United States Patent
Altermann et al.

(10) Patent No.: US 9,441,016 B2
(45) Date of Patent: Sep. 13, 2016

(54) **COMPLETE GENOME SEQUENCE OF THE METHANOGEN *METHANOBREVIBACTER RUMINANTIUM***

(75) Inventors: Eric Heinz Altermann, Palmerston North (NZ); Graeme Trevor Attwood, Ashhurst (NZ); Gregory Cook, Dunedin (NZ); Debjit Dey, Palmerston North (NZ); Scott A. Ferguson, Cambridge (GB); Petrus Hendricus Janssen, Palmerston North (NZ); William John Kelly, Ashhurst (NZ); Zhanhao Kong, Shanghai (CN); Suzanne Lambie, Palmerston North (NZ); Sinead Christine Leahy, Palmerston North (NZ); Dong Li, Palmerston North (NZ); Duncan McMillan, Dunedin (NZ); Sharla McTavish, Loughborough (GB); Diana Pacheco, Palmerston North (NZ); Robert Starr Ronimus, Palmerston North (NZ); Carrie Sang, Palmerston North (NZ); Carl Yeoman, Champaign, IL (US)

(73) Assignee: Pastoral Greenhouse Gas Research Ltd., Wellington (NZ)

( * ) Notice: Subject to any disclaimer, the term of this patent is extended or adjusted under 35 U.S.C. 154(b) by 269 days.

(21) Appl. No.: 13/392,075

(22) PCT Filed: Aug. 27, 2010

(86) PCT No.: PCT/NZ2010/000169
§ 371 (c)(1),
(2), (4) Date: May 7, 2012

(87) PCT Pub. No.: WO2011/025394
PCT Pub. Date: Mar. 3, 2011

(65) Prior Publication Data
US 2013/0217612 A1    Aug. 22, 2013

Related U.S. Application Data

(60) Provisional application No. 61/237,296, filed on Aug. 27, 2009.

(30) Foreign Application Priority Data

Aug. 27, 2009  (NZ) ......................................... 579292

(51) Int. Cl.
| C12N 15/31 | (2006.01) |
| C07K 14/195 | (2006.01) |
| C07K 16/12 | (2006.01) |
| C12N 15/74 | (2006.01) |

(52) U.S. Cl.
CPC ......... *C07K 14/195* (2013.01); *C07K 16/1267* (2013.01); *C12N 15/74* (2013.01); *G01N 2333/195* (2013.01)

(58) Field of Classification Search
None
See application file for complete search history.

(56) References Cited

U.S. PATENT DOCUMENTS

| 2003/0219467 A1 | 11/2003 | Miner et al. |
| 2010/0048595 A1 | 2/2010 | Gordon et al. |
| 2010/0172874 A1 | 7/2010 | Turnbaugh et al. |
| 2010/0184624 A1 | 7/2010 | Samuel et al. |

FOREIGN PATENT DOCUMENTS

| WO | 9511041 | 4/1995 |
| WO | 9700086 | 1/1997 |
| WO | 03038109 | 5/2003 |
| WO | 2006102350 | 9/2006 |
| WO | 2008076696 | 6/2008 |
| WO | 2008151032 | 12/2008 |
| WO | WO 2009041832 A2 * | 4/2009 |
| WO | 2010002890 | 1/2010 |
| WO | 2010030997 | 3/2010 |

OTHER PUBLICATIONS

Samuel et al., "Genomic and metabolic adaptations of Methanobrevibacter smithii to the human gut" PNAS 104:10643-10648 (2007).*
Accession No. ABQ87469, cell division control protein Cdc6 from M. smithii, accessed Jun. 22, 2013.*
Accession No. ABQ87418, 3-hexulose 6-phosphate synthase/formaldehyde activating enzyme from M. smithii, accessed Jun. 22, 2013.*

(Continued)

*Primary Examiner* — Julie Ha
*Assistant Examiner* — Kristina M Hellman
(74) *Attorney, Agent, or Firm* — Loeb & Loeb LLP

(57) ABSTRACT

The present invention includes the complete genome sequence for the methanogen, *Methanobrevibacter ruminantium*, including polynucleotides which encode *M. ruminantium* polypeptides or peptides, as well as polynucleotides from non-coding regions. Also included are the encoded *M. ruminantium* polypeptides and peptides, and antibodies directed to these peptides or polypeptides, in addition to expression vectors and host cells for producing these peptides, polypeptides, polynucleotides, and antibodies. The invention further includes methods and compositions for detecting, targeting, and inhibiting microbial cells, especially methanogen cells such as *M. ruminantium* cells, using one or more of the disclosed peptides, polypeptides, polynucleotides, antibodies, expression vectors, and host cells.

13 Claims, 42 Drawing Sheets

(56) References Cited

OTHER PUBLICATIONS

Attwood et al., "Analysis of the Methanobrevibacter ruminantium draft genome: understanding methanogen biology to inhibit their action in the rumen," Austral. J. Exper. Agricult. 48:83-88 (2008).*
Attwood, et al., "Analysis of the methanobrevibacter ruminatium draft genome: understanding methanogen biology to inhibit their action in the rumen," Austr. J. Exper. Agri. 48:83-88 (published online Jan. 2, 2008).*
UnitProt Accession No. D3E1E0 accessed Aug. 2, 2014 at URL: uniprot.org/uniprot/D3E1E0.*
Attwood, et al., "Analysis of the methanobrevibacter ruminatium draft genome: understanding methanogen biology to inhibit the ir action in the rumen," Austr. J. Exper. Agri. 48:83-88 (published online Jan. 2, 2008).*
Accession No. A5UMS1, M. smithii, accessed Jan. 17, 2014 at http://www.uniprot.org/uniprot/A5UMS1.*
Attwood G T et al: "Analysis of the Methanobrevibacter Ruminantium Draft Genome: Understanding Methanogen Biology to Inhibit Their Action in the Rumen", Australian Journal of Experimental Agriculture, Jan. 2, 2008, 48(2):83-88.
Frick W.R. et al. "The Genome Sequence of Methanosphaera Stadtmanae Reveals Why This Human Intestinal Archaeon is Restricted to Methanol and H2 for Methane Formation and ATP Synthesis," Journal of Bacteriology, Jan. 2006, 188(2):642-658.
Samuel B.S. et al. "Genomic and Metabolic Adaptations of Methanobrevibacter Smithii to the Human Gut,".PNAS, Jun. 19, 2007, 104(25):10643-10648.
Smith D.R. et al. "Complete Genome Sequence of Methanobacterium Thermoautotrophicum Delta H: Functional Analysis and Comparative Genomics," Journal of Bacteriology, Nov. 1997, 179(22):7135-7155.
International Preliminary Patentability Report corresponding to related PCT Application No. PCT/NZ2010/000169; Mailed Feb. 28, 2008; and Written Opinion of the ISA mailed Dec. 2, 2010.

Anderson, I. "Genomic Characterization of Methanomicrobiales Reveals Three Classes of Methanogens", Lawrence Berkeley National Laboratory, Oct. 6, 2009, pp. 1-33.
Attwood, G. "Methanogen genomics to discover targets for methane mitigation technologies and options for alternative H2 utilisation in the rumen", Australian Journal of Experimental Agriculture, 2008, pp. 28-37, vol. 48, Csiro Publishing.
Balch, W.E. et al., "Methanogens: Reevaluation of a Unique Biological Group", Microbiological Reviews, Jun. 1979, pp. 260-296, vol. 43, No. 2.
Balch, W.E. et al., "New Approach to the Cultivation of Methanogenic Bacteria: 2-Mercaptoethanesulfonic Acid (HS-CoM)-Dependent Grouth of Methanobacterium ruminantium in a Pressurized Atmosphere", Applied and Environmental Microbiology, Dec. 1979, pp. 781-791, vol. 32, No. 6.
Bambini, S. et al., "The use of genomics in microbial vaccine development", Drug Discovery Today, Mar. 2009, pp. 252-260, vol. 14, Nos. 5/6, Elsevier Ltd.
Dumitru R. et al., "Targeting Methanopterin Biosynthesis to Inhibit Methanogenesis", Applied and Enviornmental Microbiology, Dec. 2003, pp. 7236-7241; vol. 69, No. 12.
Leahy, S. et al., "The Genome Sequence of the Rumen Methanogen Methanobrevibacter ruminantium Reveals New Possibilities for Controlling Ruminant Methane Emissions", PLos One, Jan. 2010, pp. 1-16, vol. 5, No. 1.
Luo, H. et al., "Differential Expression of Methanogenesis Genes of Methanothermaobacter thermoautotrophicus (Formerly Methanobacterium thermoautotrophicum) in Pure Culure and in Cocultures with Fatty Acid-Oxidizing Syntrophs", Mar. 2002, pp. 1173-1179, vol. 68, No. 3.
Luo, Y. et al., "Pseudomurein endoisopeptidases PeiW and PeiP, two moderately related members of a novel family of proteases produced in Methanothermobacter strains", FEMS Microbiology Letters, 2008, pp. 47-51, Elsevier Science B.V.
Smith, P.H. et al., "Isolation and Characterization of *Methanobacterium ruminantium* N. SP", Journal of Bacteriology, 1958, pp. 713-718, vol. 75, No. 6.

* cited by examiner

Supplementary Figure. [A] Consensus sequence of forty-four C-terminal regions (200 amino acids) from adhesin-like proteins of *M. ruminantium* M

Fig 18

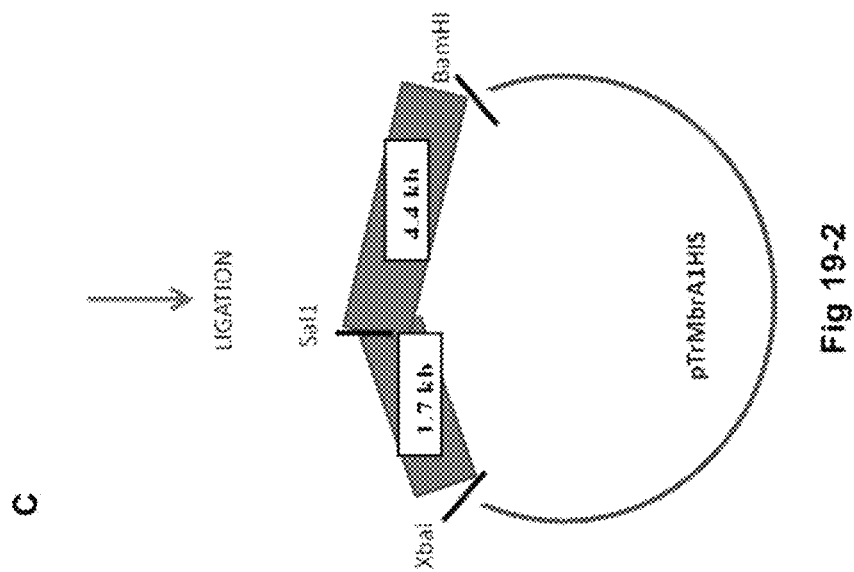

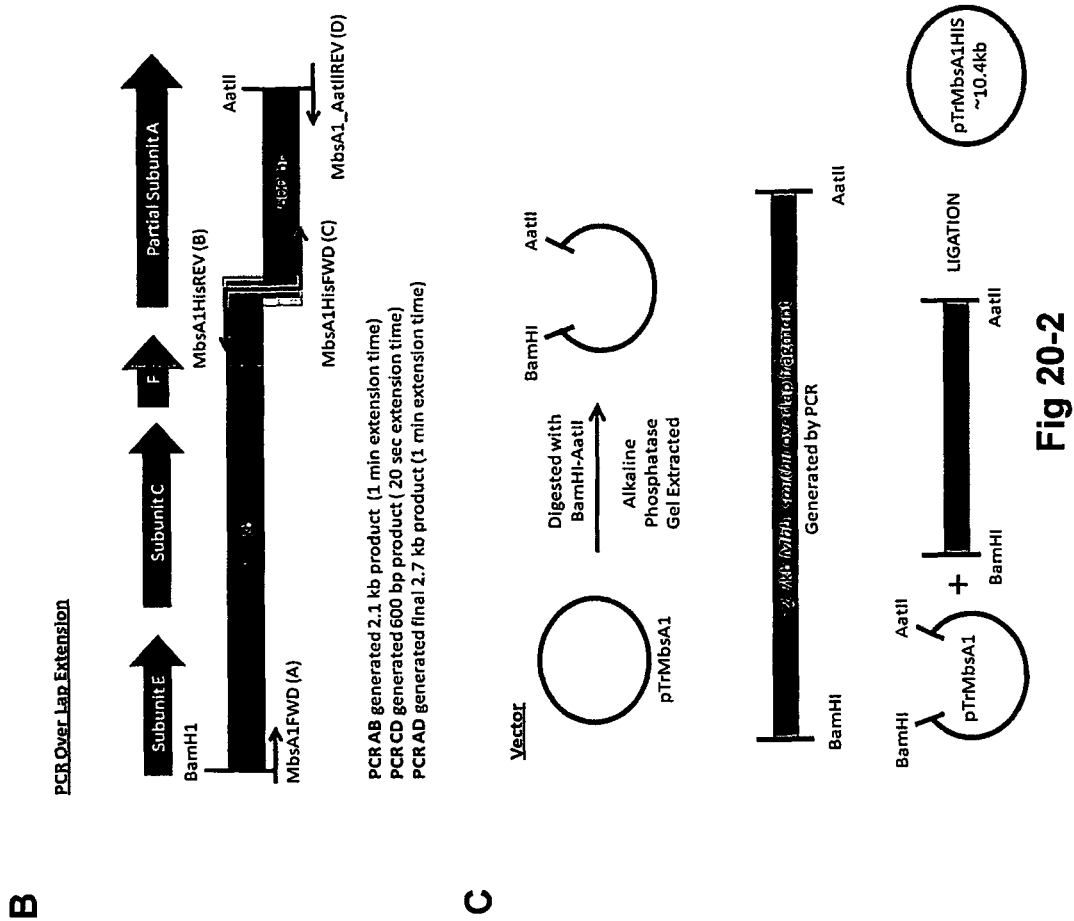

Mbb. ruminantium A₁Aₒ-ATP synthase

| Gene | Subunit | Size (Kda) | Amino Acids (bp) |
|---|---|---|---|
| atpH | H | 11.1 | 104 |
| atpI | i | 73.7 | 667 |
| atpK | k | 15.5 | 161 |
| atpE | E | 22.4 | 208 |
| atpC | C | 42.6 | 384 |
| atpF | F | 11.2 | 105 |
| atpA | A | 64.0 | 584 |
| atpB | B | 51.1 | 462 |
| atpD | D | 26.3 | 231 |

COMPLETE GENOME SEQUENCE OF THE METHANOGEN *METHANOBREVIBACTER RUMINANTIUM*

RELATED APPLICATIONS

This is a national phase application of PCT/NZ2010/000169, filed 27 Aug. 2010, which claims the benefit of U.S. Provisional Patent Application 61/237,296 filed 27 Aug. 2009 and New Zealand Provisional Patent Application 579292 filed 27 Aug. 2009, which are hereby incorporated by reference herein, in their entirety.

FIELD OF THE INVENTION

The present invention encompasses the complete genome sequence for the methanogen, *Methanobrevibacter ruminantium*. The invention encompasses polynucleotides which encode *M. ruminantium* polypeptides or peptides, as well as polynucleotides from non-coding and intergenic regions. Also encompassed are the encoded *M. ruminantium* polypeptides and peptides, and antibodies directed to these peptides or polypeptides. The invention also encompasses expression vectors and host cells for producing these peptides, polypeptides, polynucleotides, and antibodies. The invention further encompasses methods and compositions for detecting, targeting, and inhibiting microbial cells, especially methanogen cells such as *M. ruminantium* cells, using one or more of the disclosed peptides, polypeptides, polynucleotides, antibodies, expression vectors, and host cells.

BACKGROUND OF THE INVENTION

Global surface temperatures are predicted to increase between 1.1° C. to 6.4° C. during the twenty-first century primarily due to increased levels of greenhouse gases (GHGs) in the atmosphere (Solomon et al., 2007). Methane ($CH_4$) is a particularly potent GHG, having a global warming potential 21 times that of carbon dioxide ($CO_2$) (IPCC, 2007) and accounts for 16% of total global GHG emissions (Scheehle & Kruger, 2006). Methane from agriculture represents around 40% of the emissions produced by human-related activities; the single largest source of which is from enteric fermentation in livestock, mainly from ruminant animals (Steinfeld et al., 2006). The worldwide demand for meat and milk is predicted to double by 2050 (Food and Agriculture Organization of the United Nations (FAO), 2008) and ruminant-based agricultural activities are expected to continue to be an important contributor to global $CH_4$ emissions. Therefore, reducing $CH_4$ emissions from ruminants will be important in meeting international commitments under the Kyoto Protocol and also in ensuring the long-term sustainability of ruminant-based agriculture. Moreover, as $CH_4$ production in the rumen accounts for 2-12% of the ingested energy (Johnson & Johnson, 1995), it is predicted that reducing $CH_4$ emissions from ruminants will also make more energy available to the animal and therefore enhance their productivity. Ruminant animals are particularly important to agriculture in New Zealand (NZ), producing a third of NZ's commodity exports (Statistics New Zealand, 2008) and making up a large proportion of the internationally traded lamb and milk products (Leslie et al., 2008). Consequently, NZ has an unusual GHG emission profile, with ruminant $CH_4$ emissions accounting for 31% of NZ's total GHG emissions (Ministry for the Environment, 2007).

Methane is formed in the fore-stomach (reticulorumen, or more commonly known as the rumen) by methanogens, a subgroup of the Archaea. During normal rumen function, plant material is broken down by fibre-degrading microorganisms and fermented mainly to volatile fatty acids (VFAs), ammonia, hydrogen ($H_2$) and $CO_2$. Rumen methanogens principally use $H_2$ to reduce $CO_2$ to $CH_4$ in a series of reactions that are coupled to ATP synthesis. The rumen harbours a variety of different methanogen species, but analyses of archaeal small subunit ribosomal RNA genes from rumen samples of ruminants on differing diets around the world suggest the majority fall into three main groups: *Methanobrevibacter*, *Methanomicrobium* and a large, as yet uncultured, group of rumen archaea referred to as rumen cluster C (Janssen & Kirs, 2008). Sequences affiliated with *Methanobrevibacter* dominate, on average accounting for 61.6% of rumen archaea, with sequences associated with *M. gottschalkii* (33.6%) and *M. ruminantium* (27.3%) being most prominent.

Attempts have been made to inhibit the action of methanogens in the rumen using a variety of interventions but most have failed, or met with only limited success, due to low efficacy, poor selectivity, toxicity of compounds against the host, or build up of resistance to anti-methanogen compounds (McAllister & Newbold, 2008). Currently there are few practical methane reduction technologies available for housed ruminant animals, and no effective technologies for grazing animals. Methane interventions should ideally target features that are conserved across all rumen methanogens, so that no unaffected methanogens can fill the vacated niche. Interventions should also be specific for methanogens only, such that other rumen microbes continue their normal digestive functions. Whole genome sequencing allows the definition of gene targets that are both conserved and specific to rumen methanogens. It is not yet possible to obtain genome sequences of all methanogen groups present in the rumen as some are yet to be cultivated, and a rumen methanogen "metagenome" is prevented by the inability of current sequencing technologies to reassemble complete genomes from complex microbial ecosystems. Therefore, sequencing the genomes of individual rumen methanogens currently in culture is a critical step in developing $CH_4$ mitigation technologies for ruminant animals.

SUMMARY OF THE INVENTION

Here we report the genome sequence of *M. ruminantium* M1T (DSM 1093), the first rumen methanogen genome to be completely sequenced. We have included a particular emphasis on identifying targets for enteric methane mitigation technologies focusing on vaccine development and anti-methanogen drug leads.

The invention thus features the complete genome sequence for the methanogen, *Methanobrevibacter ruminantium*. The invention features, in particular, isolated peptides, polypeptides, and polynucleotides of *M. ruminantium*, as well as expression vectors, host cells, and antibodies, and methods of use thereof, as described in detail herein.

The invention specifically features an isolated peptide comprising, for example, at least a fragment of one amino acid sequence selected from the group consisting of SEQ ID NO: 5867-7584. In a particular aspect, the peptide comprises at least a fragment of an amino acid sequence of any one of SEQ ID NO: 5867-7584. In a further aspect, the peptide comprises at least a fragment of an amino acid sequence of any one of SEQ ID NO: 5867-7584. In another aspect, the peptide is a fragment, for example, comprising at least one amino acid sequence encompassing an extracellular domain of any one of SEQ ID NO: 5867-7584.

The invention specifically features an isolated polypeptide comprising, for example, at least one amino acid sequence selected from the group consisting of SEQ ID NO: 5867-7584. In a particular aspect, the polypeptide comprises the amino acid sequence of any one of SEQ ID NO: 5867-7584. In a further aspect, the polypeptide comprises the amino acid sequence of any one of SEQ ID NO: 5867-7584. In another aspect, the polypeptide is a fragment, for example, comprising at least one amino acid sequence encompassing an extracellular domain of any one of SEQ ID NO: 5867-7584.

The invention additionally features an isolated polynucleotide comprising a coding sequence for at least one peptide. In one aspect, the polynucleotide comprises a coding sequence for at least a fragment of an amino acid sequence selected from the group consisting of SEQ ID NO: 5867-7584. In a particular aspect, the polynucleotide comprises a coding sequence for at least a fragment of any one of SEQ ID NO: 5867-7584. In a further aspect, the polynucleotide comprises a coding sequence for at least a fragment of any one of SEQ ID NO: 5867-7584. In another aspect, the polynucleotide comprises a fragment of a coding sequence, for example, least one amino acid sequence encompassing an extracellular domain of any one of SEQ ID NO: 5867-7584.

The invention additionally features an isolated polynucleotide comprising a coding sequence for at least one polypeptide. In one aspect, the polynucleotide comprises a coding sequence for at least one amino acid sequence selected from the group consisting of SEQ ID NO: 5867-7584. In a particular aspect, the polynucleotide comprises a coding sequence for any one of SEQ ID NO: 5867-7584. In a further aspect, the polynucleotide comprises a coding sequence for any one of SEQ ID NO: 5867-7584. In another aspect, the polynucleotide comprises a fragment of a coding sequence, for example, least one amino acid sequence encompassing an extracellular domain of any one of SEQ ID NO: 5867-7584.

In an additional aspect, the invention features an isolated polynucleotide comprising, for example, a nucleic acid sequence selected from the group consisting of SEQ ID NO: 1-1718. In a particular aspect, the polynucleotide comprises the nucleic acid sequence of SEQ ID NO: 1-1718. In another aspect, the polynucleotide is a fragment or an oligonucleotide comprising, for example, the nucleic acid sequence encompassing an extracellular domain as encoded by any one of SEQ ID NO: 1-1718. In addition, the invention encompasses an isolated polynucleotide, or fragment thereof, which hybridizes to any one of the nucleic acid sequences of SEQ ID NO: 1-1718. The invention further encompasses an isolated polynucleotide comprising the complement, reverse complement, reverse sequence, or fragments thereof, of any one of the nucleic acid sequences.

The invention features an expression vector comprising a polynucleotide of the invention. In one aspect, the expression vector comprises a coding sequence for at least a fragment of an amino acid sequence selected from the group consisting of SEQ ID NO: 5867-7584. In a particular aspect, the expression vector comprises a coding sequence for at least a fragment of at least one of SEQ ID NO: 5867-7584. In a further aspect, the expression vector comprises a coding sequence for at least one amino acid sequence of at least one of SEQ ID NO: 5867-7584. In another aspect, the expression vector comprises a coding sequence for at least one amino acid sequence encompassing an extracellular domain of any one of SEQ ID NO: 5867-7584.

The invention also features a host cell, for example, a microbial host cell, comprising at least one expression vector.

The invention specifically features an antibody directed to a peptide, polypeptide, or polynucleotide as disclosed herein. In certain aspects, the antibody is directed to an amino acid sequence selected from the group consisting of SEQ ID NO: 5867-7584. In alternate aspects, the antibody is directed to at least a fragment of a polypeptide sequence selected from the group consisting of SEQ ID NO: 5867-7584. In a particular aspect, the antibody binds to at least a fragment of the peptide sequence of any one of SEQ ID NO: 5867-7584. In a further aspect, the antibody binds to at least a fragment of the polypeptide sequence of any one of SEQ ID NO: 5867-7584. In an alternate aspect, the antibody binds to at least a fragment of a peptide or polypeptide encompassing an extracellular domain of any one of SEQ ID NO: 5867-7584. In another aspect, the antibody includes one or more fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention additionally features modified peptides or polypeptides, e.g., for at least one of SEQ ID NO: 5867-7584, including biologically active alterations, fragments, variants, and derivatives, described herein. Also featured are polynucleotides encoding these modified peptides or polypeptides, as well as alterations, fragments, variants, and derivatives of the disclosed polynucleotides; antibodies raised using these modified peptides, polypeptides, or polynucleotides; expression vectors comprising these polynucleotides; and host cells comprising these vectors. Further featured are modified antibodies, including biologically active alterations, fragments, variants, and derivatives, described herein. In specific aspects, the compositions and methods of the invention employ these modified peptides, polypeptides, polynucleotides, antibodies, or corresponding expression vectors or host cells.

The invention features a composition comprising an isolated peptide or polypeptide, e.g., at least one of SEQ ID NO: 5867-7584. Also featured is a composition comprising an isolated polynucleotide, e.g., at least one of SEQ ID NO: 1-1718. The invention additionally features a composition comprising an antibody, e.g., directed to a peptide, polypeptide, or polynucleotide sequence disclosed herein. Further featured is a composition that includes an expression vector, or host cell comprising an expression vector, in accordance with the invention. The composition can include any one of the biologically active alterations, fragments, variants, and derivatives described herein. The compositions can include at least one cell inhibitor (e.g., as a fusion or conjugate), and can be formulated, for example, as pharmaceutical compositions, in particular, vaccine compositions.

The invention also features a composition of the invention as part of a kit for targeting and/or inhibiting microbial cells, especially methanogen cells, in accordance with the disclosed methods. The kits comprise: a) at least one composition as set out herein; and b) optionally, instructions for use, for example, in targeting cells or inhibiting cell growth or replication for methanogens or other microbes.

The invention also features a method for producing a peptide or polypeptide, e.g., at least a fragment of any one of SEQ ID NO: 5867-7584, the method comprising: a) culturing an expression vector or host cell comprising an expression vector, which comprises at least part of a coding sequence for at least one peptide or polypeptide under conditions suitable for the expression of the peptide or polypeptide; and b) recovering the peptide or polypeptide from the culture. In particular aspects, the peptide or polypeptide comprises at least one amino acid sequence selected from the group consisting of SEQ ID NO: 5867-7584, or modified sequences thereof.

The invention also features a method for producing an antibody, e.g., directed to at least a fragment of any one of SEQ ID NO: 5867-7584, the method comprising: a) culturing an expression vector or host cell comprising an expression vector, which comprises at least part of a coding sequence for at least one antibody or antibody fragment under conditions suitable for the expression of the antibody or antibody fragment; and b) recovering the amino acid sequence from the culture. In particular aspects, the antibody or antibody fragment is directed to at least one amino acid sequence selected from the group consisting of SEQ ID NO: 5867-7584, or modified sequences thereof. In an alternate aspect, the antibody is produced by administration to a host animal, as described in detail herein.

The invention additionally features a method for producing an antibody, e.g., directed to at least a fragment of any one of SEQ ID NO: 5867-7584, which comprises a fusion or conjugate with at least one cell inhibitor. Such method comprises: a) culturing an expression vector or host cell comprising an expression vector, which comprises a coding sequence for at least one antibody or antibody fragment under conditions suitable for the expression of the antibody or antibody fragment; b) forming a fusion or conjugate to the antibody or antibody fragment (e.g., by expression of the fused sequence or chemical conjugation to the cell inhibitor); and c) recovering the fusion or conjugate.

In particular aspects, the antibody is directed to at least a fragment of any one of SEQ ID NO: 5867-7584, or modified sequences thereof. In further aspects, the inhibitor is selected from anti-methanogenesis compounds (e.g., bromoethanesulphonic acid), antibodies and antibody fragments, lytic enzymes, peptide nucleic acids, antimicrobial peptides, and other antibiotics as described in detail herein. In an alternate aspect, the antibody is produced by administration to a host animal and then conjugated, as described in detail herein.

In addition, the invention features a method of inhibiting (e.g., inhibiting growth or replication) of a microbial cell, in particular, a methanogen cell, comprising: contacting the cell with antibody or antibody fragment, e.g., directed to at least a fragment of any one of SEQ ID NO: 5867-7584, or an antibody fusion or conjugate, or any modified antibody. As another method, the cell is inhibited by administration of a vaccine composition as described in detail herein.

The invention further features a method of inhibiting (e.g., inhibiting growth or replication) of a microbial cell, in particular, a methanogen cell, comprising: a) optionally, producing or isolating at least one antibody as disclosed herein; and b) contacting the cell with the antibody. In a particular aspect, the antibody is directed to at least a fragment of any one of SEQ ID NO: 5867-7584, or a modified sequence thereof. In certain aspects, the antibody further comprises at least one cell inhibitor, attached, for example, as a fusion or conjugate. In other aspects, the antibody is administered to a subject as a composition, e.g., a vaccine composition.

Additionally, the invention features a method of inhibiting (e.g., inhibiting growth or replication) of a microbial cell, in particular, a methanogen cell, comprising: a) optionally, producing or isolating at least one peptide or polypeptide as disclosed herein; and b) administering the peptide or polypeptide to a subject to induce an immune response thereto. In a particular aspect, the peptide or polypeptide comprises at least one amino acid sequence selected from the group consisting of SEQ ID NO: 5867-7584, or a modified sequence thereof. In other aspects, the peptide or polypeptide is administered to a subject as a composition, e.g., a vaccine composition.

The invention furthermore features a method of detecting and/or measuring the levels of a polypeptide, in particular, a cell surface polypeptide, or corresponding peptides or polynucleotides, comprising: 1) contacting a sample from a subject with an antibody directed to the polypeptide (e.g., at least a fragment of any one of SEQ ID NO: 5867-7584, or a modified sequence thereof), or a corresponding peptide or polynucleotide (e.g., at least a fragment of one of SEQ ID NO: 1-1718, or a modified sequence thereof); and 2) determining the presence or levels of the antibody complex formed with the corresponding polypeptide, peptide, or polynucleotide in the sample. Such methods can also be used for detecting and/or measuring the levels of a microbial cell, in particular, a methanogen cell.

The invention also features a method of detecting and/or measuring the levels of a polynucleotide, in particular, a polynucleotide encoding a cell surface component, comprising: 1) contacting a sample from a subject with a complementary polynucleotide (e.g., a sequence complementary to at least a fragment of any one of SEQ ID NO: 1-1718, or a modified sequence thereof); and 2) determining the presence or levels of the hybridization complex formed with the polynucleotide in the sample. Such methods can also be used for detecting and/or measuring the levels of a microbial cell, in particular, a methanogen cell.

In particular aspects, the methods of the invention utilize in vivo or in vitro expression components. In other aspects, the methods employ peptides, polypeptides, polynucleotides, or antibodies produced by recombinant, synthetic, or semi-synthetic means, or by endogenous means.

Other aspects and embodiments of the invention are described herein below.

BRIEF DESCRIPTION OF THE DRAWINGS

This invention is described with reference to specific embodiments thereof and with reference to the figures.

Figure 3:
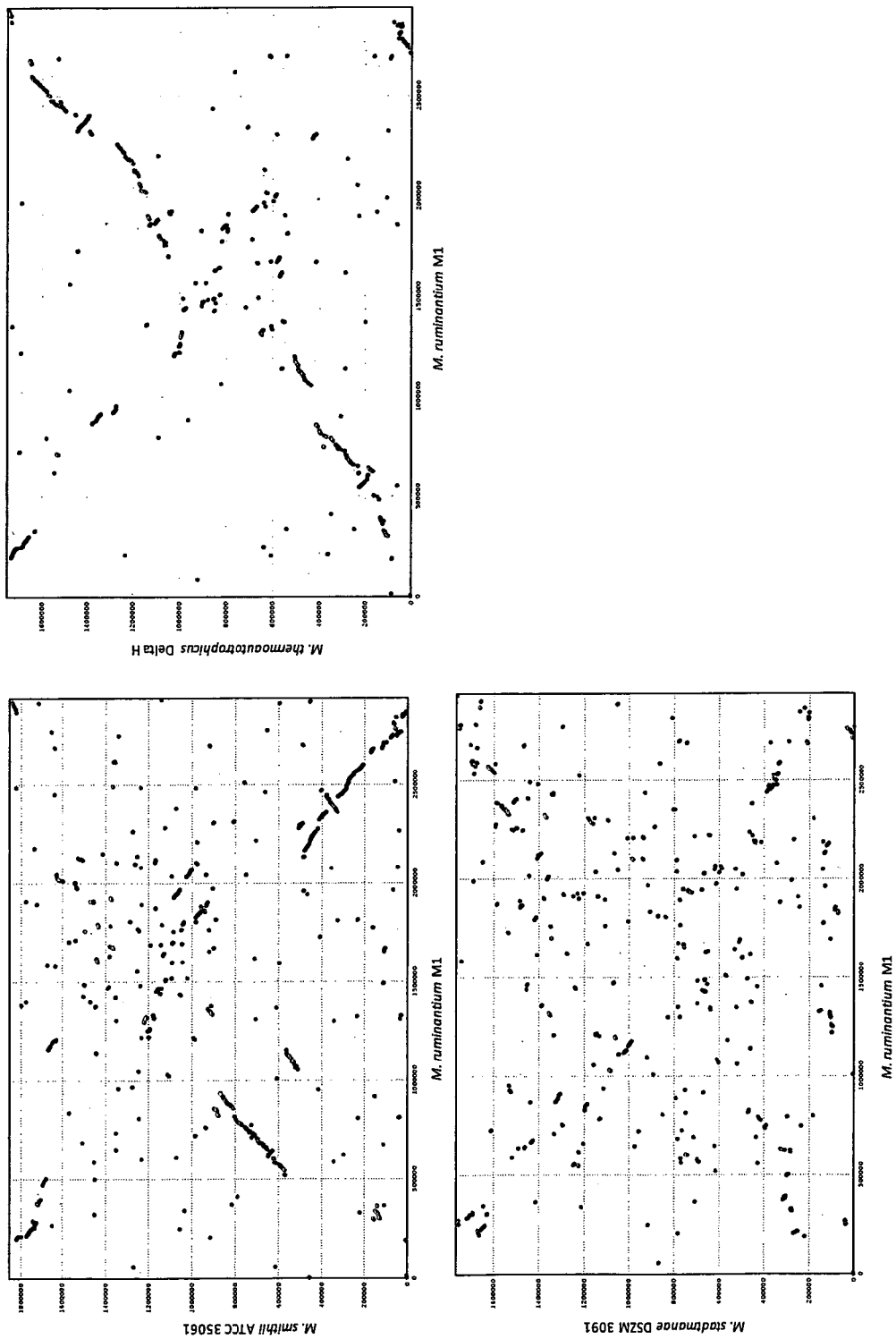

FIG. 3: PROmer alignments (Delcher et al., 2003) of *M. ruminantium* M1 against complete Methanobacteriales genomes. Whenever the two sequences agree, a shaded line or dot is plotted. The forward matches are displayed in the lighter shade, while the reverse matches are plotted in the darker shade. Where the two sequences were perfectly identical, a single lighter line would extend from the bottom left to the top right. An X-shape pattern is visible is all three synteny plots indicating moderately diverged Methanobacteriales genomes. It has been proposed that the X-pattern is generated by symmetric chromosomal inversions around the origin of replication (Emanuelsson, 2007). Units displayed in base-pairs.

Figure 4:
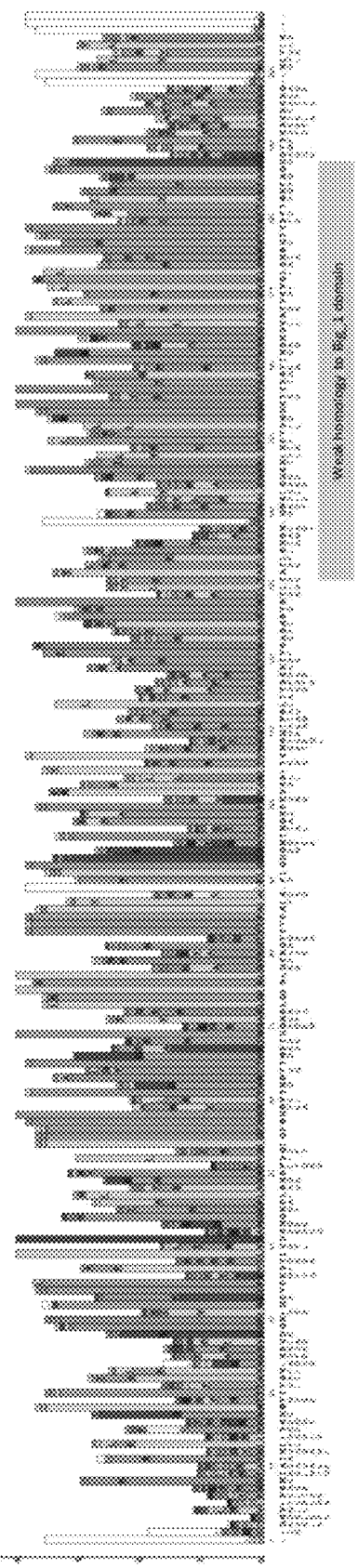

FIG. 4: Consensus sequence of forty-four C-terminal regions (200 amino acids) from adhesin-like proteins of *M. ruminantium* M1 (A). LogoBar display of this consensus. In both figures region of homology to Big_1 domain (PfamO2369) is highlighted in grey (B).

Figure 5:
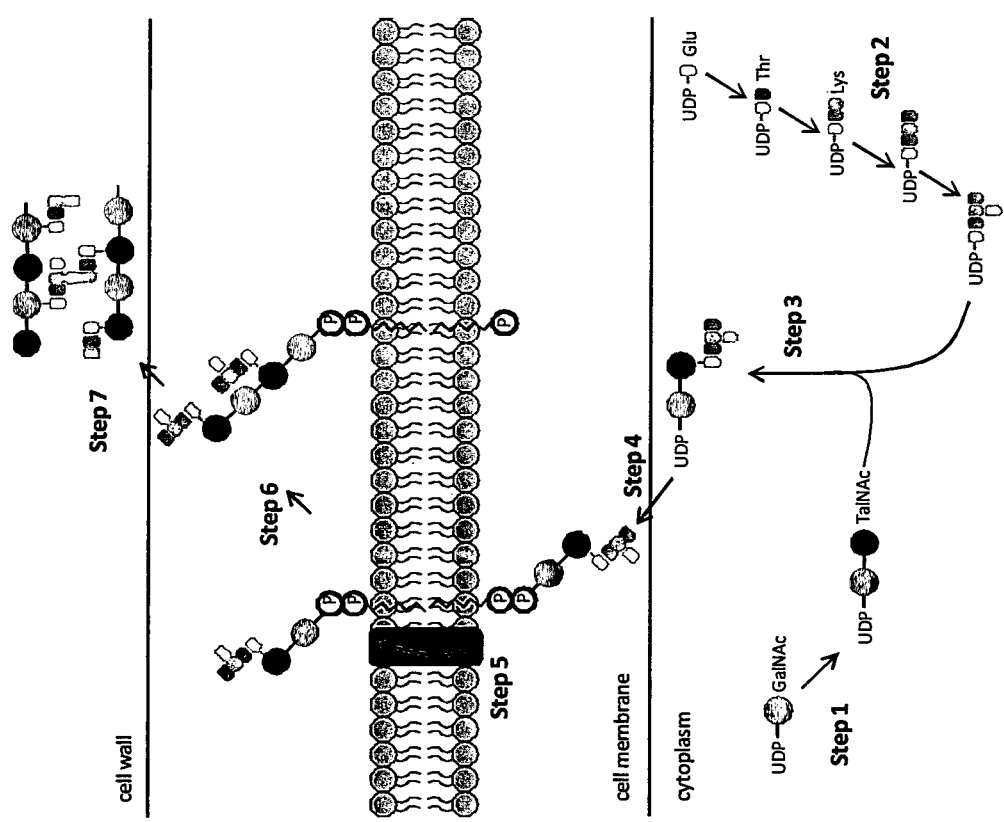

FIG. 5: Proposed biosynthetic pathway for pseudomurein in M1 (Kandler and König H, 1998; König et al., 1994). The disaccharide backbone of *M. ruminantium* M1 pseudomurein consists of N-acetylgalactosamine (GalNAc) and N-acetyltalosaminuronic acid (TalNAc) in a β(1-3) linkage. TalNac has not been detected as a monomer and it is believed to be formed during the synthesis of the disaccharide probably by epimerization and oxidation of UDP-GalNAc (Step 1). Synthesis of the pentapeptide involved in crosslinking is believed to start with UDP-glutamic acid followed by stepwise addition of L-amino acids (Step 2). The amino acids found in the pentapeptide are usually alanine, lysine (Lys) and glutamic acid (Glu), but *M. ruminantium* M1 is reported to contain threonine (Thr) instead of alanine (Kandler and König, 1978). The UDP activated pentapetide is linked to the disaccharide to give a UDP-disaccharide pentapeptide (Step 3) which is subsequently translocated to the membrane via covalent bond formation with a membrane embedded undecaprenyl phosphate (Step 4). Following their intracellular biosynthesis the pseudomurein repeating units must be exported and assembled. Homologs of the *E. coli* peptidoglycan lipid II flippase (MurJ) have been reported for pseudomurein producing methanogens (Ruiz, 2008; Step 5), but there are no genes similar to the penicillin binding proteins that carry out the transglycosylation (Step 6) and transpeptidation reactions in bacterial peptidoglycan assembly. Peptide crosslinking of pseudomurein requires removal of a terminal residue of one peptide and linkage from a glutamic acid to the lysine of an adjacent peptide (Step 7), and is probably carried out by transglutaminases. None of the enzymes involved in pseudomurein biosynthesis have been characterized, but analysis of the genome sequence has suggested candidates to carry out several of the steps. Several of these have homologs only in those methanogens with pseudomurein-containing cell walls. Two other transmembrane proteins of unknown function (mru1585 and mru1635) are also only found in pseudomurein-containing species.

Figure 6:
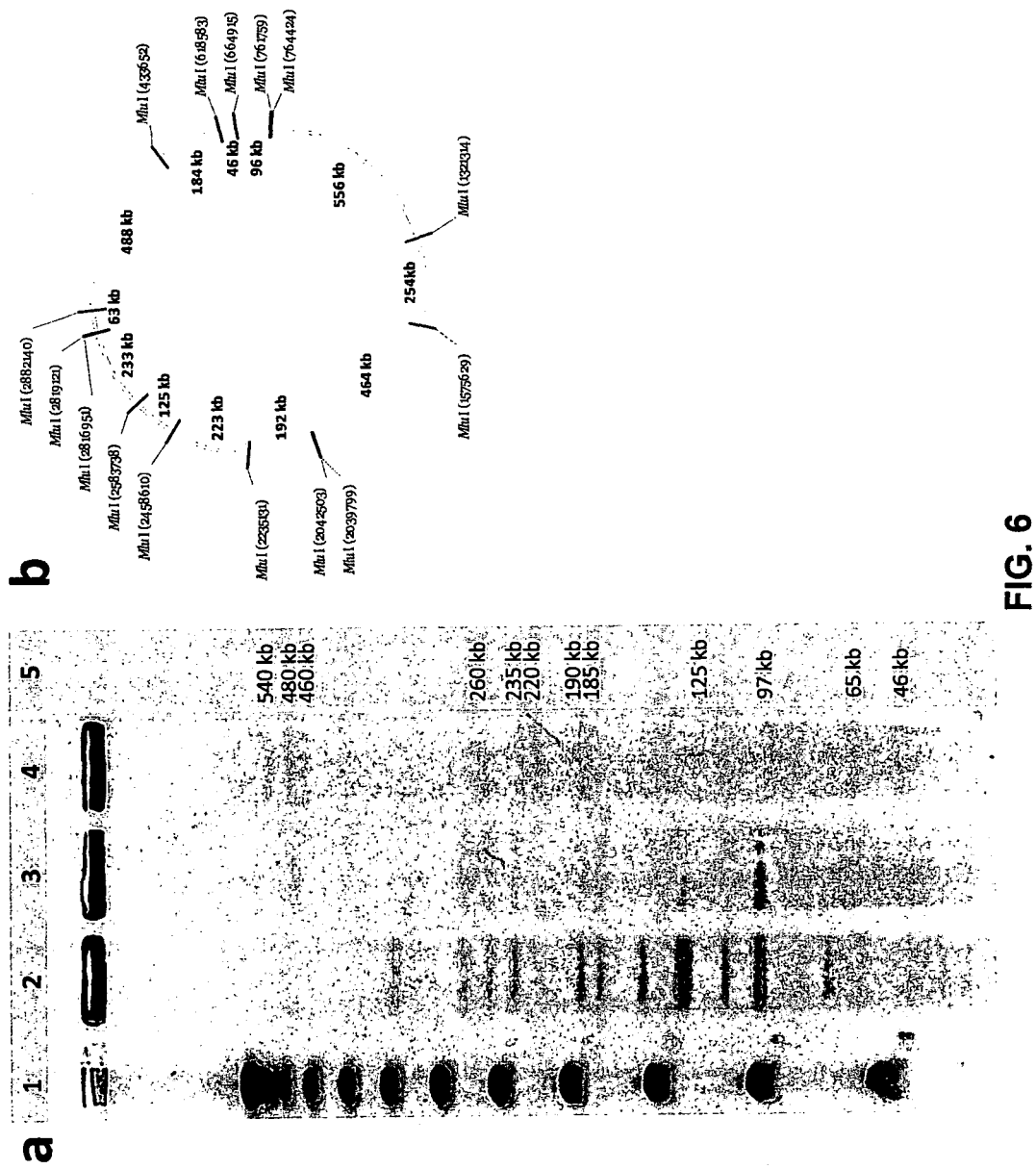

FIG. 6: (a) PFGE of genomic DNA from M1. Lane 1, λ ladder (New England Biolabs); Lane 2, ApaI/BssHII double digest; Lane 3, ApaI digest; Lane 4, MluI digest; Lane 5, Sizes of MluI fragments. The bands in the λ ladder are multiples of 48.5 kb. (b) In silico restriction map of the M1 chromosome showing the position and fragment size of the MluI digest.

Figure 7:
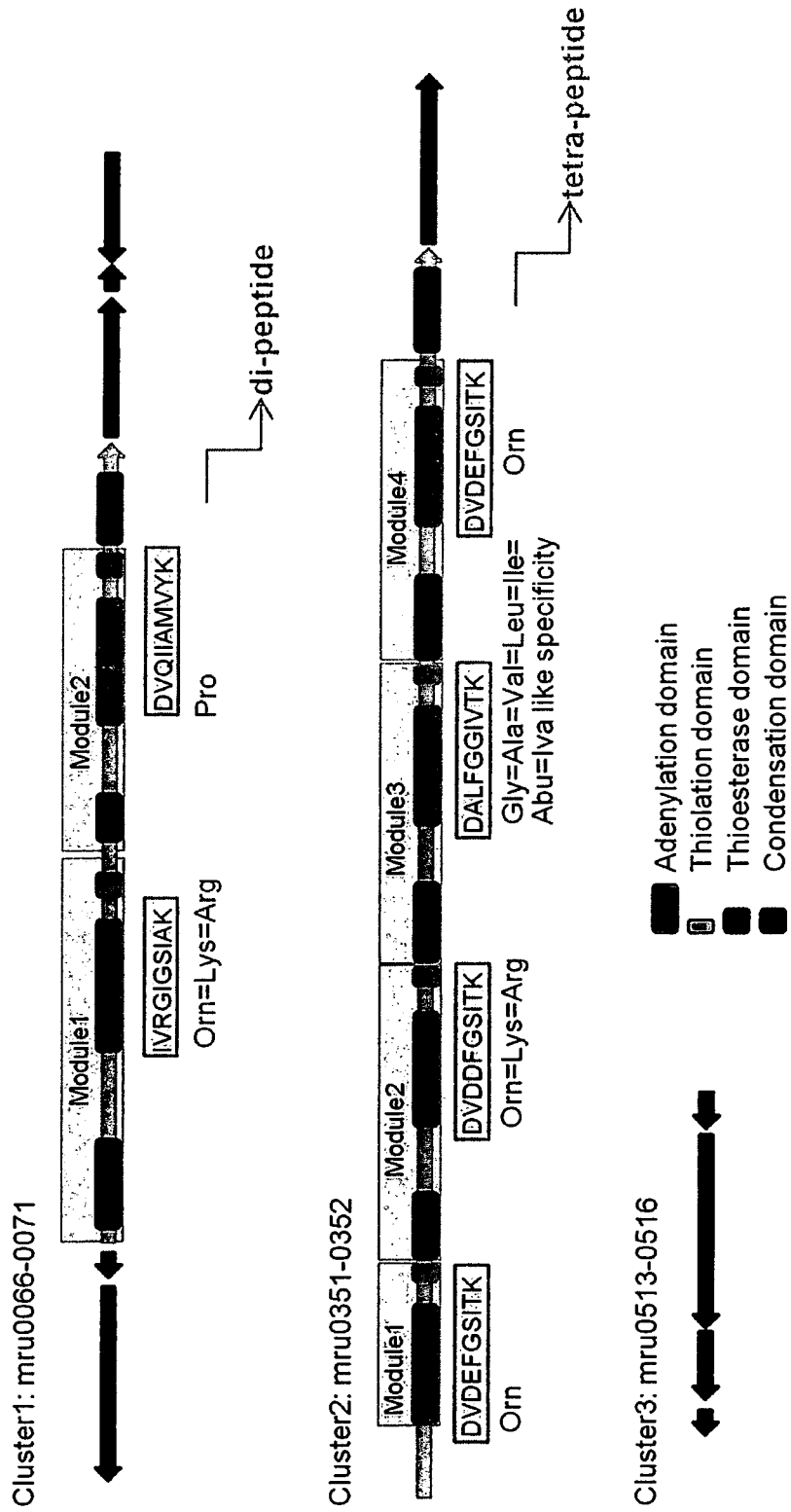

FIG. 7: Gene organisation of three clusters proposed to be involved in secondary metabolite metabolism in M1. Cluster1. Mru0068 is predicted to encode two non-ribosomal peptide synthetase (NRPS) modules, each containing condensation, adenylation and thiolation domains. The presence of a condensation domain in the first module is often associated with NRPSs that make N-acylated peptides (Steller et al., 1999). The second module is followed by a terminal thioester reductase domain which is thought to release the peptide from the final thiolation domain. Mru0068 is surrounded by genes that encode two serine phosphatases (mru0066, mru0071), an anti-sigma factor antagonist (mru0067) and a MatE efflux family protein (mru0069) which are likely to be involved in environment sensing, regulating NRPS expression and export of the NRP, respectively. Cluster2. The second NRPS gene (mru0351) contains 4 modules and a C-terminal thioester reductase domain. Immediately downstream of mru0351 is another MatE efflux family protein (mru0352), presumably involved in the efflux of the NRP. Cluster3. A small cluster of genes elsewhere in the genome (mru0513-0516) appears to encode NRPS-associated functions. The cluster includes a 4'-phosphopantetheinyl transferase (mru0514) which primes NRPSs by adding a phosphopantetheinyl group to a conserved serine within the thiolation domain, an acyltransferase (mru0512) possibly involved in NRP acylation, a serine phosphatase (mru0515), an anti-sigma factor antagonist (mru0513), and an anti-sigma regulatory factor serine/threonine protein kinase (mru0516) that may function in sensing the environment and NRPS regulation. Although the products of each NRPS are unknown, an analysis of adenylation domain amino acid sequences by NRPS predictor (Rausch et al., 2005) predicts 10 residues which are important for substrate binding and catalysis.

Figure 8:
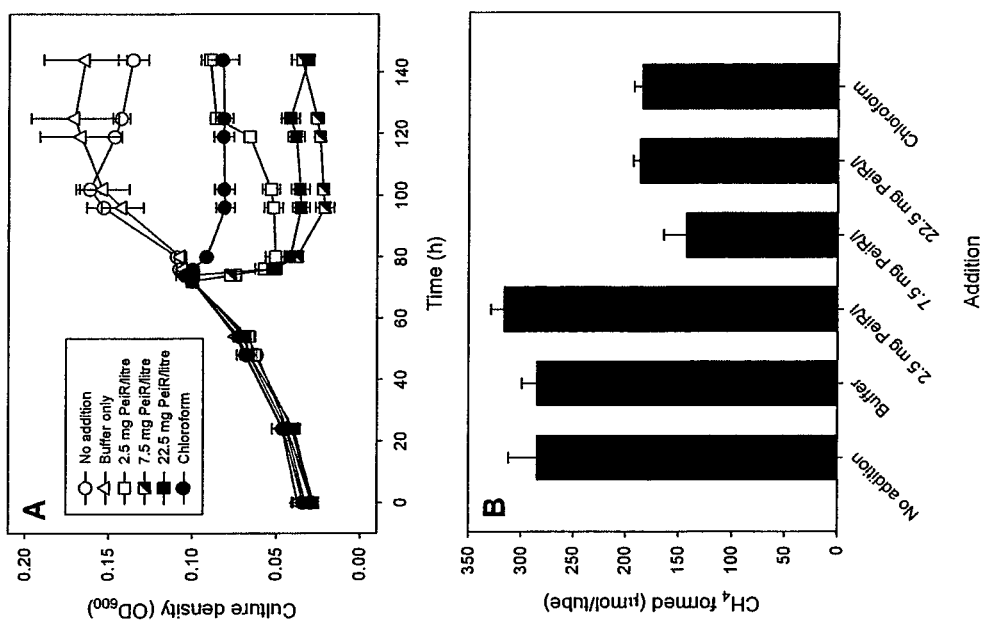

FIG. 8: Effect of the lytic enzyme PeiR on M1 growth in vitro. (A) Addition of PeiR to growing cultures at 73 h resulted in a dramatic drop in culture density, indicative of cell lysis. At a low concentration of PeiR (final concentration of 2.5 mg per liter), the cultures were able to recover, indicated by the increase in culture density after 100 h, and (B) by production of methane at levels similar to that of cultures receiving no PeiR. Addition of higher concentrations of PeiR (7.5 and 22.5 mg per liter) resulted in a lasting effect, with (A) no subsequent recovery of growth and (B) a reduced methane yield. Chloroform, a known potent inhibitor of methanogens, resulted in a similarly reduced methane yield (B), but the decrease in culture density was less (A), as expected since it halts metabolism rather than lysing cells. PeiR was added to 10 ml cultures in 0.1 ml of buffer. The buffer alone had no effect. The symbols (A) and solid bars (B) are means of 3 replicates, and the thin vertical bars represent one standard error on either side of the mean.

Figure 9:
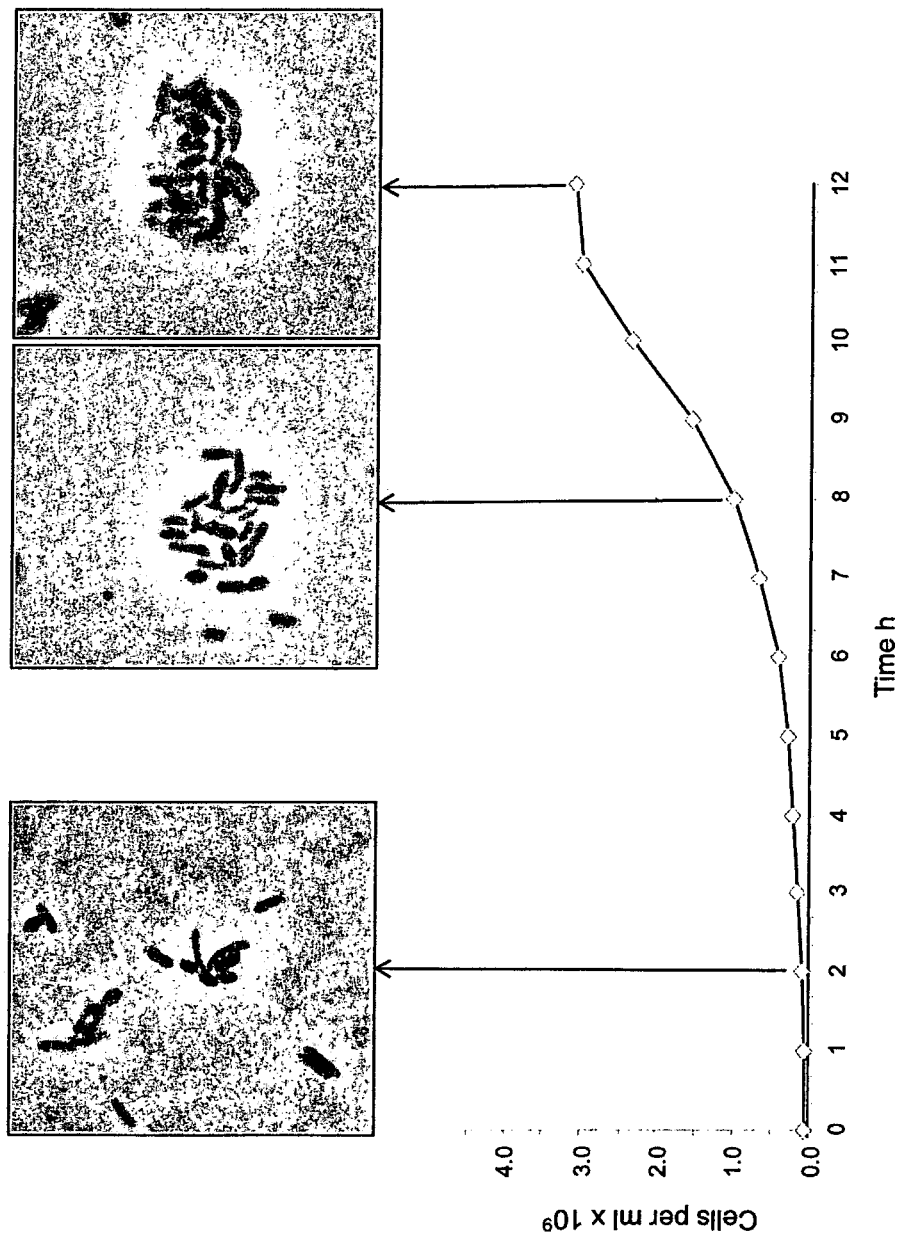

FIG. 9: Observation of interspecies interactions between *M. ruminantium* M1 and *B. proteoclasticus* B316$^T$. Graph displays growth rate of M1 in co-culture with B316. Microscopic images taken at 2, 8 and 12 h post inoculation of B316 (lighter, rod-shaped organism) into BY+ (+0.2% xylan) media containing a mid-exponential M1 culture (darker, short ovoid rod-shaped organism). Growth as determined by Thoma slide enumeration, is shown along with sampling time.

Figure 10:
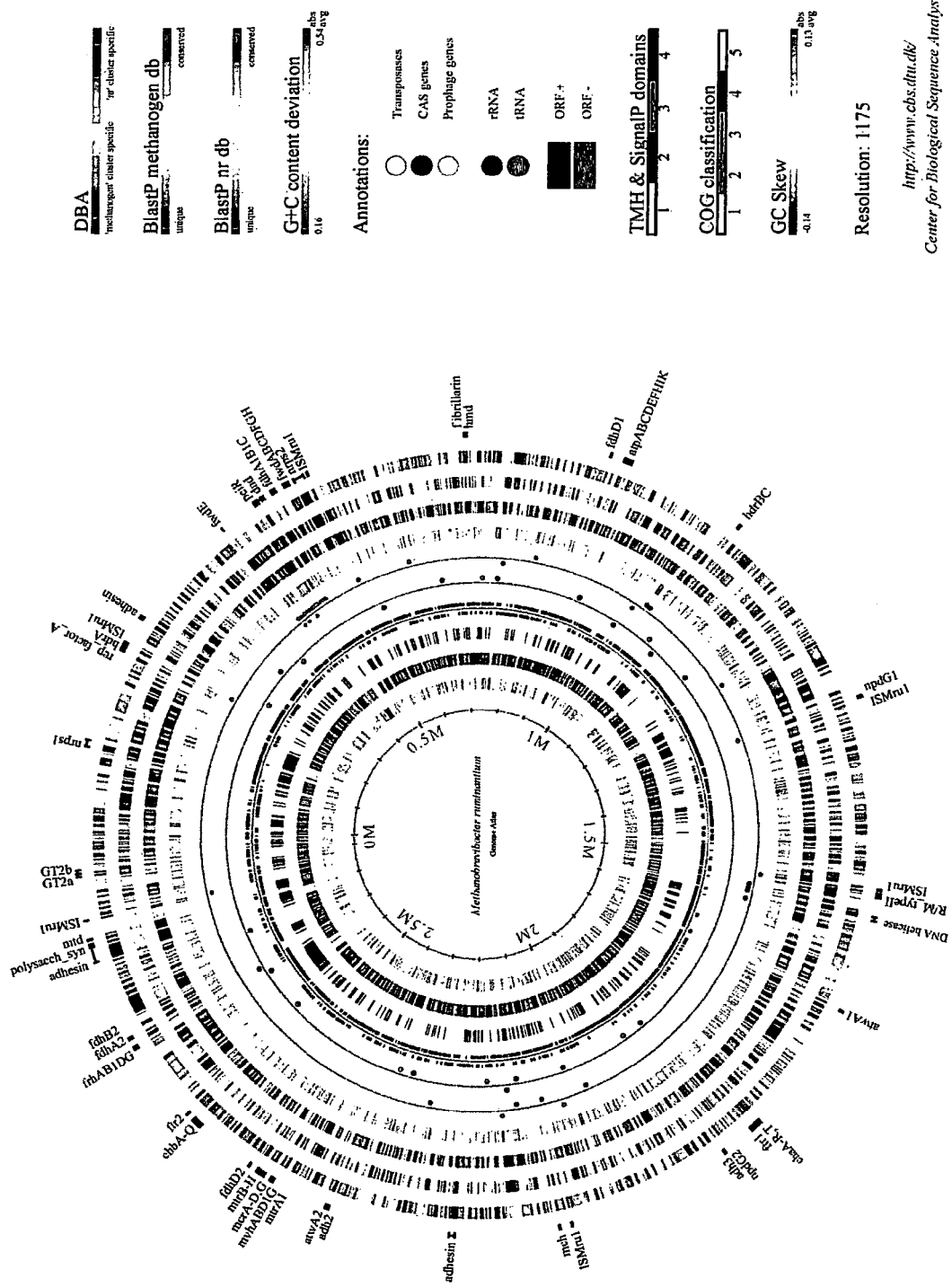

FIG. 10: Genome atlas of *M. ruminantium* M1. The circle was created using Genewiz (Jensen et al., 1999) and in house developed software. The right-hand legend describes the single circles in the top-down-outermost-innermost direction. Outermost 1$^{st}$ ring: Differential Blast Analysis between the non-redundant (nr) database (Ring 3) and a custom methanogen database (Ring 2). Regions in medium-dark shading indicate protein sequences highly conserved between *M. ruminantium* and at methanogens but not found in the nr database. Regions in darker shading indicate protein sequences conserved between *M. ruminantium* and the nr database but not present in other methanogens genomes. $2^{nd}$ ring: gapped BlastP results using a custom methanogen database consisting of publicly accessible genome project sequences (Table 10), $3^{rd}$ ring: gapped BlastP results using the non-redundant database minus published methanogen genome project sequences. In both rings, regions in medium-dark shading represent unique proteins in *M. ruminantium*, whereas highly conserved features are shown in darker shading. The degree of colour saturation corresponds to the level of similarity. $4^{th}$ ring: G+C content deviation: medium shading highlights low-GC regions, light shading high-GC islands. Annotation rings 5 and 6 indicate absolute position of functional features as indicated. $7^{th}$ ring: ORF orientation. ORFs in sense orientation (ORF+) are shown in dark shading; ORFs oriented in antisense direction (ORF−) are shown in medium-dark shading. $8^{th}$ ring: prediction of membrane bound and cell surface proteins. White: no transmembrane helices (TMH) were identified, Black: ORFs with at least one TMH, Medium-dark shading: ORFs predicted to encompass a Signal Peptide sequence and Medium shading: ORFs predicted to incorporate both TMH and SignalP domains. $9^{th}$ ring: COG classification. COG families were assembled into 5 major groups: information storage and processing (light shading); cellular processes and signalling (medium shading); metabolism (light-medium shading); poorly characterized (dark shading); and ORFs with uncharacterized COGs or no COG assignment (grey). $10^{th}$ ring: GC-skew. Innermost ring: genome size (Mb). Selected features representing single ORFs are shown outside of circle 1 with bars indicating their absolute size. Origin and terminus of DNA replication are identified in light-medium shading and dark-medium shading, respectively.

Figure 11:
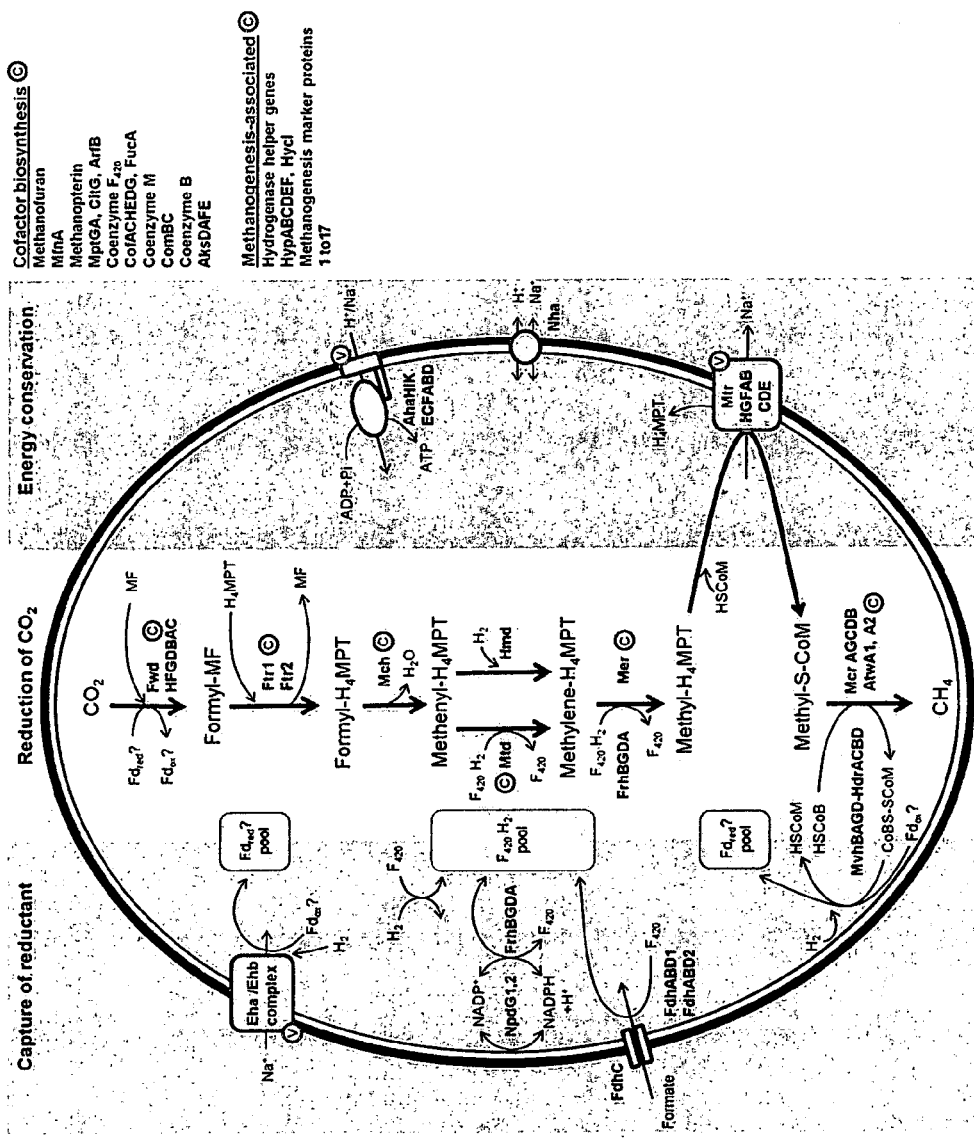

FIG. 11: Methanogenesis pathway. The predicted pathway of methane formation in M1 based on the scheme of Thauer et al. (Thauer et al., 2008) for methanogens without cytochromes. The pathway is divided into three partitions; capture of reductant (left side, medium shaded background), reduction of $CO_2$ (centre, lighter shaded background) and energy conservation (right side, darker shaded background). The main reactions are indicated by thick arrows and enzymes catalysing each step are coloured green. Cofactor participation is indicated with thin arrows. Membrane located proteins are coloured light brown and potential vaccine and chemogenomic targets are labelled with a circled V or C respectively. Small upwards arrows signify up-regulated genes during co-culture with *Butyrivibrio proteoclasticus*. Full gene names and corresponding locus tag numbers can be found in Table 9, below. $H_4MPT$; tetrahydromethanopterin; MF, methanofuran; $F_{420}$, co-factor $F_{420}$ oxidised; $F_{420}H_2$, co-factor $F_{420}$ reduced; $Fed_{(ox)}$?, unknown oxidised ferredoxin; $Fed_{(red)}$?, unknown reduced ferredoxin; HSCoM, reduced coenzyme M; HSCoB, reduced coenzyme B, CoBS-SCoM, coenzyme B-coenzyme M heterodisulphide; NADP+, nicotinamide adenosine dinucleotide phosphate non-reduced; NADPH, nicotinamide adenosine dinucleotide phosphate reduced.

Figure 12:
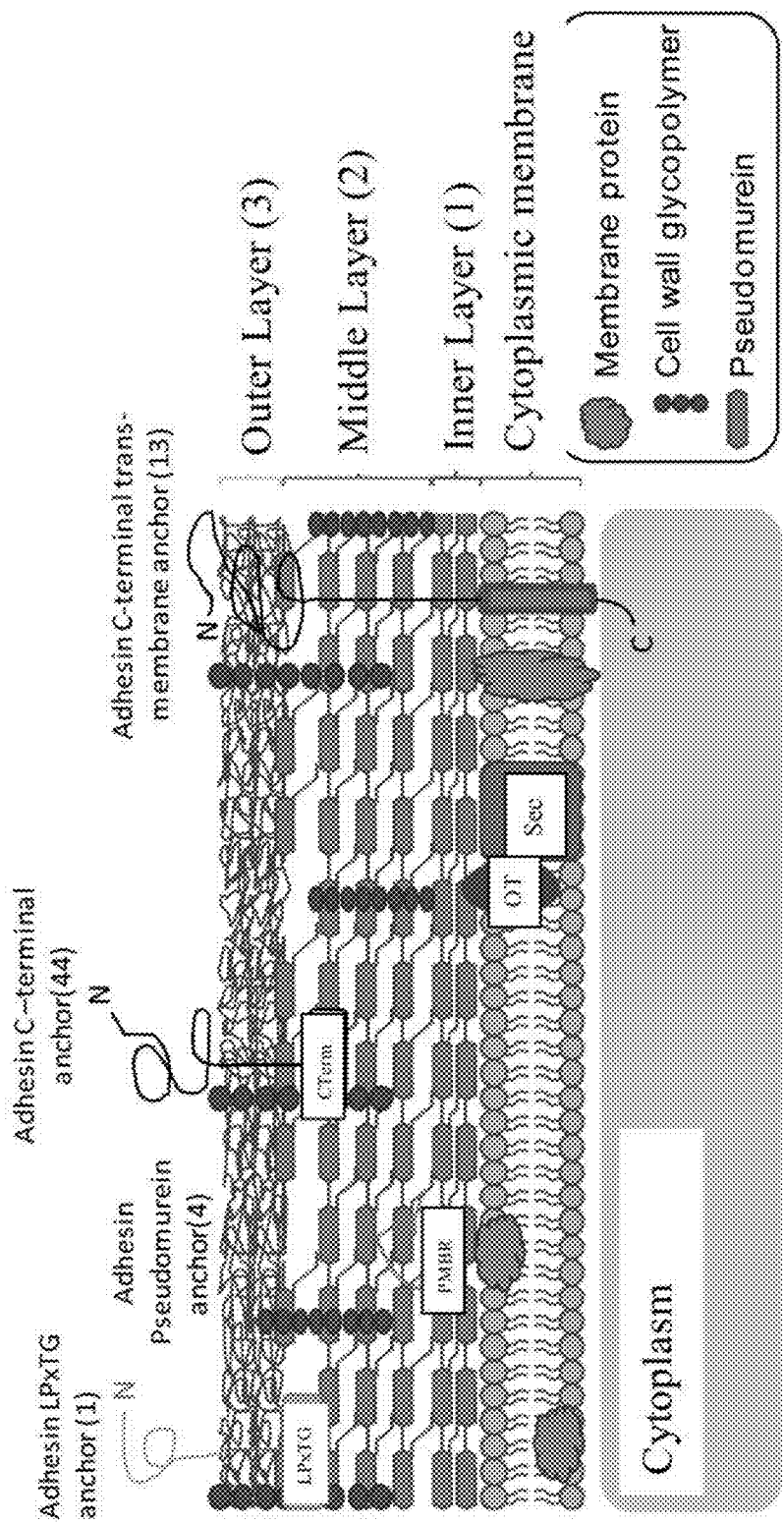

FIG. 12: Cell envelope topography of M1. Ultrastructural studies of M1 (Zeikus & Bowen, 1975; Miller, 2001) show that the cell wall is composed of three layers and is comparable to the organization seen in Gram positive bacteria (Graham & Beveridge, 1994). The three layers can be described as: (1) a thin electron-dense inner layer composed of compacted newly synthesised pseudomurein, (2) a thicker less-electron-dense middle layer which is also composed of pseudomurein, and (3) a rough irregular outer layer that is distal to the pseudomurein layers and assumed to be composed of cell wall glycopolymers, wall associated proteins and possibly other components. Representative adhesin-like proteins with different cell-anchoring domains are shown. The number of these proteins predicted in the M1 genome is shown in brackets. OT, oligosaccharyl transferase; Sec, Sec protein secretion pathway; PMBR, pseudomurein binding repeat (PF09373); M1-C, M1 adhesin-like protein conserved C-terminal domain.

Figure 13:
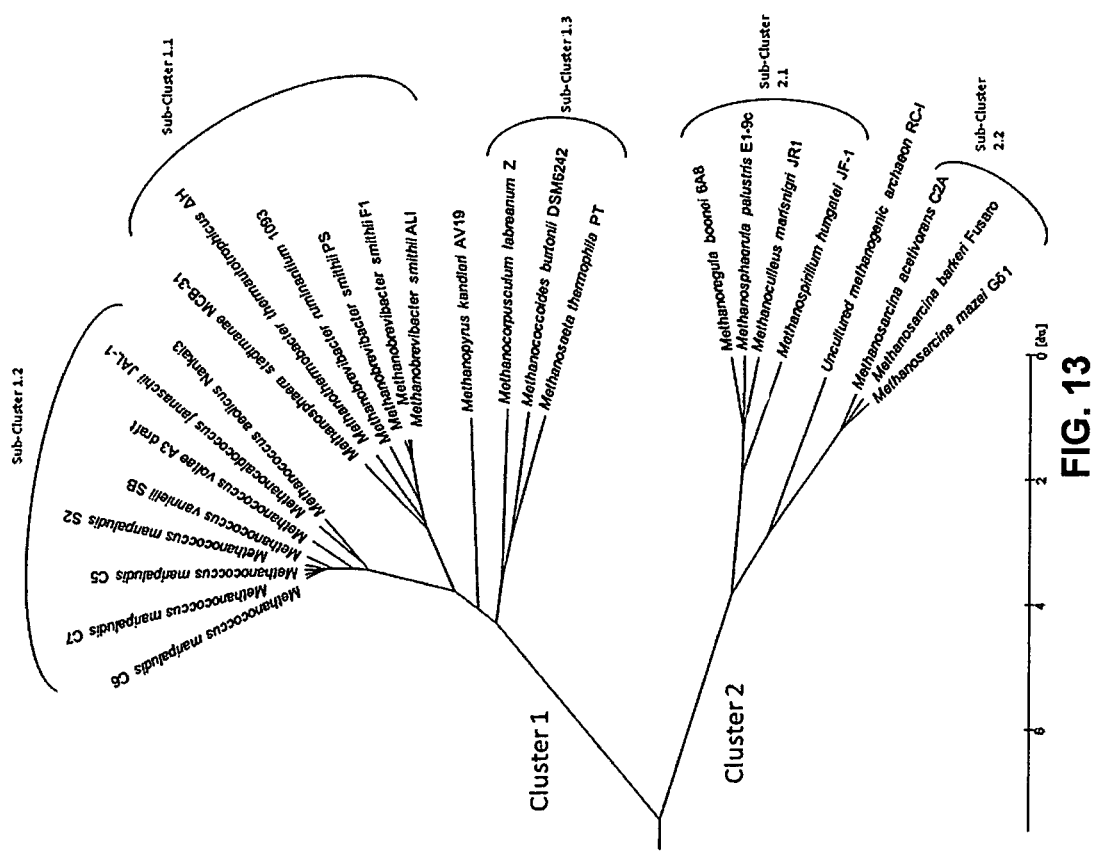

FIG. 13: Functional Genome Distribution (FGD) of 26 methanogen genomes. Publicly available complete genomes were downloaded in GenBank format were possible. Publicly available draft phase genomes were downloaded in FASTA format, concatenated using a universal spacer-stop-spacer sequence (TTAGTTAGTTAG; SEQ ID NO: 7585) and automatically annotated using GAMOLA. Predicted ORFeomes of all genomes were subjected to an FGD analysis and the resulting distance matrix was imported into MEGA4 (Samuel et al., 2007). The functional distribution was visualised using the UPGMA method (Boekhorst et al., 2005). The optimal tree with the sum of branch length=49.7 is shown. The tree is drawn to scale, with branch lengths in the same units as those of the functional distances used to infer the distribution tree. Accession numbers for individual genomes can be found in Table 10, below.

Figure 14:
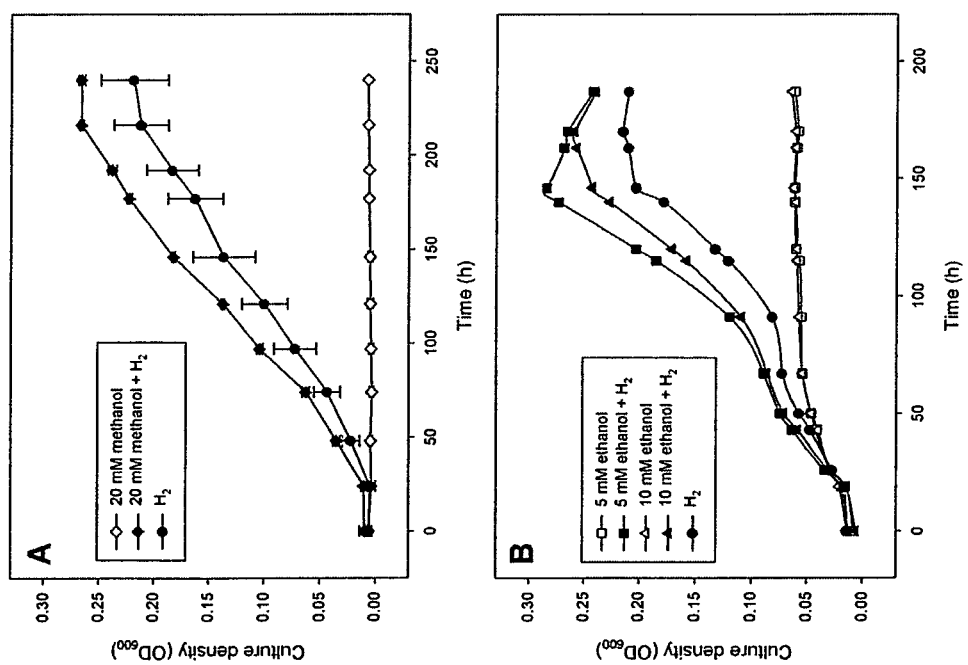

FIG. 14: Stimulation of growth of M1 by alcohols. The inclusion of (A) 20 mM methanol or (B) 5 or 10 mM ethanol when M1 was grown on H2 resulted in an increase in culture density (measured as OD600 nm) compared to cultures grown on H2 alone. H2 was added once only, at the time of inoculation, by gassing the cultures with H2+CO2 (4:1) to 180 kPa overpressure. Higher concentrations of ethanol (20 mM) resulted in some inhibition of growth (not shown), and there was no stimulation by isopropanol (5 to 20 mM; not shown). No growth occurred when cultures were supplemented with methanol (A), ethanol (B), or isopropanol (not shown) when no H2 was added, and no methane was formed by those cultures. The symbols in panel are means of 4 replicates, and the thin vertical bars in panel (A) represent one standard error on either side of the mean. Error bars are omitted from panel (B) for the sake of clarity.

Figure 15:
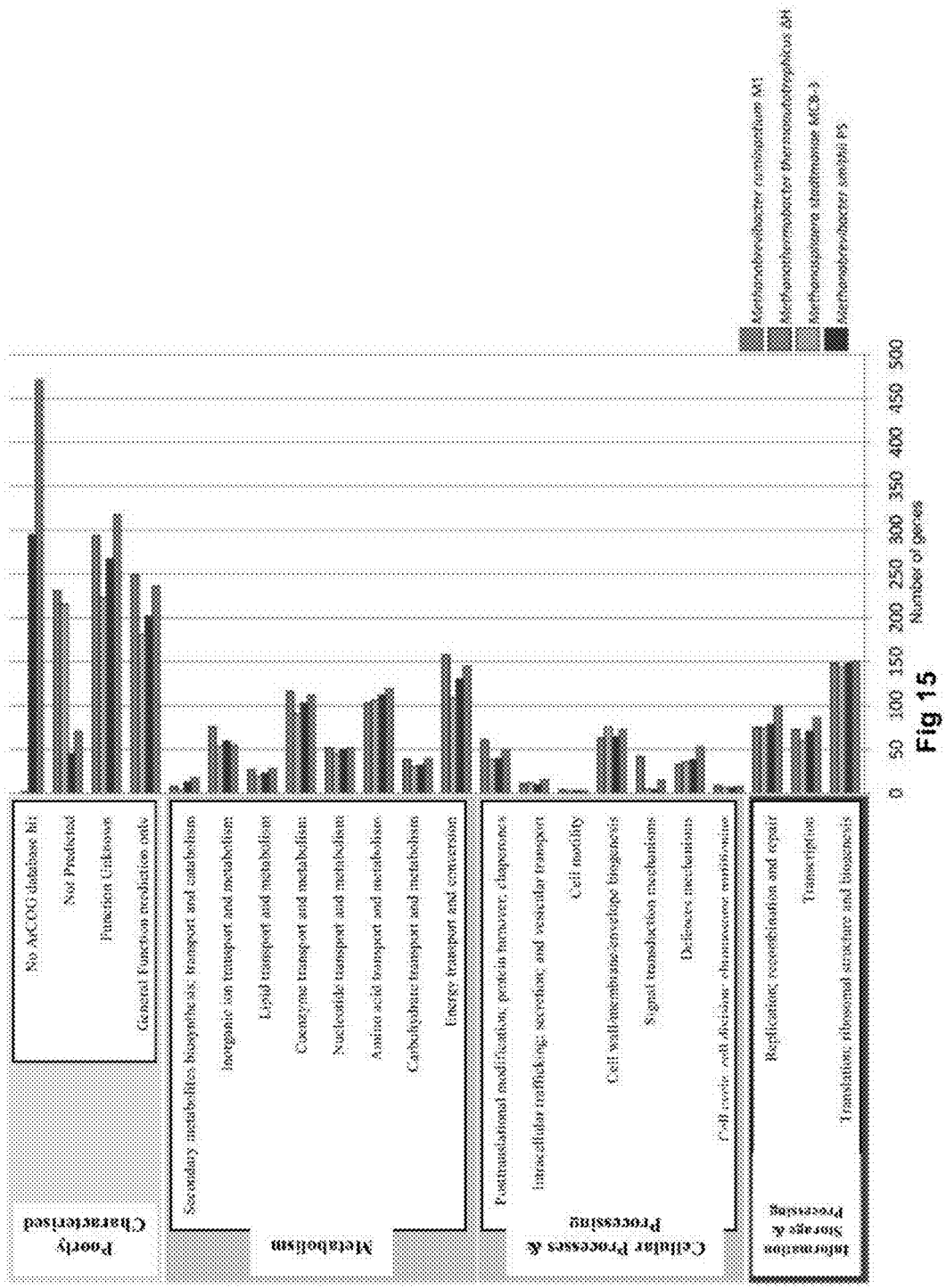

FIG. 15: Distribution of genes in the predicted ORFeomes of members of the Methanobacteriales classified according to functional categories in the archaeal COG database (Makarova et al., 2007).

Figure 16:
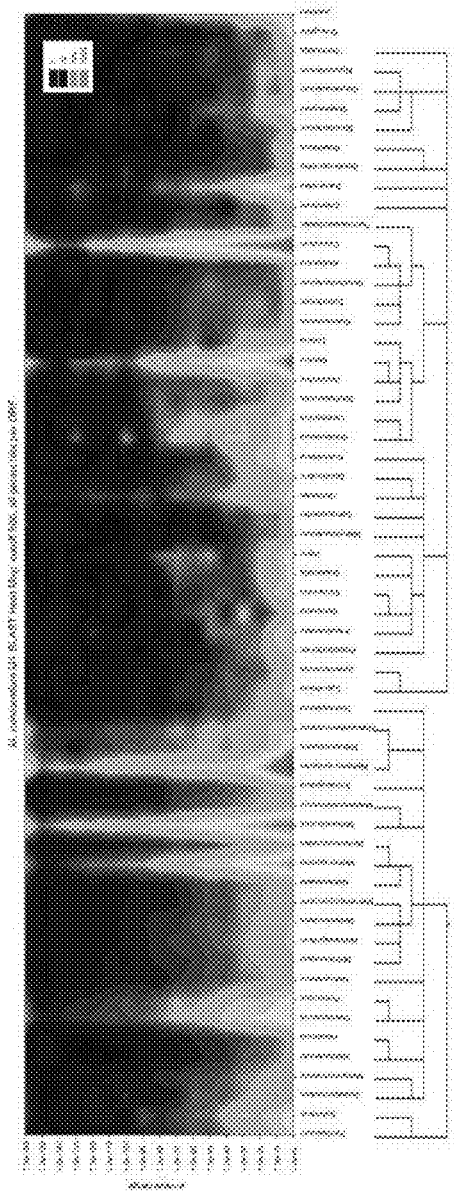
Figure 16:
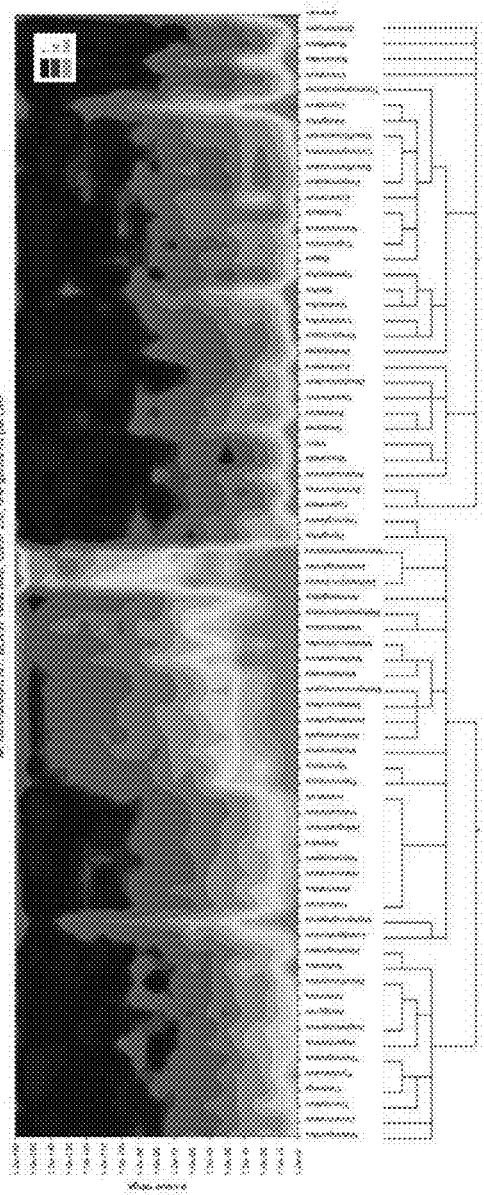

FIG. 16: BLAST Heat Map depicting BLAST-result distribution across the *M. ruminantium* M1. ORFeome. In both figures, the X-axis (horizontal axis) shows all genera with at least 500 and 250 Blast hits throughout the ORFeome, respectively. Genera are phylogenetically sorted based on a semi-dynamically re-parsed phylogenetic tree obtained from the Ribosomal Database Project II (RDP II) (hypertext transfer protocol://rdp.cme.msu.edu/hierarchy/hierarchy_browser.jsp), selecting NCBI taxonomy, level 10 genera display list and set to include archaeal sequences. Bacterial or archaeal genera not covered within the RDPII data were entered and parsed from a separate data file, where appropriate. Phylogenetic distribution and grouping of genera is indicated using an ASCII based tree-abstraction. The Y-axis indicates e-value ranges, and the Z-axis (colour coded) represents the frequency of hits for each genus in each e-value range in log-scale. Respective Log-colour-scales of frequencies are indicated in each figure, whereby warmer colours indicate higher frequencies. Figure (a) allows all BLAST hits per genus per ORF, accepting multiple genus hits per ORF. Figure (b) employs a frequency cutoff of one hit per genus per ORF, effectively limiting the hit rate to the best Blast hit found in each given ORF and genus.

Figure 17:
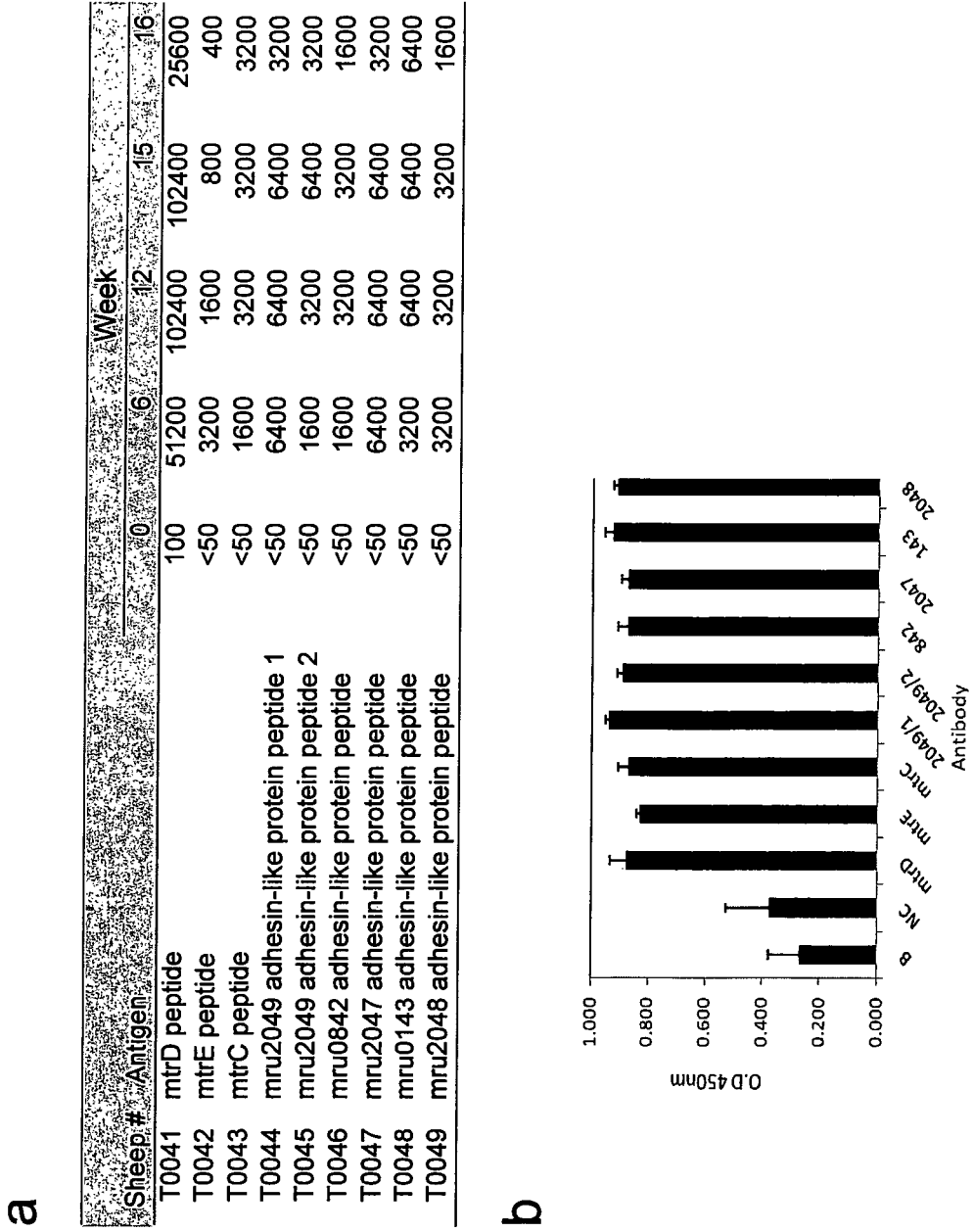
Figures 1, 19:
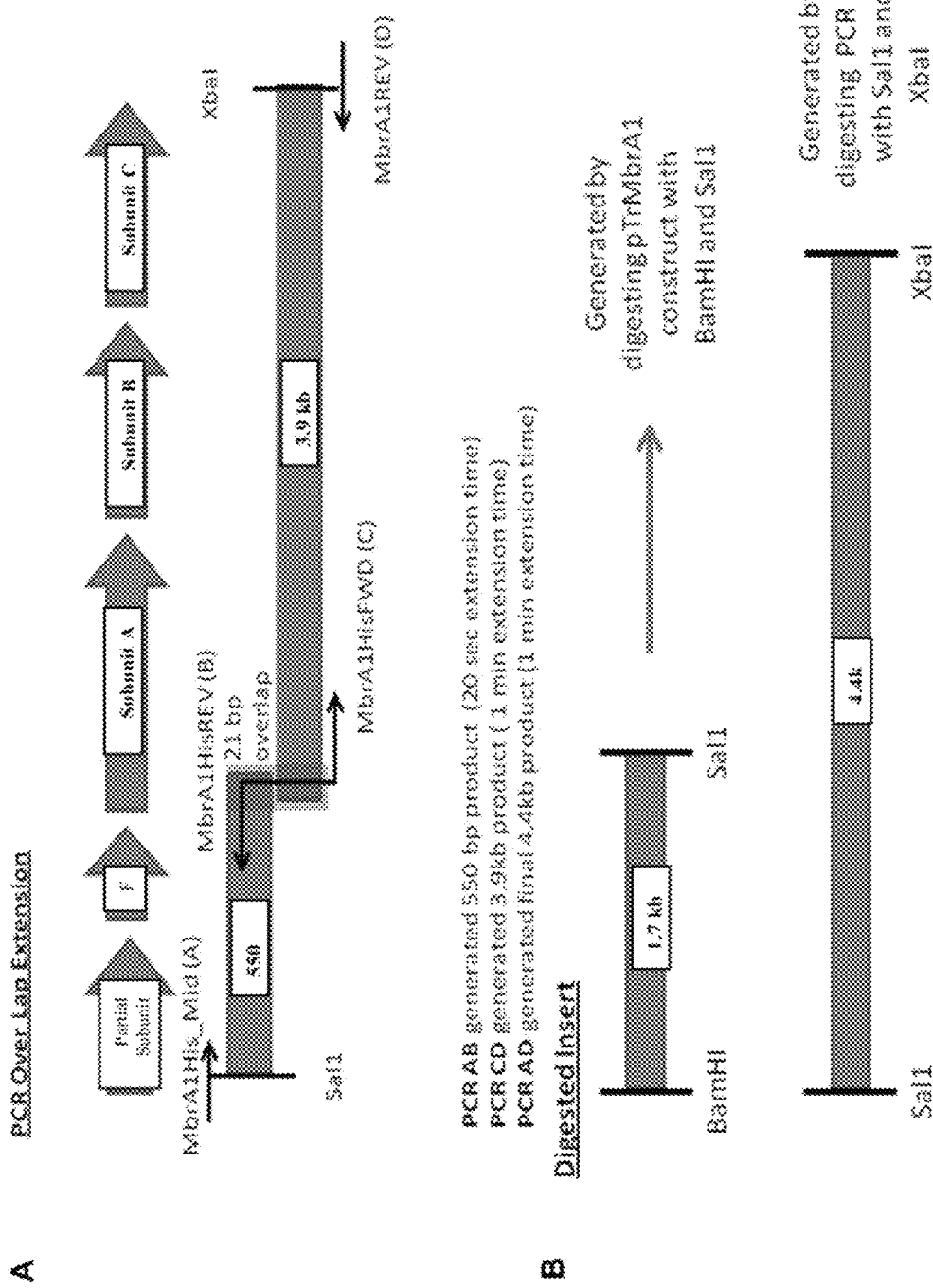
Figures 1, 20:
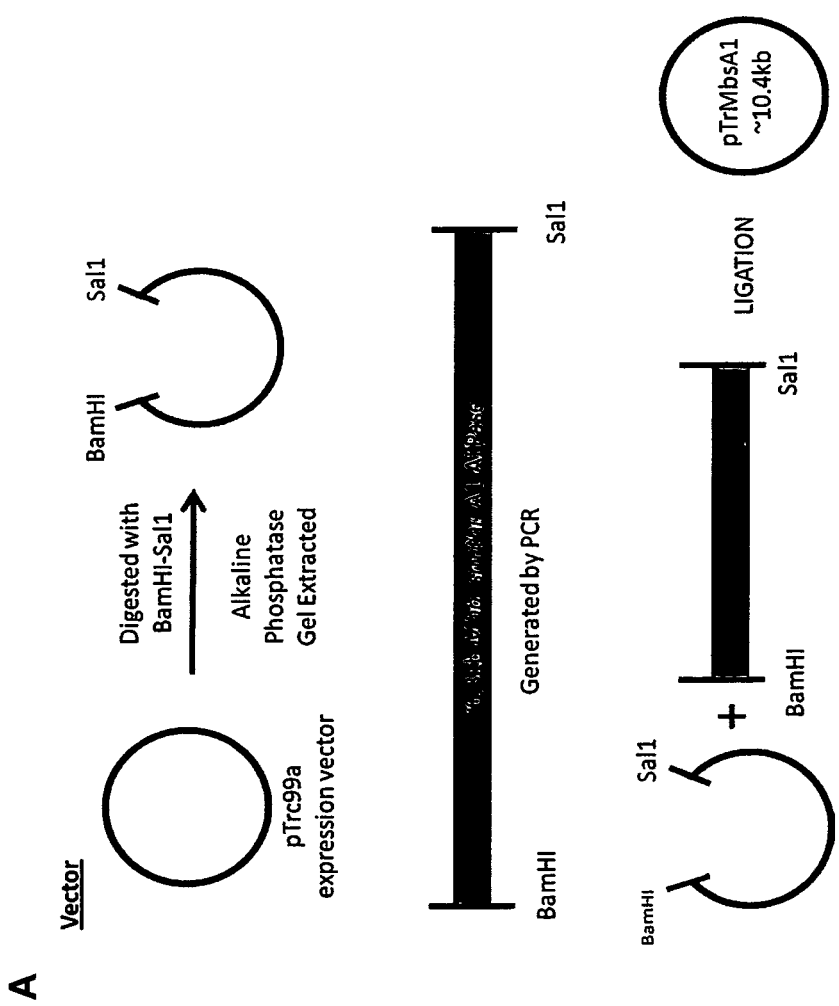
Figure 21:
Figure 22:
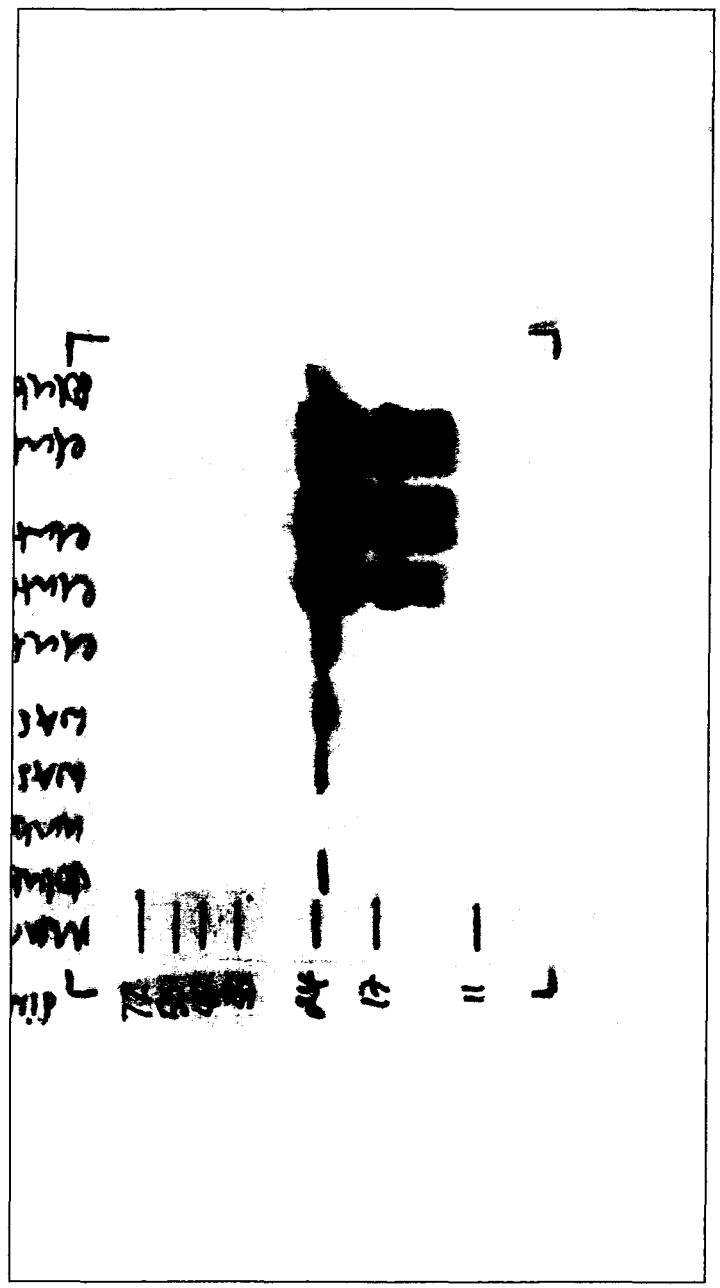
Figure 23:
Figure 33:
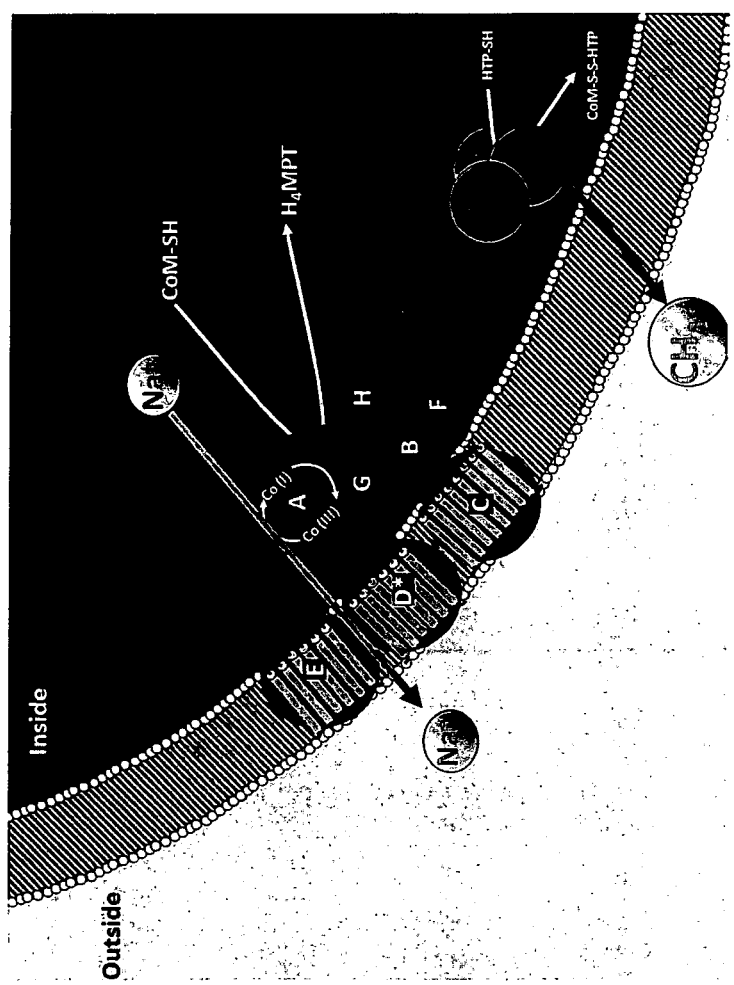

FIG. 17: Sheep antibody responses to vaccination with peptides designed against *M. ruminantium* $H_4MPT$ methyltransferase subunits (MtrCDE) and surface proteins and binding of antibodies to immobilised *M. ruminantium* cells. (a) Vaccination with peptides designed against M1 genes. (b) Binding of antibodies to immobilised M1 cells. In the antibody-binding experiment a negative control (NC) serum from a sheep which had not had colostrum as a lamb was included, as was a sample without added serum which served as a blank, B.

FIG. 18: NRPS alignment. ClustalW (Larkin et al., 2007) alignment of non-ribosomal peptide synthetetases from *M. ruminantium* M1 (mru00068) and *Syntrophomonas wolfei* subsp. *wolfei* str. Goettingen (swol1094). Alignment was visualised using Jalview (Waterhouse et al., 2009). Conserved residues are shown in medium shading. Domain organisation of *M. ruminantium* M1 is displayed via boxes (box marked with rounded brackets=condensation domain; box marked with pointed brackets=adenylation domain; box marked with triangle=phosphopantetheine attachment site; box marked with double arrow=thioester reductase domain).

FIG. 19: *Mbb. ruminantium* $A_1A_o$ ATP synthase PCR cloning and introduction of a hexa-histidine tag at the N-terminal of subunit A by PCR overlap expression; (A) PCR overlap extension; (B) digested insert; (C) ligation.

FIG. 20: *M. smithii* $A_1A_o$ ATP synthase PCR cloning and introduction of a hexa-histidine tag by PCR overlap expression. (A) Cloning; (B) PCR overlap extension; (C) digested insert and ligation.

FIG. 21: (A) pTrMbrA1HIS clone which contains the genes encoding for the *M. ruminantium* A1-ATPase in the *E. coli* expression vector pTrc99a, and includes a Hexa-Histidine tag on the N-terminal of Subunit A. (B) pTrMbrA1A0HIS9 clone.

FIG. 22: Western blot analysis of pTrMbrA1HIS expression. Lane 1: Pre-stain Protein Marker; Lane 2: Soluble Material 10 μg; Lane 3: Unbound Material 10 μg; Lane 4: Wash 1, 10 μg; Lane 5: Wash 2, 10 μg; Lane 6: Elutant 1, 10 μg (150 mM Imidazole); Lane 7: Elutant 2, 10 μg (150 mM Imidazole); Lane 8: Elutant 2, 20 μg; Lane 9: Elutant 2, 20 μg, Denatured 95° C. 5 min; Lane 10: Soluble Material 10 μg, Denatured 95° C. 5 min.

FIG. 23: Western blot analysis of pTrMbsA1HIS expression. Lane 1: Pre-stain Protein Marker; Lane 2: C41-pLysRARE/pTrMbsA1HIS starting material; Lane 3: pTrMbsA1HIS unbound material; Lane 4: pTrMbsA1HIS Wash 1, 40 mM imidazole; Lane 5: pTrMbsA1HIS Wash 2, 40 mM imidazole; Lane 6: pTrMbsA1HIS Elutant 1, 150 mM imidazole; Lane 7: pTrMbsA1HIS Elutant 2, 150 mM imidazole; Lane 8: pTrMbsA1HIS Elutant 3, 400 mM imidazole.

FIG. 24: Growth of *E. coli* strains BL21 (A), DK8 (B) and C41 (C) harbouring pTRMbbr-$A_1A_O$ at 37° C., showing the effect of induced expression of the *Mbb. ruminantium* $A_1A_O$-ATP synthase. (D) Localization of the *Mbb. ruminantium* $A_1A_O$-ATPase in DK8 by SDS-PAGE and western analysis. Samples were resolved on a 14% polyacrylamide gel in the presence of 0.1% sodium dodecyl sulfate (SDS) and either stained with Coomassie Brilliant blue or transferred for western analysis to a polyvinylidene difluoride membrane in the presence of 0.02% SDS and then immunoblotted using a penta-His antibody conjugate to detect the hexa-histidine tag on the A-subunit. Lane 1, protein molecular weight ladder; Lane 2, His-tagged TA2.A1 $F_1F_O$ ATPase purification (positive control); Lane 3, cell lysate; Lane 4, cytoplasmic fraction; Lane 5, membrane fraction.

FIG. 25: Purification (A and B) of the *Mbb. ruminantium* $A_1A_O$-ATPase.

FIG. 26: Subunits of the *Mbb. ruminantium* $A_1A_O$-ATPase.

FIG. 27: Extraction of the $A_1A_O$-ATPase K-subunit monomer.

FIG. 28: $Na^+$ binding motif in the $A_1A_O$-ATPase K-subunit.

FIG. 29: *Mbb. ruminantium* purified $A_1A_o$ ATP synthase activity. (A) Kinetics of ATP hydrolysis by purified *Mbb. ruminantium* $A_1A_o$ ATP synthase. Background ATPase activity generated by thermal hydrolysis of ATP or contaminant ATP in buffer or enzyme has been subtracted (these totaled <5% of the final value shown). (B) Influence of $Mg^{2+}$ on the kinetics of ATP hydrolysis by purified recombinant *Mbb. ruminantium* $A_1A_o$ ATP synthase. Background ATPase activity generated by thermal hydrolysis of ATP or contaminant ATP in buffer or enzyme has been subtracted (these totaled <5% of the final value shown). (C) ATPase activity over a pH range in the presence and absence of $Na^+$. Background ATPase activity generated by thermal hydrolysis of ATP or contaminant ATP in buffer or enzyme has been subtracted from the activities displayed (these totaled <5% of the final value shown). (D) Stability of the purified and membrane-bound (in DK8 membranes) *Mbb. ruminantium* $A_1A_o$ ATP synthase. Background ATPase activity generated by thermal hydrolysis of ATP or contaminant ATP in buffer or enzyme has been subtracted (these totaled <5% of the final value shown).

FIG. 30: *Mbb. ruminantium* soluble and membrane-bound $A_1A_o$ ATP synthase activity. (A and B) Effects of TBT and DCCD on ATPase activity. *E. coli* DK8 (Δatp) inverted membranes containing the recombinant $A_1A_O$-ATPase were used to determine the effects of the inhibitors TBT (200 μM) and DCCD (250 μM) at different pH values. ATPase activity was measured in presence of 130 mM $Na^+$ (A) and in absence of $Na^+$ (B). Background ATPase activity generated by thermal hydrolysis of ATP or contaminant ATP in buffer or enzyme has been subtracted (these totaled <5% of the final value shown). (C) Tributylin Inhibition of ATP Hydrolysis by Purified Recombinant *Mbb. ruminantium* $A_1A_o$ ATP synthase. Background ATPase activity generated by thermal hydrolysis of ATP or contaminant ATP in buffer or enzyme has been subtracted (these totaled <5% of the final value shown). (D) Amiloride Inhibition of ATP Hydrolysis of the *Mbb. ruminantium* $A_1A_o$ ATP synthase. Background ATPase activity generated by thermal hydrolysis of ATP or contaminant ATP in buffer or enzyme has been subtracted (these totaled <5% of the final value shown).

FIG. 31: *Mbb. ruminantium* membrane-bound $A_1A_o$ ATP synthase activity. (A) Tributylin Inhibition of ATP Hydrolysis by the *Mbb. ruminantium* $A_1A_o$ ATP synthase in DK8 and Native Membranes. Background ATPase activity generated by thermal hydrolysis of ATP or contaminant ATP in buffer or enzyme has been subtracted (these totaled <5% of the final value shown). (B) Amiloride Inhibition of ATP Hydrolysis of Purified Recombinant *Mbb. ruminantium* $A_1A_o$ ATP synthase in DK8 and Native Membranes. Background ATPase activity generated by thermal hydrolysis of ATP or contaminant ATP in buffer or enzyme has been subtracted (these totaled <5% of the final value shown).

FIG. 32: ATP synthesis in *E. coli* DK8 inverted membrane vesicles. Closed squares with no DCCD; closed triangles, a 20 min preincubation with 250 μM TBT.

FIG. 33: Model of the membrane-associated sodium ion-translocating methyltransferase complex from methanogenic archaea.

Figure 34:
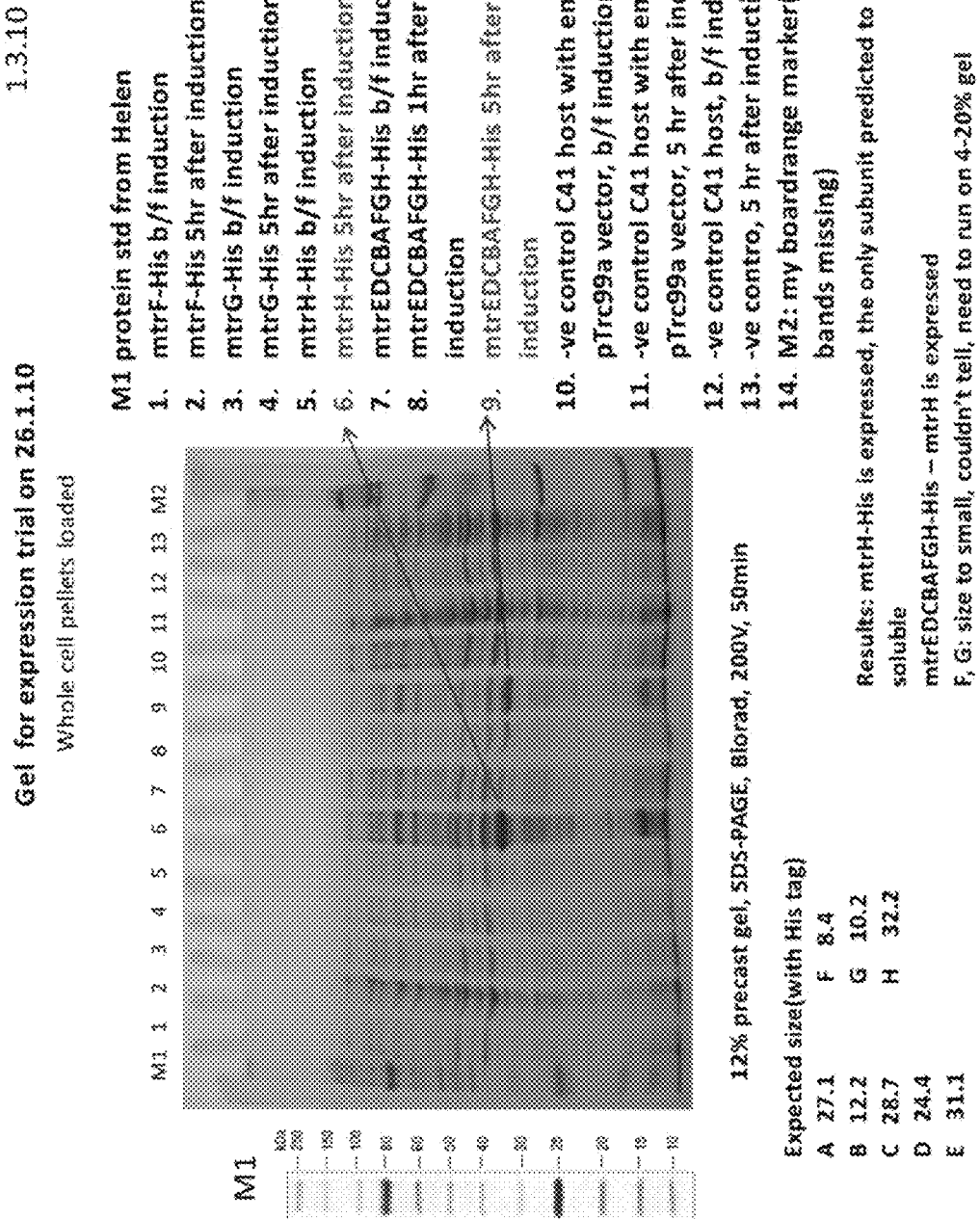

FIG. 34: SDS-PAGE analysis of mtrF-His, mtrG-His, mtrH-His and mtrEDCBAFGH-His expression in *E. coli* C41 (IPTG induction, at 37° C. for 5 hr).

Figure 35:
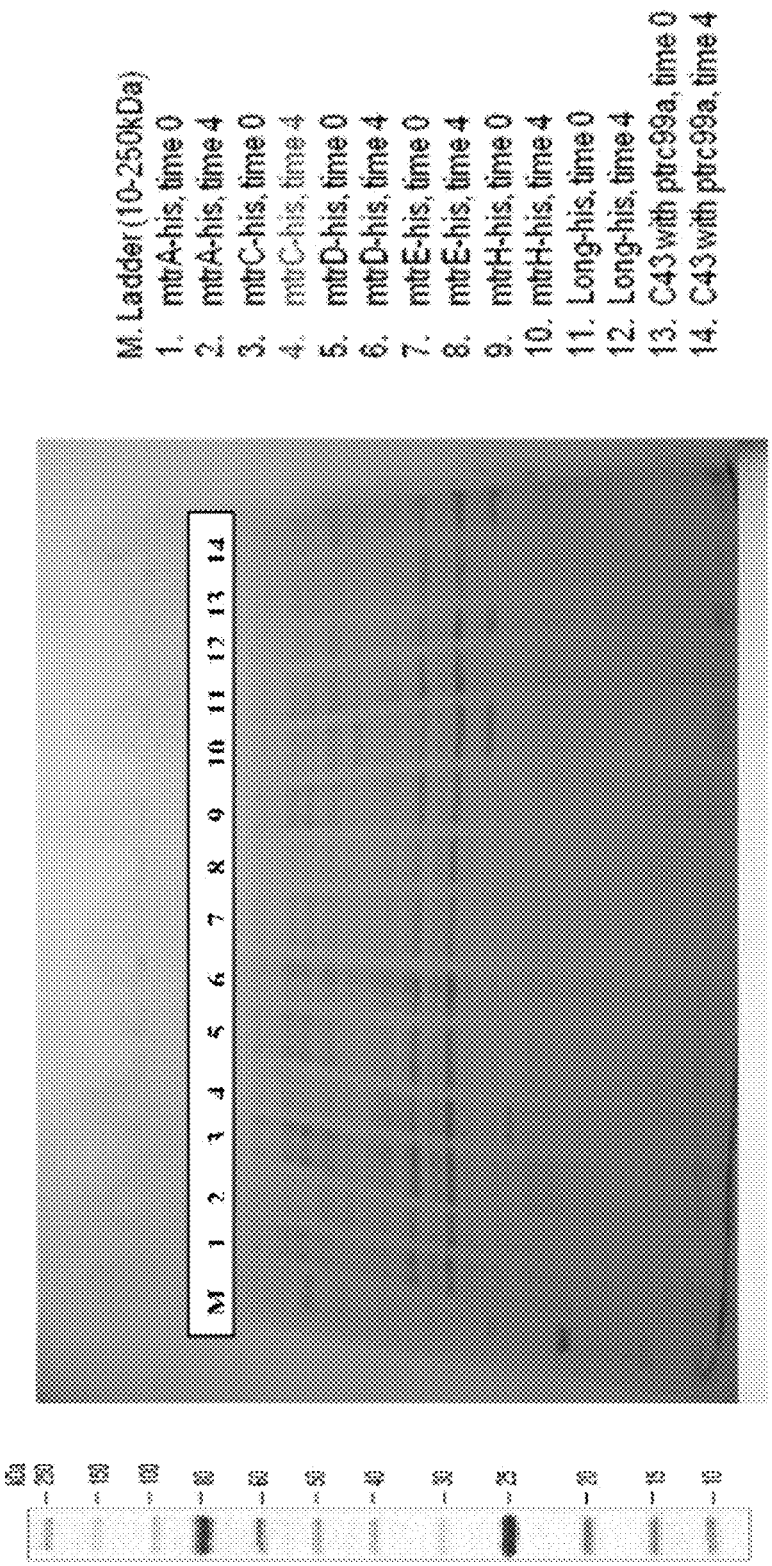

FIG. 35: SDS-PAGE analysis of mtrA-His, mtrC-His, mtrD-His, mtrE-His, mtrH-His and mtrEDCBAFGH-His expression in *E. coli* C43 (IPTG induction, at 37° C. for 4 hr).

Figure 36:
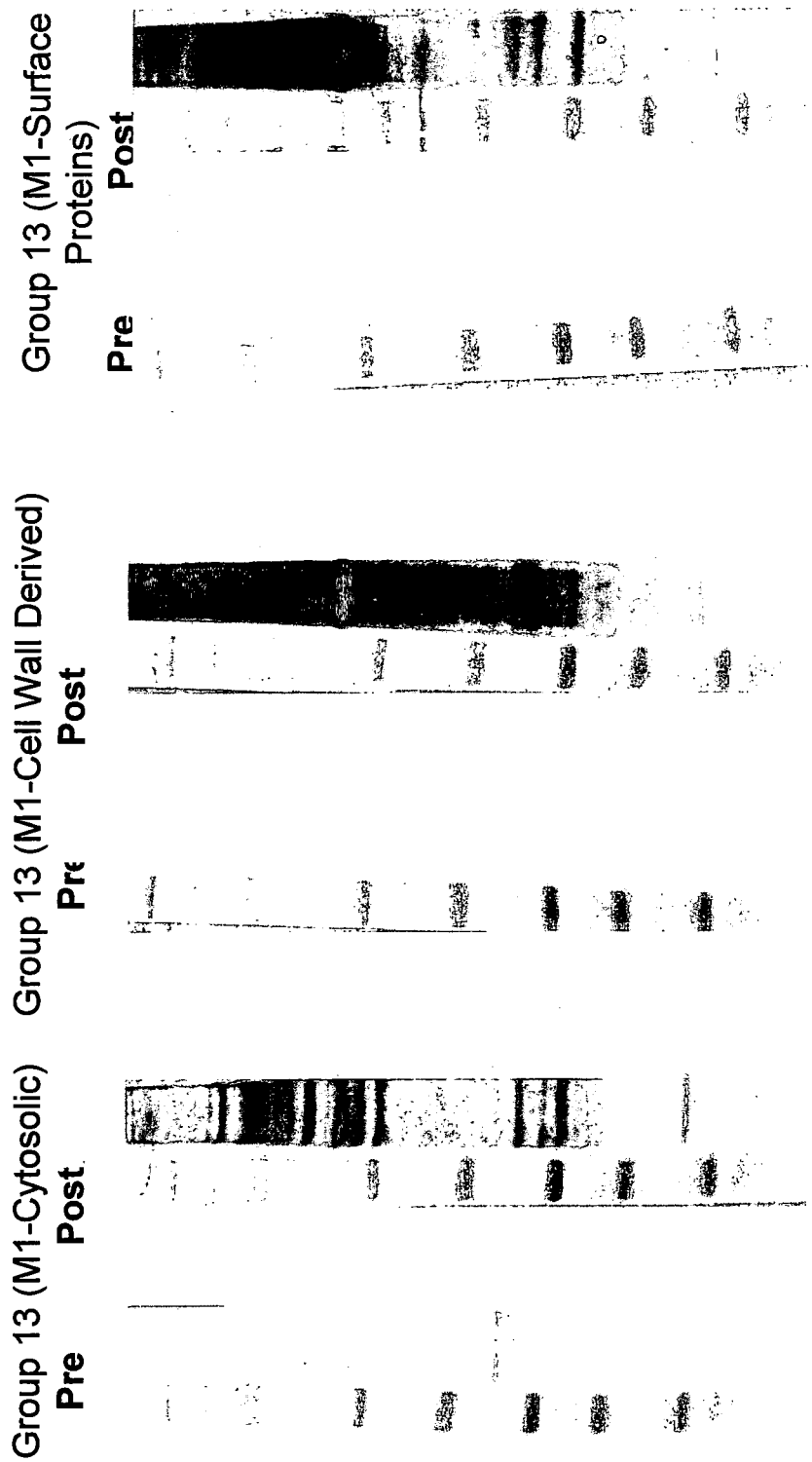

FIG. 36: Western Blot analysis of *M. ruminantium* surface protein antisera against M1 cell fraction. Pre: sera obtained before immunisation; Post: sera obtained after immunisation.

Figure 37:
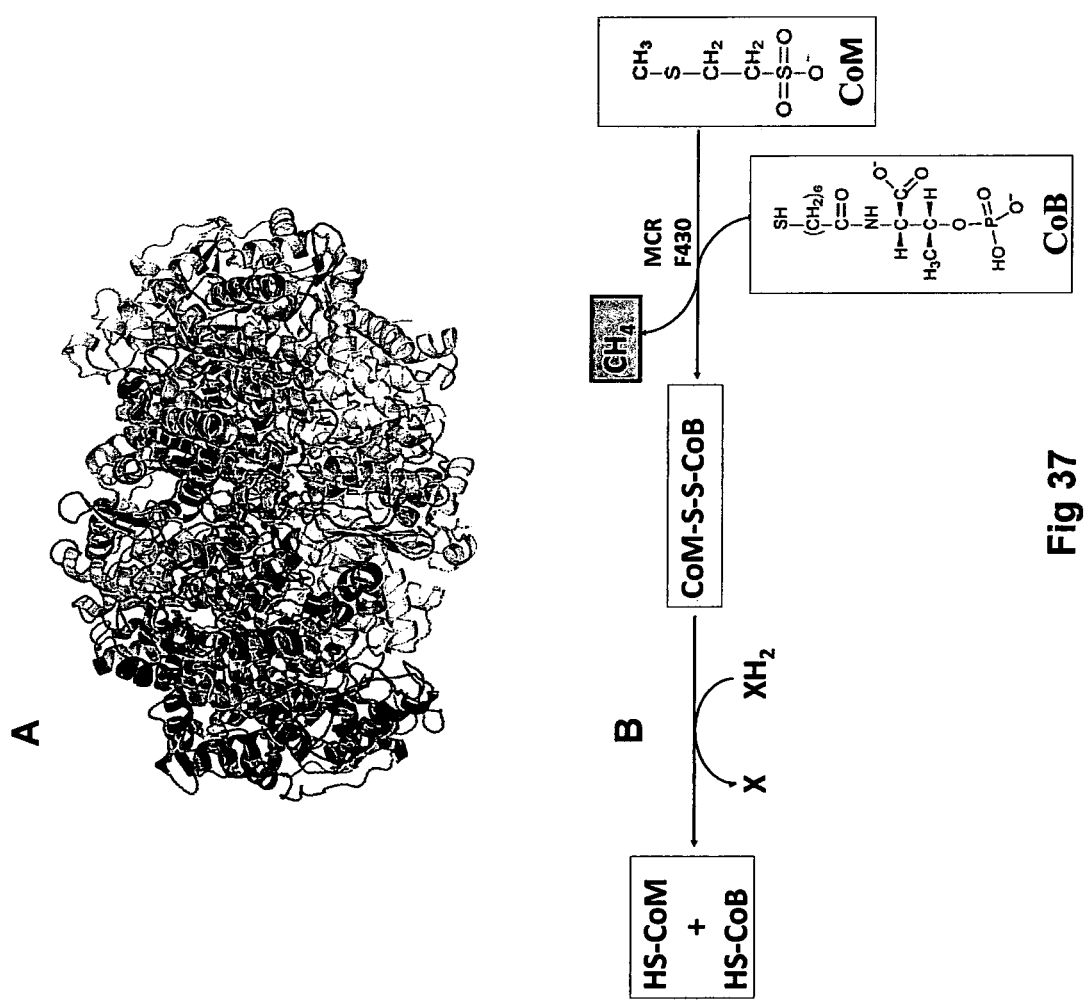

FIG. 37: (A) The α2β2γ2 subunit structure of MCR which contains two nickel porphinoid F430 rings and two molecules each of methylcoenzyme M (CoM) and coenzyme B (CoB). (B) The final reaction of the energy conserving pathway of methanogenic archaea in which CoM and CoB are converted to methane and the heterodisulfide product CoM-S-S-CoB.

Figure 38:
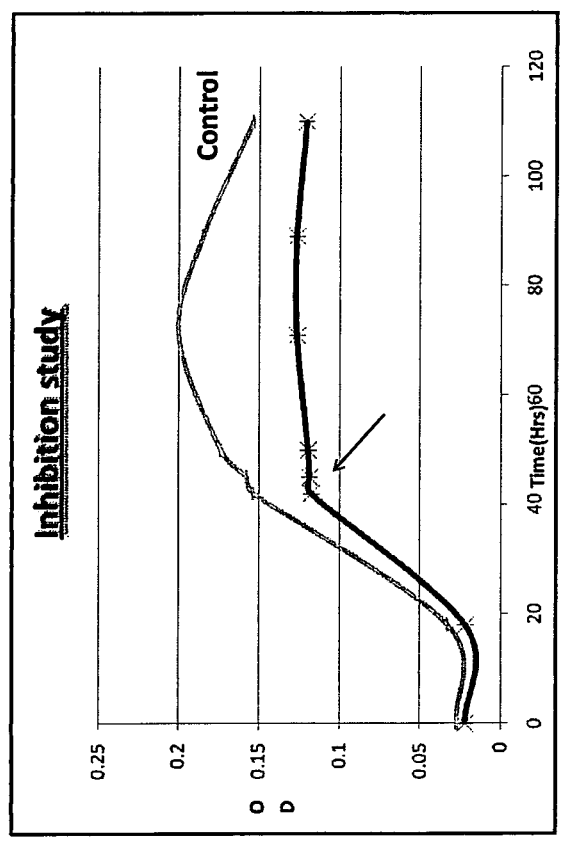

FIG. 38: Optical cell density was measured in pure culture over time to assess the effectiveness of potential inhibitors.

DETAILED DESCRIPTION OF THE INVENTION

Definitions

The term "antibody" should be understood in the broadest possible sense and is intended to include intact monoclonal antibodies and polyclonal antibodies. It is also intended to cover fragments and derivatives of antibodies so long as they exhibit the desired biological activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and Fab$_2$ fragments, and a Fab expression library.

Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., one or more mouse, human, or ruminant sequences. Further included are camelid antibodies or nanobodies. It will be understood that each reference to "antibodies" or any like term, herein includes intact antibodies, as well as any fragments, alterations, derivatives, or variants thereof.

"Altered" polynucleotides encoding peptides, polypeptides, or antibodies, as used herein, include those with deletions, insertions, or substitutions of different nucleotides resulting in a polynucleotide that encodes the same or functionally equivalent sequence.

The encoded peptide, polypeptide, or antibody may also be "altered" and contain deletions, insertions, or substitutions of amino acid residues which produce a silent change and result in a functionally equivalent sequence. Deliberate amino acid substitutions may be made on the basis of similarity in polarity, charge, solubility, hydrophobicity, hydrophilicity, and/or the amphipathic nature of the residues as long as the biological activity (e.g., cell association, membrane association) or immunogenic/immunological activity is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

The amino acid molecules as noted herein, refer to oligopeptides, peptides, polypeptides, proteins or antibodies, and any fragments thereof, and to any naturally occurring, recombinant, synthetic, or semi-synthetic molecules. These molecules of the invention comprise at least 5, 10, 15, 20, 25, 30, 35, 40, 45, 50, 100, 150, 200, 250 amino acids, preferably at least 5 to 10, 10 to 20, 20 to 30, 30 to 40, 40 to 50, 50 to 100, 100 to 150, 150 to 200, 200 to 250, or at least 300, 350, 400, 450, or 500 amino acids. Such amino acid sequences preferably retain the biological activity (e.g., effect on cell growth) or the immunogenicity/immunological activity of the molecule. The amino acid molecules noted herein are not limited to the complete, native sequence associated with the full-length molecule, but include also any fragments, alterations, derivatives, and variants thereof.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The terms "biologically active" or "functional," as used herein, refer to a peptide or polypeptide retaining one or more structural, immunogenic, or biochemical functions (e.g., cell association, membrane association) of a naturally occurring sequence.

The terms "cell inhibitor" or "inhibitor," as used herein, refer to agents that decrease or block the growth or replication of microbial cells, especially methanogen cells. A cell inhibitor can act to decrease or block, for example, cellular division. An inhibitor can decrease or block, for example, DNA synthesis, RNA synthesis, protein synthesis, or post-translational modifications. An inhibitor can also decrease or block the activity of enzymes involved in the methanogenesis pathway. An inhibitor can also target a cell for recognition by immune system components. Inhibition of a cell also includes cell killing and cell death, for example, from lysis, apoptosis, necrosis, etc. Useful inhibitors include, but are not limited to, anti-methanogenesis compounds (e.g., bromoethanesulphonic acid), antibodies and antibody fragments, lytic enzymes, peptide nucleic acids, antimicrobial peptides, and other antibiotics as described in detail herein.

The terms "complementary" or "complementarity," as used herein, refer to the natural binding of polynucleotides under permissive salt and temperature conditions by base-pairing. For the sequence A-G-T, the complementary sequence is T-C-A, the reverse complement is A-C-T and the reverse sequence is T-G-A. Complementarity between two single stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

As used herein, "computer readable media" refers to any medium which can be read and accessed directly by a computer. A "computer-based system" refers to the hardware means, software means, and data storage means used to analyze the sequence information of the present invention.

The term "derivative", as used herein, refers to the chemical modification of a nucleic acid encoding a peptide, polypeptide, or antibody, or a nucleic acid complementary thereto. Such modifications include, for example, replacement of hydrogen by an alkyl, acyl, or amino group. In preferred aspects, a nucleic acid derivative encodes a peptide, polypeptide, or antibody which retains a biological or immunogenicity/immunological activity of the natural molecule. A derivative peptide, polypeptide, or antibody is one which is modified by glycosylation, pegylation, or any similar process which retains one or more biological function (e.g., cell association, membrane association) or immunogenicity/immunological activity of the sequence from which it was derived.

The term "homology", as used herein, refers to a degree of complementarity. There may be partial homology (i.e., less than 100% identity) or complete homology (i.e., 100% identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (e.g., Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction.

The term "hybridization", as used herein, refers to any process by which a strand of nucleic acid binds with a complementary strand through base pairing.

An "immunogenic epitope" is defined as a part of a protein that elicits an antibody response when the whole protein is the immunogen. On the other hand, a region of a protein molecule to which an antibody can bind is defined as an "antigenic epitope."

An "insertion" or "addition", as used herein, refers to a change in an amino acid or nucleotide sequence resulting in the addition of one or more amino acid residues or nucleotides, respectively, as compared to the naturally occurring molecule.

A "methanogen," as used herein, refers to microbes that produce methane gas, which include *Methanobrevibacter, Methanothermobacter, Methanomicrobium, Methanobacterium*, and *Methanosarcina*. Specific methanogens include, but are not limited to, *Methanobrevibacter ruminantium* (i.e., the M1 strain (also called "M1"), or strain DSM1093 hypertext transfer protocol://www.dsmz.de/microorganisms/html/strains/strain.dsm001093.htm), *Methanobrevibacter smithii, Methanobrevibacter acididurans, Methanobrevibacter thaueri, Methanobacterium bryantii, Methanobacterium formicicum, Methanothermobacter marburgensis, Methanothermobacter wolfeii, Methanosphaera stadtmanae, Methanomicrobium mobile, Methanosarcina barkeri, Methanosarcina mazei, Methanococcoides burtonii*, and *Methanolobus taylorii*. All methanogen genera and species are encompassed by this term.

"Microbial" cells as used herein, refers to naturally-occurring or genetically modified microbial cells including archaebacteria such as methanogens, halophiles, and thermoacidophiles, and eubacteria, such as cyanobacteria, spirochetes, proteobacteria, as well as Gram positive and Gram negative bacteria.

The term "modified" refers to altered sequences and to sequence fragments, variants, and derivatives, as described herein.

The nucleic acid molecules as noted herein refer to polynucleotides, oligonucleotides, or fragments thereof, and to DNAs or RNAs of natural, recombinant, synthetic or semi-synthetic, origin which may be single or double stranded, and can represent sense or antisense strands, or coding or non-coding regions, or intergenic regions. These molecules of the invention preferably comprise at least 12, 15, 30, 45, 60, 75, 90, 105, 120, 135, 150, 300, 450, 600, 750 nucleotides, preferably at least 15 to 30, 30 to 60, 60 to 90, 90 to 120, 120 to 150, 150 to 300, 300 to 450, 450 to 600, or 600 to 750 nucleotides, or at least 800, 850, 900, 950, 1000, 1200, 1300, 1400, or 1500 nucleotides. It will be understood that a nucleic acid molecule as noted herein, will include the native, full length sequence, as well as any complements, fragments, alterations, derivatives, or variants, thereof.

The term "oligonucleotide" refers to a nucleic acid sequence of at least 6, 8, 10, 12, 15, 18, 21, 25, 27, 30, or 36 nucleotides, or at least 12 to 36 nucleotides, or at least 15 to 30 nucleotides, which can be used in PCR amplification, sequencing, or hybridization assays. As used herein, oligonucleotide is substantially equivalent to the terms "amplimers," "primers," "oligomers," and "probes," as commonly defined in the art.

The term "polynucleotide," when used in the singular or plural, generally refers to any nucleic acid sequence, e.g., any polyribonucleotide or polydeoxyribonucleotide, which may be unmodified RNA or DNA or modified RNA or DNA. This includes, without limitation, single and double stranded DNA, DNA including single and double stranded regions, single and double stranded RNA, and RNA including single and double stranded regions, hybrid molecules comprising DNA and RNA that may be single stranded or, more typically, double stranded or include single and double stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding (e.g., SEQ ID NO: 1-1718) or non-coding sequences (e.g., SEQ ID NO: 1719-3102 or SEQ ID NO:7607-7684), or intergenic sequences (e.g., SEQ ID NO: 3103-5866), or sense or antisense sequences, or iRNAs such as siRNAs. It will be understood that each reference to a "polynucleotide" or like term, herein, will include the full length sequences as well as any complements, fragments, alterations, derivatives, or variants thereof.

A "peptide" and "polypeptide," as used herein, refer to the isolated peptides or polypeptides of the invention obtained from any species, preferably microbial, from any source whether natural, synthetic, semi-synthetic, or recombinant. Specifically, a peptide or polypeptide of the invention can be obtained from methanogen cells, such as *Methanobrevibacter* cells, in particular, *M. ruminantium*, or *M. smithii* cells. For recombinant production, a peptide or polypeptide of the invention can be obtained from microbial or eukaryotic cells, for example, *Escherichia, Streptomyces, Bacillus, Salmonella*, yeast, insect cells such as *Drosophila*, animal cells such as COS and CHO cells, or plant cells. It will be understood that each reference to a "peptide" or "polypeptide," herein, will include the full-length sequence, as well as any fragments, alterations, derivatives, or variants, thereof.

"Peptide nucleic acid" or "PNA" as used herein, refers to an antisense molecule or anti-gene agent which comprises bases linked via a peptide backbone.

The term "ruminant," as used herein, refers to animals that have a rumen as a special type of digestive organ. Ruminants include, but are not limited to, cattle, sheep, goats, buffalo, moose, antelope, caribou, and deer.

The term "SEQ ID NO:" refers to a specifically numbered sequence as disclosed herein. The format of "SEQ ID NO: ##" refers to each sequence taken individually, and any combination thereof.

The terms "stringent conditions" or "stringency," as used herein, refer to the conditions for hybridization as defined by the nucleic acid, salt, and temperature. These conditions are well known in the art and may be altered in order to identify or detect identical or related polynucleotide sequences. See, e.g., Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (e.g., within a range from about 5° C. below the melting temperature of the probe to about 20° C. to 25° C. below the melting temperature). One or more factors may be varied to generate conditions of either low or high stringency different from, but equivalent to, the above listed conditions.

The term "subject" includes human and non-human animals. Non-human animals include, but are not limited to, birds and mammals, such as ruminants, and in particular, mice, rabbits, cats, dogs, pigs, sheep, goats, cows, and horses.

The terms "substantially purified" or "isolated" as used herein, refer to polypeptides, peptides, or polynucleotides, that are removed from their cellular, recombinant, or synthetic environment, and are at least 60% free, preferably 75% free, and most preferably at least 90% free or at least 99% free from other components with which they are associated in their environment. "Isolated" polynucleotides and polypeptides have been identified and separated from at least one contaminant molecule with which they are associated in their natural state. Accordingly, it will be understood that isolated polynucleotides and polypeptides are in a form which differs from the form or setting in which they are found in nature. It will further be appreciated that "isolated" does not necessarily reflect the exact extent (e.g., a specific percentage) to which the sequence has been purified.

"Transformation," as defined herein, describes a process by which exogenous DNA enters and changes a recipient cell. It may occur under natural or artificial conditions using various methods well known in the art. Transformation may rely on any known method for the insertion of foreign polynucleotides into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

"Vaccines" as used herein include all components and compositions for stimulating the immune response in a subject. Particularly useful in this regard are subunit vaccines, including peptide vaccines, and also vectored vaccines, nucleic acid vaccines, and edible vaccines. Vaccines can be used to establish or strengthen an immune response to an antigen, particularly a microbial antigen. In particular aspects, vaccines comprise antigens that evoke host-protective reactions, e.g., antibody formation, T helper, and T cell responses. Vaccines can also comprise antibodies, for example, for passive immunization.

A "variant" of a peptide, polypeptide, or antibody, as used herein, refers to an amino acid molecule that is altered by one or more amino acids. A variant polynucleotide is altered by one or more nucleotides. A variant may result in "conservative" changes, wherein a substituted amino acid has similar structural or chemical properties, e.g., replacement of leucine with isoleucine. More rarely, a variant may result in "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunogenic/immunological activity may be found using computer programs well known in the art, for example, LASERGENE software (DNASTAR).

The invention also encompasses nucleic acid and amino acid variants which retain at least one biological activity (e.g., cell association, membrane association) or immunogenicity/immunological activity. A preferred variant is one having substantially the same or a functionally equivalent sequence, for example, having at least 70%, at least 75%, at least 80%, at least 85%, and more preferably at least 90%, sequence identity to a disclosed sequence. A most preferred variant is one having at least 95%, at least 97%, at least 98%, or at least 99%, at least 99.5%, at least 99.8%, or at least 99.9% sequence identity to a sequence disclosed herein. The percentage identity is determined by aligning the two sequences to be compared as described below, determining the number of identical residues/nucleotides in the aligned portion, dividing that number by the total number of residues/nucleotides in the inventive (queried) sequence, and multiplying the result by 100. A useful alignment program is AlignX (Vector NTI).

Description of the Invention

Methane is produced in the foregut of ruminants by methanogens which act as terminal reducers of carbon in the rumen system. The multi-step methanogenesis pathway is well elucidated, mainly from the study of non-rumen methanogens. However, the adaptations that allow methanogens to grow and persist in the rumen are not well understood. *Methanobrevibacter ruminantium* (formerly *Methanobacterium ruminantium*) is the so-called type species of the *Methanobrevibacter* genus and was isolated from the bovine rumen (Smith, 1958). *M. ruminantium* is a dominant methanogen worldwide which is found in ruminants fed a wide variety of diets (Janssen, 2008). As such, *M. ruminantium* represents an important target for anti-methane technology.

We have embarked on a programme to sequence the genomes of cultured representatives of the main rumen methanogen groups. Defining gene targets within rumen methanogens for $CH_4$ mitigation technologies is somewhat akin to developing a therapeutic intervention for a microbial pathogen. Therefore, our analysis of the *M. ruminantium* genome is presented with an emphasis on identifying conserved methanogen surface proteins suitable for vaccine development via reverse vaccinology techniques (Rappuoli, 2001) and enzyme targets susceptible to small molecule inhibitors through a chemogenomics approach (Caron et al., 2001).

In view of this, we have elucidated the full genome sequence of *M. ruminantium* and have identified all of the components of the methanogenesis pathway therein. Comparison of these gene sequences with those from *Methanobacterium thermoautotrophicum* and *Methanosphaera stadtmanae* indicates methanogenesis gene organisation is conserved within the *Methanobacteriales* (FIGS. 1, 10, 13, and 15). The *M. ruminantium* genome also includes many large surface proteins which may mediate association with other rumen microbes. Based on the role of *M. ruminantium* in the rumen environment, the identified polynucleotides and polypeptides can be used as a means for inhibiting methanogens and/or methanogenesis, and to further elucidate the role of *M. ruminantium* in methane formation. Particularly useful are the disclosed polynucleotides and polypeptides identified as components involved in methanogenesis (Tables 2, 4, 5, and 9, below), as cell surface components (Tables 3, 5, 6, and 9, below), as components involved in exopolysaccharide biosynthesis (Tables 2, 4, and 9, below), as components with membrane spanning domains (Tables 3 and 9, below), as components involved in non-ribosomal peptide synthesis (Tables 7 and 9, below), as well as the polynucleotides and polypeptides for antibody production (Tables 2 and 9, below). The specific *M. ruminantium* sequences are disclosed herewith include identified ORFs (Table 11), non-coding features (Table 12), and intergenic regions (Table 13).

The M1 genome was sequenced, annotated and subjected to comparative genomic and metabolic pathway analyses. Conserved and methanogen-specific gene sets suitable as targets for vaccine development or chemogenomic-based inhibition of rumen methanogens were identified. The feasibility of using a synthetic peptide-directed vaccinology approach to target epitopes of methanogen surface proteins was demonstrated. A prophage genome was described and its lytic enzyme, endoisopeptidase PeiR, was shown to lyse M1 cells in pure culture. A predicted stimulation of M1 growth by alcohols was demonstrated and microarray analyses indicated up-regulation of methanogenesis genes during co-culture with a hydrogen (H2) producing rumen bacterium. We also report the discovery of non-ribosomal peptide synthetases in *M. ruminantium* M1, the first reported in archaeal species. The M1 genome sequence provides new insights into the lifestyle and cellular processes of this important rumen methanogen. It also defines vaccine and chemogenomic targets for broad inhibition of rumen methanogens and represents a significant contribution to worldwide efforts to mitigate ruminant methane emissions and reduce production of anthropogenic greenhouse gases.

Peptides, Polypeptides, and Polynucleotides

The invention encompasses peptides and polypeptides, including those comprising at least one of SEQ ID NO: 5867-7584, and fragments, variants, and derivatives thereof. The peptides and polypeptides of the present invention may be expressed and used in various assays to determine their biological activity. The peptides and polypeptides may be used for large-scale synthesis and isolation protocols, for example, for commercial production. Such peptides and polypeptides may be used to raise antibodies, to isolate corresponding amino acid sequences, and to quantitatively determine levels of the amino acid sequences. The peptides and polypeptides can be used for vaccines for targeting and inhibiting microbial cells, especially methanogen cells. The peptides and polypeptides can also be used for preparing antibodies to inhibit the growth or replication of such cells. The peptides and polypeptides of the present invention may also be used as compositions, for example, pharmaceutical compositions, especially vaccine compositions. In particular aspects, slow-release ruminal devices can be used in conjunction with the peptides, polypeptides, antibodies, and compositions (e.g., pharmaceutical compositions, especially vaccine compositions) of the invention.

The peptides of the present invention comprise at least one sequence selected from the group consisting of: (a) peptides comprising at least a fragment of an one amino acid sequence selected from the group consisting of SEQ ID NO: 5867-7584, or fragments, variants, or derivatives thereof; (b) peptides comprising a functional domain of at least one amino acid sequence selected from the group consisting of SEQ ID NO: 5867-7584, and fragments and variants thereof; and (c) peptides comprising at least a specified number of contiguous residues (see exemplary lengths hereinabove) of at least one amino acid sequence selected from the group consisting of SEQ ID NO: 5867-7584, or variants or derivatives thereof. In one embodiment, the invention encompasses an isolated peptide comprising the amino acid sequence of at least one of SEQ ID NO: 5867-7584. All of these sequences are collectively referred to herein as peptides of the invention.

The polypeptides of the present invention comprise at least one sequence selected from the group consisting of: (a) polypeptides comprising at least one amino acid sequence selected from the group consisting of SEQ ID NO: 5867-7584, or fragments, variants, or derivatives thereof; (b) polypeptides comprising a functional domain of at least one amino acid sequence selected from the group consisting of SEQ ID NO: 5867-7584, and fragments and variants thereof; and (c) polypeptides comprising at least a specified number of contiguous residues (see exemplary lengths hereinabove) of at least one amino acid sequence selected from the group consisting of SEQ ID NO: 5867-7584, or variants or derivatives thereof. In one embodiment, the invention encompasses an isolated polypeptide comprising the amino acid sequence of at least one of SEQ ID NO: 5867-7584. All of these sequences are collectively referred to herein as polypeptides of the invention.

The invention also encompasses an isolated polynucleotide that encodes a peptide or polypeptide of SEQ ID NO: 5867-7584. The isolated polynucleotides of the present invention have utility in genome mapping, in physical mapping, and in cloning of genes of more or less related cell surface components. Probes designed using the polynucleotides of the present invention may be used to detect the presence and examine the expression patterns of genes in any organism having sufficiently homologous DNA and RNA sequences in their cells, using techniques that are well known in the art, such as slot blot techniques or microarray analysis. Primers designed using the polynucleotides of the present invention may be used for sequencing and PCR amplifications. The polynucleotides of the invention can be used for preparing expression vectors and host cells for vaccines to target and inhibit microbial cells, especially methanogen cells. The invention further encompasses the use of the polynucleotides for the production of antibodies to inhibit the growth or replication of such cells. The polynucleotides of the present invention may also be used as compositions, for example, pharmaceutical compositions, especially vaccine compositions. In particular aspects, slow-release ruminal devices can be used in conjunction with the polynucleotides, vectors, host cells, and compositions (e.g., pharmaceutical compositions, especially vaccine compositions) of the invention.

The polynucleotides of the present invention comprise at least one sequence selected from the group consisting of: (a) sequences comprising a coding sequence for at least one amino acid sequence selected from the group consisting of SEQ ID NO: 5867-7584, or fragments or variants thereof; (b) complements, reverse sequences, and reverse complements of a coding sequence for at least one amino acid sequence selected from the group consisting of SEQ ID NO: 5867-7584, or fragments or variants thereof; (c) open reading frames contained in the coding sequence for at least one amino acid sequence selected from the group consisting of SEQ ID NO: 5867-7584, and their fragments and variants; (d) functional domains of a coding sequence for at least one amino acid sequence selected from the group consisting of SEQ ID NO: 5867-7584, and fragments and variants thereof; and (e) sequences comprising at least a specified number of contiguous residues (see exemplary lengths hereinabove) of a coding sequence for at least one amino acid sequence selected from the group consisting of SEQ ID NO: 5867-7584, or, variants thereof; and (f) sequences comprising at least a specified number of contiguous nucleotides (see exemplary lengths hereinabove) of any one of SEQ ID NO: 1-1718. Oligonucleotide probes and primers (e.g., SEQ ID NO: 7586-7607) and their variants are also provided. All of these polynucleotides and oligonucleotide probes and primers are collectively referred to herein, as polynucleotides of the invention.

It will be appreciated by those skilled in the art that as a result of the degeneracy of the genetic code, a multitude of nucleotide sequences encoding the peptides or polypeptides of the invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to naturally occurring amino acid sequences, and all such variations are to be considered as being specifically disclosed.

Nucleotide sequences which encode the peptides or polypeptides, or their fragments or variants, are preferably capable of hybridizing to the nucleotide sequence of the naturally occurring sequence under appropriately selected conditions of peptide or stringency. However, it may be advantageous to produce nucleotide sequences encoding a peptide or polypeptide, or its fragment or derivative, possessing a substantially different codon usage. Codons may be selected to increase the rate at which expression of the peptide or polypeptide occurs in a particular prokaryotic or eukaryotic host in accordance with the frequency with which particular codons are utilized by the host. Other reasons for substantially altering the nucleotide sequence encoding peptides or polypeptides and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode the peptides or polypeptides, or their fragments or variants, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a peptide or polypeptide, or any variants or fragment thereof. Also encompassed by the invention are polynucleotide sequences that are capable of hybridizing to the claimed nucleotide sequences, and in particular, those shown in SEQ ID NO: 1-1718, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase Amersham Pharmacia Biotech (Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) the ABI Catalyst and 373 and 377 DNA Sequencers (Perkin Elmer), or the Genome Sequencer 20™ (Roche Diagnostics).

The polynucleotides encoding the peptides or polypeptides may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotides or fragments thereof which encode peptides or polypeptides may be used in recombinant DNA molecules to direct expression of the peptides or polypeptides, or fragments or variants thereof, in appropriate host cells. Due to the inherent degeneracy of the genetic code, other DNA sequences which encode substantially the same or a functionally equivalent amino acid sequence may be produced, and these sequences may be used to clone and express peptides or polypeptides. The nucleotide sequences of the present invention can be engineered using methods generally known in the art in order to alter amino acid-encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, introduce mutations, and so forth.

In another embodiment of the invention, natural, modified, or recombinant nucleic acid sequences encoding peptides or polypeptides may be ligated to a heterologous sequence to encode a fusion protein. For example, it may be useful to encode a chimeric sequence that can be recognized by a commercially available antibody. A fusion protein may also be engineered to contain a cleavage site located between the peptide or polypeptide of the invention and the heterologous protein sequence, so that the peptide or polypeptide may be cleaved and purified away from the heterologous moiety.

In another embodiment, sequences encoding peptides or polypeptides may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the polypeptide itself may be produced using chemical methods to synthesize the amino acid molecule, or a fragment thereof. For example, polypeptide synthesis can be performed using various solid-phase techniques (Roberge, J. Y. et al. (1995) Science 269:202-204; Merrifield J. (1963) J. Am. Chem. Soc. 85:2149-2154) and automated synthesis may be achieved, for example, using the ABI 431A Peptide Synthesizer (Perkin Elmer). Various fragments of peptides or polypeptides may be chemically synthesized separately and combined using chemical methods to produce the full length molecule.

The newly synthesized peptide or polypeptide may be isolated by preparative high performance liquid chromatography (e.g., Creighton, T. (1983) Proteins Structures and Molecular Principles, WH Freeman and Co., New York, N.Y.). The composition of the synthetic peptides or polypeptides may be confirmed by amino acid analysis or sequencing (e.g., the Edman degradation procedure; Creighton, supra). Additionally, the amino acid sequence of the peptide or polypeptide, or any part thereof, may be altered during direct synthesis and/or combined using chemical methods with sequences from other proteins, or any part thereof, to produce a variant molecule.

In order to express a biologically active peptides or polypeptides, the nucleotide sequences encoding the sequences or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the peptide or polypeptide and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding the peptides or polypeptides of the invention. These include, but are not limited to, microorganisms such as bacteria transformed with recombinant phage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. For bacteria, useful plasmids include pET, pRSET, pTrcHis2, and pBAD plasmids from Invitrogen, pET and pCDF plasmids from Novagen, and Director™ plasmids from Sigma-Aldrich. For methanogens, useful plasmids include, but are not limited to pME2001, pMV15, and pMP1. The invention is not limited by the expression vector or host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In bacterial systems, a number of expression vectors may be selected depending upon the use intended for the peptide or polypeptide. For example, when large quantities of peptide or polypeptide are needed, vectors which direct high level expression of fusion proteins that are readily purified may be used. Such vectors include, but are not limited to, the multifunctional E. coli cloning and expression vectors such as BLUESCRIPT (Stratagene), in which the sequence encoding a polypeptide may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like.

pGEX vectors (Promega, Madison, Wis.) may also be used to express peptides or polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned peptide or polypeptide of interest can be released from the GST moiety at will. In the yeast, Saccharomyces

*cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

Specific initiation signals may also be used to achieve more efficient translation of sequences encoding the peptides or polypeptides of the invention. Such signals include the ATG initiation codon and adjacent sequences. In cases where sequences encoding a peptide or polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed peptide or polypeptide in the desired fashion. Such modifications of the sequence include, but are not limited to, acetylation, carboxylation, glycosylation, phosphorylation, lipidation, and acylation. Post-translational processing which cleaves a "prepro" form of the peptide or polypeptide may also be used to facilitate correct insertion, folding, and/or function. Different host cells which have specific cellular machinery and characteristic mechanisms for post-translational activities are available from the American Type Culture Collection (ATCC; Bethesda, Md.) and may be chosen to ensure the correct modification and processing of the sequence. Specific host cells include, but are not limited to, methanogen cells, such as *Methanobrevibacter* cells, in particular, *M. ruminantium*, or *M. smithii* cells. Host cells of interest include, for example, *Rhodotorula, Aureobasidium, Saccharomyces, Sporobolomyces, Pseudomonas, Erwinia* and *Flavobacterium*; or such other organisms as *Escherichia, Lactobacillus, Bacillus, Streptomyces*, and the like. Specific host cells include *Escherichia coli*, which is particularly suited for use with the present invention, *Saccharomyces cerevisiae, Bacillus thuringiensis, Bacillus subtilis, Streptomyces lividans*, and the like.

There are several techniques for introducing polynucleotides into eukaryotic cells cultured in vitro. These include chemical methods (Feigner et al., Proc. Natl. Acad. Sci., USA, 84:7413 7417 (1987); Bothwell et al., Methods for Cloning and Analysis of Eukaryotic Genes, Eds., Jones and Bartlett Publishers Inc., Boston, Mass. (1990), Ausubel et al., Short Protocols in Molecular Biology, John Wiley and Sons, New York, N.Y. (1992); and Farhood, Annal. NY Acad. Sci., 716:23 34 (1994)), use of protoplasts (Bothwell, supra) or electrical pulses (Vatteroni et al., Mutn. Res., 291:163 169 (1993); Sabelnikov, Prog. Biophys. Mol. Biol., 62: 119 152 (1994); Bothwell et al., supra; and Ausubel et al., supra), use of attenuated viruses (Davis et al., J. Virol. 1996, 70(6), 3781 3787; Brinster et al. J. Gen. Virol. 2002, 83(Pt 2), 369 381; Moss, Dev. Biol. Stan., 82:55 63 (1994); and Bothwell et al., supra), as well as physical methods (Fynan et al., Int J Immunopharmacol. 1995 February; 17(2):79-83; Johnston et al., Meth. Cell Biol., 43(Pt A):353 365 (1994); Bothwell et al., supra; and Ausubel et al., supra).

Successful delivery of polynucleotides to animal tissue can be achieved by cationic liposomes (Watanabe et al., Mol. Reprod. Dev., 38:268 274 (1994)), direct injection of naked DNA or RNA into animal muscle tissue (Robinson et al., Vacc., 11:957 960 (1993); Hoffman et al., Vacc. 12:1529 1533; (1994); Xiang et al., Virol., 199:132 140 (1994); Webster et al., Vacc., 12:1495 1498 (1994); Davis et al., Vacc., 12:1503 1509 (1994); Davis et al., Hum. Molec. Gen., 2:1847 1851 (1993); Dalemans et al. Ann NY Acad. Sci. 1995, 772, 255 256. Conry, et al. Cancer Res. 1995, 55(7), 1397-1400), and embryos (Naito et al., Mol. Reprod. Dev., 39:153 161 (1994); and Burdon et al., Mol. Reprod. Dev., 33:436 442 (1992)), intramuscular injection of self replicating RNA vaccines (Davis et al., J Virol 1996, 70(6), 3781 3787; Balasuriya et al. Vaccine 2002, 20(11 12), 1609 1617) or intradermal injection of DNA using "gene gun" technology (Johnston et al., supra).

A variety of protocols for detecting and measuring the expression of the peptides or polypeptides of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay can be used with monoclonal antibodies reactive to two non-interfering epitopes on the peptide or polypeptide, but a competitive binding assay can also be used. These and other assays are described, among other places, in Hampton, R. et al. (1990; Serological Methods, a laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences encoding the peptides or polypeptides, or any fragments or variants thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Expression vectors or host cells transformed with expression vectors may be cultured under conditions suitable for the expression and recovery of the peptide or polypeptide from culture. The culture can comprise components for in vitro or in vivo expression. In vitro expression components include those for rabbit reticulocyte lysates, *E. coli* lysates, and wheat germ extracts, for example, Expressway™ or RiPs systems from Invitrogen, Genelator™ systems from iNtRON Biotechnology, EcoPro™ or STP3™ systems from Novagen, TNT® Quick Coupled systems from Promega, and EasyXpress systems from QIAGEN. The peptide or polypeptide produced from culture may be secreted or contained intracellularly depending on the sequence and/or the vector used. In particular aspects, expression vectors which encode a peptide or polypeptide can be designed to contain signal sequences which direct secretion of the peptide or polypeptide through a prokaryotic or eukaryotic cell membrane. Specific signal peptides for use herein have been disclosed in detail in U.S. 60/975,104 filed 25 Sep. 2007, and in PCT/2008/000247 filed 25 Sep. 2008, which are hereby incorporated by reference herein in their entirety.

Other constructions may include an amino acid domain which will facilitate purification of the peptide or polypeptide. Such domains include, but are not limited to, metal chelating domains such as histidine-tryptophan (e.g., 6X-HIS) modules that allow purification on immobilized metals, protein A domains that allow purification on immobilized immunoglobulin, and the domain utilized in the FLAG® extension/affinity purification system (Immunex Corp., Seattle, Wash.). Useful epitope tags include 3XFLAG®, HA, VSV-G, V5, HSV, GST, GFP, MBP, GAL4, and β-galactosidase. Useful plasmids include those comprising a biotin tag (e.g., PinPoint™ plasmids from Promega), calmodulin binding protein (e.g., pCAL plasmids from Stratagene), streptavidin binding peptide (e.g., InterPlay™ plasmids from Stratagene), a c-myc or FLAG® tag (e.g., Immunoprecipitation plasmids from Sigma-Aldrich), or a histidine tag (e.g., QIAExpress plasmids from QIAGEN).

To facilitate purification, expression vectors can include cleavable linker sequences such as those specific for Factor Xa or enterokinase (Invitrogen, San Diego, Calif.). For example, the vector can include one or more linkers between the purification domain and the peptide or polypeptide. One such expression vector provides for expression of a fusion protein comprising a peptide or polypeptide of the invention and a polynucleotide encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3:263-281) while the enterokinase cleavage site provides a means for purifying the peptide or polypeptide from the fusion protein. A discussion of vectors which contain fusion proteins is provided in Kroll, D. J. et al. (1993; DNA Cell Biol. 12:441-453).

In another aspect, the invention provides a peptide or polypeptide comprising an epitope-bearing portion of a polypeptide of the invention. The epitope of this polypeptide portion can be an immunogenic (eliciting an immune response) or antigenic (antibody-binding) epitope. These immunogenic epitopes can be confined to a few loci on the molecule. It is understood that the number of immunogenic epitopes of a protein generally is less than the number of antigenic epitopes. See, for instance, Geysen et al., Proc. Natl. Acad. Sci. USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983). Antibodies that react with predetermined sites on proteins are described in Science 219: 660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., p. 661.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., p. 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using polynucleotides of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. See, e.g., Houghten, R. A. (1985) General method for the rapid solid-phase synthesis of large numbers of peptides: specificity of antigen-antibody interaction at the level of individual amino acids. Proc. Natl. Acad. Sci. USA 82:5131-5135. This process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., p. 5134

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen Virol. 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomer which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, the polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been demonstrated, e.g., for chimeric proteins consisting of the first two domains of the human CD4-polypeptide and various domains of the constant regions of the heavy or light chains of mammalian immunoglobulins (EPA 394,827; Traunecker et al., Nature 331:84-86 (1988)). Fusion proteins that have a disulfide-linked dimeric structure due to the IgG part can also be more efficient in binding and neutralizing other molecules than the monomeric protein or protein fragment alone (Fountoulakis et al., J Biochem 270:3958-3964 (1995)).

Non-Ribosomal Peptide Synthetases

As particular examples, the polypeptides of the invention may include non-ribosomal peptide synthetases. Non-ribosomal peptides are synthesized on enzymatic thiotemplates termed non-ribosomal peptide synthetases (NRPS). The non-ribosomal peptides encompass a wide range of compounds having diverse activities including, but not limited to, immunosuppressive (such as cyclosporin), surfactant (such as surfactin), siderophores (such as enterobactin), virulence factors (such as yersinabactin), antibacterial (such as penicillin and vancomycin), and anti-cancer (such as actinomycin and bleomycin) activities (Weber et al., Current Genomics 1994; 26:120-25; Ehmann et al., Proc. Nat. Acad. Sci. 2000; 97:2509-14; Gehring et al., Biochemistry 1998; 37:11637; Kallow et al., Biochemistry 1998; 37:5947-52; Trauger et al., Proc. Nat. Acad. Sci. 2000; 97:3112-17; Schauweker et al., J. Bacteriology 1999; 27:2468-74; and Shen et al., Bioorganic Chem 1999; 27:155-71). As to particular NRPS products, see Felnagle et al., Nonribosomal peptide synthetases involved in the production of medically relevant natural products, Mol. Pharm. 2008 March-April; 5(2):191-211.

Non-ribosomal peptides typically range in size from 1-11 amino acids and are produced by a variety of microbes including cyanobacteria, actinomycetes, and fungi. In many cases the non-ribosomal peptides contain non-proteogenic amino acids such as norleucine, β-alanine, ornithine, etc., for which biogenesis pathways, which are secondary to primary metabolism, are required and are post-synthetically modified (e.g., hydroxylated, methylated or acylated) by tailoring enzymes. The term proteogenic indicates that the amino acid can be incorporated into a protein in a cell through well-known metabolic pathways. The choice of including a (D)- or (L)-amino acid into a peptide of the present invention depends, in part, on the desired characteristics of the peptide. For example, the incorporation of one or more (D)-amino acids can confer increasing stability on the peptide in vitro or in vivo. The term amino acid equivalent refers to compounds which depart from the structure of the naturally occurring amino acids, but which have substantially the structure of an amino acid, such that they can be substituted within a peptide that retains biological activity. Thus, for example, amino acid equivalents can include amino acids having side chain modifications and/or substitutions, and also include related organic acids, amides or the like.

The polynucleotide sequences required to make a NRPS and the necessary tailoring enzymes have been shown in all cases to be localized to the chromosome of the producing microbe. NRPS are modular in nature, where a module may be defined as a segment of the NRPS necessary to catalyze the activation of a specific amino acid and result in the incorporation of that amino acid into a non-ribosomal peptide. A minimal module contains three domains: (1) adenylation domains (about 60 kDa), responsible for selecting and activating an amino acid and transferring the aminoacyl adenylate to a peptidyl carrying centre; (2) thiolation domains, also referred to as peptidyl carrier proteins (8-10 kDa), containing a serine residue which is post-translationally modified with a 4-phosphopantetheine group (Ppant) which acts as an acceptor for the aminoacyl adenylate; and (3) condensation domains (50-60 kDa) which catalyze peptide bond-forming chain-translocating steps between an upstream peptidyl-s-Ppant and the downstream aminoacyl-Ppant of the adjacent module (Doekel, S, and Marahiel, M. A. 2000; Chem. Biol. 7:373-384). This minimal module for chain extension is typically repeated within a synthetase and a co-linear relationship exists between the number of modules present and the number of amino acids in the final product with the order of the modules in the synthetase determining the order of the amino acids in the peptide.

The adenylation domain is typically about 60 kDa. The main function of this domain is to select and activate a specific amino acid as an aminoacyl adenylate. Based on its function, the adenylation domain regulates the sequence of the peptide being produced. Once charged (as an amino acyl adenylate moiety), the amino acid is transferred to a thiolation domain (peptidyl carrying centre). The thiolation domain is also referred to as a peptidyl carrier protein. This domain is typically 8-10 kDa and contains a serine residue that is post-translationally modified with a 4-phosphopantetheine group. This group acts as an acceptor for the aminoacyl adenylate moiety on the amino acid. A nucleophilic reaction leads to the release of the aminoacyl adenylate and conjugation of the amino acid to thiolation domain via a thioester bond. The condensation domain is typically about 50-60 kDa in size. The main function of this domain is to catalyze the formation of a peptide bond between two amino acids. In this reaction an upstream tethered peptidyl group is translocated to the downstream aminoacyl-s-Ppant and linked to the amino acid by peptide bond formation.

This minimal module for chain extension is typically repeated within a synthetase. Additionally, and typically, a co-linear relationship exists between the number of modules present and the number of amino acids in the final product with the order of the modules in the synthetase determining the order of the amino acids in the peptide. This 1:1 relationship, with every amino acid in the product having one module within the enzyme, is referred to as the co-linearity rule. Examples have been found that violate this rule, and in such cases, the NRPS contains more modules than one would expect based on the number of amino acids incorporated in the peptide product (Challis et al., Chem. Biol. 2000; 7:211-24). In some cases the minimal module also is supplemented with additional domains (epimerization, N- or C-methylation, or cyclization domain), with their position in the synthetase determining the substrate upon which they can act. In addition, it has been observed that NRPS contain inter-domain spacers or linker regions. It has been proposed that these spacers may play a critical role in communication between domains, modules, and even entire synthetases.

There are highly conserved motifs in the catalytic domains of peptide synthetases including: 10 conserved motifs in the adenylation domain; 1 conserved motif in the thiolation domain; 7 conserved motifs in the condensation domain; 1 conserved motif in the thioesterase domain; 7 conserved motifs in the epimerization domains; and 3 conserved motifs in the N-methylation domains. These are detailed in Marahiel et al., Chemical Rev. 1997; 97:2651-73. In addition to modifications such as epimerization, methylation and cyclization during peptide synthesis, post-translational modifications including methylation, hydroxylation, oxidative cross-linking and glycosylation can occur (Walsh et al., Curr. Opin. Chem. Biol. 2001; 5:525-34).

In the present invention, the polynucleotide and polypeptide sequences for NRPS from *M. ruminantium* have been characterized (see below). For use with the present invention, the enzymes may be tailored as needed. For example, after production of the core of the peptide product, the sequence may then be modified by additional enzymes which are herein termed tailoring enzymes. These enzymes alter the amino acids in the compound without altering the number or the specific amino acids present within the compound. Such tailoring enzymes may include, but are not limited to, arginine cyclase, an O-mannosyltransferase, a phenylalanine C-methyltransferase, a first isovaleryl transferase, and a second isovaleryl transferase. The present invention permits specific changes to be made, either by site directed mutagenesis or replacement, to genetically modify the peptide core. The modifications may be made in a rational manner to improve the biological activity of the peptide produced by the strain or to direct synthesis of compounds that are structurally related to the peptide. The invention also allows for the tailoring enzymes to be used for biotransformation experiments to produce enzymes to modify and possibly improve other useful compounds. As to modified NRPS products, see Velkov et al., Non-ribosomal peptide synthetases as technological platforms for the synthesis of highly modified peptide bioeffectors—Cyclosporin synthetase as a complex example, Biotechnol Annu Rev. 2003;9:151-97.

The determination of the NRPS from *M. ruminantium* also enables one of ordinary skill in the art to clone and express the pathway into a heterologous organism. Any organism may be used, although preferably a bacterial strain is used. The choice of organism is dependent upon the needs of the skilled artisan. For example, a strain that is amenable to genetic manipulation may be used in order to facilitate modification and production of the peptide product. The present invention advantageously permits specific changes to be made to individual modules of NRPS, either by site directed mutagenesis or replacement, to genetically modify the peptide core. Additionally, the NRPS modules can be used to modify other NRPS that direct the synthesis of other useful peptides through module swapping. For example, the module in NRPS that incorporates tyrosine into the peptide core of the product may be modified so as to incorporate a serine in its place.

The activity of any NRPS disclosed herein may be evaluated using any method known in the art. For example, specific modifications to the polypeptide sequence may be produced to alter the final product. Other non-limiting examples of studies that may be conducted with these proteins include (i) evaluation of the biological activity of a protein and (ii) manipulation of a synthetic pathway to alter the final product from microbes. Genetic manipulations and expression of the polypeptides discussed herein may be conducted by any method known in the art. For example, the effect of point mutations may be evaluated. The mutations may be produced by any method known in the art. In one specific method, the manipulations and protein expression may be conducted using a vector that comprises at least one origin of replication. The origins of replication allow for replication of the polynucleotide in the vector in the desired cells. Additionally, the vector may comprise a multiple cloning site that allows for the insertion of a heterologous nucleic acid that may be replicated and transcribed by a host cell. In one particular aspect, conjugation can be used for the direct transfer of nucleic acid from one prokaryotic cell to another via direct contact of cells. The origin of transfer is determined by a vector, so that both donor and recipient cells obtain copies of the vector. Transmissibility by conjugation is controlled by a set of genes in the tra region, which also has the ability to mobilize the transfer of chromosomes when the origin of transfer is integrated into them (Pansegrau et al., J. Mol. Biol., 239:623-663, 1994; Fong and Stanisich, J. Bact., 175:448-456, 1993).

The vector described previously may be used to assess the biological activity of the NRPS. The vector may be used to alter a polypeptide, either by partial or complete removal of the polynucleotide sequence encoding the protein, or by disruption of that sequence. Evaluation of the products produced when the altered polypeptide is present is useful in determining the functionality of the polypeptide. As discussed above, specific polypeptides within the biochemical pathway may be modified to assess the activity of the compounds produced by these altered polypeptides and to determine which sections of the product are important for activity and function. The present invention contemplates any method of altering any of the NRPS of the present invention. More specifically, the invention contemplates any method that would insert amino acids, delete amino acids or replace amino acids in the polypeptides of the invention. Additionally, a whole domain in a module in a NRPS may be replaced. Therefore, for example, the acylation domain that incorporates tyrosine into the final product may be replaced with a domain that incorporates serine. The modifications may be performed at the nucleic acid level. These modifications may be performed by standard techniques and are well known within the art. Upon production of the polynucleotide encoding the modified polypeptide, the amino acid sequence can be expressed in a host cell. Then the host cell can be cultured under conditions that permit production of a product of the altered pathway. Once the product is isolated, the activity of the product may be assessed using any method known in the art. The activity can be compared to the product of the non-modified biosynthetic pathway and to products produced by other modifications. Correlations may be drawn between specific alterations and activity. For example, it may be determined that an active residue at a specific position may increase activity. These types of correlations will allow one of ordinary skill to determine the most preferred product structure for specified activity. As to modification techniques for NRPS, see Dürfahrt et al., Functional and structural basis for targeted modification of non-ribosomal peptide synthetases, Ernst Schering Res Found Workshop. 2005;(51):79-106.

The present invention also contemplates a method for using an intergeneric vector to manipulate, modify, or isolate a protein involved in the synthesis of a specific product. For example, the vector of the present invention may be used to alter an enzyme which is involved in incorporation of an alanine residue into a peptide, so that a tyrosine residue is incorporated instead. The effect of this modification on peptide function may be then be evaluated for biological efficacy. In the above example, modifications to the enzyme may include, but are not limited to, removal of amino acids and/or sequences that specifically recognize alanine and/or incorporation of amino acids and/or sequences that specifically recognize tyrosine. Therefore, in general terms, the vector of the present invention may be used to alter a gene sequence by insertion of nucleic acid sequences, deletion of nucleic acid sequences, or alteration of specific bases within a nucleic acid sequence to alter the sequence of a polypeptide of interest; thereby producing a modified protein of interest. Preferably, the polypeptide of interest is involved in the synthesis of a compound of interest. The method of modifying a protein may comprise (i) transfecting a first microbial cell with the vector of the present invention, (ii) culturing the first microbial cell under conditions that allow for replication of the vector, (iii) conjugating the first microbial cell with a second microbial cell under conditions that allow for the direct transfer of the vector from the first microbial cell to the second microbial cell, and (iv) isolating the second microbial cell transformed with the vector. Other method of vector transfer are also contemplated and disclosed herein.

Antibodies and Vaccines

The antibodies of the invention may be produced using methods which are generally known in the art. In particular, purified peptides, polypeptides, or polynucleotides may be used to produce antibodies in accordance with known methods. Such antibodies may include, but are not limited to, polyclonal, monoclonal, chimeric, and single chain antibodies, Fab fragments, and fragments produced by a Fab expression library. Neutralizing antibodies, (i.e., those which inhibit function) are especially preferred for use with vaccines.

For the production of antibodies, various hosts including goats, rabbits, rats, mice, humans, and others, may be immunized by injection with a peptide, polypeptide, polynucleotide, or any fragment thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, polypeptides, or fragments used to induce antibodies have an amino acid sequence comprising at least five amino acids and more preferably at least 10 amino acids. It is also preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin and antibody produced against the chimeric molecule.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

In addition, techniques developed for the production of "chimeric antibodies", e.g., the combining of mouse antibody genes and human antibody genes to obtain a molecule with appropriate antigen specificity and biological activity can be used (Morrison, S. L. et al. (1984) Proc. Natl. Acad.

Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120-3).

Those of skill in the art to which the invention relates will appreciate the terms "diabodies" and "triabodies". These are molecules which comprise a heavy chain variable domain (VH) connected to a light chain variable domain (VL) by a short peptide linker that is too, short to allow pairing between the two domains on the same chain. This promotes pairing with the complementary domains of one or more other chains and encourages the formation of dimeric or trimeric molecules with two or more functional antigen binding sites. The resulting antibody molecules may be monospecific or multispecific (e.g., bispecific in the case of diabodies). Such antibody molecules may be created from two or more antibodies using methodology standard in the art to which the invention relates; for example, as described by Todorovska et al. (Design and application of diabodies, triabodies and tetrabodies for cancer targeting. J. Immunol. Methods. 2001 Feb. 1;248(1-2):47-66).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

Antibody fragments which contain specific binding sites may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 254:1275-1281).

Various immunoassays may be used for screening to identify antibodies having binding specificity. Numerous protocols for competitive binding or immunoradiometric assays using either polyclonal or monoclonal antibodies with established specificities are well known in the art. Such immunoassays typically involve the measurement of complex formation between a peptide, polypeptide, or polynucleotide and its specific antibody. A two-site, monoclonal-based immunoassay utilizing monoclonal antibodies reactive to two non-interfering epitopes is preferred, but a competitive binding assay may also be employed (Maddox, supra).

The antibodies described herein have the ability to target and/or inhibit cells and are also useful as carrier molecules for the delivery of additional inhibitory molecules into microbial cells. The chemistry for coupling compounds to amino acids is well developed and a number of different molecule types could be linked to the antibodies. The most common coupling methods rely on the presence of free amino (alpha-amino or Lys), sufhydryl (Cys), or carboxylic acid groups (Asp, Glu, or alpha-carboxyl). Coupling methods can be used to link the antibody to the cell inhibitor via the carboxy- or amino-terminal residue. In some cases, a sequence includes multiple residues that may react with the chosen chemistry. This can be used to produce multimers, comprising more than one cell inhibitor. Alternatively, the antibody can be shortened or chosen so that reactive residues are localized at either the amino or the carboxyl terminus of the sequence.

For example, a reporter molecule such as fluorescein can be specifically incorporated at a lysine residue (Ono et al., 1997) using N-α-Fmoc-Nε-1-(4,4-dimethyl-2,6 dioxocyclohex-1-ylidene-3-methylbutyl)-L-lysine during polypeptide synthesis. Following synthesis, 5- and 6-carboxyfluorescein succinimidyl esters can be coupled after 4,4-dimethyl-2,6 dioxocyclohex-1-ylidene is removed by treatment with hydrazine. Therefore coupling of an inhibitory molecule to the antibody can be accomplished by inclusion of a lysine residue to the polypeptide sequence, then reaction with a suitably derivatised cell inhibitor.

EDC (1-ethyl-3-(3-dimethylaminopropyl)carbodiimide hydrochloride) or the carbodiimide coupling method can also be used. Carbodiimides can activate the side chain carboxylic groups of aspartic and glutamic acid as well as the carboxyl-terminal group to make them reactive sites for coupling with primary amines. The activated antibody is mixed with the cell inhibitor to produce the final conjugate. If the cell inhibitor is activated first, the EDC method will couple the cell inhibitor through the N-terminal alpha amine and possibly through the amine in the side-chain of Lys, if present in the sequence.

m-Maleimidobenzoyl-N-hydroxysuccinimide ester (MBS) is a heterobifunctional reagent that can be used to link an antibody to cell inhibitors via cysteines. The coupling takes place with the thiol group of cysteine residues. If the chosen sequence does not contain Cys it is common to place a Cys residue at the N- or C-terminus to obtain highly controlled linking of the antibody to, the cell inhibitor. For synthesis purposes, it may be helpful for the cysteine to be placed at the N-terminus of the antibody. MBS is particularly suited for use with the present invention.

Glutaraldehyde can be used as a bifunctional coupling reagent that links two compounds through their amino groups. Glutaraldehyde provides a highly flexible spacer between the antibody and cell inhibitor for favorable presentation. Glutaraldehyde is a very reactive compound and will react with Cys, Tyr, and His to a limited extent. The glutaraldehyde coupling method is particularly useful when a polypeptide contains only a single free amino group at its amino terminus. If the antibody contains more than one free amino group, large multimeric complexes can be formed.

In one aspect, the antibodies of the invention can be fused (e.g., by in-frame cloning) or linked (e.g., by chemical coupling) to cell inhibitors such as antimicrobial agents. Included among these are antimicrobial peptides, for example, bactericidal/permeability-increasing protein, cationic antimicrobial proteins, lysozymes, lactoferrins, and cathelicidins (e.g., from neutrophils; see, e.g., Hancock and Chapple, 1999, Antimicrob. Agents Chemother. 43:1317-1323; Ganz and Lehrer, 1997, Curr. Opin. Hematol. 4:53-58; Hancock et al., 1995, Adv. Microb. Physiol. 37:135-175). Antimicrobial peptides further include defensins (e.g., from epithelial cells or neutrophils) and platelet microbiocidal proteins (see, e.g., Hancock and Chapple, 1999, Antimicrob. Agents Chemother. 43:1317-1323). Additional antimicrobial peptides include, but are not limited to, gramicidin S, bacitracin, polymyxin B, tachyplesin, bactenecin (e.g., cattle bactenecin), ranalexin, cecropin A, indolicidin (e.g., cattle indolicidin), and nisin (e.g., bacterial nisin).

Also included as antimicrobial agents are ionophores, which facilitate transmission of an ion, (such as sodium), across a lipid barrier such as a cell membrane. Two ionophore compounds particularly suited to this invention are the RUMENSIN™ (Eli Lilly) and Lasalocid (Hoffman LaRoche). Other ionophores include, but are not limited to, salinomycin, avoparcin, aridcin, and actaplanin. Other antimicrobial agents include Monensin™ and azithromycin, metronidazole, streptomycin, kanamycin, and penicillin, as well as, generally, β-lactams, aminoglycosides, macrolides, chloramphenicol, novobiocin, rifampin, and fluoroquinolones (see, e.g., Horn et al., 2003, Applied Environ. Microbiol. 69:74-83; Eckburg et al., 2003, Infection Immunity 71:591-596; Gijzen et al., 1991, Applied Environ. Microbiol. 57:1630-1634; Bonelo et al., 1984, FEMS Microbiol. Lett. 21:341-345; Huser et al., 1982, Arch. Microbiol. 132:1-9; Hilpert et al., 1981, Zentbl. Bakteriol. Mikrobiol. Hyg. 1 Abt Orig. C 2:21-31).

Particularly useful inhibitors are compounds that block or interfere with methanogenesis, including bromoethanesulphonic acid, e.g., 2-bromoethanesulphonic acid (BES) or a salt thereof, for example, a sodium salt. Sodium molybdate (Mo) is an inhibitor of sulfate reduction, and can be used with bromoethanesulphonic acid. Other anti-methanogenesis compounds include, but are not limited to, nitrate, formate, methyl fluoride, chloroform, chloral hydrate, sodium sulphite, ethylene and unsaturated hydrocarbons, acetylene, fatty acids such as linoleic and cis-oleic acid, saturated fatty acids such as behenic and stearic acid, and, also lumazine (e.g., 2,4-pteridinedione). Additional compounds include 3-bromopropanesulphonate (BPS), propynoic acid, and ethyl 2-butynoate.

Further included as antimicrobial agents are lytic enzymes, including phage lysozyme, endolysin, lysozyme, lysin, phage lysin, muralysin, muramidase, and virolysin. Useful enzymes exhibit the ability to hydrolyse specific bonds in the bacterial cell wall. Particular lytic enzymes include, but are not limited to, glucosaminidases, which hydrolyse the glycosidic bonds between the amino sugars (e.g., N-acetylmuramic acid and N-acetylglucosamine) of the peptidoglycan, amidases, which cleave the N-acetylmuramoyl-L-alanine amide linkage between the glycan strand and the cross-linking peptide, and endopeptidases, which hydrolyse the interpeptide linkage (e.g., cysteine endopeptidases) and endoisopeptidases that attack pseudomurein of methanogens from the family Methanobacteriaceae.

Additionally, PNAs are included as antimicrobial agents. PNAs are peptide-nucleic acid hybrids in which the phosphate backbone has been replaced by an achiral and neutral backbone made from N-(2-aminoethyl)-glycine units (see, e.g., Eurekah Bioscience Collection. PNA and Oligonucleotide Inhibitors of Human Telomerase. G. Gavory and S. Balasubramanian, Landes Bioscience, 2003). The bases A, G, T, C are attached to the amino nitrogen on the backbone via methylenecarbonyl linkages (P. E. Nielsen et al., Science 1991. 254: 1497-1500; M. Egholm et al., Nature 1993. 365: 566-568). PNAs bind complementary sequences with high specificity, and higher affinity relative to analogous DNA or RNA (M. Egholm et al., supra). PNA/DNA or PNA/RNA hybrids also exhibit higher thermal stability compared to the corresponding DNA/DNA or DNA/RNA duplexes (M. Egholm et al., supra). PNAs also possess high chemical and biological stability, due to the unnatural amide backbone that is not recognized by nucleases or proteases (V. Demidov et al., Biochem Pharmacol 1994. 48: 1310-1313). Typically, PNAs are at least 5 bases in length, and include a terminal lysine. PNAs may be pegylated to further extend their lifespan (Nielsen, P. E. et al. (1993) Anticancer Drug Des. 8:53-63).

In one particular aspect, the antibodies of the invention can be fused or linked to other antibodies or fragments thereof. The added antibodies or antibody fragments can be directed to microbial cells, or particularly methanogen cells, or one or more cell components. For example, cell surface proteins, e.g., extracellular receptors, can be targeted. In certain aspects, the antibodies or antibody fragments can be engineered with sequences that are specifically expressed in subjects, for example, human or ruminant sequences. Also included are chimeric antibodies, for example, monoclonal antibodies or fragments thereof that are specific to more than one source, e.g., one or more mouse, human, or ruminant sequences. Further included are camelid antibodies or nanobodies.

The antibodies of the invention find particular use in targeting a microbial cell, in particular, a methanogen cell. In certain aspects, the antibodies can be used to associate with or bind to the cell wall or membrane and/or inhibit growth or replication of the cell. As such, the antibodies can be used for transient or extended attachment to the cell, or to mediate sequestration or engulfment of the cell, and/or lysis. To effect targeting, the microbial cell can be contacted with an antibody as isolated from a host organism, or produced by expression vectors and/or host cells, or synthetic or semi-synthetic chemistry as described in detail herein. Alternately, the antibodies can be produced by the host organism itself in response to the administration or the peptides, polypeptides, or polynucleotides disclosed herein. It is understood that the antibodies of the invention, as well as the corresponding polynucleotides, expression vectors, host cells, peptides, and polypeptides, can be used to target various microbes, for example, *Methanobrevibacter ruminantium*, which is the primary methanogen in ruminants, and *Methanobrevibacter smithii*, which is the primary methanogen in humans. In particular aspects, the antibodies, or corresponding polynucleotides, expression vectors, host cells, peptides, or polypeptides, are delivered to subjects as a composition described in detail herein, for example, through use of a slow-release ruminal device.

In various aspects, the agents of the invention (e.g., one or more peptides, polypeptides, polynucleotides, and antibodies) can be included in a composition, for example, a pharmaceutical composition, and especially a vaccine composition. The composition comprises, for example: a) an isolated peptide or alteration, fragment, variant, or derivative thereof; b) an isolated polypeptide, or an alteration, fragment, variant, or derivative thereof; c) an isolated polynucleotide, or an alteration, fragment, variant, or derivative thereof; d) an expression vector comprising this polynucleotide; e) a host cell comprising this expression vector; or (f) an antibody, or an alteration, fragment, variant, or derivative thereof. The compositions of the invention can be specifically packaged as part of kits for targeting, and/or inhibiting microbial cells, especially methanogen cells, in accordance with the disclosed methods. The kits comprise at least one composition as set out herein and instructions for use in targeting cells or inhibiting cell growth or replication, for methanogens or other microbes.

For vaccines, a number of approaches can be used to increase antigen immunogenicity, for example, by use of antigen particles; antigen polymers and polymerization; emulsifying agents; microencapsulation of antigens; killed bacteria and bacterial products; chemical adjuvants and cytokines; and agents for targeting antigens to antigen presenting cells (reviewed in Paul, Fundamental Immunology, 1999, Lippincott-Raven Publishers, New York, N.Y., p. 1392-1405).

To render antigens particulate, alum precipitation can be used. With the use of aluminium hydroxide or aluminium phosphate, the antigen in question becomes incorporated into an insoluble, gel-like precipitate or else is bound to preformed gel by electrostatic interactions. Antigens can be subjected to mild heat aggregation. Antigens exhibiting self-assembly can also be used. Liposomes, virosomes, and immunostaining complexes (ISCOMs) are also useful for forming particulates.

To promote polymerization, nonionic block copolymers can be used as additives to adjuvants, e.g., polymers or polyoxypropylene and polyoxyethylene, with which antigen can be associated. These are found as components of complex adjuvant formulations by both Syntex (SAF-1, Syntex Adjuvant Formulation-1) and Ribi Chemical Co. Carbohydrate polymers of mannose (e.g., mannan) or of β1-3 glucose (e.g., glucan) can be used in similar fashion (Okawa Y, Howard C R, Steward M W. Production of anti-peptide antibody in mice following immunization of mice with peptides conjugated to mannan. J Immunol Methods 1992; 142:127-131; Ohta M, Kido N, Hasegawa T, et al. Contribution of the mannan side chains to the adjuvant action of lipopolysaccharides. Immunology 1987;60:503-507).

Various agents can be used for emulsification, including water-in-oil emulsions, such as Freund's adjuvants (e.g., Freund's incomplete adjuvant), or other mixtures comprising tiny droplets of water stabilized by a surfactant such as mannide monooleate in a continuous phase of mineral oil or other oils, such as squalane. An alternative approach is to use oil-in-water emulsions, such as MF5963 (Chiron), or other mixtures comprising oil droplets of squalene and a mixture of emulsifying agents TWEEN80 and SPAN85, and chemical immunomodulators such as derivatives or muramyl dipeptide, e.g., muramyl tripeptide-phosphatidyl ethanolamine (MTP-PE) (Valensi J-P M, Carlson J R, Van Nest G A. Systemic cytokine profiles in Balb/c mice immunized with trivalent influenza vaccine containing MF59 oil emulsion and other advanced adjuvants. J Immunol 1994;153: 4029-4039). Small amounts of polysorbate 80 and sorbitan trioleate can also be used in the mixtures. As another example, SAF-165 (Syntex) can be used, or other oil-in-water mixtures comprising Pluronic L121, squalene, and TWEEN80.

Microcapsules, in particular, biodegradable microcapsules, can be used to prepare controlled-release vaccines (Chang T M S. Biodegradable, semi-permeable microcapsules containing enzymes hormones, vaccines and other biologicals. J Bioeng 1976;1:25-32; Langer R. Polymers for the sustained release of macromolecules: their use in a single step method of immunization. Methods Enzymol 1981;73: 57-75). Cyanoacrylates are another form of biodegradable polymer. For example, poly(butyl-2-cyanoacrylate) can be used as an adjuvant for oral immunization (O'Hagan D T, Palin K J, Davis S S. Poly (butyl-2-cyanoacrylate) particles as adjuvants for oral immunization. Vaccine 1989;7:213-216). Microcapsules are useful for the mucosal administration of vaccines. Particles of very small size (nanoparticles) are particularly suitable. Digestion in the stomach can be countered by enteric coated polymers, and coating with substances that increase intestinal absorption, as needed.

Various bacteria, other than killed *M. tuberculosis*, can be used as adjuvants. Where the killed bacterial preparation is itself highly antigenic, the adjuvant properties extend to the co-administered antigen. Useful organisms include *Bordetella pertussis*, *Corynebacterium parvum*, and *Nippostrongylus brasiliensis*. Peptide and lipid components of bacteria can also be used. Exemplary components include acetylmuramyl-L-alanyl-D-isoglutamine, or muramyl dipeptide (MDP) (Ellouz F, Adam A, Ciorbaru R, Lederer E. Minimal structural requirements for adjuvant activity of bacterial peptidoglycans. Biochem Biophys Res Commun 1974;59:1317-1325), MDP (murabutide) (Chedid L, Parant M A, Audibert F M, et al. Biological activity of a new synthetic muramyl dipeptide devoid of pyrogenicity. Infect Immun 1982;35:417-424), threonyl MDP (Allison A C, Byars N E. An adjuvant formulation that selectively elicits the formation of antibodies of protective isotypes and cell-mediated immunity. J Immunol Methods 1986;95:157-168), and MTP-PE. Lipid adjuvants can comprise LPS endotoxins of gram-negative bacteria, such as *Escherichia, Salmonella*, and *Pseudomonas*. In certain approaches, the lipid A structure can be chemically modified to lower toxicity but retain adjuvanticity, e.g., as for monophosphoryl lipid A (MPL) (Johnson A G, Tomai M, Solem L, Beck L, Ribi E. Characterization of non-toxic monophosphoryl lipid. Rev Infect Dis 1987;9:S512).

Various chemicals can be used as adjuvants, including polynucleotides, such as poly-I:C and poly-A:U, vitamin D3, dextran sulphate, inulin, dimethyl dioctadecyl ammonium bromide (DDA), pyridine, carbohydrate polymers similar to mannan, and trehalose dimycolate (Morein B, Lövgren-Bengtsson K, Cox J. Modern adjuvants: functional aspects. In: Kaufmann S H E, ed. Concepts in vaccine development. Berlin: Walter de Gruyter, 1996:243-263). Also included are polyphosphazines (initially introduced as slow release-promoting agents) and a *Leishmania* protein, LeIF. Cytokines can also be used as adjuvants, for example, IL-2, IL-4, IL-6, IL-10, GM-CSF, and IFN-g.

For targeting antigen presenting cells, C3d domains, Fc domains, and CTB domains can be used (Dempsey P W, Allison M E D, Akkaraju S, Goodnow C C, Fearon D T. C3d of complement as a molecular adjuvant: bridging innate and acquired immunity. Science 1996; 271:348-350; Sun J-B, Holmgren J, Czerkinsky C. Cholera toxin B subunit: an efficient transmucosal carrier-delivery system for induction of peripheral immunological tolerance. Proc Natl Acad Sci USA 1994;91:10795-10799; Sun J-B, Rask C, Olsson T, Holmgren J, Czerkinsky C. Treatment of experimental autoimmune encephalomyelitis by feeding myelin basic protein conjugated to cholera toxin B subunit. Proc Natl Acad Sci USA 1996;93:7196-7201).

Specific adjuvants for mucosal delivery, e.g., CT, LT, and Fragment C of tetanus toxin, can also be used (Elson C J, Ealding W. Generalized systemic and mucosal immunity in mice after mucosal stimulation with cholera toxin. J Immunol 1984;132:2736-2743; Holmgren J, Lycke N, Czerkinsky C. Cholera toxin and cholera B subunit as oral-mucosal adjuvant and antigen vector systems. Vaccine 1993;11:1179-1184; Clements J D, Hartzog N M, Lyon F L. Adjuvant activity of *Escherichia coli* heat-labile enterotoxin and effect on the induction of oral tolerance in mice to unrelated protein antigens. Vaccine 1988;6:269-277; Gomez-Duarte O G, Galen J, Chatfield S N, Rappuoli R, Eidels L, Levine M M. Expression of fragment C of tetanus toxin fused to a carboxyl-terminal fragment of diphtheria toxin in *Salmonella typhi* CVD 908 vaccine strain. Vaccine 1995;13:1596-1602).

Therapeutics and Diagnostics

The peptides, polypeptides, polynucleotides, and antibodies of the present invention are considered to have health benefits. In particular aspects, vaccines that target methanogens can be used to restore energy to the subject that is normally lost as methane. The invention therefore relates to a pharmaceutical composition (especially a vaccine composition) in conjunction with a pharmaceutically acceptable carrier, for use with any of the methods discussed above. Such pharmaceutical compositions may comprise a peptide, polypeptide, or antibody in combination with a cell inhibitor. Alternatively, the pharmaceutical compositions may comprise a polynucleotide, expression vector, or host cell as described in detail herein. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject alone, or in combination with other agents, drugs (e.g., antimicrobial drugs), or hormones.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.). The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilising agents may be added, such as the crosslinked polyvinyl pyrrolidone, agar, alginic acid, or a salt thereof, such as sodium alginate.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. For administration of a composition of the invention, such labeling would include amount, frequency, and method of administration.

Pharmaceutical compositions suitable for use in the invention include compositions wherein the active ingredients are contained in an effective amount to achieve the intended purpose. For any compound, the therapeutically effective dose can be estimated initially either in cell assays, e.g., in microbial cells, or in particular, in methanogen cells, or in animal models, usually mice, rabbits, dogs, or pigs, or in ruminant species such as sheep, cattle, deer, and goats. The animal model may also be used to determine the appropriate concentration range and route of administration. Such information can then be used to determine useful doses and routes for administration. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for polynucleotides than for polypeptides. Similarly, delivery of peptides, or polypeptides, polynucleotides, or antibodies will be specific to particular cells, conditions, locations, etc.

The exact dosage will be determined by the practitioner, in light of factors related to the subject that requires treatment. Dosage and administration are adjusted to provide sufficient levels of the active agent or to maintain the desired effect. Factors which may be taken into account include the severity of the disease state, general health of the subject, age, weight, and gender, diet, time, and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. The compositions can be co-administered with one or more additional anti-microbial agents, including anti-methanogenesis compounds (e.g., bromoethanesulphonic acid), antibodies and antibody fragments, lytic enzymes, peptide nucleic acids, antimicrobial peptides, and other antibiotics as described in detail herein. Co-administration can be simultaneous or sequential, or can alternate with repeated administration.

Particularly useful for the compositions of the invention (e.g., pharmaceutical compositions) are slow release formulas or mechanisms. For example, intra-ruminal devices include, but are not limited to, Time Capsule™ Bolus range by Agri-Feeds Ltd., New Zealand, originally developed within AgResearch Ltd., New Zealand, as disclosed in WO 95/19763 and NZ 278977, and CAPTEC by Nufarm Health & Sciences, a division of Nufarm Ltd., Auckland, New Zealand, as disclosed in AU 35908178, PCT/AU81/100082, and Laby et al., 1984, *Can. J. Anim. Sci.* 64 (Suppl.), 337-8, all of which are incorporated by reference herein. As a particular example, the device can include a spring and plunger which force the composition against a hole in the end of a barrel.

As a further embodiment, the invention relates to a composition for a water supplement, e.g., drenching composition, or food supplement, e.g., ruminant feed component, for use with any of the methods discussed above. In particular aspects, the food supplement comprises at least one vegetable material that is edible, and a peptide or polypeptide of the invention. Alternatively, the food supplement comprises at least one vegetable material that is edible, and a polypeptide or peptide, or a polynucleotide encoding a peptide or polypeptide disclosed herein, for example, as an expression vector or host cell comprising the expression vector. In particular, the composition further includes a cell inhibitor, as fused or linked to the resultant sequence. The preferred vegetable material include any one of hay, grass, grain, or meal, for example, legume hay, grass hay, corn silage, grass silage, legume silage, corn grain, oats, barley, distillers grain, brewers grain, soy bean meal, and cotton seed meal. In particular, grass silage is useful as a food composition for ruminants. The plant material can be genetically modified to contain one or more components of the invention, e.g., one or more polypeptides or peptides, polynucleotides, or vectors.

In another embodiment, antibodies which specifically bind the peptides, polypeptides, or polynucleotides of the invention may be used to determine the presence of microbes, especially methanogens, or in assays to monitor levels of such microbes. The antibodies useful for diagnostic purposes may be prepared in the same manner as those described above. Diagnostic assays include methods which utilize the antibody and a label to detect a peptide or polypeptide in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring levels of a peptide, polypeptide, or polynucleotide are known in the art (e.g., ELISA, RIA, and FACS), and provide a basis for diagnosing the presence or levels of a microbe, especially a methanogen. Normal or standard levels established by combining body fluids or cell extracts taken from normal subjects, e.g., normal humans or ruminants, with the antibody under conditions suitable for complex formation. The amount of standard complex formation may be quantified by various methods, but preferably by photometric means. Quantities of peptide, polypeptide, or polynucleotide expressed in subject, control, and treated samples (e.g., samples from vaccinated subjects) are compared with the standard values. Deviation between standard and subject values establishes the parameters for determining the presence or levels of the microbe.

In another embodiment of the invention, the polynucleotides may be used for diagnostic purposes using particular hybridization and/or amplification techniques. The polynucleotides which may be used include oligonucleotides, complementary RNA and DNA molecules, and PNAs. The polynucleotides may be used to detect and quantitate gene expression in samples in which expression may be correlated with the presence or levels of a microbe. The diagnostic assay may be used to distinguish between the absence, presence, and alteration of microbe levels, and to monitor levels during therapeutic intervention.

In one aspect, hybridization with PCR probes may be used to identify nucleic acid sequences, especially genomic sequences, which encode the peptides or polypeptides of the invention. The specificity of the probe, whether it is made from a highly specific region, e.g., 10 unique nucleotides in the 5' regulatory region, or a less specific region, e.g., in the 3' coding region, and the stringency of the hybridization or amplification (maximal, high, intermediate, or low) will determine whether the probe identifies only naturally occurring sequences, alleles, or related sequences. Probes may also be used for the detection of related sequences, and should preferably contain at least 50% of the nucleotides from any of the coding sequences. The hybridization probes of the subject invention may be DNA or RNA and derived from the nucleotide sequence of SEQ ID NO: 1-1718, or complements, or modified sequences thereof, or from genomic sequences including promoter and enhancer elements of the naturally occurring sequence.

Means for producing specific hybridization probes for DNAs include the cloning of polynucleotides into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like. The polynucleotides may be used in Southern or northern analysis, dot blot, or other membrane-based technologies; in PCR technologies; or in dipstick, pin, ELISA assays, or microarrays utilizing fluids or tissues from subject biopsies to detect the presence or levels of a microbe. Such qualitative or quantitative methods are well known in the art.

In a particular aspect, the polynucleotides may be useful in various assays labelled by standard methods, and added to a fluid or tissue sample from a subject under conditions suitable for hybridization and/or amplification. After a suitable incubation period, the sample is washed and the signal is quantitated and compared with a standard value. If the amount of signal in the test sample is significantly altered from that of a comparable control sample, the presence of altered levels of nucleotide sequences in the sample indicates the presence or levels of the microbe. Such assays may also be used to evaluate the efficacy of a particular vaccination regimen in animal studies, in clinical trials, or in monitoring the treatment of a subject.

In order to provide a basis for the diagnosis of the presence or levels of a microbe, a normal or standard profile for expression is established. This may be accomplished by combining body fluids or cell extracts taken from normal subjects, with a polynucleotide or a fragment thereof, under conditions suitable for hybridization and/or amplification. Standard levels may be quantified by comparing the values obtained from normal subjects with those from an experiment where a known amount of a substantially purified polynucleotide is used. Standard values obtained from normal samples may be compared with values obtained from samples from subjects treated for microbial growth. Deviation between standard and subject values is used to establish the presence or levels of the microbe.

Once the microbe is identified and a vaccination protocol is initiated, hybridization and/or amplification assays may be repeated on a regular basis to evaluate whether the level of expression in the subject begins to decrease relative to that which is observed in the normal subject. The results obtained from successive assays may be used to show the efficacy of vaccination over a period ranging from several days to months.

Particular diagnostic uses for oligonucleotides designed from the polynucleotides may involve the use of PCR. Such oligomers may be chemically synthesized, generated enzymatically, or produced in vitro. Oligomers will preferably consist of two nucleotide sequences, one with sense orientation (5'.fwdarw.3') and another with antisense orientation (3'.fwdarw.5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate expression include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotides described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents. In one embodiment, the microarray is prepared and used according to methods known in the art such as those described in PCT application WO 95/11995 (Chee et al.), Lockhart, D. J. et al. (1996; Nat. Biotech. 14: 1675-1680) and Schena, M. et al. (1996; Proc. Natl. Acad. Sci: 93: 10614-10619).

In one aspect, the oligonucleotides may be synthesized on the surface of the microarray using a chemical coupling procedure and an ink jet application apparatus, such as that described in PCT application WO 95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may include, for example, 24, 48, 96, 384, 1024, 1536, or 6144 spots or wells (e.g., as a multiwell plate), or more, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce polynucleotides which are complementary to the nucleic acids on the microarray. If the microarray consists of cDNAs, antisense RNAs are appropriate probes. Therefore, in one aspect, mRNA is used to produce cDNA which, in turn and in the presence of fluorescent nucleotides, is used to produce fragments or antisense RNA probes. These fluorescently labeled probes are incubated with the microarray so that the probe sequences hybridize to the cDNA oligonucleotides of the microarray. In another aspect, polynucleotides used as probes can include polynucleotides, fragments, and complementary or antisense sequences produced using restriction enzymes, PCR technologies, and oligolabeling kits (Amersham Pharmacia Biotech) well known in the area of hybridization technology.

In another embodiment of the invention, the peptides or polypeptides of the invention or functional or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the peptide or polypeptide and the agent being tested, may be measured.

One technique for drug screening which may be used provides for high throughput screening of compounds having suitable binding affinity to the peptide or polypeptide of interest as described in published PCT application WO 84/03564. In this method, large numbers of different small test compounds are synthesized on a solid substrate, such as plastic pins or some other surface. The test compounds are reacted with the peptide or polypeptide, or fragments thereof, and washed. Bound peptide or polypeptide is then detected by methods well known in the art. Purified peptide or polypeptide can also be coated directly onto plates for use in the aforementioned drug screening techniques. Alternatively, non-neutralizing antibodies can be used to capture the peptide and immobilize it on a solid support.

In another technique, one may use competitive drug screening assays in which neutralizing antibodies capable of binding the peptide or polypeptide specifically compete with a test compound for binding to the peptide or polypeptide. In this manner, the antibodies can be used to detect the presence of a test compound which shares one or more antigen binding sites with the antibody.

Plant Constructs and Plant Transformants

Of particular interest is the use of the polynucleotides of this invention for plant transformation or transfection. Exogenous genetic material may be transferred into a plant cell and the plant cell regenerated into a whole, fertile, or sterile plant. Exogenous genetic material is any genetic material, whether naturally occurring or otherwise, from any source that is capable of being inserted into any organism. Such genetic material may be transferred into either monocotyledons or dicotyledons including but not limited to the plants used for animal feed, e.g., feed for sheep, cows, etc.

A variety of methods can be used to generate stable transgenic plants. These include particle gun bombardment (Fromm et al., Bio/Technology 8:833-839 (1990)), electroporation of protoplasts (Rhodes et al., Science 240:204-207 (1989); Shimamoto et al., Nature 338:274-276 (1989)), treatment of protoplasts with polyethylene glycol (Datta et al., Bio/Technology, 8:736-740 (1990)), microinjection (Neuhaus et al., Theoretical and Applied Genetics, 75:30-36 (1987)), immersion of seeds in a DNA solution (Ledoux et al., Nature, 249:17-21 (1974)), and transformation with T-DNA of *Agrobacterium* (Valvekens et al., PNAS, 85:5536-5540 (1988); Komari, Plant Science, 60:223-229 (1989)). In most, perhaps all plant species, *Agrobacterium*-mediated transformation is the most efficient and easiest of these methods to use. T-DNA transfer generally produces the greatest number of transformed plants with the fewest multi-copy insertions, rearrangements, and other undesirable events.

Many different methods for generating transgenic plants using *Agrobacterium* have been described. In general, these methods rely on a "disarmed" *Agrobacterium* strain that is incapable of inducing tumours, and a binary plasmid transfer system. The disarmed strain has the oncogenic genes of the T-DNA deleted. A Binary plasmid transfer system consists of one plasmid with the 23-base pair T-DNA left and right border sequences, between which a gene for a selectable marker (e.g. an herbicide resistance gene) and other desired genetic elements are cloned. Another plasmid encodes the *Agrobacterium* genes necessary for effecting the transfer of the DNA between the border sequences in the first plasmid. Plant tissue is exposed to *Agrobacterium* carrying the two plasmids, the DNA between the left and right border repeats is transferred into the plant cells, transformed cells are identified using the selectable marker, and whole plants are regenerated from the transformed tissue. Plant tissue types that have been reported to be transformed using variations of this method include: cultured protoplasts (Komari, Plant Science, 60:223-229 (1989)), leaf disks (Lloyd et al., Science 234:464-466 (1986)), shoot apices (Gould et al., Plant Physiology, 95:426-434 (1991)), root segments (Valvekens et al., PNAS, 85:5536-5540 (1988)), tuber disks (Jin et al., Journal of Bacteriology, 169: 4417-4425 (1987)), and embryos (Gordon-Kamm et al., Plant Cell, 2:603-618 (1990)).

In the case of *Arabidopsis thaliana* it is possible to perform in plant germline transformation (Katavic et al., Molecular and General Genetics, 245:363-370 (1994); Clough et al., Plant Journal, 16:735-743 (1998)). In the simplest of these methods, flowering *Arabidopsis* plants are dipped into a culture of *Agrobacterium* such as that described in the previous paragraph. Among the seeds produced from these plants, 1% or more have integration of T-DNA into the genome.

Monocot plants have generally been more difficult to transform with *Agrobacterium* than dicot plants. However, "supervirulent" strains of *Agrobacterium* with increased expression of the virB and virG genes have been reported to transform monocot plants with increased efficiency (Komari et al., Journal of Bacteriology, 166:88-94 (1986); Jin et al., Journal of Bacteriology, 169:417-425 (1987)

Most T-DNA insertion events are due to illegitimate recombination events and are targeted to random sites in the genome. However, given sufficient homology between the transferred DNA and genomic sequence, it has been reported that integration of T-DNA by homologous recombination may be obtained at a very low frequency. Even with long stretches of DNA homology, the frequency of integration by homologous recombination relative to integration by illegitimate recombination is roughly 1:1000 (Miao et al., Plant Journal, 7:359-365 (1995); Kempin et al., 389:802-803 (1997)).

Exogenous genetic material may be transferred into a plant cell by the use of a DNA vector or construct designed for such a purpose. Vectors have been engineered for transformation of large DNA inserts into plant genomes. Binary bacterial artificial chromosomes have been designed to replicate in both *E. coli* and *Agrobacterium* and have all of the features required for transferring large inserts of DNA into plant chromosomes. BAC vectors, e.g. a pBACwich, have been developed to achieve site-directed integration of DNA into a genome.

A construct or vector may also include a plant promoter to express the gene or gene fragment of choice. A number of promoters that are active in plant cells have been described in the literature. These include the nopaline synthase (NOS) promoter, the octopine synthase (OCS) promoter, a caulimovirus promoter such as the CaMV 19S promoter and the CaMV 35S promoter, the figwort mosaic virus 35S promoter, the light-inducible promoter from the small subunit of ribulose-1,5-bis-phosphate carboxylase (ssRUBISCO), the Adh promoter, the sucrose synthase promoter, the R gene complex promoter, and the chlorophyll a/b binding protein gene promoter.

For the purpose of expression in source tissues of the plant, such as the leaf; seed, root, or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase (FBPase) promoter from wheat, the nuclear photosynthetic ST-LS1 promoter from potato, the phenylalanine ammonia-lyase (PAL) promoter and the chalcone synthase (CHS) promoter from *Arabidopsis thaliana*.

Also reported to be active in photosynthetically active tissues are the ribulose-1,5-bisphosphate carboxylase (RbcS) promoter from eastern larch (*Larix laricina*), the promoter for the cab gene, cab6, from pine, the promoter for the Cab-1 gene from wheat, the promoter for the CAB-1 gene from spinach, the promoter for the cab1R gene from rice, the pyruvate, orthophosphate dikinase (PPDK) promoter from *Zea mays*, the promoter for the tobacco Lhcb1*2 gene, the *Arabidopsis thaliana* SUC2 sucrose-$^{H+}$ symporter promoter, and the promoter for the thylacoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435 and 4,633,436, all of which are herein incorporated in their entirety.

Constructs or vectors may also include, with the coding region of interest, a nucleic acid sequence that acts, in whole or in part, to terminate transcription of that region. For example, such sequences have been isolated including the Tr7 3' sequence and the nos 3' sequence or the like. It is understood that one or more sequences of the present invention that act to terminate transcription may be used.

A vector or construct may also include other regulatory elements or selectable markers. Selectable markers may also be used to select for plants or plant cells that contain the exogenous genetic material. Examples of such include, but are not limited to, a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil, a mutant acetolactate synthase gene (ALS) which confers imidazolinone or sulphonylurea resistance; and a methotrexate resistant DHFR gene.

A vector or construct may also include a screenable marker to monitor expression. Exemplary screenable markers include a .beta.-glucuronidase or uidA gene (GUS), an R-locus gene, which encodes a product that regulates the production of anthocyanin pigments (red colour) in plant tissues; a beta-lactamase gene, a gene which encodes an enzyme for which various chromogenic substrates are known (e.g., PADAC, a chromogenic cephalosporin); a luciferase gene, a xylE gene which encodes a catechol dioxygenase that can convert chromogenic catechols; an alpha-amylase gene, a tyrosinase gene which encodes an enzyme capable of oxidizing tyrosine to DOPA and dopaquinone which in turn condenses to melanin; an alpha-galactosidase, which will turn a chromogenic alpha-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., alpha-amylase, beta-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

Thus, any of the polynucleotides of the present invention may be introduced into a plant cell in a permanent or transient manner in combination with other genetic elements such as vectors, promoters enhancers etc. Further any of the polynucleotides encoding a protein or fragment thereof or homologs of the present invention may be introduced into a plant cell in a manner that allows for expression (e.g., overexpression) of the protein or fragment thereof encoded by the polynucleotide.

Computer Related Uses

In one embodiment, a nucleotide or amino acid sequence of the present invention can be recorded on computer readable media. This takes into account any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a sequence of the present invention.

A skilled artisan can readily adopt any of the presently know methods for recording information on computer readable medium to generate manufactures comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium.

As non limiting examples, the sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing the sequence of any SEQ ID NO: herein, or a representative fragment thereof, or any variant thereof, in computer readable form, a skilled artisan can routinely access the sequence information for a variety of purposes. Computer software is publicly available which allows a skilled artisan to access sequence information provided in a computer readable medium. For example, software can be used to implement the BLAST (Altschul et al., J. Mol. Biol. 215:403-410 (1990)) and BLAZE (Brutlag et al., Comp. Chem. 17:203-207 (1993)) search algorithms, e.g., on a Sybase system to identify, open reading frames (ORFs) which contain homology to ORFs or proteins from other organisms. Such ORFs may be protein encoding sequences which are useful in producing commercially important proteins such as enzymes.

The present invention further provides systems, particularly computer-based systems, which contain the sequence information described herein. Such systems are designed to identify commercially important sequences of the M. ruminantium genome. This includes the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As stated above, the computer-based systems of the present invention comprise a data storage means having stored therein a nucleotide sequence of the present invention and the necessary hardware means and software means for supporting and implementing a search means. This refers to memory which can store nucleotide sequence information of the present invention, or a memory access means which can access manufactures having recorded thereon the nucleotide sequence information of the present invention. Searching can include one or more programs which are implemented on the computer-based system to compare a target sequence or target structural motif with the sequence information stored within the data storage means.

Search means are used to identify fragments or regions of the M. ruminantium genome which match a particular target sequence or target motif, e.g., antibody targets. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBIA). A skilled artisan can readily recognize that any one of the available algorithms or implementing software packages for conducting homology searches can be adapted for use in the present computer-based systems.

The target sequence can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments of the *M. ruminantium* genome, such as sequence fragments involved in gene expression and protein processing, may be of shorter length.

A target structural motif, or target motif includes any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

A variety of structural formats for the input and output means can be used to input and output the information in the computer-based systems of the present invention. A preferred format for an output means ranks fragments of the *M. ruminantium* genome possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the *M. ruminantium* genome. In particular aspects, software can be used implement the BLAST and BLAZE algorithms (Altschul et al., J. Mol. Biol. 215:403-410. (1990)) and to identify open reading frames. A skilled artisan can readily recognize that any one of the publicly available homology search programs can be used as the search means for the computer-based systems of the present invention The computer system may include a processor connected to a bus. Also connected to the bus may be a main memory (preferably implemented as random access memory, RAM) and a variety of secondary storage devices, such as a hard drive and a removable medium storage device. The removable medium storage device may represent, for example, a floppy disk drive, a CD-ROM drive, a magnetic tape drive, etc. A removable storage medium (such as a floppy disk, a compact disk, a magnetic tape, etc.) containing control logic and/or data recorded therein may be inserted into the removable medium storage device. The computer system may include appropriate software for reading the control logic and/or the data from the removable medium storage device once inserted in the removable medium storage device.

A sequence of the present invention may be stored in a well known manner in the main memory, any of the secondary storage devices, and/or a removable storage medium. Software for accessing and processing the genomic sequence (such as search tools, comparing tools, etc.) reside in main memory during execution.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1

Materials and Methods

Strain Information and Growth Conditions

*Methanobrevibacter ruminantium* $M1^T$ (DSM1093) was obtained from the German Collection of Microorganisms and Cell Cultures (DSMZ), Braunschweig, Germany. The original description of *Methanobacterium ruminantium* was made by Smith and Hungate (Smith & Hungate, 1958) and the genus designation later changed to *Methanobrevibacter* (Balch et al., 1979). *Methanobrevibacter ruminantium* $M1^T$ (DSM1093) was isolated from bovine rumen contents by Bryant (Bryant, 1965). It is designated the neotype strain for this species because the original strain of Smith and Hungate was not maintained. *M. ruminantium* strain $M1^T$ was routinely grown in basal medium (Joblin et al., 1990) with added trace elements (Balch et al., 1979), ($BY^+$ medium), with $H_2$ plus $CO_2$ (4:1) at 180 kPa overpressure. The culture tubes were incubated on their sides, at 39° C. in the dark, on a platform shaken at 200 rpm.

Co-Culture of *M. ruminantium* and *Butyrivibrio proteoclasticus*

M1 was grown in co-culture with Butyrivibrio proteoclasticus $B316^T$ (DSM14932) to examine gene expression under rumen-like conditions. Eighteen pure cultures of M1 were grown in $BY^+$ medium with $H_2$ plus $CO_2$ (4:1) at 180 kPa overpressure in 100 ml volumes in 125 ml serum bottles sealed with blue butyl septum stoppers and aluminium seals (Bellco Glass, Vineland, N.J., USA). When the cultures reached mid-exponential phase, as measured by optical density at 600 nm (Ultrospec 1100 pro UV/Vis spectrophotometer, Amersham Biosciences, Little Chalfont, Buckinghamshire, UK) they were flushed with $O_2$-free 100% $CO_2$ gas until $H_2$ was not detectible by gas chromatography. All 18 cultures were supplemented with oat spelt xylan (Sigma-Aldrich, St. Louis, Mo., USA) to 0.2% (w/v) final concentration, then nine of the cultures were inoculated with 0.5 ml of a late-exponential phase culture of *B. proteoclasticus*. The other nine were re-pressurized to $H_2$ plus $CO_2$ (4:1) at 180 kPa overpressure. Three further serum bottles of $BY^+$ medium supplemented with 0.2% (w/v) xylan were also inoculated with an equivalent inoculum of *B. proteoclasticus*. Growth in the co-culture was monitored periodically by Thoma slide enumeration (Webber Scientific International Ltd., Teddington, England). Mid-exponential phase co-cultures and monocultures were harvested by centrifugation (10,000×g, 5 min at 4° C.), and the cell pellets resuspended in 10 ml of $BY^+$ medium (+0.2% [w/v] xylan) and 20 ml of RNAprotect (Qiagen, Hilden, Germany). These were incubated for 5 min at room temperature, and were immediately processed for RNA extraction.

Microarray Analyses

RNA Isolation, cDNA Synthesis and Labelling. Cells of M1 and *B. proteoclasticus* from mono- or co-cultures prepared as described above, were pelleted by centrifugation (5,000×g, 10 min room temperature), air-dried and frozen under liquid $N_2$. Frozen pellets were ground in a sterile pre-chilled (−20° C.) mortar and pestle under liquid $N_2$, and the ground samples resuspended in excess TRIzol (Invitrogen, Carlsbad, Calif., USA). The mixtures were incubated at 20° C. for 5 min. Chloroform (200 µl) was then added, mixed vigorously, and incubated for a further 3 min. The samples were centrifuged (12,000×g, 15 min, 4° C.) and the aqueous phases transferred to fresh tubes, mixed with 0.5 volumes isopropanol and incubated at 20° C. for 10 min to precipitate the RNAs. Precipitated RNAs were pelleted by centrifugation (12,000×g, 10 min, 4° C.), the supernatants removed and the RNAs washed with 5 ml of 75% (v/v) ethanol before being re-pelleted by centrifugation. Ethanol was removed, the pellets air dried on ice and finally each resuspended in 1 ml of diethyl pyrocarbonate (DEPC) treated Milli-Q water. The RNAs were further purified using an RNeasy Midi kit (Qiagen, Hilden, Germany) and quantified using an Agilent 2100 Bioanalyzer (Agilent Technologies, Santa Clara, Calif., USA) following the respective manufacturer's instructions. cDNA synthesis, labeling and purification were carried out using the Invitrogen cDNA labelling purification kit, while the Cy3 and Cy5 dyes were from GE Healthcare (Uppsala, Sweden).

Quantification of Co-Culture mRNA. The relative quantities of RNAs contributed by each organism to the co-culture samples were determined by quantitative PCR of the *B. proteoclasticus* butyryl-CoA dehydrogenase (bcd) gene (using primers bcdqfp: tgagaagggaacacctggat; SEQ ID NO: 7586, and bcdqrp: ttgctcttccgaactgctt; SEQ ID NO: 7587), and the M1 gene encoding $N^5,N^{10}$-methenyl-$H_4$MPT cyclohydrolase (mch) (using primers mchqfp: gtattgcctggtgaagatgt; SEQ ID NO: 7588 and mchqrp: gtcgatttggtagaagtca; SEQ ID NO: 7589). Homologs of both genes have previously been shown to be constitutively expressed in closely related species (Reeve et al., 1997; Asanuma et al., 2005). The mono-culture RNAs were then combined in equal proportions to normalise mRNA abundance with their co-culture replicates.

Probe Synthesis and Slide Printing. Oligonucleotide 70mer probes were designed against the draft genomes of M1 and *Butyrivibrio proteoclasticus* B316$^T$ using ROSO software (Reymond et al., 2004) and synthesised by Illumina (San Diego, Calif., USA). Oligonucleotides were spotted onto epoxy-coated slides (Corning, Lowell, Mass., USA) using an ESI robot (Engineer Service Inc., Toronto, Ontario, Canada).

Microarray Hybridization and Scanning. Microarrays were replicated 6 times (3 biological replicates per treatment, each with a dye swap) and each gene was represented on the array 3 to 7 times. Microarray slides were pre-warmed in microarray prehybridization buffer (50° C. for 30 min), and transferred into hybridization chambers (Corning, Lowell, Mass., USA) and lifter cover slips (Erie Scientific, Portsmouth, N.H., USA) were laid over the probe areas. Samples of RNA to be compared (e.g., Cy3 co-culture versus combined Cy5 individual mono-cultures) were combined, denatured at 95° C. for 10 min, and mixed with 60 µl of pre-warmed (68° C.) Slide Hyb buffer #1 (Ambion, Austin, Tex., USA). The mixture was loaded onto the slide, the hybridization chamber sealed, and incubated in a water bath at 50° C. for 24 h. Following hybridization, the slides were washed by vigorous shaking by hand in pre-warmed (50° C.) wash solutions 1 to 3 (wash solution 1: 10% SDS, 2×SSC; wash solution 2: 1×SSC; wash solution 3: 0.1× SSC), 7 min per wash in aluminium foil-covered Falcon tubes (Becton, Dickinson and Co. Sparks, Md., USA). Following the third wash, the slides were dried by low speed centrifugation (1,500×g, 4 min) followed by incubation for 20 min in a 37° C. vacuum oven (Conthemn, Wellington, NZ) in the dark. Microarray slides were scanned using a GenePix® Professional 4200 scanner and GenePix Pro 6.0 software (Molecular Devices, Sunnyvale, Calif., USA) and analysed using the Limma package in Bioconductor (Smyth, 2005). Genes with an up- or down-regulation of 2 fold or greater and an FDR value <0.05 were deemed statistically significant.

Growth Experiments to Test Effects of PeiR and Alcohols

M1 was grown in medium RM02 in anaerobic culture tubes (16 mm internal diameter, 18 mm outer diameter, 150 mm long; Bellco Glass, Vineland, N.J., USA), essentially as described by Balch and Wolfe, 1976. The mineral salts base of RM02 contained (per liter of medium): 1.4 g of $KH_2PO_4$, 0.6 g of $(NH_4)_2SO_4$, 1.5 g of KCl, 1 ml trace element solution SL10 (Widdel et al., 1983), 1 ml of selenite/tungstate solution (Tschech and Pfennig, 1984) and 4 drops of 0.1% (w/v) resazurin solution. This solution was mixed and then boiled under $O_2$-free 100% $CO_2$, before being cooled in an ice bath while it was bubbled with 100% $CO_2$. Once the medium was cool, 4.2 g of $NaHCO_3$ and 0.5 g of L-cysteine.HCl.$H_2O$ was added per liter. The medium was dispensed into the culture tubes while being gassed with 100% $CO_2$, at 9.5 ml of medium per tube, and the tubes sealed with blue butyl septum stoppers and aluminium seals (Bellco), with a headspace of 100% $CO_2$. These tubes were sterilised by autoclaving for 20 min at 121° C. Before use, the tubes were stored in the dark for at least 24 h. Sodium acetate (20 mM final conc.), sodium formate (60 mM final conc.), coenzyme M (10 µM final conc.), and vitamin-supplemented clarified rumen fluid were added to sterile media, before inoculation with 0.5 ml of an actively growing culture of *M. ruminantium*, then gassed with $H_2$ plus $CO_2$ (4:1) to 180 kPa overpressure. In some experiments, the formate was omitted, and alcohols were added, as noted in the experimental descriptions accompanying the results. The culture tubes were incubated on their sides, at 39° C. in the dark, on a platform shaken at 200 rpm.

To prepare the clarified rumen fluid, rumen contents were collected from a ruminally-fistulated cow that had been fed hay for 48 h after being on a rye-grass clover pasture. Feed was withheld from the animal overnight and rumen contents collected the next morning. The material was filtered through a single layer of cheesecloth and then fine particulate material removed by centrifugation at 10,000×g for 20 min. The supernatant was stored at −20° C. Before further use, it was thawed, and any precipitates removed by centrifugation at 12,000×g for 15 min. The supernatant was bubbled for 10 min with 100% $N_2$ gas, before being autoclaved under 100% nitrogen for 15 min to remove viruses. The following was then added per 100 ml of rumen fluid while stirring under air: 1.63 g of $MgCl_2.6H_2O$ and 1.18 g of $CaCl_2.2H_2O$. The resulting heavy precipitate was removed by centrifuging at 30,000×g and 4° C. for 60 min. The supernatant was designated the clarified rumen fluid. Two grams of yeast extract powder was added, and the mixture then bubbled with $N_2$ gas for 15 min, before being transferred to a $N_2$-flushed sterile serum vial through a 0.2-µm pore size sterile filter using a syringe and needle.

Two ml of Vitamin 10 concentrate was then added per 100 ml of preparation by syringe and needle. Vitamin 10 concentrate contained 1000 ml of distilled water, 40 mg of 4-aminobenzoate, 10 mg of D-(+)-biotin, 100 mg of nicotinic acid, 50 mg of hemicalcium D-(+)-pantothenate, 150 mg of pyridoxamine hydrochloride, 100 mg of thiamine chloride hydrochloride, 50 mg of cyanocobalamin, 30 mg of D,L-6,8-thioctic acid, 30 mg of riboflavin and 10 mg of folic acid. After preparation, the solution was well mixed and then bubbled with $N_2$ gas for 15 min, before being transferred to a $N_2$-flushed sterile serum vial through a 0.2 µm pore size sterile filter using a syringe and needle.

Growth of M1 was followed by measuring the culture density at 600 nm by inserting the tubes directly into an Ultrospec 1100 pro UV/Vis spectrophotometer (Amersham Biosciences, Little Chalfont, Buckinghamshire, UK). Tubes containing 10 ml of medium RM02 were inoculated with 0.5 ml of an actively growing culture of M1, then gassed with $H_2$ plus $CO_2$ (4:1) to 180 kPa overpressure. Additions of PeiR in 0.1 ml of buffer (20 mM 3-[N-morpholino]propane sulfonic acid: 1 mM dithiothreitol: 0.3 M NaCl, 20% glycerol [v/v], pH 7.0 with NaOH), 0.1 ml of buffer only, or 0.1 ml of chloroform were made when the cultures had grown to mid-exponential phase (optical density at 600 nm [$OD_{600}$] ~0.1, 16 mm path length). In the experiments testing the effects of PeiR addition, the culture densities were mathematically normalised to an $OD_{600}$ of 0.1 at the time the additions were made, and all other readings corrected by the same ratio. This was done to remove the effect of lack of absolute synchronicity between cultures, a common phenomenon when culturing methanogens. This normalisation was not done for experiments testing the utilisation of alcohols. Methane was measured by gas chromatography, taking a 0.3 ml sample from the culture headspace, at the pressure in the culture tube, and injecting it into an Aerograph 660 (Varian Associates, Palo Alto, Calif., USA) fitted with a Porapak Q 80/100 mesh column (Waters Corporation, Milford, Mass., USA) and a thermal conductivity detector operated at 100° C. The column was operated at room temperature with $N_2$ as the carrier gas at 12 cm$^3$/min.

DNA Extraction

Genomic DNA was extracted from M1 grown on BY medium with $H_2$ plus $CO_2$ (4:1), using the liquid $N_2$ freezing and grinding method (Jarrell et al., 1992). Briefly, M1 cultures were harvested by centrifugation at 27,000×g for 20 min at 4° C. and cell pellets combined and placed into 40 ml Oakridge centrifuge tubes (Thermo Fisher Scientific, Inc.). The cells were frozen at −20° C. and kept frozen for at least 4 days. The frozen cell pellets were placed in a sterile, pre-cooled (−85° C.) mortar and liquid $N_2$ poured over the pellet. After the $N_2$ had evaporated, the pellet was ground to a powder with a sterile glass rod. Immediately, 0.5 ml of TES buffer (10 mM. Tris-HCl: 1 mM EDTA:0.25 M sucrose, pH 7.5) was added to the powdered cell pellet and mixed gently into a slurry. Sodium dodecyl sulfate was added to a final concentration of 1% (w/v) and Proteinase K (Roche Diagnostics, Mannheim, Germany) added to a final concentration of 50 µg/ml. The mixture was incubated at 60° C. for 30 min. NaCl was added to a final concentration of 0.5 M and the lysate was placed on ice for 1 h. The lysate was centrifuged at 25,000×g for 15 min at 4° C. and the supernatant recovered carefully. An equal volume of cold (4° C.) isopropanol was added to the supernatant, and the precipitated DNA was collected by centrifugation at 12,000×g for 10 min at room temperature and re-dissolved in TE buffer (10 mM Tris-HCl: 1 mM EDTA, pH 7.5). The DNA was treated with RNase (10 µg/ml), (Sigma-Aldrich) for 30 min at 37° C., and extracted twice with an equal volume of phenol/chloroform/isoamyl alcohol (25:24:1) and twice with an equal volume of chloroform alone. NaCl was added to a final concentration of 0.5 M and the DNA precipitated by adding 2.5 volumes of cold (4° C.) ethanol. The precipitated DNA was collected by centrifugation at 14,000×g for 10 min at 4° C. and re-dissolved in TE buffer.

Pulsed-Field Gel Electrophoresis (PFGE)

Standard PFGE protocol involves embedding cells in agarose and lysis with lysozyme and/or proteases, but this was not possible with M1 because its pseudomurein-containing cell wall was resistant to lysis by commercially available enzymes. In order to overcome this, the cell pellet from a centrifuged 50 ml culture was frozen with liquid $N_2$ and very gently ground in a pestle and mortar to damage the cell wall. The ground material was allowed to thaw, 2 ml of 1 M NaCl plus 10 mM Tris (pH 7.6) was added and 300 µl aliquots were mixed with an equal volume of 2% (w/v) low melt agarose (Bio-Rad Laboratories, Hercules, Calif., USA). Embedded cells were treated with 0.1 mg ml$^{-1}$ Proteinase K in lysis buffer (50 mM Tris-HCl: 50 mM EDTA: 1% [w/v] sarkosyl, pH 8.0) at 50° C. for up to 24 h. The agarose plugs were washed twice with sterile water and three times with TE buffer (10 mM Tris-HCl: 1 mM EDTA, pH 8.0) before storage in 10 mM Tris-HCl: 100 mM EDTA (pH 8.0) at 4° C. DNA embedded in agarose was digested for 16 h with 1.0 U of ApaI, BssHII or MluI (New England Biolabs, Beverly, Mass., USA) in 100 µl of restriction enzyme buffer, loaded into wells of 1% (w/v) agarose gels (SeaKem Gold agarose, Cambrex Bio Science, Rockland, Me., USA), and run at 200 V for 20 h at 14° C. in 0.5×Tris-borate buffer using a CHEF DR III PFGE apparatus and model 1000 mini chiller (Bio-Rad). Double-digest combinations of these enzymes were digested and run in the same way. DNA was visualized by staining with ethidium bromide and the image captured using a Gel Doc 1000 system (Kodak Gel Logic 200 Imaging System, Eastman Kodak, Rochester, N.Y., USA).

Genome Sequencing, Assembly and Validation

The genome sequence of M1 was determined using a whole genome shotgun strategy (Agencourt Biosciences, USA) and a pyrosequencing approach (Macrogen, USA). A hybrid assembly (Goldberg et al., 2006) was performed utilising the Staden package (Staden & Bonfield, 2000), Phred (Ewing et al., 1998), Phrap (hypertext transfer protocol://www.phrap.org), Paracel (Paracel Inc.) and Repeatmasker (hypertext transfer protocol://repeatmasker.org) resulting in a 27 contig assembly. Gaps were closed using additional sequencing by PCR-based techniques. Quality improvement of the genome sequence was performed using standard PCR to ensure correct assembly and the resolution of any remaining base conflicts. Assembly validation was confirmed by pulsed-field gel electrophoresis (see above).

Genome Analysis and Annotation

A GAMOLA (Altermann and Klaenhammer, 2003) Artemis (Rutherford et al., 2000) software suite was used to manage genome annotation. Protein-encoding open reading frames (ORFs) were identified using the ORF-prediction program Glimmer (Delcher et al., 1999) and BLASTX (Gish & States, 1993). A manual inspection was performed to verify or, if necessary, redefine the start and stop of each ORF. Assignment of protein function to ORFs was performed manually using results from the following sources; BLASTP (Altschul et al., 1990) to both a non-redundant protein database provided by the National Centre for Biotechnology Information (NCBI) (Sayers et al., 2009) and clusters of orthologous groups (COG) (Tatusov et al., 2000) database. HMMER (Eddy, 1998) was used to identify protein motifs to both the PFAM (Finn et al., 2008) and TIGRFAM (Haft et al., 2003) libraries. TMHMM (Krogh et al., 2001; hypertext transfer protocol://www.cbs.dtu.dk/services/TMHMM/) was used to predict transmembrane sequences, and SignalP (Bendtsen et al., 2004) was used for the prediction of signal peptides.

Ribosomal RNA genes were detected on the basis of BLASTN searches to a custom GAMOLA ribosomal database. Transfer RNA genes were identified using tRNAscan-SE (Lowe & Eddy, 1997). Miscellaneous-coding RNAs were identified using the Rfam database utilizing the INFERNAL software package (Eddy, 2002). Insertion sequence elements were identified using Repeatfinder (Volfovsky et al., 2001) and BLAST and annotated manually. Genome atlas visualisations were constructed using GENEWIZ (Jensen et al., 1999). Horizontal gene transfer studies were performed using Darkhorse (Podell & Gaasterland, 2007), GC % content (Rice et al., 2000) and the Codon Adaptation Index (Sharp & Li, 1987). A BLAST analysis was performed against the arCOG (Makarova et al., 2007) database. Analysis of non-ribosomal peptide synthetases (NRPSs) was performed using NRPSpredictor (Rausch et al., 2005). An LPxTG-HMM (Boekhorst et al., 2005) was used for the identification of LPxTG motifs. Metabolic pathway reconstructions were performed using Pathway Voyager (Altermann & Klaenhammer, 2005) and the KEGG (Kyoto Encyclopedia of Genes and Genomes) database (Kanehisa & Goto, 2000) combined with an extensive review of the literature. Identification of open reading frames (ORFs) as vaccine and drug targets was performed as described. Genome sequences used in comparative studies were downloaded from the National Centre for Biotechnology Information (NCBI) FTP website and are listed in Table 10, below.

Genome sequence was prepared for NCBI submission using Sequin (Benson et al., 2009). The adenine residue of the start codon of the Cdc6-1 (mru0001) gene was chosen as the first base for the M1 genome. For GC skew and synteny analysis, the sequences of genomes of other members of the order Methanobacteriales were rotated to begin at the same location. GC skew analysis was performed by circular_diagram.pl (Rutherford, K, Sanger Centre software) and synteny plots were generated using MUMmer3.0 (Delcher et al., 2003).

Vaccine Target ORF Identification

Vaccine targets are likely to be surface exposed or membrane associated and conserved among methanogens or archaeal species. Methanogens are the only known resident archaea in the rumen and therefore archaeal specific candidates were not omitted from target lists, likewise when present, sequence homology to proteins associated with known vaccine or drug design remained a strong element for target selection regardless of other criteria. To identify the surface-exposed or membrane-associated ORFs of M1 a combination of methods was utilized. To date, there is no signal peptide model for archaea. There are simply too few experimentally verified secretory proteins available for Archaea to train a specific model. For this reason ORF sequences were analysed for the presence of signal peptides using SignalP Version 3.0 (Bendtsen et al., 2004) trained against the Gram-positive, Gram-negative and Eukaryotic models and the results combined. SignalP-HMM (hidden markov models) was used to discriminate between signal peptide and non-signal peptide ORFs whereas SignalP-NN (neural networks) was utilized for the prediction of cleavage sites as described by Emanuelsson et al., 2007 (Emanuelsson et al., 2007). TMHMM (Krogh et al., 2001; hypertext transfer protocol://www.cbs.dtu.dk/services/TMHMW) was used for the prediction of transmembrane domains and (Nakai & Horton, 1999) PSORT trained on a Gram-positive model was used to predict a protein's subcellular localization. BLASTP results were analyzed to identify methanogen specific ORFs.

Chemogenomics Target ORF Identification

Three different approaches were utilized to identify candidate chemogenomics targets.

Metabolic Profiling Analyses. Several factors were taken into consideration when performing this analysis. Utilizing the metabolic reconstruction of M1 and an extensive review of the literature, archaeal- or methanogen-specific enzymes, or enzymes with sufficient structural or biochemical differences compared to their bacterial or eukaryl counterparts were identified. Some methanogen enzymes or pathways that have been previously targeted by researchers for inhibition demonstrating the essentiality of certain enzymes/pathways were also taken into consideration. In addition, a few enzymes which represent key enzymes to several pathways or are well known validated targets in pathogenic bacteria or parasites, whilst still retaining sufficient sequence divergence to potentially be able to be targeted effectively were also included. Most of the cell wall enzymes are listed as the majority of successful antibiotics that have been developed against pathogenic bacteria target cell wall biosynthesis. Methanobacterial cell wall synthesis, despite apparently sharing some common enzymes (e.g., mur ligases) is widely divergent in biochemical terms from bacterial cell wall synthesis and the homologous enzymes share only limited sequence homology. The degree to which strain M1, or other rumen methanogens, are able to utilize amino acids, vitamins, or purine or pyrimidine compounds in rumen fluid is under investigation.

Functional Genome Distribution (FGD). A FGD analysis (Altermann 2009, manuscript in preparation) was performed using 26 publicly available draft and complete methanogen genome sequences (dbMethano, Table 10). In contrast to an evolutionary phylogeny, FGD analyzes the functional relationship between microbes based on their predicted ORFeomes. FGD is a comparative genomics approach to genome-genome comparisons, emphasizing functional relationships rather than ancestral lineages. Briefly, pooled ORFeomes are subjected to all-vs-all analyses, evaluating the level and quality of amino-acid similarities between individual ORFs pairings. Individual results for each genome-genome combination are then combined into a symmetrical distance matrix and can be visualized using the Unweighted Pair Group Method with Arithmetic mean (UPGMA) method (Sneath and Sokal, 1973) Numerical Taxonomy. Freeman, San Francisco. Strain and cluster conserved and specific gene sets were mined based on respective BLAST e-values, using custom developed software.

Differential Blast Analysis (DBA). The reference genome of M1 was subjected to analysis against two BLASTP databases using GAMOLA (Altermann and Klaenhammer, 2003). The first amino-acid database employed all methanogen ORFeomes used in the FGD analysis (dbMethano), while the second database was comprised of the non-redundant database (nr) as provided by NCBI, excluding hits to genera used in dbMethano. E-values of best BLASTP hits for both database sets were consolidated into an empirically determined e-value trust level range ($[T_{e\text{-}value}]$) and their respective differential calculated as follows: $\Delta = T_{nr}$ −T$_{dbMethano}$). Results were visualized on a genome atlas using Genewiz (Jensen et al., 1999) and software developed in-house.

Peptide Vaccine Methods

The use of synthetic peptides to raise antibodies against predicted M1 surface proteins was investigated. The M1 proteins encoding the membrane-spanning subunits of tetrahydromethanopterin S-methyltransferase (MtrCDE, mru1921, 1922 and 1923), adhesin-like proteins (mru2049, 0842, 0143 and 2048) and a magnesium chelatase subunit H (BchH, mru2047) containing N-terminal and C-terminal TMHs, were analysed to identify extracellular peptide sequences which might serve as potential antibody binding sites. Nine suitable peptide sequences from extracellular regions of these eight proteins were identified and used to guide the manufacture of the corresponding synthetic peptides. Each peptide was coupled to the Keyhole Limpet hemocyanin (KLH) protein via an additional N- or C-terminal cysteine residue and a maleimidocaproyl-N-hydroxysuccinimide linker and used to raise antibodies in sheep (Invitrogen, USA). The conjugated peptides (200 µg) were injected intradermally (ID) into sheep (1-3 yr age) in Complete Freund's Adjuvant (CFA) at 10-15 sites on day 0, and secondary boosters in CFA were given on day 14. Six ID injections of 200 µg KLH-peptide in Incomplete Freund's Adjuvant at 10-15 sites were given at days 28, 56, 70, 84, 98 and 112. Test bleeds (2-5 ml) were taken on days 42, 56, 84, and 112 for ELISA analyses.

Antibody titer was determined with an ELISA with Peptide-GGG (goat gamma globulin) bound in solid phase (0.1 µg/100 µl/well) on high binding 96 well plates. The serum was first diluted 50-fold and then further diluted in 2-fold serial dilutions. The ELISA titer is the estimated dilution factor that resulted in an OD$_{405}$ nm of 0.2 and is derived from nonlinear regression analysis of the serial dilution curve. Detection was obtained using an HRP (horseradish peroxidase)-conjugated secondary antibody and ABTS (2,2'-azino-bis(3-ethylbenzthiazoline-6-sulphonic acid). In the antibody-binding experiment M1 cells (40 µl of cells in 2 ml of sodium carbonate buffer) were immobilised on Maxisorp ELISA plates and antibody binding was determined by ELISA. Serum samples were diluted 1/20 in diluent (1% w/v casein in PBS Tween 20 (g/l NaCl, 8.0; KCl, 0.2; Na2HPO4, 1.15; KH2PO4, 0.2; pH 7.2-7.4; Tween 20, 0.5 ml) and incubated at room temperature for 1 hr. Plates were washed 6 times with PBS Tween 20 and conjugate (donkey anti-sheep/goat IgG HRP, 50 µl/well of a 1/5000 diluted solution) and substrate (3, 3',5,5'tetramethyl benzidine, 50 µl/well) were added. After incubation at room temperature in the dark for 15 min, stop solution (50 µl/well of 0.05 M H2SO4) was added and OD$_{450}$ nm readings were taken.

Accession Numbers and Sequence Listing

The nucleotide sequence of the *M. ruminantium* M1 chromosome has been deposited in GenBank under Accession Number CP001719. Microarray data has been submitted to the Gene Expression Omnibus (GEO) in accordance with MIAME standards under GEO Accession Number GSE18716. The specific *M. ruminantium* sequences are disclosed herewith as a text file (.txt) for the sequence listing. The contents of sequence listing are hereby incorporated by reference herein in their entirety.

Example 2

Results

General Genome Characteristics

The genome sequence of M1 consists of a single 2.93 megabase (Mb) circular chromosome, the assembly of which has been verified by pulsed-field gel electrophoresis (FIG. 6). The general features of the M1 genome compared to other genomes of species within the order Methanobacteriales are summarized in Table 1, below, and FIG. 10. M1 has the largest genome of the Methanobacteriales sequenced to date. This increased genome size is due in part to a lower overall coding density, but also to a large number of genes encoding surface adhesin-like proteins, the presence of a prophage, and a variety of genes unique to the M1 genome. M1 encodes 2217 open reading frames (ORFs) and a functional classification of each ORF is presented in Table 9, below, and FIG. 15. Genomes of the Methanobacteriales display a GC skew similar to bacterial chromosomes (Lobry, 1996) (FIG. 2) and an X-shaped synteny pattern that is characteristic of moderately diverged genomes (FIG. 3). Analysis of potential horizontal gene transfer (HGT) events in M1 identified a number of genes which show high sequence similarity to non-methanogens, typically from members of the bacterial phylum Firmicutes (Table 4, below, and FIG. 16). These potential HGT events can be visualized in a BLAST heat map analysis (FIG. 16). Several approaches were used to define potential gene targets for $CH_4$ mitigation from M1. An integral part of this process was the analysis of genes which are conserved across methanogen genomes (FIG. 13 and Table 8, below). Coupled with this, chemogenomic targets (FIG. 1*a*) were selected on the basis of detailed metabolic analysis (Table 2, below), while potential vaccine targets (FIG. 1*b*) were chosen from proteins predicted to be associated with the M1 cell surface. Examination of the M1 genome has revealed a number of features and targets that could lead to an effective enteric methane mitigation technology, and these are discussed below.

Growth and Methanogenesis

Many of the enzymes involved in the methanogenesis pathway are strongly conserved and found only among methanogens, and therefore present good targets for $CH_4$ mitigation technologies. Although this pathway has been well studied in methanogens from a range of other environments (Thauer et al., 2008), the M1 genome shows for the first time details of this pathway in a rumen methanogen. M1 can grow with $H_2$+$CO_2$ and formate (Smith & Hungate, 1958) and encodes the enzymes, and most of the cofactors, required for conversion of these substrates through to methane according to the metabolic scheme presented in FIG. 11. Consistent with this hydrogenotrophic lifestyle, M1 lacks the methanophenazine-reducing [Ni—Fe] hydrogenase (VhoACG) and methanophenazine-dependant heterodisulphide reductase (HdrDE) found in methanophenazine-containing species within the order Methanosarcinales (Abken et al., 1998).

Surprisingly, M1 has two NADPH-dependent $F_{420}$ dehydrogenase (npdG1, 2) genes and three NADP-dependent alcohol dehydrogenase (adh1, 2 and 3) genes. In some methanogens, these enzymes allow growth on ethanol or isopropanol via $NADP^+$-dependent oxidation of the alcohol coupled to $F_{420}$ reduction of methenyl-$H_4$MPT to methyl-$H_4$MPT (Berk & Thauer, 1997) (FIG. 11). M1 is reported as not being able to grow on ethanol or methanol (Smith & Hungate, 1958), although a ciliate-associated *M. ruminan-*

*tium*-like isolate was able to use isopropanol to a limited degree but data were not presented (Tokura et al., 1999). Our attempts to grow M1 on alcohols indicate that ethanol and methanol stimulate growth in the presence of limiting amounts of $H_2+CO_2$, but they do not support growth when $H_2$ is absent (FIG. 14). M1 does not contain homologues of the mta genes known to be required for methanol utilization in other methanogens (Fricke et al., 2006). The adh genes may play a role in alcohol metabolism but the mechanism is under assessment.

Hydrogenotrophic methanogens usually encode a methyl coenzyme reductase II (mcrII or mrt), an isoenzyme of the methyl CoM reductase I (mcrI) enzyme which is differentially regulated during growth (Reeve et al., 1997) to mediate methane formation at high partial pressures of $H_2$. Interestingly, M1 does not encode a mail system. In the rumen, methanogens depend on fermentative microbes to supply $H_2$, usually at very low concentrations, and M1 appears to have adapted its lifestyle for growth at low levels of $H_2$ using the mcrI system only.

To examine the expression of genes involved in methanogenesis, in the presence of a $H_2$-forming rumen bacterium, M1 was grown in co-culture with *Butyrivibrio proteoclasticus* B316 (Moon et al., 2008) in a medium containing xylan as the sole carbon source, and gene expression was analysed by microarrays. Formylmethanofuran dehydrogenase (fwdA), methyl CoM reductase (mcrB-CDG), methyl viologen-reducing hydrogenase (mvhG), and $H_4$MPT methyltransferase (mtrABCH) were significantly up-regulated (≥2 fold) in the co-culture compared to the monoculture of M1 grown with $H_2+CO_2$ (Table 5, below). Interestingly, formate utilisation (fdhAB) genes were also up-regulated, suggesting that formate formed by *B. proteoclasticus* was an important methanogenic substrate transferred during this syntrophic interaction.

Genes encoding enzymes in the methanogenesis pathway that are potential targets are highlighted in FIG. 11. Several methanogenesis marker proteins found in methanogen genomes, with hypothetical function, were also included in the target list. Many of the enzyme subunit targets are predicted to be within the cell cytoplasm, and therefore best pursued via a chemogenomics approach (FIG. 11). However, several, subunits including those of the Aha, Eha, Ehb and Mtr enzyme complexes, are membrane-located and may be suitable as vaccine targets. Mtr catalyses the transfer of the methyl group from methyl-$H_4$MPT to CoM and couples this to the efflux of $Na^+$ ions (Reeve et al., 1997). Three of the Mtr subunits (MtrEDC) are predicted to be membrane-spanning in M1 and in each of the membrane-spanning regions the transmembrane helices have peptide loops located outside the cell membrane. These loops are potential antibody binding sites. Synthetic peptides corresponding to the loop regions of MtrE, MtrD and MtrC have been coupled to a carrier protein and used as antigens to vaccinate sheep. The resulting immune sera were shown to bind specifically to immobilized M1 cells (FIG. 17), demonstrating the feasibility of such a peptide-directed reverse vaccinology approach.

Analysis of the M1 genome has helped explain the growth requirements of M1 for acetate, 2-methylbutyrate and coenzyme M (CoM) (Bryant et al., 1971). Acetate is required for cell carbon biosynthesis after activation to acetyl CoA (acs, acsA), followed by reductive carboxylation to pyruvate (porABCDEF, Table 9, below). Reductive carboxylation of 2-methylbutyrate is probably the route for isoleucine biosynthesis (Robinson & Allison, 1969), as M1 lacks a gene encoding a homoserine kinase needed for the usual pathway from threonine (Table 9, below). Exogenously supplied CoM is essential for M1 growth as two genes needed in the CoM biosynthetic pathway, phosphosulfolactate synthase (comA) and sulfopyruvate decarboxylase (comDE) (Graham et al., 2002), are missing in M1 (FIG. 11).

Cell Envelope

The methanogen cell envelope serves as the interface between the organism and its rumen environment, and as such represents a key area for the identification of vaccine and drug targets. The main structural component of the cell envelope of M1 (FIG. 12), as with other Gram-positive methanogens, is pseudomurein. This is structurally analogous, but chemically different, to peptidoglycan, which performs the comparable function in bacteria (König et al., 1994). Bacterial peptidoglycan biosynthesis has long been a major target of antimicrobials but these compounds are largely ineffective against pseudomurein-containing cells (Kandler & König, 1998). The pathway for pseudomurein biosynthesis and its primary structure have been proposed (Kandler & König, 1998), but the enzymes involved have not been characterized. Our genomic analysis has identified several genes encoding enzymes likely to be involved both in the intracellular biosynthesis of the pseudomurein precursors and the processes involved in exporting and assembling these into the cell wall (FIG. 5).

The original description of *M. ruminantium* reported the existence of a capsule surrounding the cells, and chemical analysis of the cell walls showed that galactose and rhamnose together with lower amounts of glucose and mannose were present in addition to pseudomurein (Kandler & König, 1978; Kandler & König, 1985). The cell walls are also reported to contain high levels of phosphate, comparable to that found in bacterial cell walls containing teichoic acid (Kandler & König, 1978). M1 contains homologs of genes involved in teichoic acid production in Gram positive bacteria (Bhavsar & Brown, 2006; Weidenmaier & Peschel, 2008) (Table 9, below), suggesting the presence of as-yet unidentified cell wall glycopolymers. Additionally, several genes are predicted to be involved in exopolysaccharide production, sialic acid biosynthesis and protein glycosylation (Table 9, below). The genome contains a homolog of the eukaryal oligosaccharyl transferase (mru0391), a membrane protein believed to be involved in glycosylating proteins translocated via the Sec pathway (Yurist-Doutsch, 2008) (FIG. 12). Glycoproteins derived from the cell wall of M1 have been shown to be highly immunogenic in sheep. The resulting antisera agglutinated M1 cells and significantly reduced their ability to grow and produce methane in vitro (Wedlock et al., in preparation). Overall, polysaccharides and glycosylated molecules are a major component of the M1 cell envelope, and their accessibility at the cell surface make these polymers viable methane mitigation targets.

Genomes of human gut methanogens encode large surface proteins that have features similar to bacterial (Fricke et al., 2006; Samuel et al., 2007) adhesins. Similarly, M1 has an array of large adhesin-like proteins, much greater in number than those reported from other gut methanogens (Table 1, below). In the co-culturing experiments described above, six M1 adhesin-like proteins were upregulated (Table 5, below), and microscopic examination showed co-aggregation of M1 and *B. proteoclasticus* cells (FIG. 9). In addition, immune sera produced by small peptides synthesized to correspond to four M1 adhesin-like proteins were shown to bind specifically to immobilized M1 cells (FIG. 17). Identifying highly conserved methanogen-specific features of these adhesin-like proteins may present a pathway to vaccine development. Sixty two adhesin-like proteins are predicted to be extracellular and contain a cell-anchoring domain (FIG. 12). These proteins represent a significant component of the M1 cell envelope (Table 3). The largest group of these (44) contain a conserved C-terminal domain (M1-C, FIG. 4) with weak homology to a Big_1 domain (Pfam accession number PF02369) which may be involved in attachment to the cell wall, possibly by interaction with pseudomurein or cell wall glycopolymers. Several of these proteins also contain a papain family cysteine protease domain (PF00112), and their role may be in the turnover of pseudomurein cell walls.

A second group of 14 proteins is predicted to contain a C-terminal transmembrane domain, suggesting they are anchored in the cell membrane. Curiously, the genome contains one adhesin-like protein (mru2147) with a cell wall LPxTG-like sorting motif and three copies of a cell wall binding repeat (PF01473), both of which are commonly found in Gram-positive bacteria. There has only been one other report of a LPxTG-containing protein in a methanogen, the pseudomurein containing *Methanopyrus kandleri* (Boekhorst et al., 2005). Our analysis of the *M. smithii* PS genome revealed the presence of two LPxTG containing proteins (msm0173 and msm0411). Such proteins are covalently attached to the cell wall by membrane associated transpeptidases, known as sortases. Sortase activity has been recognised as a target for anti-infective therapy in bacteria (Maresso & Schneewind, 2008) and a sortase (mru1832) has been identified in the M1 genome.

Prophage

Phage exert a significant ecological impact on microbial populations in the rumen, and have been suggested as biocontrol agents for rumen methanogens (Klieve & Hegarty, 1999). M1 has 70 ORFs (mru0256-0325) over a 62 Kb GC-rich (39% G+C content) region of the genome that encode a prophage genome, designated φmru. Based on a functional annotation, φmru is partitioned into distinct modules encoding integration, DNA replication, DNA packaging, phage capsid, lysis and lysogenic functions (Attwood et al., 2008). Within the lysis module, a gene encoding a putative lytic enzyme, endoisopeptidase PeiR (mru0320), was identified. Recombinant phage lytic enzymes have been used for controlling antibiotic-resistant bacterial pathogens (Hermoso et al., 2007), and a methanogen phage lytic enzyme may be a viable biocontrol option. We have confirmed the ability of recombinant PeiR to lyse M1 cells in pure culture (WO 09041831A1) (FIG. 8). PeiR represents a novel enzyme, as it does not show significant homology to any sequence currently in public databases. The variety of methanogen cell wall types means a combination of different lytic enzymes will be required for effective methanogen lysis in the rumen. However, the expression of PeiR and demonstration of its effectiveness against a major rumen methanogen is an important step towards this goal. PeiR will also be useful in increasing the permeability of pseudomurein-containing cell walls of methanogens to aid development of genetic systems for performing gene knockouts to validate targets, while the φmru phage itself might be useful as a genetic tool for *M. ruminantium*. The prophage has also been disclosed in detail in U.S. 60/989,840 filed 22 Nov. 2007, and in PCT/2008/000248 filed 25 Sep. 2008, which are hereby incorporated by reference herein in their entirety.

Non-Ribosomal Peptide Synthetases

Figure 18:
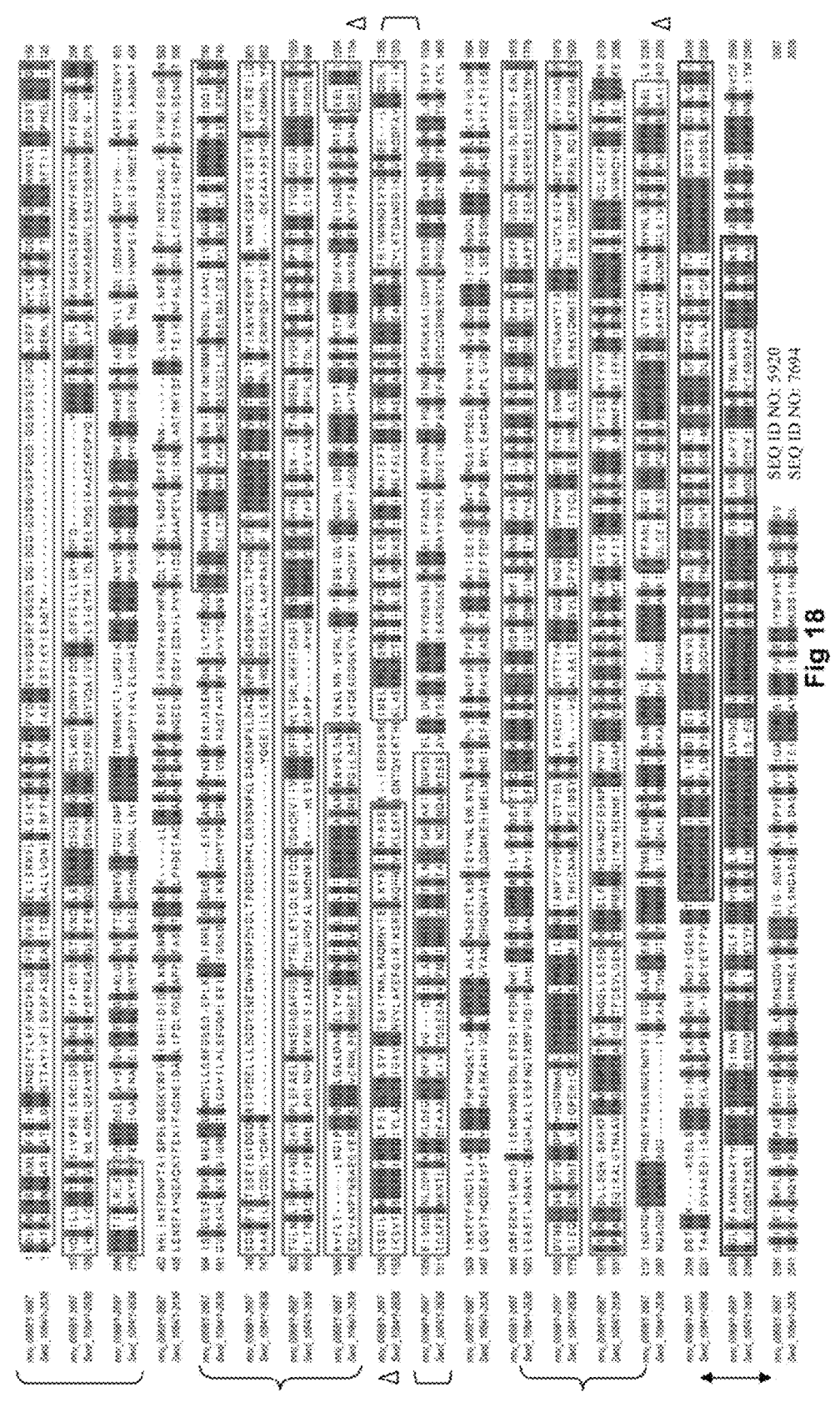

An unforeseen and novel feature of M1 is the presence of two large proteins (mru0068 and mru0351) showing the distinctive domain architecture of non-ribosomal peptide synthetases (NRPS) (FIG. 7). To our knowledge, this is the first report of NRPS genes identified in an archaeal genome. HGT studies indicate that these genes may be bacterial in origin (Table 4, below). NRPSs produce a wide variety of small molecule natural products that have biotechnological applications as peptide antibiotics, siderophores, immunosupressants or antitumor drugs (Amoutzias et al., 2008). The NRPS encoded by mru0068 is predicted to encode two modules, each containing condensation, adenylation and thiolation domains. The presence of a condensation domain in the first module is often associated with NRPSs that make N-acylated peptides (Fischbach and Walsh, 2006). The second module is followed by a terminal thioesterase domain which is thought to release the peptide from the final thiolation domain. Mru0068 is surrounded by genes that encode two serine phosphatases (mru0066, mru0071), an anti-sigma factor antagonist (mru0067), and a MatE efflux family protein (mru0069), which are likely to be involved in environment sensing, regulating NRPS expression and export of the NRP, respectively. Mru0068 displays full length protein alignment with a putative NRPS from *Syntrophomonas wolfei* subsp. *wolfei* strain Göttingen (FIG. 18), a Gram-positive bacterium known to participate in syntrophic interactions with methanogens (McInerney et al., 1979).

The second NRPS gene (mru0351) contains 4 modules and a thioesterase domain. Downstream of mru0351 is another MatE efflux family protein (mru0352), presumably involved in NRP export. A third, smaller cluster of genes located elsewhere in the genome (mru0513-0516) appear to encode NRPS-associated functions. This cluster includes a 4'-phosphopantetheinyl transferase (mru0514) which primes NRPSs by adding a phosphopantetheinyl group to a conserved serine within the thiolation domain, an acyltransferase (mru0512) possibly involved in NRP acylation, a serine phosphatase (mru0515), an anti-sigma factor antagonist (mru0513), and an anti-sigma regulatory factor serine/threonine protein kinase (mru0516) that may function in sensing the environment and NRPS regulation. Although the products of each NRPS are unknown, an analysis of adenylation domain amino acid sequences predicts 10 residues (boxed, FIG. 7) which are important for substrate binding and catalysis. HGT studies indicate that these genes may be bacterial in origin (Table 4).

Thus, several genes in M1 are possibly involved in sensing the environment, and in the regulation and transport of the NRP (FIG. 7) and such genes are also present in the *S. wolfei* genome. Although the actual roles of these genes have not been defined conclusively, NRPs are known to contribute to microbial growth and ecological interactions, thus may provide a means to manage methane emissions from livestock.

Comparative Genomics Analysis

To functionally compare *M. ruminantium* to other methanogens, 25 publicly accessible complete and draft phase genome sequences were subjected to a Functional Genome Distribution (FGD) analysis (Altermann, submitted) (FIG. 13). Together with *Methanobrevibater smithii, Methonsphaera stadtmanae*, and *Methanothermobacter thermoautotrophicus, M. ruminantium* formed a functional cluster. Within this cluster, a large number of predicted genes were found to be conserved (low e-value cutoff 1e-100, Table 8, below). The majority of these conserved genes were classified into core biological categories, such as amino acid biosynthesis, cell cycle, central carbon metabolism, nucleic acid metabolism, protein fate and synthesis and purine and pyrimidine biosynthesis. Similarly, genes involved in energy metabolism, especially in the methanogenesis pathway were commonly shared within this functional cluster.

Most notably, only one fourth of this gene set was found to be conserved when compared with other functional clusters. A similar observation was found for conserved genes involved in the biosynthesis of vitamins and co-factors. 23 genes were found to be highly conserved within the *M. ruminantium* functional cluster, whereas only two genes involved in cobalamin and thimaine biosynthesis were shared with methanogens outside this cluster, respectively. It is also interesting to note that, apart from *Methanopyrus kandleri*, pseudomurein containing methanogens have been functionally grouped together in the *M. ruminantium* cluster. This is clearly reflected in the 14 highly conserved genes involved in pseudomurein and exopolysaccharide biosynthesis. Outside this functional cluster only one gene, a glucosamine-fructose-6-phosphate aminotransferase, GlmS2, was found to be conserved at this level.

While conserved gene sets cause functional clustering, strain or cluster specific genes are responsible for differentiation. When compared to all other members of its own cluster, *M. ruminantium* was found to harbour 468 strain specific genes (high e-value cutoff 1e-10). While the vast majority (341 genes) was assigned to genes with hypothetical or unknown functional categories, a significant number of genes were identified assigned to relevant biological functions. Mobile elements such a transposases and prophage elements were identified as strain specific to *M. ruminantium*. Strain-specific genes involved in the production of exopolysaccharides and cell surface proteins are likely to endow *M. ruminantium* with surface and adhesion properties distinctly different from other members of the *M. ruminantium* functional cluster. Similarly, ten unique transport systems were identified ranging from generic multidrug transporter to predicted pH homeostasis systems. Also 22 regulatory proteins (16 involved in protein interaction and five transcriptional regulators) were detected. When extending the search for strain specific genes outside its own functional cluster, the number of identified ORFs dropped down significantly. Only three genes coding for adhesion-like proteins and two genes involved in the production of exopolysaccharides (a sialyltransferase and a glycosyl transferase) were found to be *M. ruminantium* specific.

Comparing pseudomurein producers (PMP) to all other methanogens using a relaxed parameter set (low e-value cutoff 1e-60; high e-value cutoff 1e-10; mismatch tolerance 2) revealed an interesting set of genes functionally specific to this subset. A number of genes involved in pseudomurein biosynthesis were identified to be functionally specific to PMPs. In addition, two genes coding for adhesion-like proteins, four genes predicted to be involved in exopolysaccharide production and one gene coding for a poly-gamma-glutamate biosynthesis protein, likely to be involved in capsule synthesis, were found to be cluster specific. These genes coding for cell surface structures represent prime targets for vaccination based methane mitigation strategies, as their gene products are likely to reflect unique structures with the potential to induce specific antibodies. Interestingly, a gene coding for the energy-converting hydrogenase A subunit R was found to be PMP specific (including *M. thermoautotrophicus* and *M. kandleri*). This gene product is involved in electron transfer by reducing a ferredoxin. The Eha/Ehb complex is already being targeted for the development of a methanogen vaccine (FIG. 11).

Currently a bias exists for pseudomurein producing methanogen genomes. With the exception of *Methanothermobacter thermoautotrophicus* (isolated from sewage sludge) and *Methanopyrus kandleri* (isolated from a submarine hydrothermal vent) all PMP methanogens were isolated either from rumen, the gastrointestinal tract or from faeces. It stands to reason that these closely related ecological niches facilitate common lifestyle adaption events. Such an event was detected in the presence of a highly conserved bile salt hydrolase which is predicted to hydrolyse the amide linkage between the bile acid carboxyl group and the glycine or taurine amino group. The presence of a bile salt hydrolase explicitly implies that *M. ruminantium* (and other rumen methanogens) is well adapted for a passage from the rumen environment through to the gastrointestinal tract. Functionally conserved oxidative stress response genes such as rubredoxin rub1 further suggest a certain tolerance of methanogens to aerobic environments and a life-cycle from oral intake, biological activity in rumen and gastrointestinal tract ecologies, excretion into the aerobic environment and a subsequent—potentially time limited—waiting period for the next oral intake event may be proposed. How strictly anaerobic organisms such as methanogens survive exposure to high stress levels remains subject to further evaluation.

A recently published phylogenetic tree based on seven core enzymes (Miller, 2001) deviates in part significantly from the functional clustering shown in FIG. 13. Anderson et al. propose three classes of methanogens, based on the resulting phylogenetic approximation. In contrast, the FGD analysis revealed the presence of only two major functional clusters which can each be split into further sub-clusters (FIG. 13). Most notably, *Methanocorpusculum labreanum*, *Methanococcoides burtonii* and *Methanosaeta thermophila* form a distinct functional cluster under the FGD analysis (FIG. 13, sub-cluster 1.3) but are separated into Class II and Class III, respectively, based on the phylogenetic analysis. These differences clearly highlight the importance of whole genome analyses to address lifestyle adaptation processes (as described above) and genomic plasticity within a biotechnological context.

To investigate the broader phylogenetic placement of *M. ruminantium* and assess the potential level of horizontal gene transfer between archaea and archaea and eubacteria, a Blast Heat Map analysis was performed based on the non-redundant amino-acid database (FIG. 16). Significant heat flares were detected within archaea for the genera of *Methanococcus*, and, to lesser degrees for *Methanosarcina* and *Thermococcus* (FIG. 16A). Surprisingly, considerable levels of high sequence similarities were detected for the eubacterial genera of *Clostridium* and *Bacillus*, commonly found in ecological niches inhabited by *M. ruminantium*. These heat flares infer a profound level of shared and functionally similar gene sets and fortify the notion that genetic exchange between microbial domains is a common event, likely driven by lifestyle adaption forces. Analysing the relative quality of sequence similarity levels revealed a core set of genes commonly shared among phylogenetically diverse methanogenic archaea (FIG. 16B). Interestingly, individual heat flares of other archaea such as Halobacteria sharing highly conserved gene sets to *M. ruminantium* appear similar in shape than flares observed for *Clostridium* and *Bacillus*, further strengthening the model of genetic exchange between domains. Interestingly, a more detailed analysis of the *M. ruminantium* M1 ORFeome to bacterial sequences highlighted a series of gene sets not commonly found in other Methanobacteriales such as genes involved in biotin and cobalamin biosynthesis (Table 8, below).

Based on these observations we conducted a differential Blast Analysis (DBA) using the non-redundant database and the 26 methanogen genomes as references. While a DBA analysis is more liberal than FGD, it is able to highlight gene products present in at least one methanogen genome comprising dbMethano but not present in any other organism (nr database) and vice versa. Therefore, gene sets found to be present in methanogens but not in other microbes might represent prime targets for methane mitigation strategies. Using a minimum DBA value of four, 117 gene targets were identified to be conserved between *M. ruminantium* and methanogens but not present in other organisms. Notably, 21 genes predicted to be associated to the cell envelope were identified, including cell surface proteins and genes involved in exopolysaccharide and pseudomurein biosynthesis. One gene coding for a polysaccharide biosynthesis protein and two adhesion-like proteins were among the most prominent targets (DBA value of −6). All three genes are involved in cell-cell interaction and could represent targets for methanogen modulation. Interestingly, a single adhesion like protein was identified near the origin of DNA replication, conserved between *M. ruminantium* and other organisms but absent in methanogens (FIG. 10).

Closest hits were found to *Coprococcus eutactus* (Acc: ZP_02205388.1, isolated from human faeces), *Streptococcus sanguinis* (Acc: YP_001036038.1, isolated from human dental plaque), *Peptostreptococcus micros* (renamed as: *Parvimonas micra*, Acc: ZP_02093886.1, isolated from human gut), *Arcanobacterium pyogenes* (Acc: AA043108.1, commonly found on mucosal surfaces of livestock) and *Bacillus weihenstephanensis* (Acc: YP_001647931.1, human pathogen). All of those organisms are able to interact with either animal or human hosts and it is tempting to speculate that this adhesion reflects a specific lifestyle adaptation of *M. ruminantium* to the rumen and, possibly, to the gastrointestinal tract environment. This clearly strengthens the previous hypothesis modelled on the Blast Heat Map proposing a significant level of genetic exchange between *M. ruminantium* and certain genera of Eubacteria. Similarly, two adjacent glycosylhydrolases of the GT2 family were found to be shared in a similar way. For both proteins, top Blast hits link to Clostridia and Bacilli while their function was associated to the transfer of sugar units to teichoic acids which in turn are covalently linked to the cell wall thus providing *M. ruminantium* with a methanogen-unique outer cell-surface structure.

Genes predicted to be involved in hydrogen metabolism and methanogenesis such as the energy-converting hydrogenase B (Ehb) and the tungsten formylmethanofuran dehydrogenase (Fwd) were found to be methanogen specific. Also, another gene involved core functions, a Fibrillarin-like archaeal protein, commonly thought to participate in processing pre-ribosomal rRNA, was found to be methanogen specific. This is interesting, as only methanogen genera were excluded from the non-redundant database, but not other archaea. Therefore, this gene might present an opportunity to target methanogens at an essential function. An in-depth analysis of the presence/absence of this gene in the methanogen genomes revealed an interesting distribution pattern. With the exception of *Methanospitillum hungatei* members of functional cluster 4 (FIG. 13) do not harbours this gene, while cluster 3 predominantly features this archaeal gene, with the notable exception of *Methanococcoides burtonii*, *Methanosaeta thermophila* and *Methanosphaera stadtmanae*. It might be noteworthy, that within methanogens this gene is either absent or present, creating a highly conserved target with low genetic drift. Although not universally conserved, this gene might offer the opportunity to specifically target the majority of cluster 3 methanogens, thus including those of rumen origin, for methane mitigation strategies.

Identification of Targets for Methane Mitigation

Figure 1:
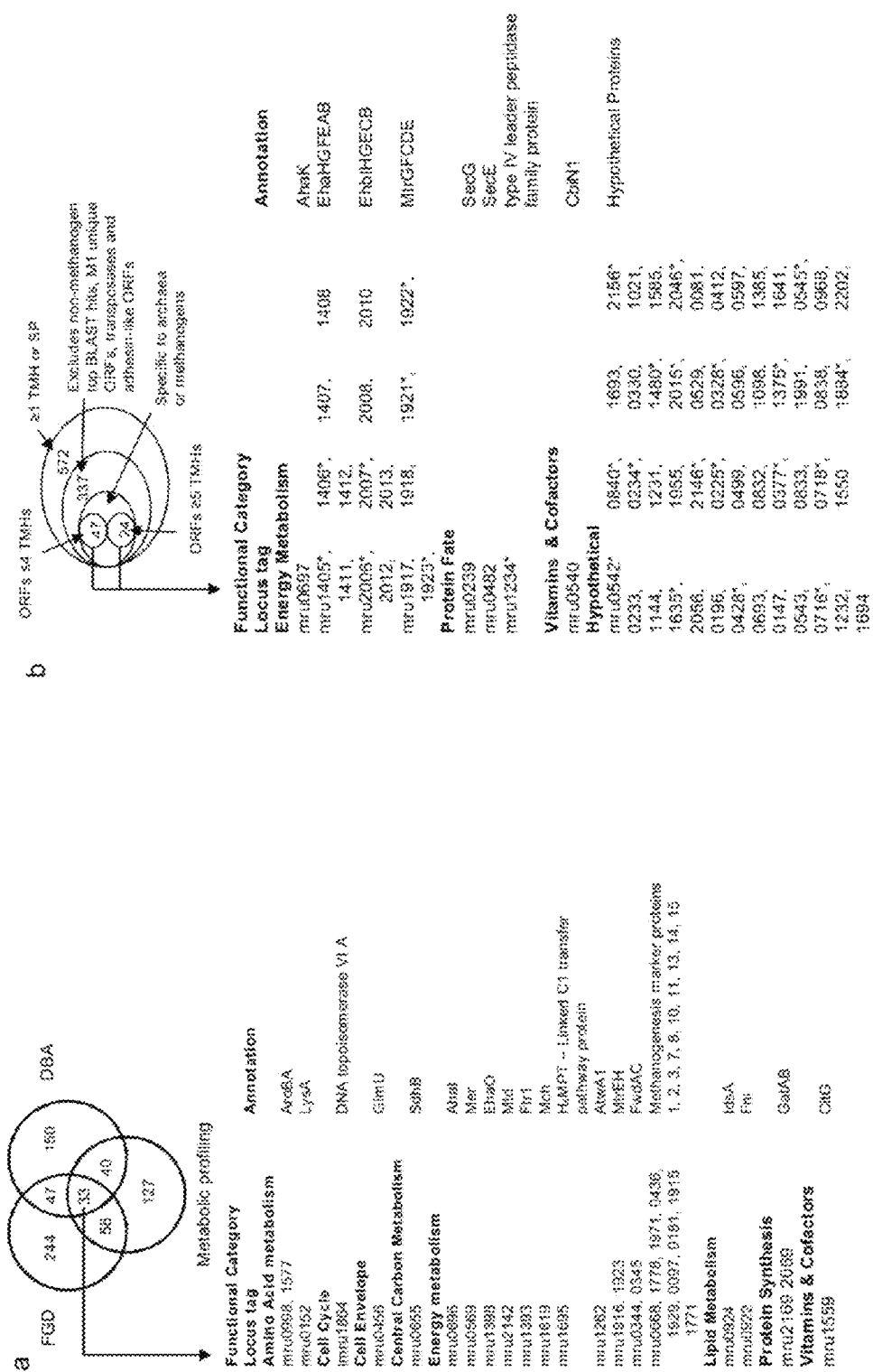
FIG. 1: Chemogenomic and vaccine gene targets within M1. The number of genes identified by each analysis is shown in the Venn diagram and a selection of the gene targets are summarized in the tables grouped by functional category (a) Chemogenomic gene targets were defined by identification of genes that occurred across three separate analyses; the Functional Genome Distribution (FGD), Differential BLAST analysis (DBA) and metabolic profiling. (b) Vaccine target genes were defined as described and discussed below. TMH, transmembrane helices, SP, signal peptide.
Figure 2:
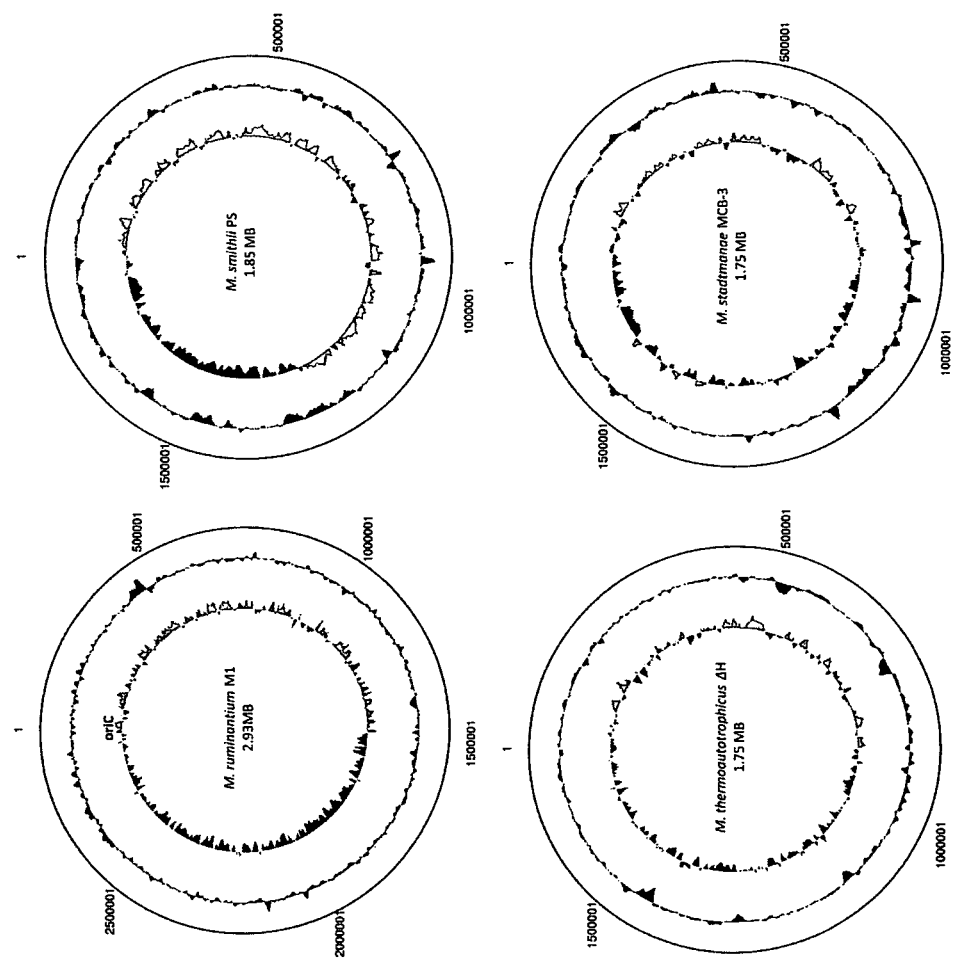
FIG. 2: GC analysis. Base-pair scale (outer circle), G+C content (middle circle) and GC skew (inner circle, (G−C/G+C), darker shade indicates values >1, lighter shade <1. Genomes of the Methanobacteriales order display a DNA skew similar to bacterial chromosomes. In *M. ruminantium* M1 the origin of replication (oriC) was identified as being immediately upstream of the Cdc6-1 gene (mru0001) based on GC skew analysis and homology to the origin of replication experimentally verified for *M. thermoautotrophicus* (Reymond et al., 2004). As with other Methanobacteriales genomes, *M. ruminantium* M1 contains a second Cdc6 homolog (mru0423). It also contains a truncated third Cdc6 homolog within the prophage sequence.

Several approaches were used to define potential gene targets from M1 for $CH_4$ mitigation via chemogenomic and vaccine approaches (FIG. 1). Genes suitable as chemogenomics targets were identified using a combination of metabolic profiling, review of the literature pertaining to the biochemistry and physiology of methanogens, and comparative genomics. The 33 candidate genes commonly identified by these approaches are shown in FIG. 1A. The full list of ORFs identified as chemogenomic targets by metabolic profiling of M1 and literature can be found in Table 5. Comparative studies were based on M1 and 26 complete and draft phase methanogen genome sequences, using a functional genome distribution (FGD) analysis (Table 3, FIG. 13). This analysis of whole genome gene conservation among methanogens showed that M1 and other members of the Methanobacteriales formed a functional cluster that shared a large number of conserved genes predicted to be involved in core biological functions (low e-value cut-off 1e-100, Table 3). In addition, a differential blast analysis (DBA) was conducted using the non-redundant (nr) database and a methanogen genome sequence database (dbMethano). The DBA analysis highlighted genes present in at least one methanogen genome within dbMethano but not present in any other organism within the nr database and vice versa (FIG. 10), thus identifying methanogen-specific genes. The majority of the 33 selected conserved and methanogen-specific genes encode enzymes that fall within the energy metabolism category, mainly within the methanogenesis pathway (Table 9). This also included several methanogenesis marker proteins found in methanogen genomes, but currently without defined function. Most of these methanogenesis enzymes are located within the cell cytoplasm, and therefore have been tagged as key targets for inhibitor discovery via a chemogenomics approach (FIG. 11).

The alternative approach of inducing the ruminant immune system to produce salivary antibodies against conserved features of rumen methanogens is an attractive methane mitigation strategy. The rumen epithelium is not immunologically active, and rumen contents do not contain complement proteins, therefore specific immune responses in the rumen do not occur. The effectiveness of a vaccination approach relies on the binding of salivary antibodies to methanogen surface features which results in their inactivation or clearance from the rumen. Vaccines are typically composed of proteins or polysaccharides derived from killed or attenuated whole cells or components presented on the outside of the cell such as flagella, capsules, cell walls, fimbrae, or secreted toxins. In the case of rumen methanogens, the primary vaccine targets are likely to be surface-exposed or membrane-associated proteins that are conserved among methanogens or archaeal species and which encode functions vital to methanogen growth and survival in the rumen. In silico analysis of the M1 ORFeome (all ORFs) identified an initial pool of 572 ORFs containing one or more transmembrane helices (TMH) or signal peptide (SP) indicating a cell membrane or cell surface location and therefore potential vaccine targets. Those ORFs with a top BLAST hit to a non-methanogen or with no homology to the nr database were removed from the analysis, as were transposase sequences (which are unlikely to represent good vaccine targets), while adhesin-like ORFs are dealt with separately above. This gave a new total of 337 ORFs. Examination of the remaining 337 ORFs, assessing their predicted function, degree of conservation among methanogens and the nature of their transmembrane structures, refined the list to 71 ORFs (FIG. 1B). Heterologous expression of membrane proteins with more than 4 TMHs has been difficult in RV studies of other microbes (Vivona et al., 2008). Therefore, a cut-off of 4 THMs was applied to define two final groups: Group A with 47 ORFs with 4 or fewer TMHs suitable for cloning and heterologous expression studies; and Group B composed of 24 ORFs with more than 4 TMHs more suitable for a synthetic peptide-directed vaccine approach.

The majority of vaccine targets identified above correspond to hypothetical proteins of unknown function. While these ORFs are presumed to be of value to M1, their importance to M1 growth and survival in the rumen is not evident, and therefore they are of lower priority as vaccine candidates. Of the remaining ORFs, those involved in energy metabolism are again prime vaccine candidates (FIG. 11). Of particular interest is the Mtr enzyme complex, which catalyses the essential methanogen function of transferring the methyl group from methyl-$H_4$MPT to CoM, coupled to the efflux of $Na^+$ ions (Lienard et al., 1996). Three of the Mtr subunits (MtrEDC) are each predicted to have >4 membrane-spanning regions and, in each of the membrane-spanning regions, the transmembrane helices have peptide loops located outside the cell membrane. These loops are potential antibody binding sites. We synthesised peptides corresponding to the loop regions of MtrE, MtrD and MtrC which were coupled to a carrier protein and then used as antigens to vaccinate sheep. The resulting immune sera bound specifically to immobilized M1 cells (FIG. 17), demonstrating the feasibility of such a peptide-directed RV approach.

Vaccine Target Identification Results

TMHMM predicted 542 ORFs to contain one or more transmembrane (TM) domains, 243 of which are also predicted to contain a signal peptide (SP). A further 30 ORFs were predicted to contain a signal peptide but no TM domain. This gave a total pool of 572 ORFs as potential vaccine candidates for the *M. ruminantium* M1 genome. Blast analyses revealed ORFs that had a top blast hit to a non-methanogen or had no homology to the NR database. These ORFs were removed from the analysis at this point as were transposase sequences (which are unlikely to represent a good vaccine target) and adhesin-like ORFs which were dealt with separately. This gave a new total of 339 ORFs. Those genes which are presently only found in *M. ruminantium* M1 and provide important information about rumen methanogens.

Methanogens are strict anaerobes and are thus present challenges for culturing in vitro and genetic techniques for validating both drug and vaccine targets particularly the Methanobacteria with their thick cell walls are still being established. As such, a further manual analysis of the 339 ORFs functions was undertaken re-examining their functional annotation, their conservation among methanogens and the prediction of their transmembrane structures and subcellular location which refined the target list to 71 ORFs which are presently specific to methanogens or archaea. Because expression can be challenging for membrane proteins, a cut-off of four TM domains was applied to expression studies of *M. ruminantium* M1 (multiple TMs can be indicative of a surface exposed protein, but conversely, they are known to impair heterologous expression in *Escherichia coli*) This resulted in a final two groups; Group A—47 vaccine targets (less than or equal to 4 TM) suitable for further cloning and expression studies and Group B—24 vaccine targets (greater than 4 TM) more suitable for a synthetic peptide directed vaccine approach. The adhesin-like ORFs were treated as a separate vaccine target list. Vaccine targets have also be disclosed in detail in U.S. 60/989,841 filed 22 Nov. 2007, and in PCT/2008/000249 filed 25 Sep. 2008, which are hereby incorporated by reference herein in their entirety.

Example 3

Overview

Genome Sequencing

*Methanobrevibacter ruminantium* was chosen for genome sequencing because of its prevalence in the rumen under a variety of dietary conditions (based on cultivation and molecular detection data), the availability of cultures, its amenity to routine growth in the laboratory, and the relatively large amount of previous studies and background literature available for this organism. A significant number of the genes within the *M. ruminantium* have been assigned a function, and have thereby allowed a detailed picture of this organism's lifestyle within the rumen. *M. ruminantium*'s dependence on simple substrates ($H_2+CO_2$, formate) and its interaction with the rumen environment via surface proteins and exopolysaccharides are important targets for inhibition. Similarly, the SPIDRs hold promise for both specific targeting of *M. ruminantium* and for future genetic manipulations to assist in determining gene function. The sequence data elucidates the metabolism of this organism and how it interacts with other microbes, and points to conserved systems and components among methanogens that can be inactivated to prevent or reduce methane formation in the rumen.

Drug Discovery for Reducing Rumen Methane Emissions

The completion of the *M. ruminantium* genome now enables the full power of '-omic' approaches to be used for developing novel drugs for reducing methane emissions. A rational drug discovery approach to the development of effective methane mitigation agents, analogous to the established approaches utilised for developing novel antibiotics against human pathogens, should proceed through several stages including: target identification; target/pathway validation; lead identification; verification of effectiveness of lead in rumen-like conditions; and ultimately, testing in animal trials (Gerdes et al. 2006; Pucci 2006; Galperin 2007). A priori, it is important to know the breadth of methanogen diversity in the rumen, and this has recently been summarised in a meta-analysis incorporating data from 14 phylogenetic studies (Janssen and Kirs, 2008). The study has shown that the vast majority of rumen archaea (92.3%) fall into three clades, the genera *Methanobrevibacter* (61.6%) and *Methanomicrobium* (14.9%) and an uncultured group termed rumen cluster C (15.8%) of as yet unknown physiology (Janssen and Kirs, 2008). Methanogens typically only account for approximately 1-4% of the total microbial community (Janssen and Kirs 2008).

Inter-genome comparisons of representative organisms, including relevant gut methanogens (e.g., *Methanobrevibacter smithii, Methanospirillim hungatei* and *Methanosphaera stadtmanae*), other rumen microorganisms (bacterial, fungal and prozoal) and mammals can aid in the identification of suitable targets (Samuel et al. 2007; Fricke et al. 2006). Overall, rumen methanogens should be somewhat easier to inhibit than bacteria, fungi or protozoa given that they are the only resident archaea in the rumen and are well known to possess several unique traits including distinctive cofactors, cell wall chemistries and lipids. Furthermore, they tend to have smaller genomes with less metabolic capability, tend to be less adaptable with fewer regulatory systems and are probably less able to develop resistance to drugs.

Given the diversity of methanogens in the rumen, the aim of developing a full spectrum anti-methanogen 'magic bullet' for complete mitigation of emissions would necessitate the targeting of enzymes that are essential to all rumen methanogens under normal rumen growth conditions. However, partial inhibition may also be desirable for extended periods of time, due to the potential decrease in the efficiency of feed conversion resulting from feedback inhibition of ruminal fermentation (Hegarty 1999; Russell and Rychlik, 2005). Significant partial reductions in methane emissions which might be more sustainable could also possibly be achievable by limiting the targeting to specific phylogenetic groups, such as the dominant Methanobrevibacteria. Methanogens grow slowly compared to rumen bacteria and are prone to being flushed out of the rumen (Janssen and Kirs 2008).

Analysis of the *M. ruminantium* genome, combined with the genome comparison and a consideration of the literature that has identified archaeal/methanogen-specific enzymes or has demonstrated the essentiality of enzymes/pathways has allowed us to generate a list of targets of interest (Tables 2 and 3, below). General targets areas include the methanogenesis pathway, energy metabolism, transcription, protein synthesis, cell wall synthesis, lipid synthesis, cofactor synthesis, and some key central carbon metabolic enzymes that are important links between essential pathways. Target prioritisation for introducing enzymes into the work stream is based on the ultimate aim of obtaining enzymes for high-throughput screening and crystal structure determinations for in silico lead identification. Targets are spread over multiple susceptible pathways to minimise risk. Prioritisation takes into consideration the presumed essentiality of target, the expected ease of expression of the proteins (e.g., size, number of subunits and presence of transmembrane domains), availability of assays, expected 'druggability' and availability crystal structures of homologous enzymes (Pucci, 2006; Hopkins and Groom, 2002).

There are several factors relevant to the development of future small molecule inhibitors of methanogens. These include that they should have minimal toxicity to the host animals, minimal accumulation or toxicity in any downstream products for human consumption, minimal deleterious effects on beneficial microorganisms responsible for normal fermentation in the rumen, and minimal downstream environmental impact. Ideally, they should also be inexpensive, given the current cost of carbon, be impervious to the large hydrolytic capacity of the rumen and should have reduced potential for allowing resistance to develop amongst the rumen methanogens. In the best circumstances, the concentration of inhibitor required should be low enough to prevent any rumen microbes from utilising the inhibitor as a substrate for growth and minimise overall costs (Weimer, 1998). It would be very beneficial if future anti-methanogen compounds that satisfy the above criteria can also help to reduce methane emissions emanating from other sources such as rice paddies. The goal of providing long term reductions in rumen methane emissions over decades will likely require a suite of non over-lapping anti-methanogen compounds. Compounds that are shown to inhibit an enzyme in an in vitro high-throughput assay should sequentially be verified for their effectiveness in pure culture experiments, followed by in vitro rumen simulations, and finally in short term and long term animal trials.

In the last decade there has been growing concern, as evidenced by recent EU legislation banning their use (McAllister and Newbold, 2008), about the use of antibiotics and other feed additives as growth promoters largely due to the development of antibiotic resistance. Consequently, even though methanogens are usually not thought to be directly implicated as a causative agent in pathogenic disease (Macario and Macario, 2008), it may be wise to avoid over-reliance on anti-methanogen agents that seek to inhibit enzymes that are common between them such as those in pseudomurein and peptidoglycan synthesis. Significantly, approximately two-thirds of antibiotics in use today against pathogenic microorganisms target cell wall synthesis, many of these the transpeptidation reaction catalysing the closure of bacterial peptidoglycan, but enzymes that catalyse earlier steps are being increasingly investigated as alternatives (Hammes et al. 1979). One of the main reasons for this is that the final steps of cell wall synthesis occurs extracellularly and are therefore the drugs are less prone to inactivation.

The recent development of an anti-*Mycobacterium tuberculosis* drug that targets the E subunit of the $F_0F_1$-ATPase that is also present in humans highlights the fact that even relatively small differences in structure could possibly be exploited to discover novel anti-methanogen compounds (Andries et al. 2005). The implication of this finding is that many essential methanogen enzymes that are not methanogen-specific. Targets that share <30-40% identity with their bacterial or eukaryal counterparts could ultimately be exploited for designing effective inhibitors.

The number of enzymes or pathways in methanogens demonstrated to be essential to help guide prioritisation of targets is relatively limited. Historically, the methanogenesis pathway itself has been targeted in numerous experiments using halogenated compounds such as chloroform that inhibit the terminal step of methanogenesis catalysed by methyl coenzyme M reductase, but these are not sustainable due to toxicity and environmental concerns (hypertext transfer protocol:///www.mafgovt.nz/mafnet/rural-nz/sustainable-resource-use/climate/green-house-gas-migration/ghg-mitigation-05.htm). In only a couple of other cases has a methanogen enzyme inhibitor been used to check whether rumen methanogen isolates hare also inhibited in pure culture, for example the targeting of the RFA-P synthase (Dumitru et al. 2003) and HMG CoA reductase with statins (Miller and Wolin, 2001). In addition, some additional understanding of growth characteristics of methanogens in the rumen may be needed. For example, researchers are still determining the extent to which rumen methanogens utilise amino acids in the rumen, which vitamins are used or enhance growth or the degree, if any, to utilise purines and pyrimidines. Thus at the moment, it may less desirable to target enzymes dedicated to the synthesis of amino acids, purines or pyrimidines.

The analysis of the M1 genome has provided new perspectives on the lifestyle and cellular processes of this prominent rumen methanogen. The genome sequence confirms the hydrogenotrophic lifestyle of M1 and gene expression data indicate that formate may be an important substrate for methanogenesis during syntrophic interaction with *B. proteoclasticus*. The ability of short chain alcohols to stimulate growth on $H_2$ but not support growth themselves is intriguing. We speculate that methanol or ethanol are oxidised by the NADP-dependent alcohol dehydrogenases and the reducing potential used to form $F_{420}H_2$ using NADPH-dependent $F_{420}$ dehydrogenase, thus augmenting the cellular pool of $F_{420}H_2$. This metabolism of alcohols could spare some of the $H_2$ or formate normally used to produce $F_{420}H_2$ and would explain the stimulation of growth by alcohols in the presence of $H_2$. The lack of a means of reducing ferredoxins with electrons from alcohols would explain why growth is not possible on alcohols alone. Further work will be required to test this hypothesis.

The abundance of genes encoding adhesin-like proteins in M1 indicates a significant ability to modulate cell surface topology. While the exact role of these proteins is currently unknown, initial observations from co-culture experiments indicate that at least some are involved in mediating close associations with hydrogen-producing bacteria in the rumen and others may be concerned with similar interactions with rumen protozoa and fungi.

The φmru prophage sequence within the M1 genome yielded the PeiR enzyme which is able to lyse methanogen cells. The variety of methanogen cell wall types means a combination of different lytic enzymes would be required for effective methanogen lysis in the rumen. However, the expression of PeiR and demonstration of its effectiveness against a major rumen methanogen is an important step towards this goal. The PeiR enzyme and the φmru phage may also be useful in increasing the permeability of M1 and other pseudomurein-containing methanogens to facilitate DNA entry and for developing tools for genetic manipulation of M1.

Methanogens are not known as producers of secondary metabolites, so the discovery of two NRPS genes was surprising, and to our knowledge, they are the first reported in an archaeal genome. Non-ribosomal peptides (NRPs) are known to contribute to microbial growth and ecological interactions and therefore their function is of interest as they could lead to a means of modulating methanogen growth.

The metabolic profiling and comparative genomics carried out in this study identified several sets of conserved, methanogen-specific genes that are currently being investigated further in our laboratory. Chemogenomic targets are being investigated via heterologous expression of genes in *Escherichia coli* coupled with the development of bioassays for screening these enzymes against libraries of chemical compounds to find specific inhibitors with efficacy at low concentrations. Vaccine candidate proteins with <4 TMHs are being investigated via heterologous expression in *E. coli* and vaccination of sheep. We have also shown the use of synthetic peptides in a reverse vaccinology approach to elicit specific antibody responses against M1 proteins with >4 TMHs. This demonstrates that membrane-embedded M1 proteins, that are unlikely to be amenable to expression in a heterologous host, are viable targets as vaccine antigens.

A wider representation of rumen methanogen genomes will be essential to verify that the selected vaccine and chemogenomics targets are conserved among other rumen methanogens, and ensure a successful, long-term $CH_4$ mitigation technology for the rumen. The wealth of biological information provided by the M1 genome represents a significant advancement for ruminant methane mitigation efforts, aimed at identifying anti-methanogen technologies' with broad efficacy.

Example 4

$A_1A_o$ ATP Synthase Cloning and Characterisation

We designed and developed an over-expression system for the $A_1A_O$-ATPase from *Methanobrevibacter ruminantium* and *Methanobrevibacter smithii* to allow the subsequent purification and characterisation of the $A_1A_O$-ATPase. *Methanobrevibacter ruminantium* and *Methanobrevibacter smithii* PCR Cloning And Introduction of Hexa-his Tag by PCR Overlap Extension To study the biochemical properties of the *M. ruminantium* $A_1$-ATPase, we prepared inverted membrane vesicles and tested for ATP hydrolysis activity. We were unable to detect any significant levels of ATP hydrolysis activity from inverted membrane vesicles of *M. ruminantium*. Due to the limited amount of cells that can be prepared at any given time for *M. ruminantium*, we undertook a heterologous over-expression approach to produce the $A_1$-ATPase. For this, we cloned the *M. ruminantium* $A_1$-ATPase genes as a 6.3 kb BamH1-Xba1 PCR product into the expression vector pTrc99a, generating plasmid pTrMbrA1. To insert the HIS-tag at the N-terminal of Subunit-A PCR overlap extension was conducted. Using this approach, we generated a clone named pTrMbrA1HIS which contains the genes encoding for the *M. ruminantium* $A_1$-ATPase in the *E. coli* expression vector pTrc99a, and introduced a Hexa-Histidine tag onto the N-terminal of Subunit A. We also cloned the $A_o$ genes with the $A_1$ genes to construct a full-length $A_1A_o$ ATP synthase expression plasmid. This was named pTrMbbr$A_1A_o$His9. In addition, we cloned the $A_1$-ATPase of *Methanobrevibacter smithii* as a 6.3 kb PCR product into the *E. coli* expression vector pTrc99a generating the plasmid pTrMbsA1. To facilitate purification, we introduced a Hexa-Histidine tag onto the N-terminal of the *M. smithii* Subunit-A by PCR overlap extension. This was named pTrMbsA1HIS. The lists of primers and plasmids from this study are shown below.

Primers

| Primer Name | Primer | Modifications | SEQ ID NO: |
|---|---|---|---|
| MbrA1FWD | AAATTTGGATCCGGAATCTTAGGTTAGGAGGTCAAT | (BamHI) | 7590 |
| MbrA1REV | AAATTTTCTAGATAACAAGCAAAATATGAATTGC | (XbaI) | 7591 |
| MbrA1HisFWD | ATGCATCATCATCATCATCATAGAGGAACTCAAATGTATGAA | HEXA-HIS TAG | 7592 |
| MbrA1HisREV | ATGATGATGATGATGATGCATCCCATCTGCGACGATAACAGG | HEXA-HIS TAG | 7593 |
| MbrA1His_MID | TTAGACAAGTTCTTAGTCGACTCTG | (Sal) | 7594 |
| MbrAOREV | AGAGACAATTTTATCTGCCCCAGAGCTCAT | (Sac) | 7595 |
| MbrA1FWD | ATTTAATTACCATGGTGATTTATTATGGCA | (Nco) | 7596 |

-continued

| Primer Name | Primer | Modifications | SEQ ID NO: |
|---|---|---|---|
| MbrA1ASeq1 | ATTGCAGGTCCTGTTATCGTC | | 7597 |
| MbrA1ASeq2 | GGACATTCCACTTATTACCGC | | 7598 |
| MbrA1ASeq3 | ACTTATCCGAACCGGTTACTC | | 7599 |
| MbsA1FWD | AAATTTTAAGGATCCAATCTGTATGAGCTCAG | BamHI | 7600 |
| MbsA1REV | AAATTTGTCGACCAATTACACAAAAAGATGAGCCGTTAC | SalI | 7601 |
| MbsA1HisFWD | ATGATTCATCATCATCATCATCATATCGAAGGAAAAATTATTAAA | HEXA-HIS TAG | 7602 |
| MbsA1HisREV | ATGATGATGATGATGATGAATCATTTAACCATCTCTACCCCAATA | HEXA-HIS TAG | 7603 |
| MbsA1_AatIIREV | ATTTATCCACATATGGACGTCCTTTCCTTA | (AatII) | 7604 |
| MbsA1Seq1 | CCTCTGAAGGATCATCTGAT | | 7605 |
| MbsA1Seq2 | AGCATTGCTTCTGAAGGTGAA | | 7606 |
| MbsA1Seq3 | GAGTAAACACTATTGGTACTA | | 7607 |

Plasmids

| Plasmid Name | Details | Features |
|---|---|---|
| pTrMbrA1 | *Methanobrevibacter ruminantium* $A_1$-ATPase cloned into expression vector pTrc99a as a 6.3 kb Bam/Xba fragment | |
| pTrMbrA1HIS | *Methanobrevibacter ruminantium* $A_1$-ATPase, cloned into expression vector pTrc99a as a 6.3 kb Bam/Xba fragment. N-terminal Hexa-Histidine tag on Subunit A | Hexa-His Tag |
| pTrMbrA1AO | *Methanobrevibacter ruminantium* $A_1A_o$-ATPase cloned into expression vector pTrc99a as a Nco/Xba fragment. N-terminal Hexa-Histidine tag on Subunit A | Hexa-His Tag |
| pTrMbsA1 | *Methanobrevibacter smithii* $A_1$-ATPase cloned into expression vector pTrc99a as a 6.3 kb Bam/Sal fragment | |
| pTrMbsA1HIS | *Methanobrevibacter smithii* $A_1$-ATPase cloned into expression vector pTrc99a as a 6.3 kb Bam/Sal fragment. N-terminal Hexa-Histidine tag on Subunit A | Hexa-His Tag |

Over-Expression and Purification of pTrMbrA1HIS and pTrMbsA1HIS as Analysed by Western Blotting As noted above, we generated a clone named pTrMbrA1HIS which contains the genes encoding for the *M. ruminantium* $A_1$-ATPase in the *E. coli* expression vector pTrc99a, and introduced a Hexa-Histidine tag onto the N-terminal of Subunit A. We expressed the plasmid pTrMbrA1HIS in the *E. coli* strain DK8, and purified the expressed protein complex by Ni-affinity chromatography. We were able to detect Subunit-A via both Western and MALDI-TOF/TOF analysis. Subunit-A was found to be running at an incorrect molecular mass of approximately 24 kDa compared to the 65 kDa predicted molecular mass. We found that this discrepancy was caused by a mutation within Subunit-A. This mutation has now been corrected, and we have repeated the over-expression and purification with the new construct. Furthermore, we have also created a clone to express the full length $A_1A_O$-ATPase in *E. coli*. The purification and characterisation of the $A_1A_O$-ATPase from *M. ruminantium* has proceeded accordingly.

From Western analysis of the *M. smithii* over-expression, two dominant bands can be observed. One protein band runs above the 72 kDa marker, and the other runs at approximately 33 kDa. The expected size of the *M. smithii* Sub-unit-A is 64.8 kDa, therefore the protein band running at approximately 72 kDa is likely the *Mbb. smithii* Subunit-A, and the lower band running at 33 kDa is likely a breakdown product, or unassembled Subunit-A which still retains the HIS-tag. We are proceeding to further purify the Ni-affinity eluted fractions, through either PEG-fractionation or gel filtration with the aim to remove the lower contaminating band, while still retaining $A_1$-ATPase activity. We have assayed the ATPase activity of the eluted *M. smithii* $A_1$-ATPase and found the sample to hydrolyse with a specific activity of approximately 0.4 Units/mg.

*Mbb. ruminantium* $A_1A_o$ ATP Synthase Expression in a Foreign Host

Figure 24:
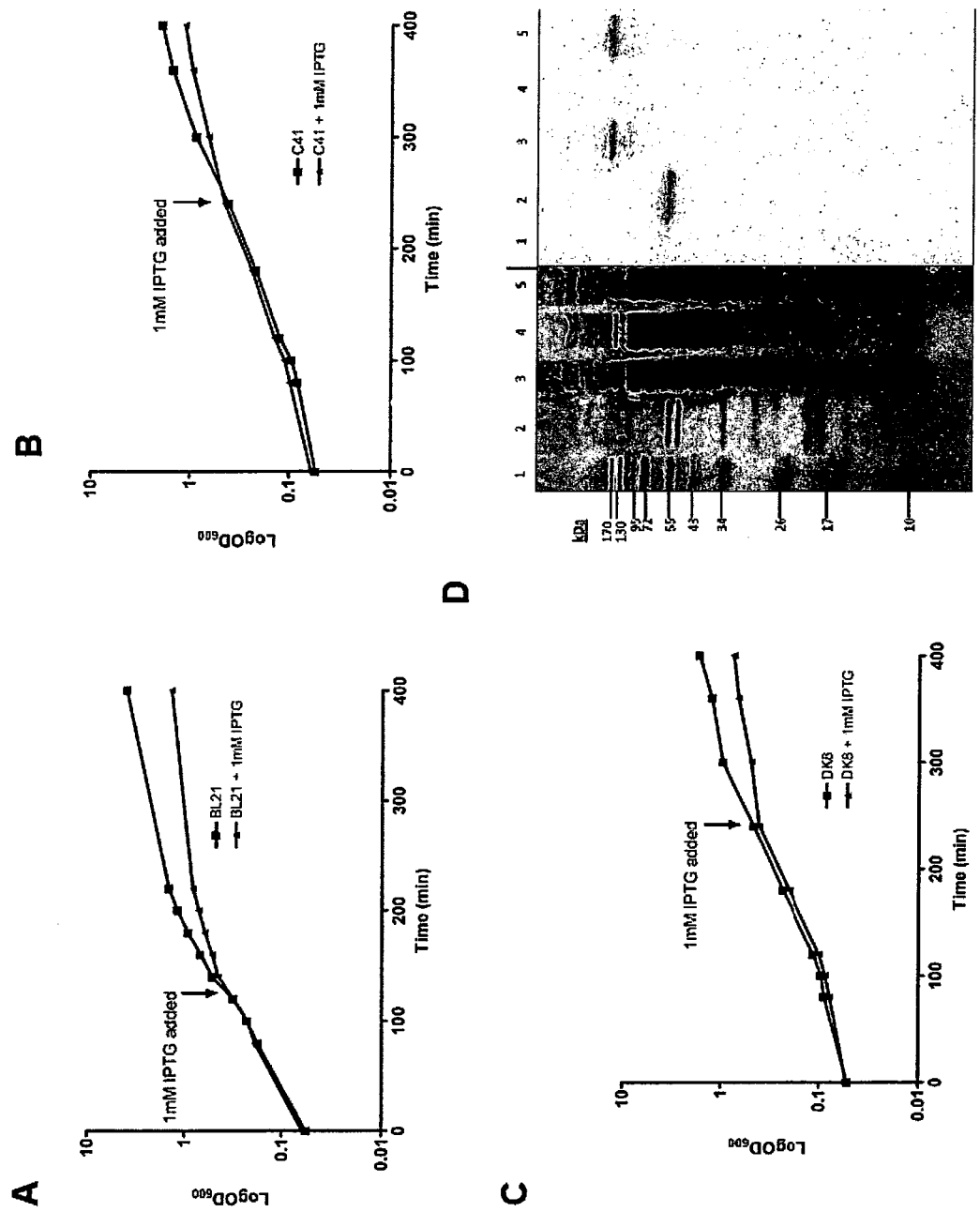

The *Mbb. ruminantium* $A_1A_O$-ATPase was expressed in *E. coli* strains DK8 (Δatp), BL21 and C41 (FIG. 24A-D). All strains showed a decrease in growth after induction of expression with 1 mM IPTG. BL21 showed the best growth (FIG. 24A) and expression of the $A_1A_O$-ATP synthase and therefore was chosen as a suitable expression host for subsequent purification. Growth of the induced cultures (BL21, C41 or DK8/pIrMbbr$A_1A_o$His9) is at a reduced rate compared to the non-induced control culture in all 3 strains (see FIG. 24A-C), a phenomenon that is a good indication of foreign protein over-expression in *E. coli*. To examine the localization of the recombinant $A_1A_O$-ATP synthase in *E. coli* the cell debris, cytoplasm and membranes were examined by SDS-PAGE and immunoblotting. Purified $F_1F_o$-ATPase (his-tag on β-subunit) from TA2.A1 enzyme was used as a positive control (FIG. 24D). The enzyme was localized in the membranes and not in the cytoplasm indicating the presence of a properly assembled enzyme. pTrMbbr$A_1A_o$His9 was able to be expressed in *E. coli* strains BL21, C41 or DK8, with the best growth and overexpression in BL21 (data not shown). These results also show the $A_1A_O$-ATP synthase is specifically localizing to the membrane preparation in both BL21 and DK8 cells.

Extraction of the $A_1A_O$-ATP Synthase from Cell Membranes

Figure 25:
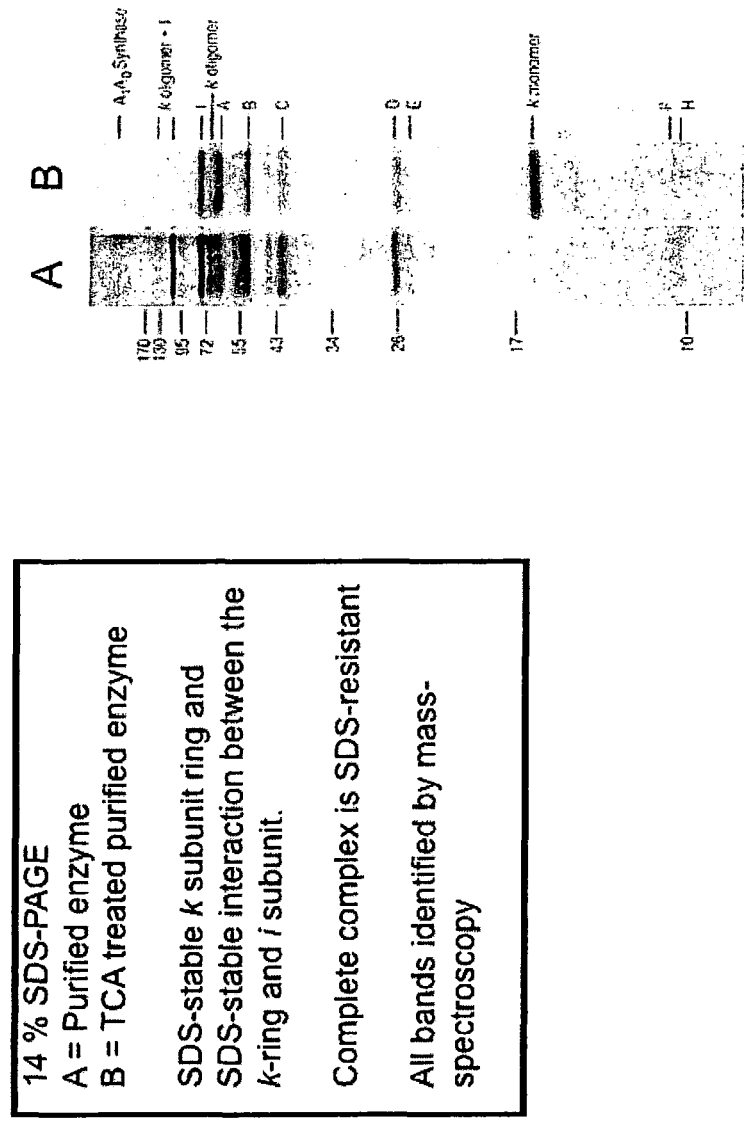
Figure 26:
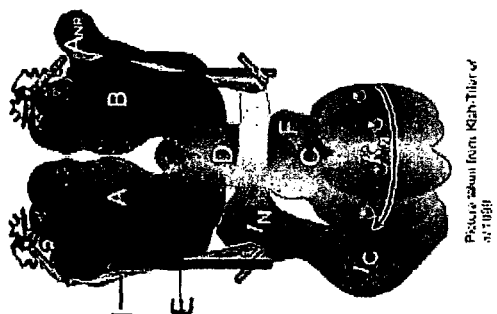

The *Mbb. ruminantium* $A_1A_O$-ATPase was expressed in the *E. coli* DK8 (Δatp) and BL21 (FIG. 24A-D). Previously, we were able to solubilize the *Mbb. ruminantium* $A_1A_o$ using 2% DDM, and we are able to semi-purify the *Mbb. ruminantium* $A_1A_o$ ATP synthase by exploiting the introduced hexa-histidine tag on the A subunit (elution at 120 mM imidazole, see FIG. 25). However, solubilisation was considered limited with only about 40% of the tagged protein being extracted from membranes. Therefore, to determine the detergent with the optimal solubilisation effect, *E. coli* BL21 inverted membrane vesicles were diluted in solubilisation buffer supplemented with different detergents to concentrations of 0.5, 1, 2 or 4%, and a concentration of 5 mg protein/ml. Solubilisation was performed under gentle stirring overnight at 4° C. or at room temperature with DM, DDM, Triton X-100, Cymal-6, CHAPS, cholate, octylglucoside and fos-choline. SDS was used as a positive control as it solubilized 100% of the membranes. The soluble and insoluble fractions were analyzed by SDS-PAGE and immunoblotting. Comparison of the immunoblots revealed that fos-choline had the best solubilisation effect (90-100%), followed by DDM (40%), DM (35%) and cymal-6 (39%). Triton X-100 and octylglucoside were weak (>20%). CHAPS and cholate led to a significant degradation of the enzyme (a smear) and were therefore not feasible. However, after activity was measured of the solubilized membrane protein, the best detergent was DDM or cymal-6 both liberating 40% of the ATPase and maintaining activity the highest activity. The Fos-choline samples did not contain enzyme activity regardless of concentration.

Purification of the *Mbb. ruminantium* $A_1A_o$-ATPase

BL21 containing pTrMbbr$A_1A_o$His9 induced with 1 mM IPTG and expression conducted for 4 hours at 37° C. Membranes were prepared by French-press, and solubilized with 2% DDM at 4° C. overnight in the presence of 0.1% TCEP (a reductant). The purification was then routinely performed by IMAC and the bound protein subjected to 10, 20, 40 then 60 mM imidazole wash steps before elution at 100 mM imidazole. It should be noted that elution of a significant amount of $A_1A_o$ protein is observed at 60 mM imidazole, however to ensure a very clean preparation this step was essential to remove contaminating proteins. To remove additional contaminants, the eluant was PEG-precipitated for 1 h at room temperature with 10% $PEG_{6000}$ followed by 15% $PEG_{6000}$. The first step precipitation removed contaminating proteins (fraction split), the second precipitates the $A_1A_o$ ATPase.

Figure 27:
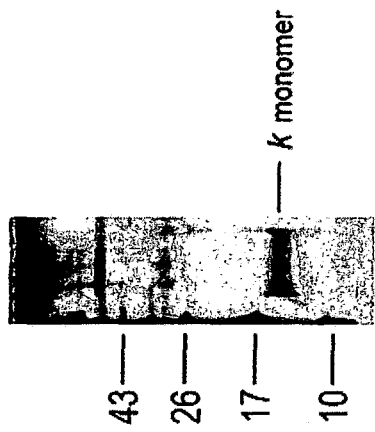
Figure 28:
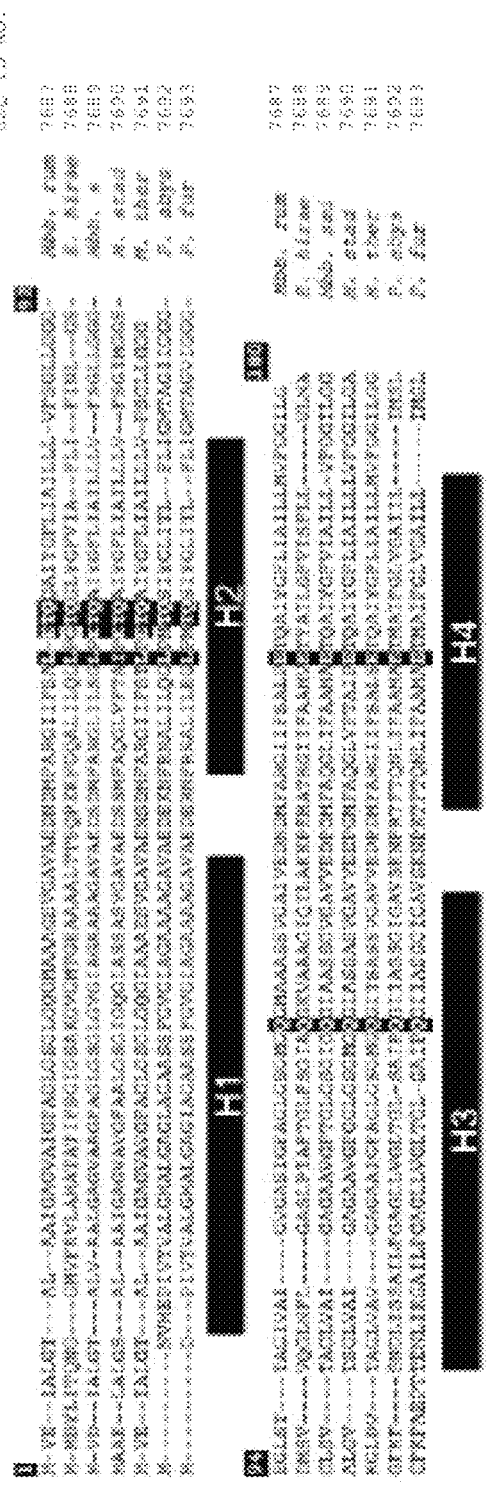

The purified *Mbb. ruminantium* $A_1A_o$-ATPase contained all 9 subunits, which was confirmed by MS/MS (FIGS. 25A and B). The K-subunit appears both as a monomer and as an oligomer on a 14% SDS-PAGE gel. When this enzyme preparation was TCA-treated, the oligomers were no longer seen, and a strong band of the K monomer was observed. This observation is indicative of an SDS-stable K ring. This was further confirmed by isolation of monomers of the K-subunit by methanol/chloroform extraction (FIG. 27). This K ring preparation is being used for antibody trials.

Purified *Mbb. ruminantium* $A_1A_o$ ATP Synthase Characterization

Two enzyme preparations were studied. Purified ATP synthase from BL21 and recombinant enzyme expressed in *E. coli* DK8 membranes. Purified $A_1A_o$ ATP synthase was examined for ATPase activity using the inorganic phosphate assay. After examining current literature on the *Methanosarcina mazei* and *Methanococcus jannaschii* $A_1A_o$ ATP synthases, it was decided to examine activity at 39° C. and a pH value of 6.5 in a buffering system that mimics the $Na^+$ concentration in the rumen (70-137 mM $Na^+$).

Figures 1, 29:
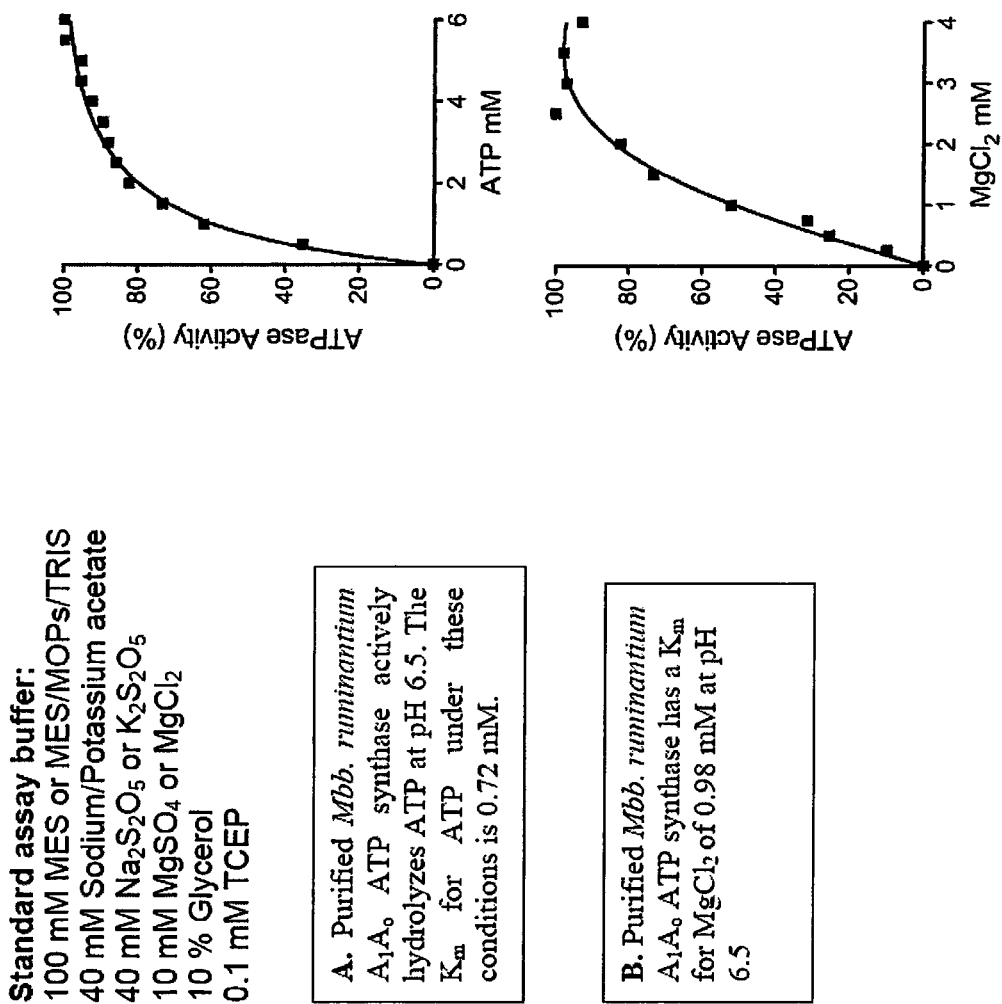
Figures 2, 29:
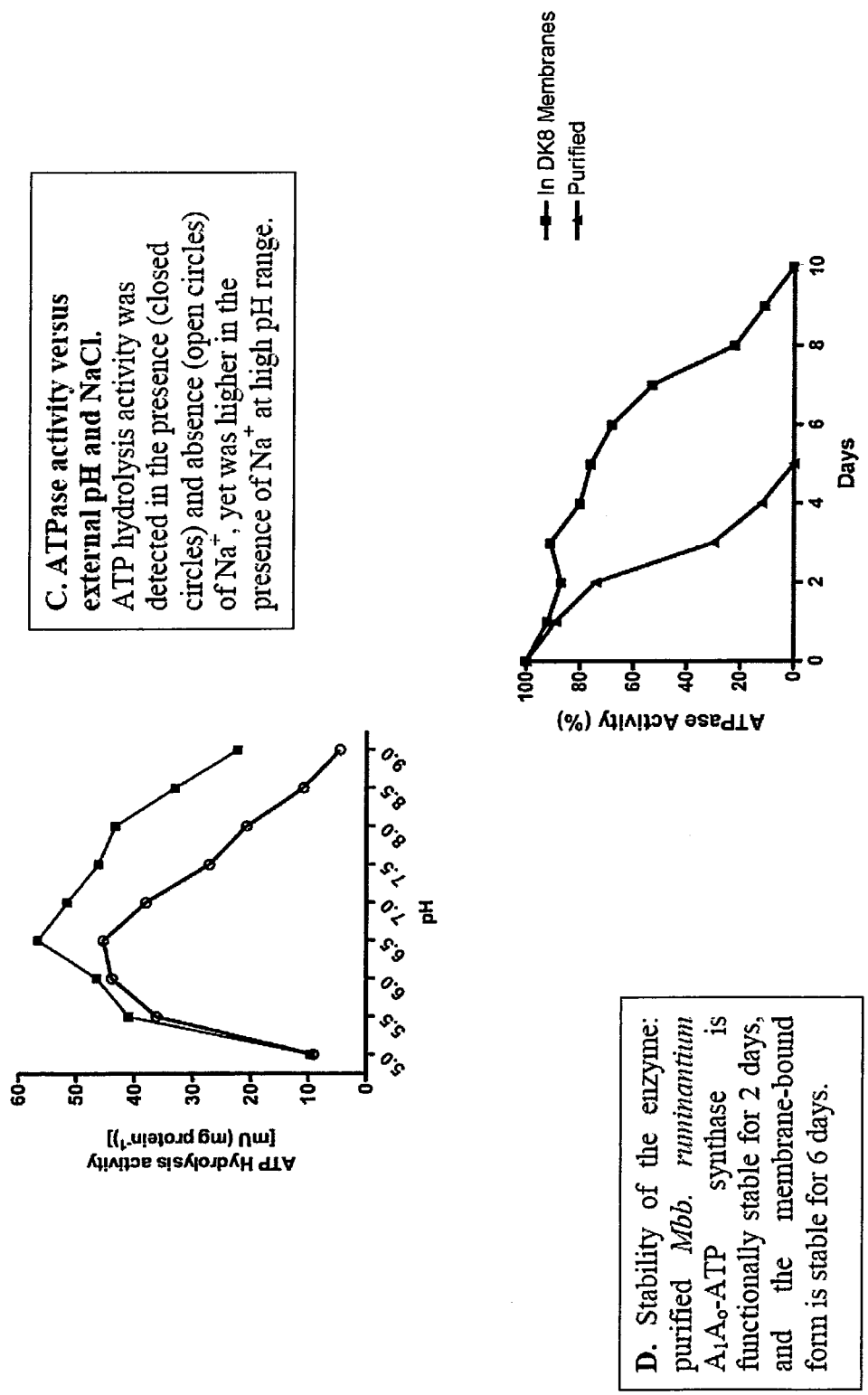

To determine the kinetics of ATP hydrolysis, the reaction was started at 39° C. by addition of $Na_2$-ATP to a final concentration of 2.5 mM. 16 µg of protein was used in each end-point assay. Background ATPase activity generated by thermal hydrolysis of ATP or contaminant ATP in buffer or enzyme was subtracted (these totaled <5% of the final value shown; FIG. 29A). The influence of $Mg^{2+}$ on the kinetics of ATP hydrolysis was also evaluated. The reaction was started by addition of Tris-ATP to a final concentration of 2.5 mM. 16 µg of protein was used in each end-point assay. Background ATPase activity generated by thermal hydrolysis of ATP or contaminant ATP in buffer or enzyme was subtracted (these totaled <5% of the final value shown; FIG. 29B).

ATPase activity was tested over a pH value range from 5.5 to 8.5 and in presence and absence of $Na^+$ using the purified recombinant $A_1A_o$-ATPase. The reaction was started at 39° C. by addition of $Na_2$-ATP or Tris-ATP to a final concentration of 2.5 mM. 16 µg of protein was used in each end-point assay. Background ATPase activity generated by thermal hydrolysis of ATP or contaminant ATP in buffer or enzyme was subtracted (these totaled <5% of the final value shown; FIG. 29C). The stability of the purified and membrane-bound (in DK8 membranes) *Mbb. ruminantium* $A_1A_o$ ATP synthase was also tested. ATPase activity was examined each day after the preparation of either purified recombinant or DK8 membrane bound *Mbb. ruminantium* $A_1A_o$ ATP synthase. The reaction was started at 39° C. by addition of $Na_2$-ATP to a final concentration of 2.5 mM. 16 µg of purified protein or 0.5 mg inverted membrane vesicles was used in each end-point assay. Background ATPase activity generated by thermal hydrolysis of ATP or contaminant ATP in buffer or enzyme was subtracted (these totaled <5% of the final value shown; FIG. 29D).

To gain insight to whether the purified or membrane-bound *Mbb. ruminantium* $A_1A_o$ ATP synthase is functionally coupled to an ionic driving force ($H^+$ or $Na^+$), tributylin (TBT) was tested as an inhibitor. TBT is a well characterized $F_o$ and $A_o$ channel inhibitor of ATP synthases. To examine the coupling ion used by the *Mbb. ruminantium* $A_1A_o$ ATP synthase, the effect of amiloride, a known $Na^+$-coupled V-type ATPase and $Na^+$ channel inhibitor was also examined.

Figures 1, 30:
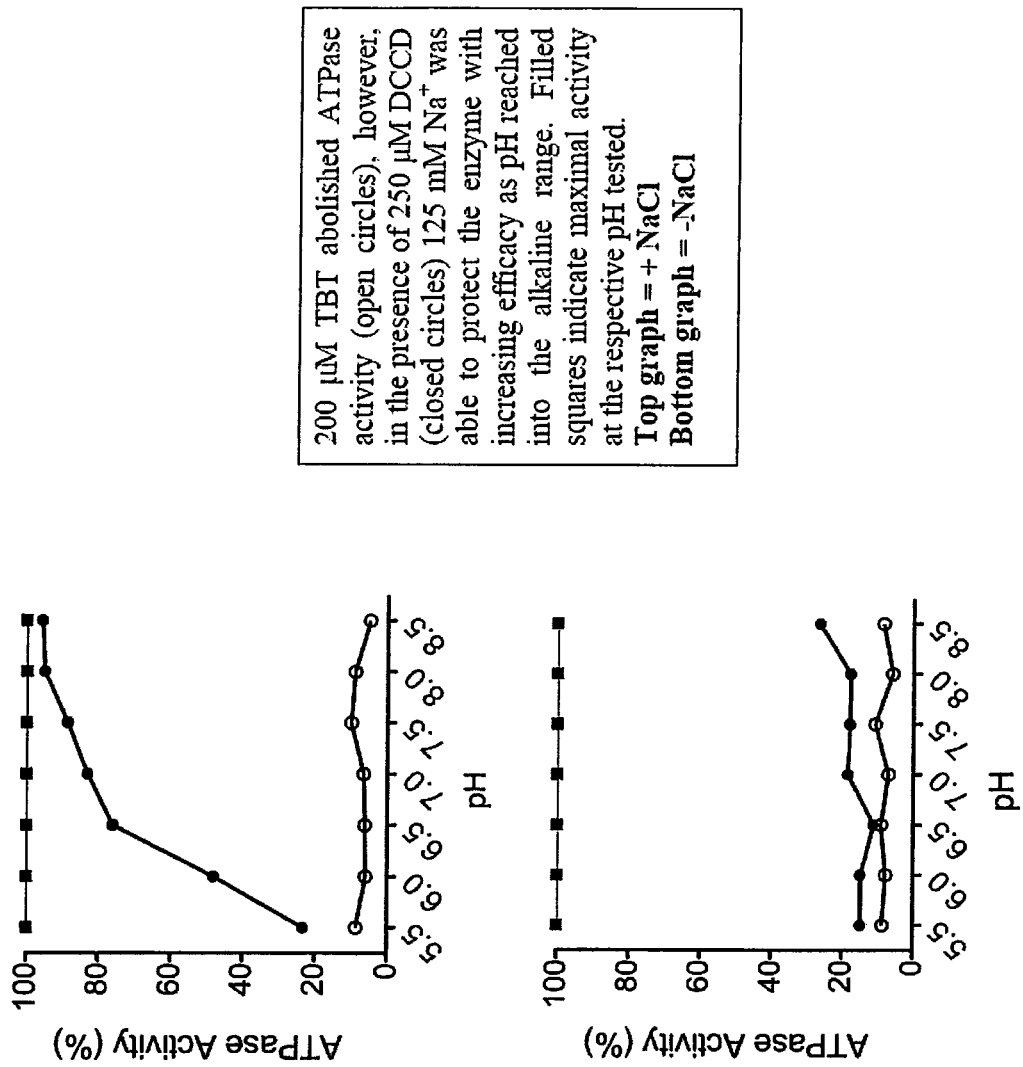
Figures 2, 30:
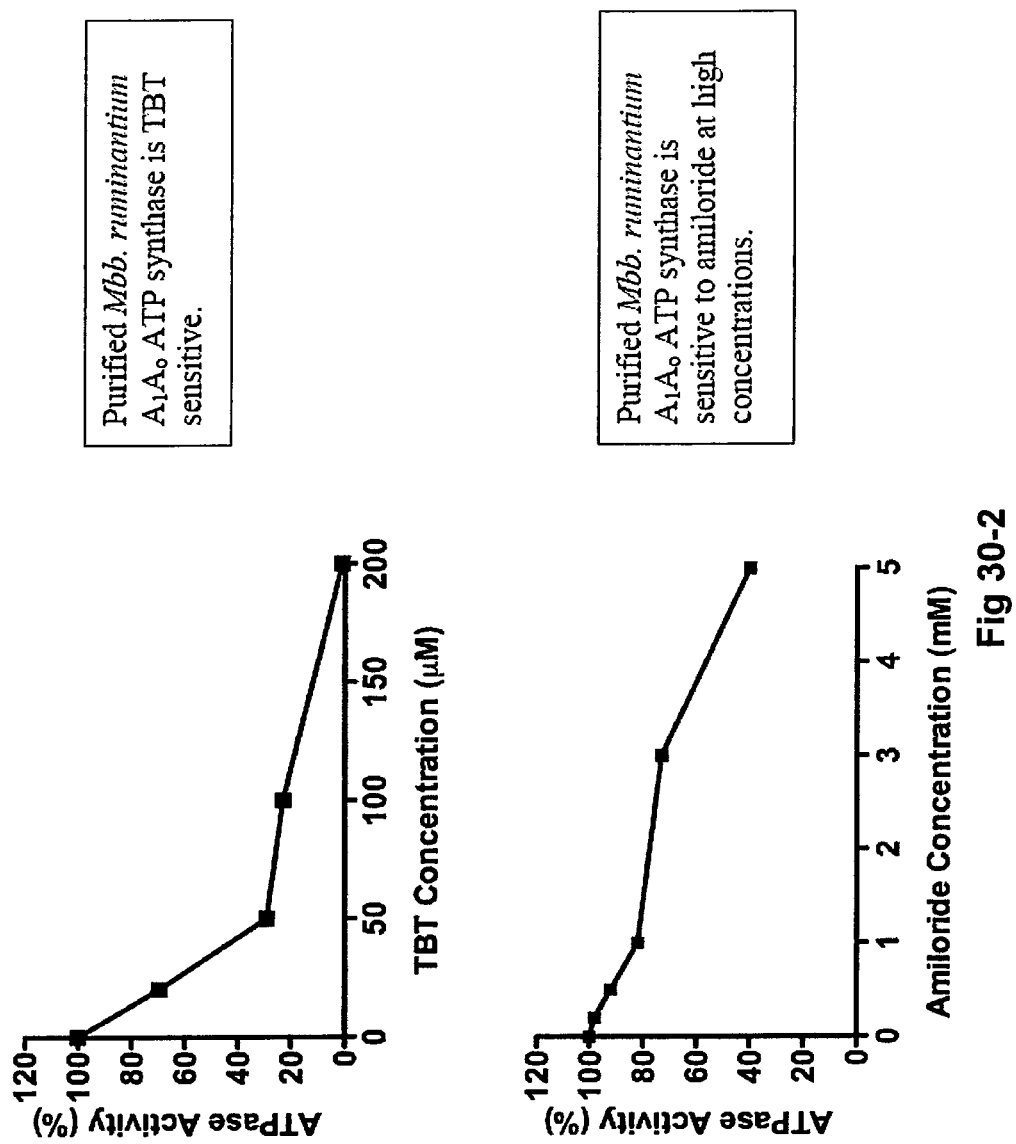

The effects of TBT and DCCD on ATPase activity were investigated as follows. *E. coli* DK8 (Δatp) inverted membranes containing the recombinant $A_1A_o$-ATPase were used to determine the effects of the inhibitors TBT (200 µM) and DCCD (250 µM) at different pH values. ATPase activity was measured in presence of 130 mM $Na^+$ (FIG. 30A) and in absence of $Na^+$ (FIG. 30B). After preincubation with the inhibitor for 20 min at room temperature (TBT or DCCD), the reaction was started at 39° C. by addition of $Na_2$-ATP or Tris-ATP to a final concentration of 2.5 mM. 0.5 mg inverted membrane vesicles was used in each end-point assay. Background ATPase activity generated by thermal hydrolysis of ATP or contaminant ATP in buffer or enzyme has been subtracted (these totaled <5% of the final value shown; FIGS. 30A and 30B).

Tributylin inhibition of ATP hydrolysis by purified recombinant *Mbb. ruminantium* $A_1A_o$ ATP synthase was then evaluated. After preincubation with the inhibitor tributylin (TBT) for 20 min at room temperature, the reaction was started at 39° C. by addition of $Na_2$-ATP to a final concentration of 2.5 mM. 16 µg of protein was used in each end-point assay. Background ATPase activity generated by thermal hydrolysis of ATP or contaminant ATP in buffer or enzyme was subtracted (these totaled <5% of the final value shown; FIG. 30C). Amiloride inhibition of ATP hydrolysis of the *Mbb. ruminantium* $A_1A_o$ ATP synthase was evaluated next. After preincubation with the inhibitor tributylin (TBT) for 20 min at room temperature, the reaction was started at 39° C. by addition of $Na_2$-ATP to a final concentration of 2.5 mM. 16 µg of protein was used in each end-point assay. Background ATPase activity generated by thermal hydrolysis of ATP or contaminant ATP in buffer or enzyme was subtracted (these totaled <5% of the final value shown; FIG. 30D).

Figure 31:
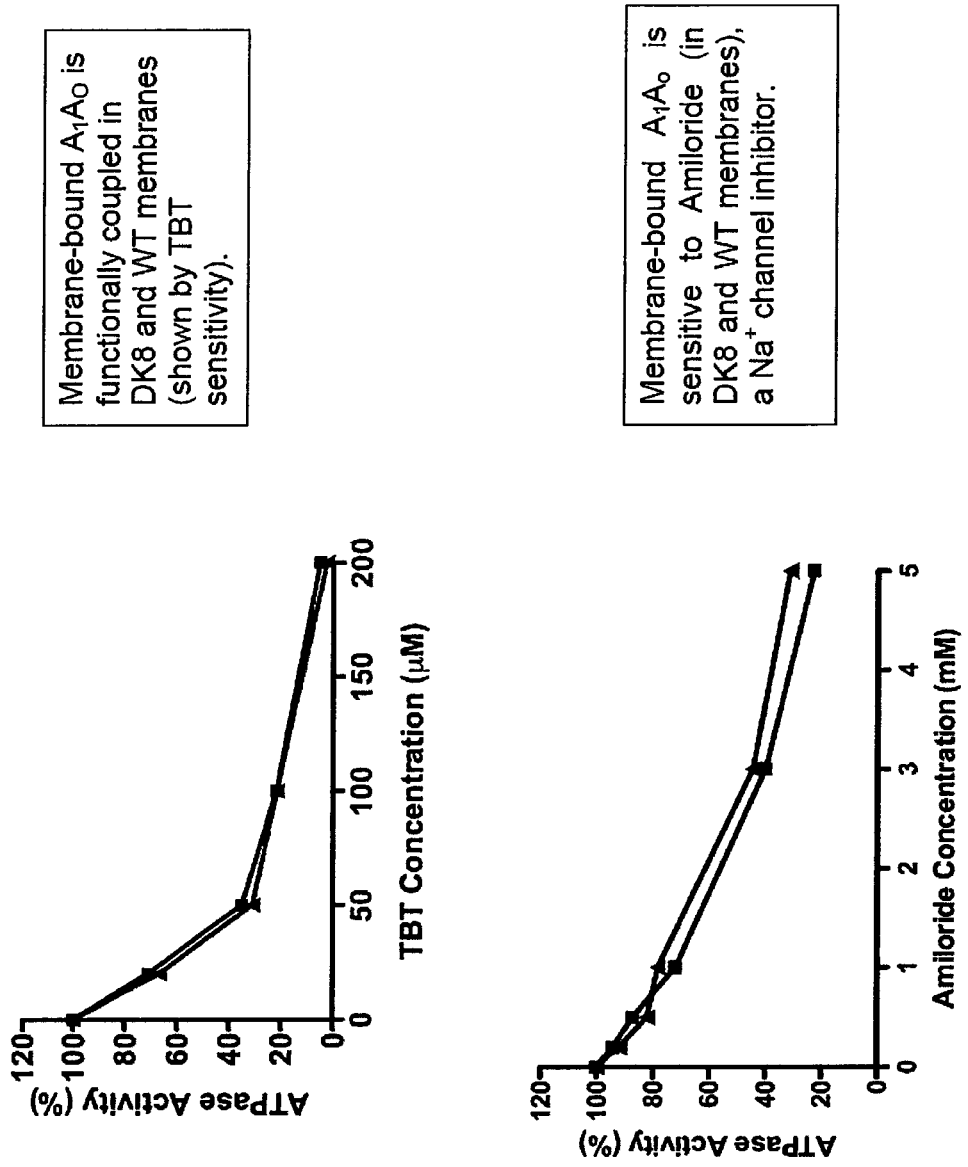

Tributylin inhibition of ATP hydrolysis by the *Mbb. ruminantium* $A_1A_o$ ATP synthase was also tested in DK8 and native membranes. After preincubation with the inhibitor tributylin (TBT) for 20 min at room temperature, the reaction was started at 39° C. by addition of $Na_2$-ATP to a final concentration of 2.5 mM. 0.5 mg inverted membrane vesicles was used in each end-point assay. Background ATPase activity generated by thermal hydrolysis of ATP or contaminant ATP in buffer or enzyme was subtracted (these totaled <5% of the final value shown; FIG. 31A). Amiloride inhibition of ATP hydrolysis of purified recombinant *Mbb. ruminantium* $A_1A_o$ ATP synthase was further tested in DK8 and native membranes. After preincubation with the inhibitor tributylin (TBT) for 20 min at room temperature, the reaction was started at 39° C. by addition of $Na_2$-ATP to a final concentration of 2.5 mM. 0.5 mg inverted membrane vesicles was used in each end-point assay. Background ATPase activity generated by thermal hydrolysis of ATP or contaminant ATP in buffer or enzyme was subtracted (these totaled <5% of the final value shown; FIG. 31B).

Figure 32:
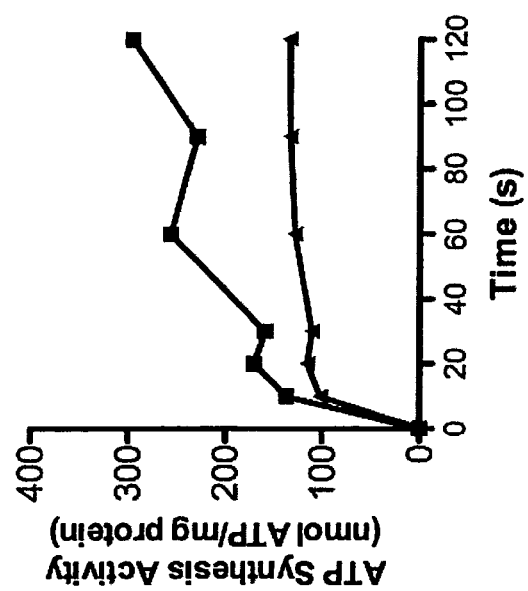

ATP synthesis in *E. coli* DK8 inverted membrane vesicles was further evaluated. Time-course of ATP synthesis was assessed at pH 6.5, 125 mM $Na^+$ and 39° C. with 0.5 mg of inverted membrane vesicles using the ATP synthesis inverted membrane vesicle assay using NADH as a driving force. Membranes were preincubated for 2 min with 2.5 mM NADH with stirring before the reaction was initiated using 0.75 mM ADP and 2.5 mM $P_i$. Closed squares with no DCCD; closed triangles, a 20 min preincubation with 250 µM TBT (FIG. 32).

Overview

We have successfully cloned, expressed and characterized the $A_1A_o$-ATP synthase from *Mbb. ruminantium*. SDS-PAGE revealed 9 subunits and an SDS-stable K ring, which was purified. The $A_1A_o$ synthase is active in both synthesis and hydrolysis, but the enzyme activities can be improved. This is consistent with other published $A_1A_o$-ATP synthases from methanogens. The coupling ion for the enzyme is being identified with studies suggesting both $H^+$ and $Na^+$ ions being important. ATP hydrolysis activity is sensitive to TBT, DCCD, and amiloride in high concentrations, suggesting these inhibitors will be ineffective against the growth of methanogens, hence the need to find a better inhibitor.

We will proceed to test antibodies generated towards the $A_1A_o$-ATP synthase in sheep against the purified enzyme in a Western blot. The antibodies have been directed against the soluble $A_1$ part of the enzyme and therefore are probably inaccessible during growth inhibition studies. This suggests that targeting the $A_1$ portion will be ineffective. We will also use the membrane-embedded sector (K ring) of the enzyme for new sheep antibody trials. This component would be accessible in the whole cell, so could be very useful as a target. We will also use the recombinant enzyme to identify inhibitors of activity using LOPAC1280™ which is a versatile compound library for assay validation and high throughput screening.

Example 5

Cloning and Expression of Non-Ribosomal-Peptide-Synthase (NRPS) Genes

Experiments are being performed to obtain expression of full-length NRPS genes, isolate the expression product and submit for structural determination and activity testing. Two non-ribosomal peptide synthetase gene sequences have been identified in *M. ruminantium* M1 (Leahy et al., 2010). We have been able to clone and amplify most of the functional modules of the NRPS1 gene of *M. ruminantium*. This allows us to investigate the substrate specificity and mode-of-action of individual NRPS domains. We have also completed the design and in vitro assessment of predicted synthetic peptides from both the NRPS1 and NRPS2 gene products from *M. ruminantium* M1. The unexpected outcomes of these experiments (an opposed reaction to known siderophores) has prompted significant interest in the nature of these NRPs and their native molecular structure.

We have shown the presence of the native NRPs in *M. ruminantium* M1 growth supernatant, and are obtaining further information on secondary and tertiary native structures and on any further modification to the peptide backbone, such as cyclisation or acylation. Therefore, expression of full length NRPS genes in a heterologous expression system will give us an opportunity to purify the active peptide compounds synthesized and make the genes available for large scale production.

Suitable primer sets were designed to ensure full length amplification and subsequent cloning into suitable expression systems. We have obtained full length amplification of the M1 NRPS2 gene and are carrying out further experiments to clone this amplicon into a vector system. Small amounts of NRPS1 from M1 have been amplified and inserted into entry vectors. These vectors are now being sequenced to confirm that the inserted amplicons reflect the NRPS gene and are free of non-silent nucleotide mutations.

We are also synthesizing NRPS genes using GeneArt's gene optimization service. This optimization not only adapts codon usage to the heterologous expression host *E. coli* but also accounts for factors that may compromise the stability of mRNA, such as extreme GC content, ribosomal binding sites, repeats and secondary structures. Substrate feeding studies with *E. coli* crude extract and *E. coli* II *M. ruminantium* crude extract mix will be carried out to evaluate the amount of functional NRPS units. Biological active NRP molecules will subsequently be detected using the CAS colorimetric assay.

We are also working to induce gene expression by providing a range of stimuli (i.e., increasing amounts of ion chelators) in the growth medium and monitor gene expression levels. An alternative approach to isolate the non-ribosomal peptides is to identify induction conditions of the NRPS genes via Northern Blot analyses. Induction of those genes will lead to increased mRNA levels, more active NRPS units and, subsequently, more NRP molecules in the growth supernatant. Based on our preliminary results reported earlier, we have identified two initial stress conditions to test. The interaction of NRP1 and 2 with Chrome Azure S (CAS) and Fe-ions, make iron scavengers and chelators such as Desferal and EDTA prime candidates for initial induction testing. The addition of both compounds to the growth medium may trigger the NRPS sensor system and cause elevated gene expression.

For these experiments, *M. ruminantium* M1 was grown to an $OD_{600}$ of 0.1 and then aliquoted in 5 mL amounts into anaerobic tubes. Different concentrations of EDTA and Desferal were added to the cultures. Each culture was sampled at 1, 2, and 4 hours and overnight after the addition of EDTA or Desferal. Samples were centrifuged to pellet the cells, supernatant was removed and the samples stored at −80° C. Subsequently, total RNA has been isolated and tested for integrity. To test semi-quantitatively the level of gene expression, RNA dilution series for each sampled time point and each inducer concentration will be established in a Northern Dot Blot system.

Three different probes have been designed targeting one house-keeping gene as positive control, and both NRPS genes. We are currently in the process of labelling these probes and will commence testing. When appropriate induction conditions have been established, we will purify the native non-ribosomal peptides from *M. ruminantium* culture supernatant using HPLC and assess for functionality using CAS assays. Furthermore, purified NRPs will be subjected to structural analyses were possible. A comparison between the non-ribosomal peptides from *M. ruminantium* and those purified from the heterologous gene expression system will allow upscaling the production of NRPs and derivatives thereof.

Example 6

Vaccination of Sheep Using Candidate Proteins Identified from the *M. ruminantium* Genome and Other Rumen Methanogens Experiments are being performed to use up to ten selected gene targets from *M. ruminantium* for heterologous expression, vaccinate sheep and test resulting serum antibodies against methanogen cultures. The first step in identifying candidate proteins for vaccine development is to determine which *M. ruminantium* proteins are cell surface-located and potentially accessible to antibody binding. In silico analysis of the *M. ruminantium* M1 open reading frames (ORFs) identified an initial pool of 572 ORFs containing one or more transmembrane helices (TMH) or signal peptide (SP) indicating a cell membrane or cell surface location. Those ORFs with a top BLAST hit to a non-methanogen or with no homology to the non-redundant database were removed and adhesin-like ORFs were dealt with separately. This gave a new total of 337 ORFs. Examination of the remaining 337 ORFs, assessing their predicted function, degree of conservation among methanogens and the nature of their transmembrane structures, refined the list to 71 ORFs (Leahy et al., 2010). Heterologous expression of membrane proteins with more than 4 TMHs has been difficult in reverse vaccinology studies of other microbes, so a cut-off of 4 THMs was applied to define two final groups: Group A with 47 ORFs with 4 or fewer TMHs suitable for cloning and heterologous expression studies; and Group B composed of 24 ORFs with more than 4 TMHs more suitable for a synthetic peptide-directed vaccine approach (see below).

*M. ruminantium* Surface and Membrane Proteins Selected as Vaccine Targets

| Functional Category and Locus tag | Annotation |
|---|---|
| Energy Metabolism | |
| mru0697 | AhaK |
| mru1405*, 1406*, 1407, 1408, 1411, 1412 | EhaHGFEAB |
| mru2006, 2007, 2008, 2010, 2012, 2013 | EhbIHGECB |
| mru1917, 1918, 1921*, 1922*, 1923* | MtrGFCDE |
| Protein Fate | |
| mru0239 | SecG |
| mru0482 | SecE |
| mru1234* | type IV leader peptidase family protein |
| Vitamins & Cofactors | |
| mru0540 | CbiN1 |
| Hypothetical | |
| mru0542*, 0840*, 1693, 2156*, 0233, 0234*, 0330, 1021, 1144, 1231, 1480*, 1585, 1635*, 1955, 2015*, 2046*, 2056, 2146* 0529 0081, 0196, 0225*, 0328*, 0412, 0428*, 0499, 0596, 0597, 0693, 0832, 1098, 1385, 0147, 0377*, 1375*, 1641, 0543, 0833, 1991, 0545*, 0716*, 0718*, 0838, 0968, 1232, 1550, 1884*, 2202, 1694 | Hypothetical proteins |

*ORFs ≥ 5 TMHs

Many of these candidate genes correspond to proteins whose function is under investigation. However, some are involved in energy production and are therefore prime candidates for vaccine development (FIG. 11). Of particular interest are the membrane-embedded ATP synthase enzyme complex which generates ATP from either a sodium or proton gradient (Aha), the $H_4MPT$ methyl transferase enzyme complex that catalyses the second to last step in the methanogenesis pathway (Mtr) and two membrane-bound energy converting [Ni—Fe] hydrogenases (Eha and Ehb).

The $H_4MPT$ methyl transferase enzyme complex is the penultimate step in the methanogenesis pathway. The methanogenic archaea use this pathway to generate energy (FIG. 11). The first five steps result in the sequential reduction of $CO_2$ by electrons sourced from $H_2$ to form N5-methyl-H4MPT, then the methyl group is transferred to coenzyme M via the action of the methyl-H4MPT:CoM-methyltransferase. Mtr is made up of multiple enzyme subunits (Mtr E, D, C, B, A, F, G, H; FIG. 33) and couples the methyl transfer reaction to the efflux of $Na^+$ ions out of the methanogen cell. This creates a $Na^+$ gradient that is used, either directly, or via a $Na^+$-$H^+$ antiporter, to drive ATP synthesis. Our analyses indicate that Mtr subunits are sufficiently conserved and specific to methanogens to be prime candidates for vaccine development. Therefore we are sub-cloning and expressing these subunits in order to obtain protein to vaccinate into sheep.

In order to clone the genes into the pTrc99A vector, 2 pairs of primers were designed for each of the 9 target ORFs (8 individual subunits and complete operon-mtrED-CBEFGH). One set of primers introduces a His (6×Histidine) tag to the N-terminal of the translated proteins, while the other set of primers do not include this tag. The primers were designed for insertion of the fragments between the NcoI site and XbaI site of the pTrc99A vector. Each open reading frame (ORF) from the mtr operon was amplified from *M. ruminantium* M1 genomic DNA, and ligated into the appropriately digested vector. The ligation products were transformed into DH5$^{\alpha}$ competent cells and insert-containing colonies were selected and analysed to verify insertion of the correct gene. In order to improve the chances of mtr gene expression, a codon-optimised mtr construct was designed for synthesis by GENEART (Germany) and cloned into pTrc99A. Each mtr gene contains an RBS site, an N-terminal 6×His tag, a TEV protease cleavage site, and is flanked by unique restriction site compatible with sub-cloning individual synthetic ORFs into the pTrc99A.

The table below summarises the mtr gene cloning and expression results. All 9 ORFs were successfully amplified with the two pairs of primers, giving 18 constructs, of which 17 were successfully cloned into the pTrc99A vector. All constructs were sequenced to confirm correct gene inserts.

Mtr Cloning and Expression

| Constructs | Cloned | Sequenced | Expression |
|---|---|---|---|
| mtrA-His | ☑ Yes | ☑ Yes | In progress |
| mtrB-His | ☑ Yes | ☑ Yes | In progress |
| mtrC-His | ☑ Yes | ☑ Yes | ☑ Yes |
| mtrD-His | ☑ Yes | ☑ Yes | In progress |
| mtrE-His | ☑ Yes | ☑ Yes | In progress |
| mtrF-His | ☑ Yes | ☑ Yes | In progress |
| mtrG-His | ☑ Yes | ☑ Yes | In progress |
| mtrH-His | ☑ Yes | ☑ Yes | ☑ Yes |
| mtrEDCBAFGH-His | ☑ Yes | ☑ Yes | In progress |
| mtrA | ☑ Yes | ☑ Yes | In progress |
| mtrB | ☑ Yes | ☑ Yes | In progress |
| mtrC | ☑ Yes | ☑ Yes | In progress |
| mtrD | ☑ Yes | ☑ Yes | In progress |
| mtrE | ☑ Yes | ☑ Yes | In progress |
| mtrF | ☑ Yes | ☑ Yes | In progress |
| mtrG | ☑ Yes | ☑ Yes | In progress |
| mtrH | ☑ Yes | ☑ Yes | ☑ Yes |

Only the complete mtr operon without the 6×His tag failed to clone from the PCR product. Expression of all 17 mtr constructs has been obtained using the expression host OverExpress C41 (DE3) (Lucigen) cells grown in YT medium and induced by IPTG at either 37° C. or 30° C. MtrH with or without the 6×His tag was successfully overexpressed, and there also appeared to be some mtrH expression from the mtrEDCBAFGH-His construct (FIG. 34).

The MtrC construct with 6×His tag had low level expression in the OverExpress C43 (DE3) (Lucigen) expression host (FIG. 35). After lysis of the cells expressing the mtrH and mtrC proteins, the two proteins were solubilised and put through the nickel columns for purification, but the proteins did not bind well to the columns, preventing column purification. The codon-optimised mtr synthetic construct has also been tested for expression in OverExpress C43 (DE3) (Lucigen) cells in YT medium, and Rosetta II (DE3), OverExpress C43 (DE3), OverExpress C41 (DE3), OverExpress C43 (DE3) pLysS, OverExpress C41 (DE3) pLysS cells in auto-induction medium (ZYP5052). No expression from any of the mtr genes was detected under any of these conditions. Further expression of codon-optimised mtr synthetic construct in Rosettall (DE3) and induction temperature at 20 to 37° C. for a range of induction times (4 to 16 hrs), with IPTG concentration ranging from 0.1 mM to 1 mM is being assessed. We also plan to sub-clone each of the individual mtr subunits from the synthetic construct and obtain expression individually.

Example 7

Vaccination of Sheep Using Cell Surface Protein Fractions Isolated from *M. ruminantium* Cells Traditional vaccine development against bacteria relies on using cell fractions to elicit antigenic responses in the host animal. This approach, while generally accepted, carries the inherent risk of contamination from other cell fractions. As an alternative to traditional cell fractionation, cell surface proteins isolated via non-destructive treatment are investigated for their ability to create effective and specific antigens. Chaotropic salts, such as guanidine hydrochloride, have been widely used to remove non-covalently bound proteins such as S-layers from the cell surface, while maintaining viable microbial cells.

In our experiments, *M. ruminantium* M1 cells have been subjected to chaotropic salt treatment removing non-covalently bound proteins from the cell surface. In a second step the treated methanogen cells have been subjected to a trypsin digest. This cleaved off exposed protein epitopes from the cell surface, without disrupting the cell wall or cell membrane. For this protocol, *M. ruminantium* M1 cells were grown in RM02 media for 7 days. The culture was then centrifuged to spin down the cells and the supernatant discarded. The cell pellet was washed three times in sterile distilled water, resuspended in 2 mL of 4M guanidine-HCl pH 7.0 and incubated at 37° C. for 1 hour. The suspension was centrifuged in a microfuge at 13 000 rpm. The supernatant (containing non-covalently bound surface proteins) was carefully removed and dialysed twice against 100 mM ammonium bicarbarbonate buffer (pH 8). A sample was run on an SDS-PAGE to estimate number and quantity of isolated proteins.

These samples have been used in a sheep vaccination trial. A Western blot analysis of M1 cell fractions against sheep antisera from the trial has been carried out and a significant level of cross-reaction has been observed (FIG. 36).

A trypsin digest was then carried out for both the non-covalently bound isolated proteins and the exposed cell-surface epitopes. This digest also served to prepare the samples for subsequent MALDI-TOF analyses. Trypsin was added at an approximate ratio of 1:50 relative to estimated amount of protein (based on SDS-PAGE). 10% (v/v) HPLC grade acetonitrile was added and the samples were incubated at 37° for 12 hours. The digests were centrifuged, supernatants were collected and subsequently dialysed against 100 mM ammonium bicarbonate buffer (pH 8). Where appropriate, DTT (dithiothreitol) was added to a final concentration of 50 mM and the samples were incubated at 60° C. for 30 minutes to reduce disulphides. IAM (iodoacetamide) was then added to a final concentration of 150 mM and samples were incubated in the dark at room temperature for 30 minutes. DTT and IAM were removed from the sample by dialysis or washing with 100 mM ammonium bicarbonate buffer (pH 8). Both preparations were sent to Dr Stefan Clerens (AgResearch, Lincoln) for MALDI-TOF.

Protein fragments were subsequently compared to the non-redundant amino-acid database hosted by NCBI and a custom ORFeome based *M. ruminantium* database (Leahy et al., 2010), associating epitopes with their respective ORFs.

Six independent culture trials were conducted, including cells from normal growth conditions, cells from medium supplemented with methanol and cell subjected to oxygen stress. A total of 57 fragments could be assigned to their respective *M. ruminantium* M1 genes (see table, below). It is noteworthy that a significant level of variety in identified ORFs was encountered in between the individual protein isolations. This may be caused by a sensitive and rapid adaptation of *M. ruminantium* to even small changes in culture conditions. Notable targets such as adhesion-like proteins or an ABC transporter substrate-binding protein were detected which will be merged into the priority target list. Interestingly, a number of cytosolic proteins (i.e., ribosomal proteins and other predicted highly expressed genes) were also detected, indicating a certain amount of ongoing cell lysis during the sample preparation. In this context, we also identified the M1 bacteriophage φmru integrase protein, pointing to a continued phage lysis process. This is supported by the detection of φmru particle in culture supernatant during normal growth conditions. The active prophage not only points to a highly stressed *M. ruminantium* cell condition but also may cause an altered biochemical and phenotypical profile.

It therefore is important to improve culture conditions and also develop a prophage-free strain that lacks the potential of accelerated and uncontrolled cell lysis. Consequently, we have initiated a phage curing experiment which aims to create a phage-free *M. ruminantium* derivative. Because *M. ruminantium* cannot be cultivated on solid media traditional phage curing methods cannot be employed. We have therefore opted for an evolutionary approach that uses ProteinaseK to remove free phage particles and continuous minimal subculturing. We will enrich for a prophage-free *M. ruminantium* population that eventually evolves in a fully cured derivative. This derivative would then also be used in further experiments, such as the assessment of the prophage ϕmru. Most interestingly, we were also able to identify the M1 NRPS1 gene product, indicating that the NRPS system can be active and expressed under laboratory growth conditions.

List of Open Reading Frames Identified by MALDI-TOF Analyses.

| ORF number | Annotation | Count |
|---|---|---|
| 82 | Adhesin-like protein+ | 1 |
| 113 (1228) | Exopolysaccharide biosynthesis polyprenyl glycosylphosphotransferase^ | 1 |
| 115 | RadA DNA repair and recombination protein+ | 1 |
| 117 | HdrA CoB-CoM heterodisulfide reductase subunit A*** | 7 |
| 201 | ModA molybdate ABC transporter substrate-binding protein+ | 1 |
| 205 | Copper ion binding protein^ | 1 |
| 247 | ThiC1 thiamine biosynthesis protein*** | 7 |
| 256 | Phage integrase*** | 5 |
| 326 | Adhesin-like protein*** | 2 |
| 333 | FdhA1*** | 3 |
| 334 | FdhB1*** | 3 |
| 351 | Nrps1+ | 1 |
| 455 | Acetyltransferase+ | 1 |
| 481 | FtsZ cell division protein+ | 1 |
| 498 | Fbp fructose 1,6-bisphosphatase*** | 3 |
| 520 | Translation elongation factor aEF-1 beta+ | 1 |
| 526 | Hmd coenzyme F420-dependent N(5),N(10)-methenyltetrahydromethanopterin reductase*** | 5 |
| 550 | PorA pyruvate ferredoxin oxidoreductase alpha subunit*** | 4 |
| 551 | PorB pyruvate ferredoxin oxidoreductase beta subunit*** | 2 |
| 569 | Mer 5,10-methylenetetrahydromethanopterin reductase*** | 7 |
| 582 | PhoU phosphate uptake regulator PhoU*** | 2 |
| 595 | PurP+ | 1 |
| 629 | Hypothetical protein+ | 1 |
| 735 | Rbr1+ | 1 |
| 727 (2191) | Adhesin-like protein with cysteine protease domain^ | 1 |
| 774 | Archaeal histone+ | 1 |
| 816 | HdrC CoB-CoM heterodisulfide reductase subunit C*** | 6 |
| 817 | HdrB*** | 3 |
| 851 | Rpl3p ribosomal protein L3P+ | 1 |
| 872 | Rps5p ribosomal protein S5P+ | 1 |
| 949 | BtcC bicarbonate ABC transporter substrate-binding protein*** | 8 |
| 1052 | Transcriptional regulator+ | 1 |
| 1091 | SucD^ | 2 |
| 1490 | Ribosomal protein L7Ae+ | 1 |
| 1228 | Hypothetical protein^ | 1 |

-continued

| ORF number | Annotation | Count |
|---|---|---|
| (113) | | |
| 1371 | Hypothetical protein+ | 1 |
| 1491 | Archaeal histone*** | 8 |
| 1499 | Adhesin-like protein with transglutaminase domain+ | 1 |
| 1570 | Acs, ADP-dependent acetyl-CoA synthetase*** | 5 |
| 1645 | Thermosome subunit*** | 2 |
| 1683 | Hypothetical protein*** | 3 |
| 1686 | Archaeal histone*** | 2 |
| 1691 | MoaA molybdenum cofactor biosynthesis protein+ | 1 |
| 1730 | Heat shock protein Hsp20+ | 1 |
| 1805 | Translation elongation factor aEF-1 alpha*** | 7 |
| 1836 | Cell shape determining protein MreB/MrI family*** | 3 |
| 1888 | PycB+ | 1 |
| 1897 | PpsA1 phosphoenolpyruvate synthase+ | 1 |
| 1900 | Hypothetical protein+ | 1 |
| 1901 | Peptidyl-prolyl cis-trans isomerase+ | 1 |
| 1906 | MvhA methyl viologen-reducing hydrogenase alpha*** | 7 |
| 1907 | MvhG methyl viologen-reducing hydrogenase gamma*** | 4 |
| 1916 | MtrH tetrahydromethanopterin S-methyltransferase*** | 9 |
| 1919 | MtrA1 tetrahydromethanopterin S-methyltransferase*** | 4 |
| 1920 | MtrB tetrahydromethanopterin S-methyltransferase+ | 1 |
| 1921 | MtrC tetrahydromethanopterin S-methyltransferase*** | 2 |
| 1924 | McrA methyl-coenzyme M reductase alpha subunit*** | 5 |
| 1925 | McrG methyl-coenzyme M reductase gamma subunit*** | 12 |
| 1928 | McrB methyl-coenzyme M reductase beta subunit*** | 9 |
| 1993 | CBS domain-containing protein+ | 1 |
| 1994 | CBS domain-containing protein*** | 8 |
| 2022 | Ftr2 formylmethanofuran-tetrahydromethanopterin formyltransferase*** | 7 |
| 2074 | FdhA2 formate dehydrogenase alpha chain+ | 1 |
| 2110 | IlvC ketol-acid reductoisomerase+ | 1 |
| 2121 | Hcp hydroxylamine reductase*** | 5 |
| 2131 | Fae/Hps bifunctional formaldehyde-activating enzyme/3-hexulose-6-phosphate synthase+ | 1 |
| 2142 | Mtd F420-dependent methylenetetrahydromethanopterin dehydrogenase*** | 11 |
| 2159 | TrpB2 tryptophan synthase beta subunit*** | 6 |
| 2191 (727) | CDP-glycerol:poly(glycerophosphate) glycerophosphotransferase^ | 1 |

ORF number indicates the respective locus tag within the *M. ruminantium* M1 genome;
Annotation shows the corresponding functional annotation;
Count highlights the number of occurrences found for each ORF throughout the six individual runs.
***ORFs found multiple times,
+unique hits,
^Hits with sequence mismatch to M1 deduced aa sequences. ORF numbers in brackets indicate ambiguous hits.

Example 8

Expression and Purification of Enzymes from the Methanogen *M. ruminantium* for the Discovery of Inhibitors Novel inhibitors have great potential to provide mitigation of the greenhouse gas methane from ruminants. This area of research has significance in the stabilisation of greenhouse gas concentrations in the atmosphere to prevent climate change. The principal methane forming organisms in the rumen are archaea belonging to the genus *Methanobrevibacter*. We are targeting genes of rumen methanogens for cloning and expression in *E. coli* with the aim of obtaining purified enzymes that can be used for: high-throughput screening (HTS) assays of chemical compound libraries; and in silico screening of inhibitors. The majority of the targets are from five main functional classes; methanogenesis/energy metabolism, central carbon metabolism, cofactor synthesis, cell wall synthesis and lipid synthesis. Work will continue to advance the targets through the pipeline. This project brings together diverse disciplines including chemogenomics, in silico modelling, structural biology, and the in vitro biological screening of targeted compounds to formulate the development of potent anti-methanogen compounds that are non-toxic to host ruminant animals and have negligible environmental impact.

Our aim is to discover small molecule inhibitors of methanogens, based on genomics, biochemistry, and structural biology. This is a powerful means to search for inhibitors of methanogens, which are difficult to culture and are not amenable to high-throughput screening with cells. In this study, a number of enzymes from *Methanobrevibacter ruminantium* were found to be solubly expressed in *E. coli* e.g. 3-hydroxy-3-methylglutaryl-CoA reductase (HMGR), methenyltetrahydromethanopterin cyclohydrolase (MCH), 3-hexylose-6-phosphate isomerise (PHI) and bifunctional formaldehyde-activating enzyme/3-hexylose-6-phosphate synthase (FAE/HPS). HMGR catalyzes the rate-limiting step in the synthesis of isoprenoid units, which are components of archaeal membrane lipids. MCH is an enzyme involved in the methanogenesis pathway. PHI and FAE/HPS are key enzymes of the ribulose monophosphate pathway, used by methanogens to generate ribose for nucleotide synthesis.

As a first step, we made a selection of targets. Information from literature and genome of *Methanobrevibacter ruminantium* (Leahy et. al., 2010) was studied and 34 targets (see table in Example 9, below) were chosen. Next, we carried out cloning in *E. coli*. Genes were amplified and cloned into expression vector pET151D (Invitrogen). Plasmids were used to transform *E. coli* BL21-Rosetta 2 cells (Novagen). From this, 27 positive clones (see table, below) were obtained. We then looked for expression of recombinant proteins. Cells were grown in auto induction medium ZYP-5052 (Studier, 2005), with shaking at 25° C. or 30° C. for approx 16 hr. Cells were lysed using lysozyme at 4° C. The hexa-histidine-tagged enzymes were then purified from cell free extracts by nickel-affinity chromatography. Imidazole was removed and buffer was exchanged. We found 15 proteins were expressed while 10 (12) were soluble (see table, below). Clones that failed to express were grown in LB media induced with IPTG. Clones with insoluble expression were subjected to varying lysis conditions. To overcome the lack of expression in some clones, the genes have been synthesised for optimum expression in *E. coli* (GeneArt).

Biochemical characterisation of HMGR has also been carried out. This included assays to measure the oxidation of NADHP (366 nm, ε3,300 M-1 cm-1), which were performed at 37° C. Activity was expressed in U mg-1 of enzyme. One unit was defined as the turnover of one μmol of NADPH per minute (2 NADPH molecules are required to reduce 1 HMG-CoA). Standard assays contained 50 mM BTP (Bis-Tris propane) pH 6.5, 400 mM NaCl, 0.05 mM DTT, 2.5% glycerol, 338 μM NADPH and 250 μM (R,S)-HMG-CoA. Prior to use, the enzyme stock (0.6 mg/mL) was incubated in 400 mM NaCl and 10 mM DTT for 2 hours at 4° C. and for 20 minutes at 37° C. then kept on ice. Assays were carried out in duplicate. HMGR was susceptible to oxidation and could be reactivated by incubation with 10 mM dithiothreitol for two hours. Highest activity was found at pH 6.5 and at 0.4-1.5 M NaCl. HMGR was able to oxidize NADPH but not NADH. The enzyme had Km values of 165±35 and 12.4±1.83 μM for NADPH and HMG-CoA, respectively. The statins simvastatin and lovastatin inhibit HMGR with high Kic values of 3.7±0.65 and 8.5±1.1 μM, respectively. Statins have previously been shown to inhibit the growth of strains of rumen *Methanobrevibacter* (Wolin and Miller, 2006). Notably, structure-based alignment showed that the enzyme is a Class I HMGR.

Example 9

In Silico Modelling of Enzymes from the Methanogen *Methanobrevibacfer ruminantium* for the Discovery of Novel Inhibitors Analysis of the *Methanobrevibacter ruminantium* genome (Leahy et. al., 2010) has revealed archaeal and methanogen-specific enzyme pathways involved in methane production, energy metabolism, protein, lipid, cofactor and cell wall synthesis. Making comprehensive use of this genomic data, essential protein targets have been analysed based on already available structural data of related enzymes for homology modelling, or when possible, purified protein has been submitted to protein crystallisation trials for x-ray structure determination.

The presence of published crystal structures that are similar in sequence is a factor for selecting targets, due to the fact that they can be used to guide the determination of our own crystal structures, thus saving time. In addition, high-resolution structures can also be used as models to develop inhibitors, as is now being performed. For example, ODcase (orotidine-5'-phosphate decarboxylase; PyrF) is a key enzyme in the biosynthesis of the pyrimidine uridine-5'-monophosphate (UMP) (Nyce and White. 1996). ODcase from other sources have provided crystal structures and high-quality work on developing inhibitors as part of its kinetic characterisation (Wu and Pai, 2002; Poduch et al., 2006; Poduch et al., 2008; Fujihashi et al., 2009; Bello et al., 2007). Other researchers are using ODcase for the development of novel anti-pathogenic compounds based on small differences between the pathogen and mammalian structures (Bello et al., 2007). There are over 40 crystal structures for methanogen ODcases. Similarly, HMG CoA reductase from other sources has been identified as the presumed target of statins (Miller and Wolin, 2001). The work of Miller and Wolin validated HMG CoA reductase as a target in methanogens, and indeed, the entire mevalonate pathway for lipid synthesis. There are >20 HMG CoA reductase crystal structures available.

The target sn-glycerol-1-phosphate dehydrogenase (NAD(P)-dependent glycerol-1-phosphate dehydrogenase, EgsA) is a well known archaeal enzyme that forms the stereo-specific glycerol-1-phosphate backbone for archaeal lipids (Koga and Morii, 2007). GGPS (geranylgeranylphosphate synthase) is another lipid synthesis enzyme that is being targeted as it also has an archaeal stereospecific catalytic site (Koga and Morii, 2007). A crystal structure is available for a methanogen GGPS (Payandeh et al. 2006). As another example, DAPDC (diaminopimelate decarboxylase; LysA) helps catalyse the formation of lysine which is a key cross-linking component of *M. ruminantium* cell walls. Lysine is an essential amino acid in mammals and therefore the lysine biosynthesis pathway has been targeted for the development of novel antibiotics (Hutton et al., 2007). A crystal structure is available for DAPDC (Ray et al., 2002). The methanopterin biosynthesis pathway enzyme RFA-P synthase has been validated as a target in other systems, and a vast array of potential inhibitors have been identified (Dumitru et al., 2003; Dumitru and Ragsdale, 2004; Scott and Rasche, 2002; Miner et al., 2003). The methanopterin pathway enzyme CitG is presumed to be essential and is nearly-methanogen specific (Chistoserdova et al., 2003, Chistoserdova et al., 2004, Schneider et al., 2000). HisAF is also indicated to be part of the methanopterin pathway (Chistoserdova et al., 2003, 2004).

The F420 biosynthesis pathway includes the targets of CofA, PLT (CofD), CofC (PLGT), and creatinine amidohydrolase (CA) and FucA are nearly methanogen-specific and presumed to be essential for methanogen survival (Graham and White 2002). Most of the remainder of the F420 pathway is also being targeted. A crystal structure is available for PLT (Forouhar et al. 2008). Several methanogenesis pathway enzymes are included which are encoded by single genes. These are essential for survival and there are crystal structures for all four (Hiromoto et al., 2009; Shima et al., 2008; Grabarse et al., 1999; Aufhammer et al., 2005; Hegemeier et al., 2003). The Coenzyme M (CoM) pathway is also thought to be essential for survival and crystal structures are available for ComA and ComC (Irimia et al. 2004; Wise et al. 2003). The Coenzyme B biosynthesis pathway is the only methanogen cofactor pathway that is fully methanogen-specific and should be absolutely essential (Graham and White, 2002). Despite this, all the known enzymes (AksA, AksD, AksE and AksF) share significant homology with bacterial proteins, and three have some homology with mammalian enzymes (AksD, AksE and AksF have some homology with mammalian aconitase subunits and/or isocitrate dehydrogenase).

The RuMP, or ribulose monophosphate pathway, is used by methanogens to generate ribose for nucleotide synthesis. Although it is not methanogen-specific it is only found in a very limited number of organisms and these are not typically found in the rumen (Werken et al., 2008; Growchowski and White, 2005). Several of the key enzymes of the pathway are of interest, and in *M. ruminantium* two of these are linked to form a bifunctional enzyme (HPS-FAE, formaldehyde-activating enzyme/hexylose-6-phosphate synthase). Phi1 (hexylose-6-phosphate isomerase) is also being targeted and is also part of the RuMP pathway. Interestingly, *M. ruminantium* also, has another Phi (Phi2), although sequence analyses suggests that Phi1 is the more likely to be involved in the RuMP pathway. A methanogen crystal structure is available for Phi (Martinez-Cruz et al., 2002).

The targets Mur 53, 78, 520, 873 and 874 are murein ligases involved in synthesising the amino acid peptide linkages of the cell walls of members of the *Methanobacteriales*. Murein ligases are also found in bacteria. Disruption of cross-linking peptide biosynthesis would be akin to discovering an 'anti-methanogen antibiotic' with similar effects to penicillin-like drugs (Zoeiby et al., 2003; Hartmann and König, 1990). Most of these, methanogen murein ligases (53, 520, 873 and 874) are quite distinct from their bacterial homologues, whereas Mur 78 retains quite high levels of homology with its bacterial counterparts. Interestingly, Mur 520 is also found in some *Methanococci* and *Methanosarcina*. Bacterial murein ligase structures (>40) are available that could be used as scaffolds for performing molecular replacement, thus aiding future structure determination of the methanogen enzymes.

Several enzymes are targeted as they are considered 'key' enzymes that are central to metabolism (gluconeogenesis that is required for amino acid, cell wall sugar synthesis, DNA and RNA synthesis and the TCA cycle), and therefore essential. Most of these have relatively easy spectrophotometric assays (Acs, PEP syn, AcsA, SdhA/SdhB). Acs and SdhA/B have archaeal-specific features (Bobik and Wolfe, 1989; Musfeldt and Schönheit, 2002). GatD and GatE are involved in translation and are archaeal-specific and provide glutaminyl-tRNA for protein synthesis (Possot et al. 1988). tRNA synthetases have been successfully targeted for the development of novel antibiotics (Ahel et al. 2005). There is a methanogen crystal structure for GatD/E (Oshikane et al. 2006).

The current targets (see below) represent 12 different cellular processes or metabolic pathways with a large share (16 targets) being derived from methanogen cofactor synthesis pathways. Taking everything into consideration, methanogen cofactors represent strong targets overall as they are typically restricted to methanogens, are likely to be essential and the cofactors themselves are fairly small molecules. Advantages of small molecules are that it can be easier to synthesise substrates for enzyme assays and easier to synthesise potential inhibitors that share similar structural features. Due to potential off-target effects, we have decided to avoid most vitamin synthesis pathways as almost all of the methanogen enzymes have counterparts in bacteria and therefore, inhibitors would have a high chance of also inhibiting beneficial rumen bacteria.

Current Chemogenomics Targets

| Target | pathway | PCR | clone | expressed/soluble | Pure | X-tal | comments |
|---|---|---|---|---|---|---|---|
| ODcase (PyrF) | pyrimidines | no | | | | | early target |
| HMG CoA red | lipids | yes | yes | yes/yes | yes | yes | early target |
| sn-G1P deh2 | lipids | yes | yes | no | | | GA; early target |
| DAPDC (LysA) | lysine/CW | yes | yes | yes/yes | yes | | early target |
| RFA-P (MptG) | methanopterin | yes | yes | yes/no | | | GA |
| PLT (CofD) | F420 | yes | yes | no | | | GA |
| CofA(1093) | F420 | yes | yes | | | | GA |
| FucA | F420 | yes | yes | yes/yes | | | |
| Phi1 | RuMP | yes | yes | yes/yes | yes | yes | |
| Hmd | methanogenesis | yes | yes | no | | | GA |
| Mch | methanogenesis | yes | yes | yes/yes | yes | yes | |
| Mer | methanogenesis | yes | yes | yes/no | | | GA |
| Mtd | methanogenesis | yes | yes | | | | GA |
| AksA | Coenzyme B | yes | | | | | |
| AksD | Coenzyme B | yes | yes | yes/no | | | |
| AksE | Coenzyme B | yes | | | | | |
| AksF | Coenzyme B | yes | yes | no | | | |
| CitG | methanopterin | yes | yes | yes/yes | | | |
| ComA (Homolog) | coenzyme M | yes | yes | yes/yes | | | |
| ComB (Homolog) | coenzyme M | yes | yes | no | | | GA |
| ComC (Homolog) | coenzyme M | yes | yes | yes/yes | yes | | |
| ComD (Homolog) | coenzyme M | yes | yes | no | | | GA |
| ComE (Homolog) | coenzyme M | yes | yes | no | | | GA |

| Target | pathway | PCR | clone | expressed/ soluble | Pure | X-tal | comments |
|---|---|---|---|---|---|---|---|
| Hps-Fae | RuMP | yes | yes | yes/yes | yes | yes | |
| Acs | key enzyme | yes | | | | | |
| AcsA | key enzyme | yes | | | | | |
| PEP syn | key enzyme | yes | yes | yes/yes | | | |
| GGPS | lipids | yes | yes | yes/ some | | | |
| SdhA | TCA | yes | | | | | |
| SdhB | TCA | yes | | | | | |
| Mur 53 | cell wall | yes | yes | | | | GA |
| Mur 78 | cell wall | yes | yes | yes/ some | yes | | |
| Mur 520 | cell wall | yes | yes | | | | |
| Mur 873 | cell wall | no | | | | | GA |
| Mur 874 | cell wall | no | | | | | GA |
| GatD | translation | yes | yes | | | | |
| GatE | translation | yes | | | | | |
| CofC | F420 | no | | | | | |
| CA | F420/riboflavin | no | | | | | |
| HisAF | methanopterin | no | | | | | |

GA, gene synthesised by GeneArt and will be recloned;
CA, creatinine amidohydrolase For specific experiments, in silico screening of large commercial compound libraries using the docking programme GOLD (Verdonk et. al., 2003; Cole, J. C. et. al., 2005) has formed the basis of our selection and design of high affinity ligands for our modelled proteins. Work is currently underway for evaluating the essential methanogen enzyme methyl-coenzyme M reductase (MCR), an enzyme that catalyzes the terminal step in methane production. A number of enzymes are being crystallised and include 3-hydroxy-3-methylglutaryl-CoA reductase (HMGR), the rate-limiting step in the synthesis of isoprenoid units, which are components of archaeal membrane lipids. Others include 3-hexylose-6-phosphate isomerase (PHI), a key enzyme of the ribulose monophosphate pathway and methenyltetrahydromethanopterin cyclohydrolase (Mch), an enzyme involved in the methanogenesis pathway.

The programme GOLD (Verdonk et. al., 2003; Cole, J. C. et. al., 2005) has been tasked in carrying out the in silico docking process in order to obtain novel inhibitors of archaeal and methanogen-specific enzymes, in particular MCR (Grabarse et. al., 2001; FIG. 37A). MCR has an α2β2γ2 subunit structure which contains two nickel porphinoid F430 rings which forms the centre of enzyme activity and two molecules each of methylcoenzyme M (CoM) and coenzyme B (CoB). These cofactors operate under strictly anaerobic conditions to carry out the final reaction of the energy conserving pathway of methanogenic archaea in which CoM and CoB are converted to methane and the heterodisulfide product CoM-S-S-CoB (FIG. 37B). This product is subsequently reduced with H2 back to the thiol forms of the separate cofactors by heterodisulfide reductase.

A number of structural databases from commercial suppliers have been downloaded from the ZINC (Irwin and Shoichet, 2005) website hypertext transfer protocol://zinc.docking.org/index.shtml and screened with GOLD (Verdonk et. al., 2003; Cole, J. C. et. al., 2005). Commercial databases available from the zinc website such as Asinex, Chembridge building blocks and the LOPAC library of proven pharmacologically-active compounds were screened with MCR. Utilizing a ruminant model of MCR based on a crystal structure from Methanothermobacter marburgensis (pdb code 1HBM4) active site regions were subjected to specific and targeted docking attempts to find inhibitors that could mimic the natural substrates and product of the enzyme. The effectiveness of candidate inhibitors were then monitored in pure culture experiments. Cell density was measured over time to assess the effectiveness of potential inhibitors (FIG. 38).

Lengthy table referenced here

US09441016-20160913-T00001

Please refer to the end of the specification for access instructions.

Lengthy table referenced here

US09441016-20160913-T00002

Please refer to the end of the specification for access instructions.

Lengthy table referenced here

US09441016-20160913-T00003

Please refer to the end of the specification for access instructions.

Lengthy table referenced here

US09441016-20160913-T00004

Please refer to the end of the specification for access instructions.

Lengthy table referenced here

US09441016-20160913-T00005

Please refer to the end of the specification for access instructions.

Lengthy table referenced here

US09441016-20160913-T00006

Please refer to the end of the specification for access instructions.

Lengthy table referenced here

US09441016-20160913-T00007

Please refer to the end of the specification for access instructions.

Lengthy table referenced here

US09441016-20160913-T00008

Please refer to the end of the specification for access instructions.

Lengthy table referenced here

US09441016-20160913-T00009

Please refer to the end of the specification for access instructions.

Lengthy table referenced here

US09441016-20160913-T00010

Please refer to the end of the specification for access instructions.

Lengthy table referenced here

US09441016-20160913-T00011

Please refer to the end of the specification for access instructions.

Lengthy table referenced here

US09441016-20160913-T00012

Please refer to the end of the specification for access instructions.

Lengthy table referenced here

US09441016-20160913-T00013

Please refer to the end of the specification for access instructions.

REFERENCES

Abken H J, Tietze M, Brodersen J, Bäumer S, Beifuss U et al. (1998) Isolation and characterization of methanophenazine and function of phenazines in membrane-bound electron transport of *Methanosarcina mazei* Gö1. J Bacteriol 180: 2027-2032.

Acharya, P., Warkentin, E., Ermler, U., Thauer, R. K. & Shima, S. The structure of formylmethanofuran: tetrahydromethanopterin formyltransferase in complex with its coenzymes. J. Mol. Biol. 357, 870-879 (2006).

Ahel, D., Slade, D., Mocibob, M., S. D. & Weygand-Durasevic, I. Selective inhibition of divergent seryl-tRNA synthetases by serine analogues. FEBS Lett. 579, 4344-4348 (2005).

Ahel I, Stathopoulos C, Ambrogelly A, Sauerwald A, Toogood H et al. (2002) Cysteine activation is an inherent in vitro property of prolyl-tRNA synthetases. J Biol Chem 277:34743-34748.

Alex, L. A., Reeve, J. N., Orme-Johnson, W. H. & Walsh, C. T. Cloning, sequence determination and expression of the genes encoding the subunits of the nickel-containing 8-hydroxy-5-deazaflavin reducing hydrogenase from *Methanobacterium thermoautotrophicum*. Biochem. 29, 7237-7244 (1990).

Altermann E, Klaenhammer T R (2005) PathwayVoyager: pathway mapping using the Kyoto Encyclopedia of Genes and Genomes (KEGG) database. BMC Genomics 6:60-66.

Altermann E, Klaenhammer T R (2003) GAMOLA: a new local solution for sequence annotation and analyzing draft and finished prokaryotic genomes. Omics 7: 161-169.

Altschul S F, Madden T L, Schaffer A A, Zhang J, Zhang Z, Miller W, Lipman D J (1997) Gapped BLAST and PSI-BLAST: a new generation of protein database search programs. Nucleic Acids Research 25, 3389-3402.

Altschul, S. F., Gish, W., Miller, W., Myers, E. W. & Lipman, D. J. Basic local alignment search tool. Journal of molecular biology 215, 403-410 (1990).

Ambrogelly, A., Kamtekar, S., Stathopoulos, C., Kennedy, D. & Söll, D. Asymmetric behavior of archaeal proly-tRNA synthetase. FEBS Lett. 579, 6017-6022 (2005).

Ammelburg M, Hartmann M D, Djuranovic S, Alva V, Koretke K K et al. (2007) A CTP-dependent archaeal riboflavin kinase forms a bridge in the evolution of cradle-loop barrels. Structure 15:1577-9150.

Amoutzias, G. D., Van de Peer, Y. & Mossialos, D. Evolution and taxonomic distribution of nonribosomal peptide and polyketide synthases. Future Microbiol. 3, 361-370 (2008).

Amoutzias G D, Van de Peer Y, Mossialos D (2008) Evolution and taxonomic distribution of nonribosomal peptide and polyketide synthases. Future Microbiol 3: 361-370.

Anderson I, Ulrich L E, Lupa B, Susanti D, Porat I et al. (2009) Genomic characterization of Methanomicrobiales reveals three classes of methanogens. PLoS One 4:e5797.

Andreesen, J. R. & Makdessi, K. Tungsten, the surprisingly positively acting heavy metal element for prokaryotes. Ann. N.Y. Acad. Sci. 1125, 215-29 (2008).

Andries K., Verhasselt P., Guillemont J., Göhlmann. H. W., Neefs J. M., Winkler H., Van Gestel J., Timmerman P., Zhu M., Lee E., Williams P., de Chaffoy D., Huitric E., Hoffner S., Cambau E., Truffot-Pemot C., Lounis N., Jarlier V. A diarylquinoline drug active on the ATP synthase of *Mycobacterium tuberculosis*. Science 307, 223-227 (2005).

Angelaccio S, Chiaraluce R, Consalvi V, Buchenau B, Giangiacomo L et al. (2003) Catalytic and thermodynamic properties of tetrahydromethanopterin-dependent serine hydroxymethyltransferase from *Methanococcus jannaschii*. J Biol Chem 278:41789-97.

Ansorg, R., Rath, P-M., Runde, V. & Beelen, D. W. Influence of intestinal decontamination using metronidazole on the detection of methanogenic Archaea in bone marrow transplant recipients. Bone Marr. Transplant. 31, 117-119 (2003).

Asanuma N, Ishiwata M, Yoshii T, Kikuchi M, Nishina Y et al. (2005) Characterization and transcription of the genes involved in butyrate production in Butyrivibrio fibrisolvens type I and type II strains. Curr Microbiol 51:91-94.

Ataide, S. F. & Ibba, M. Small molecules: big players in the evolution of protein synthesis. ACS Chem. Biol. 1, 285-297 (2006).

Attwood, G. & McSweeney, C. Methanogen genomics to discover targets for methane mitigation technologies and options for alternative H2 utilisation in the rumen. Aust. J. Exper. Agric. 48, 28-37 (2008).

Attwood, G. T., Kelly, W. J., Altermann, E. H. and Leahy, S. C. Analysis of the Methanobrevibacter ruminantium draft genome: understanding methanogen biology to inhibit their action in the rumen. Aust. J. Exp. Agric. 48(2), 83-88 (2008).

Aufhammer S W, Warkentin E, Ermler U, Hagemeier C H, Thauer R K et al. (2005) Crystal structure of formylmethanofuran: tetrahydromethanopterin formyltransferase in complex with coenzyme F420: architecture of the F420/FMN binding site of enzymes within the nonprolyl cis-peptide containing bacterial luciferase family. Pro Sci 14:1840-1849.

Balch W E, Wolfe R S (1976) New approach to cultivation of methanogenic bacteria: 2-mercaptoethanesulfonic acid (HS-CoM)-dependent growth of Methanobacterium ruminantium in a pressurized atmosphere. Appl Environ Microbiol 32:781-791.

Balch W E, Fox G E, Magrum L J, Woese C R, Wolfe R S (1979) Methanogens: reevaluation of a unique biological group. Microbiological Reviews 43, 260-296.

Bambini, S. & Rappuoli, R. The use of genomics in microbial vaccine development. Drug discovery today 14, 252-260 (2009).

Baresi, L. and Bertani, G. (1984) Isolation of a bacteriophage for a methanogenic bacterium. In Abstracts of the Annual Meeting of the American Society for Microbiology. Washington D.C.: American Society for Microbiology, p. 133.

Barkley S. J., Cornish R. M. & Poulter, C. D. Identification of an Archaeal type II isopentenyl diphosphate isomerase in Methanothermobacter thermoautotrophicus. J. Bacteriol. 186, 1811-1817 (2004).

Bauer M, Lombardot T, Teeling H, Ward N L, Amann R I et al. Archaea-like genes for C1-transfer enzymes in Planctomycetes: phylogenetic implications of their unexpected presence in this phylum. J Mol Evol 59:571-586 (2004).

Becher, B., Muller, V. & Gottschalk, G. N5-methyltetrahydromethanopterin:coenzyme M methyltransferase of Methanosarcina strain Go1 is an Na(+)-translocating membrane protein. Journal of bacteriology 174, 7656-7660 (1992).

Beifuss, U., Tietze, M., Baumer, S. & Deppenmeier, U. Methanophenazine: Structure, Total Synthesis, and Function of a New Cofactor from Methanogenic Archaea This work was supported by the Deutsche Forschungsgemeinschaft (Sonderforschungsbereich 416; grants De 488/6-1 and De 488/4-2) and the Fonds der Chemischen Industrie. We are grateful to Drs. J. Paust and H. Jaedicke (BASF AG, Ludwigshafen) and Dr. R. K. Muller (Hoffmann-La Roche Ltd., Basel) for generously providing chemicals. Angewandte Chemie (International ed 39, 2470-2472 (2000).

Bello, A. M., Poduch, E., Fujihashi, M., Amani, M., Li, Y., Crandall, I., Hui, R., Lee, P. I., Kain, K. C., Pai, E. F., Kotra, L. P. A potent, covalent inhibitor of orotidine 5'-monophosphate decarboxylase with antimalarial activity. J. Med. Chem. 50, 915-21 (2007).

Bendtsen, J. D., Nielsen, H., von Heijne, G. & Brunak, S. Improved prediction of signal peptides: SignalP 3.0. Journal of molecular biology 340, 783-795 (2004).

Benson D A, Karsch-Mizrachi I, Lipman D J, Ostell J, Sayers E W (2009) Genbank. Nucleic Acids Res 37:D26-31.

Berk, H. & Thauer, R. K. Function of coenzyme F420-dependent NADP reductase in methanogenic archaea containing an NADP-dependent alcohol dehydrogenase. Archives of microbiology 168, 396-402 (1997).

Bhaysar, A. P. & Brown, E. D. Cell wall assembly in Bacillus subtilis: how spirals and spaces challenge paradigms. Molecular microbiology 60, 1077-1090 (2006).

Bickle, T. A. and D. H. Kruger. 1993. Biology of DNA restriction. Microbiol. Rev. 57:434-450.

Bobik, T. A. & Wolfe, R. S. An unusual thiol-driven fumarate reductase in Methanobacterium with the production of the heterodisulfide of coenzyme M and N-(7-mercaptoheptanoyl)threonine-O3-phosphate. J. Biol. Chem. 264, 18714-8 (1989).

Bock, A-K., Kunow, J., Glasemacher, J. & Schönheit, P. Catalytic properties, molecular composition and sequence alignments of pyruvate:ferredoxin oxidoreductase from the methanogenic archaeon Methanosarcina barkeri (strain Fusaro). Eur. J. Biochem. 237, 35-44 (1996).

Boekhorst J, de Been M W, Kleerebezem M, Siezen R J (2005) Genome-wide detection and analysis of cell wall-bound proteins with LPxTG-like sorting motifs. J Bacteriol 187: 4928-4934.

Bonanno J B, Edo C, Eswar N, Pieper U, Romanowski M J et al. Structural genomics of enzymes involved in sterol/isoprenoid biosynthesis: Proc Natl Acad Sci USA 98:12896-12901 (2001).

Born, T. L. & Blanchard, J. S. Structure/function studies on enzymes in the diaminopimelate pathway of bacterial cell wall biosynthesis. Curr. Opin. Chem. Biol. 3, 607-613 (1999).

Boucher, Y., Kamekura, M. & Doolittle, W. F. Origins and evolution of isoprenoid lipid biosynthesis in archaea. Molec. Microbiol. 52, 515-527 (2004).

Bouhss, A., Trunkfield, A. E., Bugg, T. D. & Mengin-Lecreulx, D. The biosynthesis of peptidoglycan lipid-linked intermediates. FEMS Microbiol. Rev. 32, 208-33 (2008).

Bredel, M. & Jacoby, E. Chemogenomics: an emerging strategy for rapid target and drug discovery. Nat Rev Genet 5, 262-275 (2004).

Bryant, M. P. Rumen methanogenic bacteria. In Dougherty, R. W., Allen, R. S., Burroughs, W., Jaskson, N. L. & McGillard (ed). Physiology of digestion of the ruminant, (1965) Butterworths Publishing Inc., Washington, D.C.

Bryant, M. P., Tzeng, S. F., Robinson, I. M. & Joyner, Jr. A. E. Nutritional requirements of methanogenic bacteria, p. 23-40. In F. G. Pohland (ed.), Anaerobic biological treatment processes. Advances in chemistry series 105. American Chemical Society, Washington, D.C. (1971).

Buckel, W. & Golding, B. T. Radical enzymes in anaerobes. Annu. Rev. Microbiol. 60, 7-49 (2006).

Bult C J, et al. (1996) Complete genome sequence of the methanogenic archaeon, Methanococcus jannaschii. Science 273, 1058-1073.

Campbell, J. W. & Cronan, Jr., J. E. Bacterial fatty acid biosynthesis: targets for antibacterial drug discovery. Annu. Rev. Microbiol. 55, 305-332 (2001).

Candela, T. & Fouet, A. Poly-gamma-glutamate in bacteria. Mol. Microbiol. 60, 1091-1098 (2006).

Caron P R, Mullican M D, Mashal R D, Wilson K P, Su M S et al. (2001) Chemogenomic approaches to drug discovery. Curr Opin Chem Biol 5: 464-470.

Chistoserdova L, Jenkins C, Kalyuzhnaya M G, Marx C J, Lapidus A et al. (2004) The enigmatic Planctomyctes may hold a key to the origins of methanogenesis and methylotrophy. Mol Biol Evol 21:1234-1241.

Chistoserdova, L., Che, S-W., Lapudis, A. & Lidstrom, M. E. Methylotrophy in *Methylobacterium extorquens* AM1 from a genomic point of view. J. Bacteriol. 185, 2980-2987 (2003).

Chistoserdova, L., Vorholt, J., Thauer, R. K. & Lidstrom, M. E. C1 transfer enzymes and coenzyme linking methylotrophic bacteria and methanogenic archaea. Science 281, 99-102 (1998).

Cole, J. C. et al. Virtual Screening in Drug Discovery (Eds. B. Shoichet, Alvarez), Taylor & Francis CRC Press, Boca Raton, Fla., USA (2005).

Coskun U, Grüber G, Koch M H, Godovac-Simmermann J, Lemker T et al. (2002) Cross-talk in the A1-ATPase from *Methanosarcina mazei*. Göl due to nucleotide binding. J Biol Chem 277:17327-17333.

Coskun U, Chaban Y L, Lingi A, Müller V, Keegstra W et al. (2004) Structure and subunit arrangement of the A-type ATP synthase complex from the archaeon *Methanococcus jannaschii* visualized by electron microscopy. J Biol Chem 279:38644-38648.

Coutinho P M, Henrissat B (1999) Carbohydrate-active enzymes: an integrated database approach. In 'Recent Advances in Carbohydrate Bioengineering' (Eds H J Gilbert, G Davies, B Henrissat and B Svensson) pp. 3-12 (The Royal Society of Chemistry, Cambridge) (Carbohydrate Active Enzymes database, hypertext transfer protocol:// world wide web.cazy.org/).

Daiyasu, H., Hiroike, T., Koga, Y. & Toh, H. Analysis of membrane stereochemistry with homology modeling of sn-glycerol-1-phosphate dehydrogenase. Prot. Eng. 15, 987-995 (2002).

Daniel, R. A. & Errington, J. Control of cell morphogenesis in bacteria: two distinct ways to make a rod-shaped cell. Cell. 2003 113, 767-76.

Daugherty, M., Vonstein, V., Overbeek, R. & Ostermann, A. Archaeal shikimate kinase, a new member of the GHMP-kinase family. J. Bacteriol. 183, 292-300 (2001).

de Kruijff, B., van Dam, V. & Breukink, W. Lipid II: a central component in bacterial cell wall synthesis and a target for antibiotics. Prostagland, Leukot. Essent. Fatty Acids 79, 117-121 (2008).

de Macario E. C. & de Macario A. J. L. Methanogenic archaea in health and disease: a novel paradigm of microbial pathogenesis. Internat. J. Med. Microbiol. 299, 99-108 (2009).

de Poorter, L. M. I., Geerts, W. G., Theuvenet, A. P. & Keltjens J. T. Bioenergetics of the formyl-methanofuran dehydrogenase and heterodisulfide reductase, reactions in *Methanothermobacter thermoautotrophicus*. Eur. J. Biochem. 270, 66-75. (2003).

de Ruyck, J. & Wouters, J. Structure-based design targeting biosynthesis of isoprenoids: a crystallographic state of the art of the involved enzymes. Curr. Pro. Pep. Sci. 9, 117-137 (2008).

Delcher A L, Harmon D, Kasif S, White O, Salzberg S L (1999) Improved microbial gene identification with GLIMMER. Nucleic Acids Research 27, 4636-4641.

Delcher, A. L., Salzberg, S. L. & Phillippy, A. M. Using MUMmer to identify similar regions in large sequence sets. Current protocols in bioinformatics/editorial board, Andreas D. Baxevanis et al. Chapter 10, Unit 10 13 (2003).

Deppenmeier, U. Redox-driven proton translocation in methnaogenic Archaea. Cell Mol. Life Sci. 59, 1513-1533 (2002).

Deppenmeier, U. The unique biochemistry of methanogens. Prog. Nucl. Acid. Res. Mol. Biol. 71, 223-283 (2002).

Dermouni, H. L. & Ansorg, R. A. M. Isolation and antimicrobial susceptibility testing of fecal strains of the archaeon *Methanobrevibacter smithii*. Chemother. 47, 177-183 (2001).

DiMarco, A. A., Bobik, T. A. & Wolfe, R. S. Unusual coenzymes of methanogenesis. Annu. Rev. Biochem. 59, 355-394 (1990).

DiMarco, A. A., Donnelly, M. I. & Wolfe, R. S. Purification and properties of the 5,10-methenyltetrahydromethanopterin cyclohydrolase from *Methanobacterium thermoautotrophicum*. J. Bacteriol. 168, 1372-1377 (1986).

Divakaruni, A. V., Baida, C., White, C. L. & Gober, J. W. The cell shape proteins MreB and MreC control cell morphogenesis by positioning cell wall synthetic complexes. Mol Microbiol. 66, 174-88 (2007).

Donnelly, M. I., Escalante-Semerena, J. C., Rinehart, K. L., Jr. & Wolfe R. S. Methenyl-tetrahydromethanopterin cyclohydrolase in cell extracts of *Methanobacterium*. Arch. Biochem. Biophys. 242, 430-439 (1985).

Drevland, R. M., Jia, Y., Palmer, D. R. J. & Graham, D. E. Methanogen homoaconitase catalyses both hydrolase reactions in Coenzyme B biosynthesis. J. Biol. Chem. 283, 28888-28896 (2008).

Dumitru R, Palencia H, Schroeder S D, DeMontigny B A, Takacs J M, Rasche M E, Miner J L, Ragsdale S W. Targeting methanopterin biosynthesis to inhibit methanogenesis. Appl. Environ. Microbiol. 69, 7236-41. (2003).

Dumitru, R. V. & Ragsdale, S. W. Mechanism of 4-(beta-D-ribofuranosyl)aminobenzene 5'-phosphate synthase, a key enzyme in the methanopterin biosynthetic pathway. J. Biol. Chem. 279, 39389-95 (2004).

Eddy, S. R. A memory-efficient dynamic programming algorithm for optimal alignment of a sequence to an RNA secondary structure. BMC bioinformatics 3, 18 (2002).

Eddy, S. R. Profile hidden Markov models. Bioinformatics (Oxford, England) 14, 755-763 (1998).

Eggen, R. I., Geerling, A. C., Boshoven, A. B., de Vos, W. M. Cloning, sequence analysis, and functional expression of the acetyl coenzyme A synthetase gene from *Methanothrix soehngenii* in *Escherichia coli*. J. Bacteriol. 173, 6383-9 (1991).

Eichler, J. & Adams, M. W. Posttranslational protein modification in Archaea. Microbiol Mol Biol Rev 69, 393-425 (2005).

Eisen, J. A., Heidelberg, J. F., White, O. & Salzberg, S. L. Evidence for symmetric chromosomal inversions around the replication origin in bacteria. Genome Biol. 1(6), RESEARCH0011 (2000).

Ellermann, J., Hedderich, R., Bocher, R & Thauer, R. K. The final step in methane formation. Investigations with highly purified methyl-CoM reducatse (component C) from *Methanobacterium thermoautotrophicum* (strain Marburg). Eur. J. Biochem. 172, 669-677 (1988).

Emanuelsson, O., Brunak, S., von Heijne, G. & Nielsen, H. Locating proteins in the cell using TargetP, SignalP and related tools. Nature protocols 2, 953-971 (2007).

Ermler, U. On the mechanism of methyl-coenzyme reductase. Dalton Trans. 21, 3451-3458 (2005).

Ermler, U., Grabarse, W., Shima, S., Goubeaud, M. & Thauer, R. K. Crystal structure of methyl-coenzyme reductase: the key enzyme of biological methane formation. Science 278, 1457-1462 (1997).

Esposito, C., Caputo, I. & Troncone, R. New therapeutic strategies for coeliac disease: tissue transglutaminase as a target. Curr. Med. Chem. 14, 2572-80 (2007).

Ewing, B., Hillier, L., Wendl, M. C. & Green, P. Base-calling of automated sequencer traces using phred. I. Accuracy assessment. Genome research 8, 175-185 (1998).

FAO The State of Food Insecurity in the World. http://www.fao.org/docrep/011/i0291e/i0291e00.htm. Accessed 2009 Sep. 30 (2006).

Ferry, J. G. Enzymology of one-carbon metabolism in methanogenic pathways. FEMS Microbiol. Rev. 23, 13-38 (1999).

Finn R D, Tate J, Mistry J, Coggill P C, Sammut S J et al. (2008) The Pfam protein families database. Nucleic adds research 36, D281-288.

Fischbach M A, Walsh C T (2006) Assembly-line enzymology for polyketide and nonribosomal peptide antibiotics: logic, machinery and mechanisms. Chem Rev 106:3468-3496.

Fischer M, Schott A K, Römisch W, Ramsperger A, Augustin M et al. (2004) Evolution of vitamin B2 biosynthesis. A novel class of riboflavin synthase in Archaea. J Mol Biol 343:267-78.

Fischer M, Römisch W, Illarionov B, Eisenreich W, Bacher A (2005) Structures and reaction mechanisms of riboflavin synthases of eubacterial and archaeal origin. Biochem Soc Trans 33:780-784.

Fleischmann et al., 1995. Whole-genome random sequencing and assembly of *Haemophilus influenzae* Rd Science 269:496-512.

Food and Agriculture Organization of the United Nations (FAO). The State of Food Insecurity in the World. Available: http://www.fao.org/docrep/011/10291e/i0291e00.htm (2008).

Forouhar F, Abashidze M, Xu H, Grochowski L L, Seetharaman J et al. (2008) Molecular insights into the biosynthesis of the F420 coenzyme. J Biol Chem 283: 11832-11840.

Fricke W F, Seedorf H, Henne A, Kruer M, Liesegang H, Hedderich R, Gottschalk G, Thauer R K (2006) The genome sequence of *Methanosphaera stadtmanae* reveals why this human intestinal archaeon is restricted to methanol and H2 for methane formation and ATP synthesis. Journal of Bacteriology 188, 642-658.

Friesen, J. A. & Rodwell, J. A. The 3-hydroxy-3-methyl-glutaryl coenzyme-A (HMG-CoA) reductases. Genome Biol. 5, 248-(2004).

Fujihashi, M., Wei, L., Kotra, L. P., Pai, E. F. Structural characterisation of the molecular events during a slow substrate-product transition in orotidine 5'-monophosphate decarboxylase. J. Mol. Biol. 387, 1199-1210 (2009).

Gadelle, D., Bocs, C., Graille, M. & Forterre, P. Inhibition of archaeal growth and DNA topoisomerase VI activities by the Hsp90 inhibitor radicicol. Nucl. Acids Res. 33, 2310-2317 (2005).

Galperin M. Y. Using archaeal genomes to fight global warming and clostridia to fight cancer. Environ. Microbiol. 9, 279-286 (2007).

Gardner P P, Daub J, Tate J G, Nawrocki E P, Kolbe D L et al. Rfam: updates to the RNA families database. Nucleic acids research 37, D136-140 (2009).

Gerdes S., Edwards R., Kubal M., Fonstein M., Stevens R. & Osterman A. Essential genes on metabolic maps. Curr. Opin. Biotechnol. 17, 448-56 (2006).

Gilles, H. & Thauer, R. K. Uroporphyrinogen III, an intermediate in the biosynthesis of the nickel-containing factor F430 in *Methanobacterium thermoautotrophicum*. Eur. J. Biochem. 135, 109-112 (1983).

Girodeau, J-M., Agouridas, C., Masson, M., Pineau, R. & Le Goffic, F. The lysine pathway as target for a new genera of synthetic antibacterial antibiotics? J. Med. Chem. 29, 1023-1030 (1986).

Gish, W. & States, D. J. Identification of protein coding regions by database similarity search. Nature genetics 3, 266-272 (1993).

Global New Zealand International Trade, Investment and Travel Profile. (2008).

Godde J S, Bickerton A (2006) The repetitive DNAe called CRISPRs and their associated genes: evidence of horizontal transfer among prokaryotes. Journal of Molecular Evolution 62, 718-729.

Goenrich M, Mahlert F, Duin E C, Bauer C, Jaun B et al. (2004) Probing the reactivity of Ni in the active site of methyl-coenzyme M reductase with substrate analogues. J. Biol. Inorg. Chem. 9:691-705.

Goenrich M, Thauer R K, Yurimoto H, Kato N (2005) Formaldehyde activating enzyme (Fae) and hexylose-6-phosphate synthase (Hps) in *Methanosarcina barkeri*: a possible function in ribose-5'-phosphate biosynthesis. Arch Microbiol 184:41-48.

Goldberg S M, Johnson J, Busam D, Feldbylum T, Ferriera S et al. A Sanger/pyrosequencing hybrid approach for the generation of high-quality draft assemblies of marine microbial genomes. Proc Natl Acad Sci USA 103: 11240-11245.

Gottschalk, G. & Thauer, R. K. The Na(+)-translocating methyltransferase complex from methanogenic archaea. Biochimica et biophysica acts 1505, 28-36 (2001).

Grabarse W, Vaupel M, Vorholt J A, Shima S, Thauer R K, Wittershagen A, Bourenkov G, Bartunik H D, Ermler U. The crystal structure of methenyltetrahydromethanopterin cyclohydrolase from the hyperthermophilic archaeon *Methanopyrus kandleri*. Structure. 7, 1257-68 (1999).

Grabarse W, Mahlert F, Duin E C, Goubeaud M, Shima S et al. On the mechanism of biological methane formation: structural evidence for conformational changes methyl-co-enzyme M reductase upon substrate binding. J Mol Biol 309:315-330 (2001).

Graham, D. E, & White, R. H. Elucidation of methanogenic coenzyme biosyntheses: from spectroscopy to genomics. Nat. Prod. Rep. 19, 133-147 (2002).

Graham, D. E., Xu, H. & White, R. H. A member of a new class of GTP cyclohydrolases produces formylaminopyrimidine nucleotide monophosphates. Biochem. 41, 15074-15084 (2002).

Graham, D. E., Xu, H. & White, R. H. Identification of coenzyme M biosynthetic phosphosulfolactate synthase: a new family of sulfonate-biosynthesizing enzymes. The Journal of biological chemistry 277, 13421-13429 (2002).

Graham, D. E., Xu, H. & White, R. H. Identification of the 7,8-didemethyl-8-hydroxy-5-deazariboflavin synthase required for coenzyme F420 biosynthesis. Arch. Microbiol. 180, 455-464 (2003).

Graham, D. E., Xu, H. & White, R. H. *Methanococcus jannaschii* uses a pyruvoyl-dependent arginine decarboxylase in polyamine biosynthesis. J. Biol. Chem. 28, 277, 23500-7 (2002).

Graham, L. L. & Beveridge, T. J. Structural differentiation of the *Bacillus subtilis* 168 cell wall. J. Bacteriol. 176(5), 1413-1421 (1994).

Graille M, Cladière L, Durand D, Lecointe F, Gadelle D et al. (2008) Crystal structure of an intact type II DNA topoisomerase: insights into DNA transfer mechanisms. Struct 16:360-370.

Graupner, M. & White, R. H. The first examples of (S)-2-hydroxyacid dehydrogenases catalysing the transfer of the pro-4S hydrogen of NADH are found in the Archaea. Biochem. Biophys. Acta 1548, 169-173 (2001).

Graupner, M., Xu, H. & White, R. H. Characterization of the 2-phospho-L-lactate transferase enzyme involved in coenzyme F420 biosynthesis in *Methanococcus jannaschii*. Biochem. 41, 3754-3761 (2002).

Graupner, M., Xu, H. & White, R. H. Identification of an archaeal 2-hydroxy acid dehydrogenase catalysing reactions involved in coenzyme biosynthesis in methanoarchaea. J. Bacteriol. 182, 3688-3692 (2000).

Graupner, M., Xu, H. & White, R. H. New class of IMP cyclohydrolase in *Methanococcus jannaschii*. J. Bacteriol. 184, 1471-1473 (2002).

Griffin, M., Casadio, R. & Bergamini, C. M. Transglutaminases: nature's biological glues. Biochem J. 368, 377-396 (2002).

Grochowski L. L., Xu, H. & White, R. H. Identification and characterization of the 2-phospho-L-lactate guanyltransferase involved in coenzyme F420 biosynthesis. Biochem. 47, 3033-3037 (2008).

Grochowski, L. L. & White, R. H. Promiscuous anaerobes: new and unconventional metabolism in methanogenic archaea. Ann. N.Y. Acad. Sci. 1125, 190-214 (2008).

Grochowski, L. L., Xu, H. & White, R. H. An iron(II) dependent formamide hydrolase catalyzes the second step in the archaeal biosynthetic pathway to riboflavin and 7,8-didemethyl-8-hydroxy-5-deazariboflavin. Biochem. 48, 4181-8 (2009).

Grochowski, L. L., Xu, H. & White, R. H. Identification of lactaldehyde dehydrogenase in *Methanocaldococcus jannaschii* and its involvement in production of lactate for F420 biosynthesis. J. Bacteriol. 188, 2836-44 (2006).

Grochowski, L. L., Xu, H. & White, R. H. *Methanocaldococcus jannaschii* uses a modified mevalonate pathway for biosynthesis of isopentenyl diphosphate. J. Bacteriol. 188, 3192-3198 (2006).

Grochowski, L. L., Xu, H. & White, R. H. Ribose-5?-phosphate biosynthesis in *Methanocaldocoocus jannaschii* occurs in the absence of a pentose-phosphate pathway. J. Bacteriol. 187, 7382-7389 (2005).

Grochowski, L. L., Xu, H., White, R. H. Ribose-5-phosphate biosynthesis in *Methanocaldocoocus jannaschii* occurs in the absence of a pentose-phosphate pathway. J. Bacteriol. 187, 7382-7389 (2005).

Grochowski, L. L., Xu, H., Leung, K. & White, R. H. Characterization of an Fe2+-dependent archaeal-specific GTP cyclohydrolase, MptA, from *Methanocaldococcus jannaschii*. Biochem. 46, 6658-6667 (2007).

Grüber, G & Marshansky, V. New insights into structure-function relationships between archaeal ATP synthase (A1A0) and vacuolar type ATPase (V1V0). Bioessays 30, 1096-1109 (2008).

Guerra-Lopez, D., Daniels, L. & Rawat, M. *Mycobacterium smegmatis* mc 155 fbiC and MSMEG_2392 are involved in triphenylmethane dye decolorisation and coenzyme F420 biosynthesis. Microbiol. 153, 2724-2732 (2007).

Guo R T, Cao R, Liang P H, Ko T P, Chang T H et al. (2007) Bisphosphonates target multiple sites in both cis- and trans-prenyltransferases. Proc Natl Acad Sci USA 104: 10022-7.

Haft D H, Selengut J, Mongodin E F, Nelson K E (2005) A guild of 45 CRISPR-associated (Cas) protein families and multiple CRISPR/Cas subtypes exist in prokaryotic genomes. PLoS Computational Biology 1:474-483.

Haft, D. H., Selengut, J. D. & White, O. The TIGRFAMs database of protein families. Nucleic acids research 31, 371-373 (2003).

Hagemeier C H, Shima S, Thauer R K, Bourenkov G, Bartunik H D et al. (2003) Coenzyme F420-dependent methylenetetrahydromethanopterin dehydrogenase (Mtd) from *Methanopyrus kandleri*: a methanogenic enzyme with an unusual quarternary structure. J Mol Biol 332:1047-1057.

Hammes W. P., Winter J. & Kandler O. The sensitivity of pseudomurein-containing genus *Methanobacterium* to inhibitors of murein synthesis. Arch. Microbiol. 123, 275-279 (1979).

Harmer J, Finazzo C, Piskorski R, Ebner S, Duin E C et al. (2008) A nickel hydride complex in the active site of methyl-coenzyme M reductase: implications for the catalytic cycle. J Am Chem Soc 130:10907-10920.

Hartmann, E. & König, H. Comparison of the biosynthesis of the methanobacterial pseudomurein and the eubacterial murein. Nat. Wissenschaft. 77, 472-475 (1990).

Heath, R. J. & Rock, C. O. Fatty acid biosynthesis as a target for novel antibacterials. Curr. Opin. Investig. Drugs 5, 146-153 (2004).

Heath, R. J., White, S. W. & Rock, C. O. Lipid biosynthesis as a target for antibacterial agents. Prog. Lipid Res. 40, 467-497 (2001).

Hedderich, R., Hamann, N. & Bennati, M. Heterosulfide reductase from methanogenic archaea: a new catalytic role for an iron-sulfur cluster. Biol. Chem. 386, 961-970 (2005).

Hegarty R. S. Mechanisms for competitively reducing ruminal methanogenesis. Aust. J. Agric. Res. 50, 1299-1305 (1999).

Heim, S., Künkel, A., Thauer, R. K. & Hedderich, R. Thiol:fumarate reductase (Tfr) from *Methanobacterium thermoautotrophicum*-identification of the catalytic sites for fumarate reduction and thiol oxidation. Eur. J. Biochem. 253, 292-9 (1998).

Hendrickson, E. L. & Leigh, J. A. Roles of coenzyme F420-reducing hydrogenases and hydrogen- and F420-dependent methylenetetrahydromethanopterin dehydrogenases in reduction of F420 and production of hydrogen during methanogenesis. J. Bacteriol. 190, 4818-4821 (2008).

Hermoso J. A., García J. L. & García P. Taking aim on bacterial pathogens: from phage therapy to enzybiotics. Curr. Opin. Microbiol. 10, 461-472 (2007).

Hernández-Montes, G., Díaz-Mejía, J. J., Pérez-Rueda, & Segovia, L. The hidden universal, distribution of amino acid biosynthetic networks: a genomic perspective in their origins and evolution. Genom. Biol. 9, R95 (2008).

Hilpert, R., Winter, J., Hammes, W. & Kandler, O. The sensitivity of archaebacteria to antibiotics. Zbl. Bakt. Hyg. I Abt. Orig. C 2, 11-20 (1981).

Hiromoto T, Ataka K, Pilak O, Vogt S, Stagni M S, Meyer-Klaucke W, Warkentin E, Thauer R K, Shima S, Ermler U. The crystal structure of C176A mutated [Fe]-hydrogenase suggests an acyl-iron ligation in the active site iron complex. FEBS Lett. 583, 585-90 (2009).

Hochheimer, A., Hedderich, R. & Thauer, R. K. The formylmethanofuran dehydrogenase isoenzymes in *Methanobacterium wolfei* and *Methanobacterium thermoautotrophicum*: induction of the molybdenum isoenzyme by molybdate and constitutive synthesis of the tungsten isoenzyme. Arch. Microbiol. 170, 389-93 (1998).

Hochheimer, A., Linder, D., Thauer, R. K. & Hedderich, R. The molybdenum formylmethanofuran dehydrogenase operon and the tungsten formylmethanofuran dehydrogenase operon from *Methanobacterium thermoautotrophicum*. Structures and transcriptional regulation. European Journal of Biochemistry 242, 156-162 (1996).

Hochheimer, A., Schmitz, R. A., Thauer, R. K. & Hedderich, R. The tungsten formylmethanofuran dehydrogenase from *Methanobacterium thermoautotrophicum* contains sequence motifs characteristic for enzymes containing molybdopterin dinucleotide. Eur. J. Biochem. 234, 910-20 (1995).

Hopkins A. L. & Groom C. R. The druggable genome. Nat. Rev. Drug. Discov. 1, 727-730 (2002).

Hoshino, T., Tamegai, H., Kakinuma, K. & Eguchi, T. Inhibition of type 2 isopentenyl diphosphate isomerase from *Methanocaldococcus jannaschii* by a mechanism-based inhibitor of type I1 isopentenyl diphosphate isomerase. Bioorg. Med. Chem. 14, 6555-6559 (2006).

Howell, D. M. & White, R. H. D-erythro-neopterin biosynthesis in the methanogenic archaea *Methanococcus thermophila* and *Methanobacterium thermoautotrophicum* ?H. J. Bacteriol. 179, 5165-5170 (1997).

Howell, D. M., Graupner, M., Xu, H. & White, R. H. Identification of enzymes homologous to isocitrate dehydrogenase that are involved in Coenzyme B and leucine biosynthesis in Methanoarchaea. J. Bacteriol. 182, 5013-5016 (2000).

Howell, D. M., Harich, K., Xu, H. & White, R. H. ?-Keto acid chain elongation reactions involved in the biosynthesis of Coenzyme B (7-mercaptoheptanoyl threonine phosphate). Biochem. 37, 10108-10117 (1998).

Howell, D. M., Xu, H. & White, R. H. (R)-citramalate synthase in methanogenic Archaea. J. Bacteriol. 181, 331-333 (1999).

Hoyt, J. C., Oren, A., Escalante-Semerena, J. C. & Wolfe R. S. Tetramethanopterin-dependent serine transhydroxymethylase from *Methanobacterium thermoautotrophicum*. Arch. Microbiol. 145, 153-158 (1986).

Huang, Q., Tonge, P. J., Slayden, R. A., Kirikae, T. & Ojima, I. FtsZ: a novel target for tuberculosis drug discovery. Curr. Top. Med. Chem. 7, 527-543 (2007).

Hunter S, Apweiler R, Attwood T K, Bairoch A, Bateman A et al. (2009) InterPro: the integrative protein signature database. Nucleic Acids Res 37(Database issue):D211-215.

Hutton, C. A., Perugini, M. A. & Gerrard, J. A. Inhibition of lysine biosynthesis: an evolving antibiotic strategy. Mol. Biosyst. 3, 458-465 (2007).

IPCC (Intergovernmental Panel on Climate Change), 2007. Climate Change 2007: The Physical Science Basis, Contribution of Working Group I to the Fourth Assessment Report of the Intergovernmental Panel on Climate Change (Solomon, S., D. Qin, M. Manning, Z. Chen, M., Marquis, K. B. Averyt, M. Tignor and H. L. Miller (eds.)]. Cambridge University Press, Cambridge United Kingdom and New York, N.Y., USA, Available: http://www.ipcc.ch/publications_and_data/publications_ipcc_fourth_assessment_report_wg1_report_the_physical_science_basis.htm. Accessed 2009 Sep. 30.

Iqbal, M.a.C., Y Mitigation of ruminant methane production:current strategies, constraints and future options. World Journal of Microbiology and Biotechnology, 2747-2755 (2008).

Iranzo, M., Aguado, C., Pallotti, C., Cañizares, J. V. & Mormeneo, S. Transglutaminase activity is involved in *Saccharomyces cerevisiae* wall construction. Microbiol. 148, 1329-34 (2002).

Irimia A., Madern D., Zaccaï G., Vellieux F. M. Methanoarchaeal sulfolactate dehydrogenase: prototype of a new family of NADH-dependent enzymes. EMBO J. 23, 1234-44 (2004).

Irwin, J. J. and Shoichet, B. K. (2005) J. Chem. Inf. Model. 45(1):177-82.

Ishino, Y & Cann, I. K. O. The Euryarchaeotes, a subdomain of Archaea, survive on a single DNA polymerase: Fact or farce? Genes Genet. Syst. 73, 323-336 (1998).

Istvan, E. S. Bacterial and mammalian HMG-CoA reductases: related enzymes and distinct architectures. Curr. Opin. Struct. Biol. 11, 746-751 (2001).

Jacobson, F. S., Daniels, L., Fox, J. A., Walsh, C. T., Orme-Johnson, W. H. Purification and properties of an 8-hydroxy-5-deazaflavin-reducing hydrogenase from *Methanobacterium thermautotrophicum*. J. Biol. Chem. 257, 3385-3388 (1982).

Jansen R, Embden J D, Gaastra W, Schouls L M (2002) Identification of genes that are associated with DNA repeats in prokaryotes. Molecular Microbiology 43, 1565-1575.

Jansen R, van Embden J D, Gaastra W, Schouls L M (2002) Identification of a novel family of sequence repeats among prokaryotes. OMICS: A journal of integrative biology 6, 23-33.

Janssen P. H. & Kirs M. Structure of the archaeal community of the rumen. Appl. Environ. Microbiol. 74, 3619-3625 (2008).

Jarrell, K. F., Faguy, D., Herbert, A. M., and Kalmakoff, M. L. A general method of isolating high molecular weight DNA from methanogenic archaea (archaebacteria) Can. J. Microbiol. 38, 65-68 (1992).

Jenal U, Rechsteiner T, Pan P Y, Bühlmann E, Meile L et al. (1991) Isoleucyl-tRNA synthetase of *Methanobacterium thermautotrophicum* Marburg. J Biol Chem 266:10570-10577.

Jensen, L. J., Friis, C. and Ussery, D. W. 1999 Three views of microbial genomes. Res. Microbiol. 150, 773-777.

Joblin K N, Naylor G E, Williams A G (1990) Effect of *Methanobrevibacter smithii* on xylanolytic activity of anaerobic ruminal fungi. Applied and Environmental Microbiology 56, 2287-2295.

Joerger, A. C., Mueller-Dieckmann, C. & Schulz, G. E. Structures of L-fuculose-1-phosphate aldolase mutants outlining motions during catalysis. J. Mol. Biol. 303, 531-543 (2000).

Johnson, K. A. & Johnson, D. E. Methane emissions from cattle. Journal of animal science 73, 2483-2492 (1995).

Kadziola A, Jepsen C H, Johansson E, McGuire J, Larsen S et al. (2005) Novel class III phosphoribosyl diphosphate synthase: structure and properties of the tetrameric, phosphate-activated, non-allosterically inhibited enzyme from *Methanocaldococcus jannaschii*. J Mol Biol 354:815-828.

Kalyuzhnaya M G, Korotkova N, Crowther G, Marx C J, Lidstrom M E et al. (2005) Analysis of gene islands involved in methanopterin-linked C1 transfer reactions reveals new functions and provides evolutionary insights. J Bacteriol 187:4607-4614.

Kandler, O. & König, H. Cell envelopes of archaebacteria, in The Bacteria Volume VIII: Archaebacteria, C. R. Woese and R. S. Wolfe, Editors. Academic Press: Orlando. p. 413-457 (1985).

Kandler, O. & König, H. Cell wall polymers in Archaea (Archaebacteria). Cell Mol Life Sci 54, 305-308 (1998).

Kandler, O. & König, H. Chemical composition of the peptidoglycan-free cell walls of methanogenic bacteria. Archives of microbiology 118, 141-152 (1978).

Kandler, O. & König, H. in The Bacteria Volume VIII: Archaebacteria. (eds. C. R. Woese & R. S. Wolfe) 413-457 (Academic Press, Orlando; 1985).

Kanehisa M, Goto S, Kawashima S, Okuno Y, Hattori M (2004) The KEGG resource for deciphering the genome. Nucleic Acids Research 32, D277-D280.

Kanehisa, M. & Goto, S. KEGG: Kyoto Encyclopedia of Genes and Genomes. Nucleic Acids Res. 28, 27-30 (2000).

Kang, Y. N., Tran, A., White, R. H., & Ealick, S. E. A novel function for the N-terminal nucleophile hydrolase fold demonstrated by the structure of an archaeal inosine monophosphate cyclohydrolase. Biochem. 46, 5050-5062 (2007).

Kato, N., Yurimoto, H. & Thauer, R. K. The physiological role of the ribulose monophosphate pathway in bacteria and archaea. Biosci. Biotechnol. Biochem. 70, 10-21 (2006).

Kato, S., Kosaka, T. & Watanabe, K. Comparative transcriptome analysis of responses of Methanothermobacter thermoautotrophicus to different environmental stimuli. Environ. Microbiol. 10, 893-905 (2008).

Katz, A. H. & Caufield, C. E. Structure-based design approaches to cell wall biosynthesis inhibitors. Curr. Pharm. Design 9, 857-866 (2003).

Kenealy, W. & Zeikus, J. G. Influence of corrinoid antagonists on methanogen metabolism. J. Bacteriol. 146, 133-140 (1981).

Kengen, S. W., von den Hoff, H. W., Keltjens, J. T., van der Drift, C. & Vogels, G. D. F390 synthetase and F390 hydrolase from Methanobacterium thermoautotrophicum (strain delta H). Biofact. 3, 61-65 (1991).

Kezmarsky, N. D., Xu, H., Graham, D. E. & White, R. H. Identification and characterization of a L-tyrosine decarboxylase in Methanocaldococcus jannaschii. Biochim Biophys Acta. 1722, 175-82 (2005).

Kiener, A., König, H., Winter, J. and Leisinger, T. 1987. Purification and use of Methanobacterium wolfei pseudomurein endopeptidase for lysis of Methanobacterium thermoautotrophicum. J. Bacteriol. 169, 1010-1016.

Kim, H-S., Vothknecht, U. C., Hedderich, R., Celic, I. & Söll, D. Sequence divergence of seryl-tRNA synthetases in Archaea. J. Bacteriol. 180, 6446-6449 (1998).

Kim, S., Lee, S. W., Choi, E.-C. & Choi, S. Y. AminacyltRNA synthetases and their inhibitors as a novel family of antibiotics. Appl. Muicrobiol. Biotechnol. 61, 278-288 (2003).

Kimura, K-i. & Bugg, T. D. H. recent advances in antimicrobial nucleoside antibiotics targeting cell wall biosynthesis. Nat. Prod. Rep. 20, 252-273 (2003).

Klein, A. R., Fernández, V. M. & Thauer, R. K. H2-forming N5-N10-methylenetetrahydromethanopterin dehydrogenase: mechanism of H2 formation analyzed using hydrogen isotopes. FEBS Lett. 368, 203-206 (1995).

Klieve, A. V. & Hegarty, R. S. Opportunities for biological control of ruminal methanogenesis. Aust. J. Exp. Agri. 50, 1315-1319 (1999).

Klipcan, L., Frenkel-Morgenstern, M. & Safro, M. G. Presence of tRNA-dependent pathways correlates with high cysteine content in methanogenic Archaea. Trends Genet. 24, 59-63 (2008).

Knox, M. R. and Harris, J. E. 1986. Isolation and characterisation of a bacteriophage of Methanobrevibacter smithii. In Abstracts of the XIV International Congress on Microbiology. Manchester: International Union of Microbiological Societies.

Koga, Y. & Morii, H. Biosynthesis of ether-linked polar lipids in archaea and evolutionary considerations. Microbiol. Molec. Biol. Rev. 71, 97-120 (2007).

König, H., Hartmann, E. & Karcher, U. Pathways and principles of the biosynthesis of methanobacterial cell wall polymers. Systematic and applied microbiology 16, 510-517 (1994).

Kotnik, M., Anderluh, P. S. & Prezelj, A. Development of novel inhibitors targeting intracellular steps of peptidoglycan biosynthesis. Curr. Pharm. Des. 13, 2283-309 (2007).

Krogh, A., Larsson, B., von Heijne, G. & Sonnhammer, E. L. Predicting transmembrane protein topology with a hidden Markov model: application to complete genomes. Journal of molecular biology 305, 567-580 (2001).

Kurtz S, Schleiermacher C (1999) REPuter: fast computation of maximal repeats in complete genomes. Bioinformatics 15, 426-427.

Kwang-Pil, C., Bair, T., Bae, Y-M. & Daniels, L. Use of transposon Tn5367 mutagenesis and a nitroimidazopyranbased selection system to demonstrate a requirement for fbiA and fbiC in coenzyme F420 biosynthesis by Mycobacterium bovis BCG. J. Bacteriol. 183, 7058-7066 (2001).

Kwang-Pil, C., Kendrick, N. & Daniels, L. Demonstration that fbiC is required for Mycobacterium bovis BCG for coenzyme F420 and FO biosynthesis. J. Bacteriol. 184, 2420-2428 (2002).

Larkin M A, Blackshields G, Brown N P, Chema R, McGettigan P A et al., Clustal W and Clustal X version 2.0. Bioinformatics 23(21), 2947-2948 (2007).

Leahy S C, Kelly W J, Altermann E, Ronimus R S, Yeoman C J, et al. (2010) The Genome Sequence of the Rumen Methanogen Methanobrevibacter ruminantium Reveals New Possibilities for Controlling Ruminant Methane Emissions. PLoS ONE 5(1): e8926. doi:10.1371/journal.pone.0008926.

Lee B I, Chang C, Cho S J, Eom S H, Kim K K et al. (2001) Crystal structure of the MJ0490 gene product of the hyperthermophilic archaebacterium Methanococcus jannaschii, a novel member of the lactate/malate family of dehydrogenases. Biochem 40:10310-10316.

Lee, K. N., Fesus, L., Yancey, S. T., Girard, J. E. & Chung, S. I. Development of selective inhibitors of transglutaminase. J. Biol. Chem. 260, 14689-14694 (1985).

Lemker, T., Grüber, G., Schmid, R. & Müller, V. Defined subcomplexes of the A1 ATPase from the archaeon Methanosarcina mazei Göl: biochemical properties and redox regulation. FEBS Lett. 544, 206-209 (2003).

Lemker, T., Ruppert, C., Stöger, H. Wimmers, S. & Müller, V. Overproduction of a functional A1 ATPase from the archaeon Methanosarcina mazei Got in Escherichia coli. Eur. J. Biochem. 268, 3744-3750 (2001).

Leslie, M., Aspin, M., and Clark, H. Greenhouse gas emissions from New Zealand agriculture:issues, persepectives and industry response. Australian Journal of Experimental Agriculture, 1-5 (2008).

Lewalter, K & Müller, V. Bioenergetics of archaea: ancient energy conserving mechanisms developed in the early history of life. Biochim. Biophys. Acta 1757, 437-445 (2006).

Li, H., Graupner, M., Xu, H. & White, R. H. CofE catalyses the addition of two glutamates to F420-0 in F420 coenzyme biosynthesis in Methanococcus jannaschii. Biochem. 42, 9771-9778 (2003).

Lienard T, Becher. B, Marschall M, Bowien S, Gottschalk G (1996) Sodium ion translocation by N5-methyltetrahydromethanopterin:coenzyme M methyltransferase from Methanosarcina mazei Göl reconstituted in ether lipid liposomes. Eur J Biochem 239: 857-864.

Lin, W. & Whitman, W. B. The importance of porE and porG in the anabolic pyruvate oxidoreductase of *Methanococcus maripaludis*. Arch. Microbiol. 181, 68-73 (2004).

Lin, W. C., Yang, Y-L. & Whtman, W. B. The anabolic pyruvate oxidoreductase from *Methanococcus maripaludis*. Arch. Microbiol. 179, 444-456 (2003).

Lin, Z. & Sparling, R. Investigation of serine hydroxymethyltransferase in methanogens. Can. J. Microbiol. 44, 652-656 (1998).

Lindahl, P. A. & Chang, B. The evolution of acetyl-CoA synthase. Orig. Life Evolut. Biosph. 31, 403-434 (2001).

Lingl A, Huber H, Stetter K O, Mayer F, Kellermann J et al. (2003) Isolation of a complete A1A0 ATP synthase comprising nine subunits from the hyperthermophile *Methanococcus jannaschii*. Extremophiles 7:249-257. Lobry J R (1996) Asymmetric substitution patterns in the two DNA strands of bacteria. Mol Biol Evol 13:660-5.

Lobry J R (1996) Asymmetric substitution patterns in the two DNA strands of bacteria. Mol Biol Evol 13:660-5.

Loenen, W. and N. Murray. 1986. Modification enhancement by restriction alleviation protein (Ral) of bacteriophage lambda. J. Mol. Biol. 190:11-22.

Löwe, J. & Amos, L. A. Crystal structure of the bacterial cell-division protein FtsZ. Nature 391, 203-206 (1998).

Lowe, T. M. & Eddy, S. R. tRNAscan-SE: a program for improved detection of transfer RNA genes in genomic sequence. Nucleic acids research 25, 955-964 (1997).

Lucchini, S., F. Desiere, and H. Brussow. 1999. Comparative genomics of *Streptococcus thermophilus* phage species supports a modular evolution theory. J. Virol. 73:8647-8656.

Luo, H. W., Zhang, H., Suzuki, T., Hattori, S. & Kamagata, Y. Differential expression of methanogenesis genes of *Methanothermobacter thermoautotrophicus* (formerly *Methanobacterium thermoautotrophicum*) in pure culture and in cocultures with fatty acid-oxidizing syntrophs. Applied and environmental microbiology 68, 1173-1179 (2002).

Luo, Y. N., Pfister, P., Leisinger, T. and Wasserfallen, A. 2002. Pseudomurein endoisopeptidases PeiW and PeiP, two moderately related members of a novel family of proteases produced in *Methanothermobacter* strains. FEMS Microbiol. Lett. 208, 47-51.

Majernik, A. I. & Chong, J. P. A conserved mechanism for replication origin recognition and binding in archaea. Biochem. J. 409(2), 511-518 (2008).

Makarova K S, Grishin N V, Shabalina S A, Wolf Y I, Koonin E V (2006) A putative RNA-interference-based immune system in prokaryotes: computational analysis of the predicted enzymatic machinery, functional analogies with eukaryotic RNAi, and hypothetical mechanisms of action. Biology Direct 1:7-32.

Makarova, K. S., Aravind, L. and Koonin, E. V. 1999. A superfamily of archaeal, bacterial, and eukaryotic proteins homologous to animal transglutaminases. Protein Sci. 8, 1714-1719.

Makarova, K. S., Sorokin, A. V., Novichkov, P. S., Wolf, V. I. & Koonin, E. V. Clusters of orthologous genes for 41 archaeal genomes and implications for evolutionary genomics of archaea. Biol. Direct. 27, 2-33 (2007).

Mamat B, Roth A, Grimm C, Ermler U, Tziatzios C et al. (2002) Crystal structures and enzymatic properties of three formyltransferases from archaea: environmental adaptation and evolutionary relationship. Pro Sci 11:2168-2178.

Mareso, A. W. & Schneewind, O. Sortase as a target of anti-infective therapy. Pharmacol. Rev. 60, 128-141 (2008).

Mareso A W, Wu R, Kern J W, Zhang R, Janik D et al. (2007) Activation of inhibitors by sortase triggers irreversible modification of the active site. J Biol Chem 282:23129-23139.

Martinez-Cruz, L. A. et al. Crystal structure of MJ1247 protein from *Methanocaldococcus jannaschii* at 2 Å resolution infers a molecular function of 3-hexylose-6-phosphate isomerase. Struct. 10, 195-204 (2002).

Mashhadi, Z., Zhang, H., Xu, H. & White, R. H. Identification and characterisation of an archeal-specific riboflavin kinase. J. Bacteriol. 190, 2615-2518 (2008).

Mauer, J., Kuettner, H. C., Zhang, J. K., Hedderich, R. & Metcalf, W. W. Genetic analysis of the archaeon *Methanosarcina barkeri* reveals a central role for Ech hydrogenase and ferredoxin in methanogenesis and carbon fixation. Proc. Natl. Acad. Sci. 99, 5632-5637 (2002).

McAllister T. A. & Newbold C. J. Redirecting rumen fermentation to reduce methanogenesis. Aust. J. Exper. Agric. 48, 7-13 (2008).

McInerney, M. J., Bryant, M. P. & Pfennig, N. Anaerobic bacterium that degrades fatty acids in syntrophic association with methanogens. Arch. Microbiol. 122, 129-135 (1979).

Miller, T. L. & Wolin M. J. Inhibition of growth of methane-producing bacteria of the rumen forestomach by hydroxymethylglutaryl~SCoA reductase inhibitors. J. Dairy Sci. 84, 1445-1448 (2001).

Miller, T. L., Genus II. Methanobrevibacter, in Bergey's Manual of Systematic Bacteriology Volume One: The Archaea and the Deeply Branching and Phototrophic Bacteria., D. R. Boone and R. W. Castenholz, Editors. Springer: New York. p. 218-226 (2001).

Mills, S. D. When will the genomics investment pay off for antibacterial discovery? Biochemical pharmacology 71, 1096-1102 (2006).

Ministry for the Environment. New Zealand's greenhouse gas inventory 1990-2005 (2007) Available: http://www.mfe.govt.nz/issues/climate/greenhouse-gas-emissions/greenhouse-gas-inventory.html. Accessed 2009 Sep. 30.

Moon C D, Pacheco D M, Kelly W J, Leahy S C, Li D et al. (2008) Reclassification of *Clostridium proteoclasticum* as Butyrivibrio proteoclasticus comb. nov., a butyrate-producing ruminal bacterium. Int J Syst Evol Microbiol 58:2041-2045.

Morar, M., White, R. H. & Ealick, S. E. Structure of 2-amino-3,7-dideoxy-D-threo-hept-6-ulosonic acid synthase, a catalyst in the archaeal pathway for the biosynthesis of aromatic amino acids. Biochem. 46, 10562-71 (2007).

Morrison, S. D., Roberts, S. A., Zegeer, A. M., Montfort, W. R. & Bandarian, V. A new use for a familiar fold: the X-ray crystal structure of GTP-bound GTP cyclohydrolase III from *Methanocaldococcus jannaschii* reveals a two metal ion catalytic mechanism. Biochem. 47, 230-42 (2008).

Moser, J., Schubert, W.-D., Heinz, D. W. & Jahn, D. Tetrapyrroles: their life, birth and death. Biochem. Soc. Trans. 30, 579-584 (2002).

Mukhopadhyay, B. & Daniels, L. Aerobic purification of N5, N10-methenyltetrahydromethanopterin dehydrogenase. Separated from N5, N10-methenyltetrahydromethanopterin cyclohydrolase, from *Methanobacterium thermoautotrophicum* strain Marburg. Can. J. Microbiol. 35, 499-507 (1989).

Mukhopadhyay, B., Patel, V. J. & Wolfe, R. S. A stable archaeal pyruvate carboxylase from the hyperthermophile *Methanococcus jannaschii*. Arch. Microbiol. 174, 406-14 (2000).

Mukhopadhyay, B., Purwantini, E., Kreder, C. L. & Wolfe, R. S. Oxaloacetate synthesis in the methanarchaeon *Methanosarcina barkeri*: pyruvate carboxylase genes and a putative *Escherichia coli*-type bifunctional biotin protein ligase gene (bpl/birA) exhibit a unique organization. J. Bacteriol. 183, 3804-10 (2001).

Mukhopadhyay, B., Purwantini, E., Pihl, T. D., Reeve, J. N. & Daniels, L. Cloning, sequencing, and transcriptional analysis of the coenzyme F420-dependent methylene-5,6,7,8-tetrahydromethanopterin dehydrogenase gene from *Methanobacterium thermoautotrophicum* strain Marburg and functional expression in *Escherichia coli*. J. Biol. Chem. 270, 2827-2832 (1995).

Mukhopadhyay, B., Stoddard, S. F. &. Wolfe, R. S. Purification, regulation, and molecular and biochemical characterization of pyruvate carboxylase from *Methanobacterium thermoautotrophicum* strain deltaH. J. Biol. Chem. 273, 5155-66 (1998).

Müller, V. An, exceptional variability in the motor of archael A1A0 ATPases: from multimeric to monomeric rotors comprising 6-13 ion binding sites. Journal of bioenergetics and biomembranes 36, 115-125 (2004).

Müller, V., Ruppert, C. & Lemkar, T. Structure and function of the A0A1-ATPase from methanogenic archaea. J. Bioenerg. Biomem. 31, 15-27 (1999).

Musfeldt, M. & Schönheit, P. Novel type of ADP-forming acetyl coenzyme A synthetase in hyperthermophilic archaea: heterologous expression and characterization of isoenzymes from the sulfate reducer *Archaeoglobus fulgidus* and the methanogen *Methanococcus jannaschii*. J. Bacteriol. 184, 636-644 (2002).

Nagar-Anthal, K. R., Worrell, V. E., Teal, R. & Nagle, D. P. The pterin lumazine inhibits growth of methanogens and methane formation. Arch. Microbiol. 166, 136-140 (1996).

Nakai, K. & Horton, P. PSORT: a program for detecting the sorting signals of proteins and predicting their subcellular localization. Trends Biochem. Sci. 24(1), 34-35 (1999).

Nam Shin, J., Kim, M-J., Choi, J-a. & Chun, K. O. Characterization of aldolase from *Methanococcus jannaschii* by gas chromatography. J. Biochem. Molec. Biol. 40, 801-804 (2007).

Namboori, S. E. & Graham, D. E. Acetamido sugar biosynthesis in the Euryarchaea. J. Bacteriol. 190, 2987-2996 (2008).

New Zealand Statistics 2005 (www.stats.govt.nz)

New Zealand's Greenhouse Gas Inventory 1990-2004. The National Inventory Report and Common Reporting Format. (2006) Ministry for the Environment. Hypertext transfer protocol://www.mfe.govt.nz/publications/climate/nir-apr06/nir-apr06.pdf.

New Zealand's greenhouse gas inventory 1990-2005. (2007).

Nocek, B. et al. Structure of an amide bond forming F(420):gamma-glutamyl ligase from *Archaeoglobus fulgidus*—a member of a new family of non-ribosomal peptide synthases. J. Mol Biol. 372, 456-69 (2007).

Nyce G. W. & White R. H. dTMP biosynthesis in Archaea. J. Bacteriol. 178, 914-916 (1996).

Osborn, M. J. & Rothfield, L. Cell shape determination in *Escherichia coli*. Curr. Opin. Microbiol. 10, 606-10 (2007).

Oshikane, H. et al. Structural basis of RNA-dependent recruitment of glutamine to the genetic code. Science 312, 1950-1954 (2006).

Osterman, A. & Overbeek, R. Missing genes in metabolic pathways: a comparative genomics approach. Curr. Opin. Chem Biol. 7, 238-251 (2003).

Patent application: WO 09041831A1

Payandeh, J., Fulihashi, M., Gillon, W. & Pai, E. F. The crystal structure of (S)-3-O-geranylgeranylglyceryl phosphate synthase reveals an ancient fold for an ancient enzyme. J. Biol. Chem. 281, 6070-6078 (2006).

Payne D. J. Desperately seeking new antibiotics. Science 321, 1644-1645 (2008).

Payne, D. J., Warren, P. V., Holmes, D. J., Ji Y. & Lonsdale, J. T. Bacterial fatty acid biosynthesis: a genomics-driven target for antibacterial discovery. Drug Disc. Ther. 6, 537-544 (2001).

Perez-Bercoff, A. Koch, J. & Burglin, T. R. LogoBar: bar graph visualization of protein logos with gaps. Bioinformatics 22(1), 112-114 (2006).

Pfaltz, A., Kobelt, A., Hüster, R. & Thauer, R. K. Biosynthesis of coenzyme F430 in methanogenic bacteria. Eur. J. Biochem. 170, 459-467 (1987).

Pilak O. Mamat B, Vogt S, Hagemeier C H, Thauer Rk et al. (2006) The crystal structure of the apoenzyme of the iron-sulphur cluster-free hydrogenase. J Mol Biol 358:798-809.

Pillai B, Chemey M M, Diaper C M, Sutherland A, Blanchard J S et al. (2006) Structural insights into stereochemical inversion by diaminopimelate epimerase: an antibacterial drug target. Proc Natl Acad Sci USA 103, 8668-73.

Pisa, K. Y., Weidner, C., Maischak. H., Kavermann, H. & Müller, V. The coupling ion in the methanoarchaeal ATP synthase: H+ vs Na+ in the A0A1 ATP synthase from the archaeon *Methanosarcina mazei* Gö1. FEMS Miccrobiol. Lett. 277, 56-63 (2007).

Podell, S. & Gaasterland, T. Darkhorse: a method for genome-wide prediction of horizontal gene transfer. Genome Biol. 8(2), R16 (2007).

Poduch, E., Bello, A. M., Tang, S., Fujihashi, M., Pai, E. F., Kotra, L. P. Design of inhibitors of orotidine monophosphate decarboxylase using bioisosteric replacement and determination of inhibition kinetics. J. Med. Chem. 49, 4937-4945 (2006).

Poduch, E., Wei, L, Pai, E. F., Kotra, L. P. Structural diversity and plasticity associated with nucleotides targeting orotidine monophosphate decarboxylase. J. Med. Chem. 51, 432-438 (2008).

Pohlmann, J. & Brötz-Oesterhelt, H. New aminoacyl-tRNA synthetase inhibitors as antibacterial agents. Curr. Drug Targets-Infect. Dis. 4, 261-272 (2004).

Porat I, Kim W, Hendrickson E L, Xia Q, Zhang Y et al. (2006) Disruption of the operon encoding Ehb hydrogenase limits anabolic CO2 assimilation in the archaeon *Methanococcus maripaludis*. J Bacteriol 188:1373-1380.

Porat I, Sieprawska-Lupa M, Teng Q, Bohanon F J, White R H et al. (2006) Biochemical and genetic characterization of an early step in a novel pathway for the biosynthesis of aromatic amino acids and p-aminobenzoic acid in the archaeon *Methanococcus maripaludis*. Mol Microbiol 62:1117-31.

Porat, I., Waters, B. W., Teng, Q. & Whitman, W. B. The biosynthetic pathways for aromatic amino acid in the archaeon *Methanococcus maripaludis*. J. Bacteriol. 186, 4940-4950 (2004).

Possot, O., Gernhardt, P., Klein, A. & Sibold, L. Analysis of drug resistance in the archaebacterium *Methanococcus voltae* with respect to potential use in genetic engineering. Appl. Environ. Microbiol. 54, 734-74 (1998).

Prætorius-Ibba, M. & Ibba, M. Aminoacyl-tRNA synthesis in archaea: different but not unique. Molec. Microbiol. 48, 631-637 (2003).

Prins, R. A., van Nevel, C. J. & Demeyer, D. I. Pure culture studies of inhibitors for methanogenic bacteria. Anton. Leeuwen. 38, 281-287 (1972).

Pucci M. J. Use of genomics to select antibacterial targets. Biochem. Pharmacol. 71, 1066-1072 (2006).

Ragsdale, S. W. Pyruvate ferredoxin oxidoreductase and its radical intermediate. Chem. Rev. 103, 2333-2346 (2003).

Rappuoli, R. Reverse vaccinology, a genome-based approach to vaccine development. Vaccine 19, 2688-2691 (2001).

Rasche, M. E. & White, R. H. Mechanism for the enzymatic formation of 4-(beta-D-ribofuranosyl)aminobenzene 5'-phosphate during the biosynthesis of methanopterin. Biochem. 37, 11343-51 (1998).

Rausch C, Weber T, Kohlbacher O, Wohlleben W, Huson D H (2005) Specificity prediction of adenylation domains in nonribosomal peptide synthetases (NRPS) using Transductive Support Vector Machines (TSVM). Nucleic Acids Res 33:5799-5808.

Rawlings, N. D., Morton, F. R. and Barrett, A. J. 2006. MEROPS: the peptidase database. Nucleic Acids Res. 34, D270-D272.

Ray, S. S., Bonanno, J. B., Rajashankar, K. R., Pinho, M. G, He, G., De Lencastre, H., Tomasz, A., Burley, S. K. Cocrystal structures of diaminopimelate decarboxylase: mechanism, evolution, and inhibition of an antibiotic resistance accessory factor. Structure. 10, 1499-508 (2002).

Reeve J N, Nolling J Morgan R M, Smith D R (1997) Methanogenesis: genes, genomes and who's on first? Journal of Bacteriology 179, 5975-5986.

Reymond N, Charles H, Duret L, Calevro F, Beslon G et al. (2004) ROSO: optimizing oligonucleotides probes for microarrays. Bioinformatics 20:271-273.

Rice, P., Longden, I. & Bleasby, A. EMBOSS: The European Molecular Biology Open Software Suite. Trends Genet. 16 (6), 276-277 (2000).

Robinson, I. M & Allison, M. J. Isoleucine biosynthesis from 2-methylbutyric acid by anaerobic bacteria from the rumen. J. Bacteriol. 97(3), 1220-1226 (1969).

Römisch-Margl, W., Eisenreich, W., Haase, I, Bacher, A. & Fischer, M. 2,5-diamino-6-ribitylamino-4(3H)-pyriinidinone 5?-phosphate synthases of fungi and archaea. FEBS J. 275, 4403-4414 (2008).

Rospert, S., Voges, M., Berkessel, A., Albracht, S. P. J. & Thauer, R. K. Substrate-induced changes in the nickel-EPR spectrum of active methyl-coenzyme-M reductase from Methanobacterium thermoautotrophicum. Eur. J. Biochem. 210, 101-107 (1992).

Rother M. & Metcalf W. M. Genetic technologies for archaea. Curr. Opin. Microbiol. 8, 745-751 (2005).

Ruiz, N. Bioinformatics identification of MurJ (MviN) as the peptidoglycan lipid II flippase in Escherichia coli. Proc. Natl. Acad. Sci. 105, 15553-15557 (2008).

Russell J. B. & Rychlik J. L. Factors that alter rumen microbial ecology. Science 292, 1119-1122 (2001).

Rutherford K, Parkhill J, Crook J, Horsnell T, Rice P et al. (2000) Artemis: sequence visualization and annotation. Bioinformatics 16: 944-945.

Samuel B S, Hansen E E, Manchester J K, Coutinho P M, Henrissat B et al. (2007) Genomic and metabolic adaptations of Methanobrevibacter smithii to the human gut. Proc Natl Acad Sci USA 104:10643-10648.

Sarkar N, Langley D, Paulus H. Biological function of gramicidin: selective inhibition of RNA polymerase. Proc. Natl. Acad. Sci. U.S.A. 74(4):1478-82 (1977)

Sauer, F. D. Inhibition of methylcoenzyme M methylreductase by a uridine 5?-diphospho-acetylglucosamine derivative. Biochem. Biophys. Res. Comm. 174, 619-624 (1991).

Sayers E W, Barrett T, Benson D A, Bryant S H, Canese K et al. (2009) Database resources of the National Center for Biotechnology Information. Nucleic Acids Res 37:D5-15.

Schäfer I B, Bailer S M, Düser M G, Börsch M, Bernal R A (2006) Crystal structure of the archaeal A1A0 ATPase synthase subunit B from Methanosarcina mazei G61: implications of the nucleotide-binding differences in the major A1A0 subunits A and B. J Mol Biol 358:725-740.

Schäfer, I. B., Engelhard, M. & Müller, V. Bioenergetics of the Archaea. Microbiol. Molec. Biol. 63, 570-620 (1999).

Schäfer I B, Rössle M, Bioković G, Müller V, Grüber G (2006) Structural and functional analysis of the coupling subunit F in solution and topological arrangements of the stalk domains of the methanogenic A1A0 ATP synthase. J Bioenerg Biomem 38:83-92.

Scheehle E A, K. D. Global anthropogenic methane and nitrous oxide emissions. The Energy Journal, 33-44 (2006).

Schmitt, E., Panvert, M., Blanquet, S. & Mechulam, Y. Structural basis for tRNA-dependent amidotransferase function. Struct. 13, 1421-33 (2005).

Schneider, K., Dimroth, P. & Bott, M. Identification of triphosphoribosyl-dephospho-CoA as precursor of the citrate lyase prosthetic group. FEBS Lett. 483, 165-168 (2000).

Scholte, A. A., Eubanks, L. M., Poulter, C. D. & Vederas, J. C. Synthesis and biological activity of isopentenyl diphosphate analogues. Bioorg. Medic. Chem. 12, 763-770 (2004).

Schulz, J. O., Schubert, W-D., Moser, J., Jahn, D. & Heinz, D. W. Evolutionary relationship between initial enzymes of tetrapyrrole biosynthesis. J. Molec. Biol. 358, 1212-1220 (2006).

Schümperli, M., Pellaux, R. & Panke, S. Chemical and enzymatic routes to dihydroxyacetone phosphate. Appl. Microbiol. Biotechnol. 75, 33-45 (2007).

Scorpio A, Chabot D J, Day W A, O'brien D K, Vietri N J et al. (2007) Poly-gamma-glutamate capsule-degrading enzyme treatment enhances phagocytosis and killing of encapsulated Bacillus anthracis. Antimicrob. Agents Chemother 51: 215-222.

Scott, J. W., & Rasche, M. E. Purification, overproduction, and partial characterisation of RFAP synthase, a key enzyme in the methanopterin biosynthesis pathway. J. Bacteriol. 184, 4442-4448 (2002).

Selmer T, Kahnt J, Goubeaud M, Shima S, Grabarse W et al. The biosynthesis of methylated amino acids in the active site region of methyl-coenzyme M reductase. J Biol Chem 275:3755-3760.

Shah, N. N. & Clark, D. S. Partial purification and characterization of two hydrogenases from the extreme thermophile Methanococcus jannaschii. Appl. Environ. Microbiol. 56, 858-863 (1990).

Sharp, P. M. & Li, W. H. The codon Adaptation Index-a measure of directional synonymous codon usage bias, and its potential applications. Nucleic Acids Res. 15(3), 1281-1295 (1987).

Sheppard, K. et al. From one amino acid to another: tRNA-dependent amino acid biosynthesis. Nucl. Acids Res. 36, 1813-1825 (2008).

Sheppard, K., Sherrer, R. L., & Söll, D. Methanothermobacter thermoautotrophicus tRNAGln confines the amidotransferase GatCAB to asparaginyl-tRNAAsn formation. J. Mol. Biol. 377, 845-853 (2008).

Shieh, J. S., Whitman, W. B. Pathway of acetate assimilation in autotrophic and heterotrophic methanococci. J. Bacteriol. (1987) 169(11):5327-9.

Shima S, Pilak O, Vogt S, Schick M, Stagni M S et al. (2008) The crystal structure of [Fe]-hydrogenase reveals the geometry of the active site. Science 321:572-5.

Shima, S., Warkentin, E., Thauer, R. K. & Ermler, U. Structure and function of enzymes involved in the methanogenic pathway utilizing carbon dioxide and molecular hydrogen. J. Biosci. Bioeng. 93, 519-530 (2002).

Shokes J E, Duin E C, Bauer C, Jaun B, Hedderich R et al. (2005) Direct interaction of coenzyme M with the active-site Fe—S cluster of heterodisulfide reductase. FEBS Lett 579:1741-1744.

Silver, L. L. Does the cell wall of bacteria remain a viable source of targets for novel antibiotics? Biochem. Pharm. 71, 996-1005 (2006).

Sment, K. A. & Konisky, J. Excretion of amino acids by 1,2,4-triazole-3-alanine-resistant mutants of *Methanococcus voltae*. Appl. Environ. Microbiol. 55, 1295-1297 (1989).

Smit, A. & Mushegian, A. Biosynthesis of isoprenoid via mevalonte in archaea: the lost pathway. Genom. Res. 10, 1465-1484 (2000).

Smith D R, et al. (1997) Complete genome sequence of *Methanobacterium thermoautotrophicum* H: Functional analysis and comparative genomics. Journal of Bacteriology 179, 7135-7155.

Smith P H, Hungate R E (1958) Isolation and characterization *Methanobacterium ruminantium* n. sp. Journal of Bacteriology 75, 713-718.

Smith, C. A. Structure, function and dynamics in the mur family of bacterial cell wall ligases. J. Mol. Biol. 362, 640-655 (2006).

Smyth G K (2005) Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, 397-420.

Sneath, P. H. A. & Sokal. R. R. Numerical Taxonomy. Freeman, San Francisco (1973).

Soderberg T (2005) Biosynthsis of ribose-5'-phosphate and erythrose-4-phosphate in archaea: a phylogenetic analysis of archaeal genomes. Archaea 1:347-352.

Sprott, G. D. & Jarrell, K. F. Sensitivity of methanogenic bacteria to dicyclohexylcarbodiimide. Can. J. Microbiol. 28, 982-986 (1982).

Sprott, G. D., McKellar, R. C., Shaw, K. M., Giroux, J. & Martin, W. G. Properties of malate dehydrogenase isolated from *Methanospirillum hungatei*. Can. J. Microbiol. 25, 192-200 (1979).

Staden R, Beal K F, Bonfield J K (1998) The Staden Package. Methods in Molecular Biology Bioinformatics Methods and Protocols 132, 115-130.

Staden, R., Beal, K. F. & Bonfield, J. K. The Staden package, 1998. Methods in molecular biology (Clifton, N.J. 132, 115-130 (2000).

Statistics New Zealand. Global New Zealand International Trade, Investment and Travel Profile. New Zealand Ministry of Foreign Affairs & Trade. Available: http://www.stats.govt.nz/products-and-services/global-new-zealand/2008/global-new-zealand-Dec08.htm (2008).

Steenbakkers P. J., Geerts W. J., Ayman-Oz N. A. & Keltjens, J. T. Identification of pseudomurein cell wall binding domains. Mol Microbiol. 62, 1618-30 (2006).

Steinfeld, H., Gerber, P., Wassenaar, T., Castel, V., Rosales, M. et al. Livestock's Long Shadow Environmental Issues and Options. Rome: Food and Agriculture Organization of the United Nations (2006).

Steller, S. et al. Structural and functional organization of the fengycin synthetase multienzyme system from *Bacillus subtilis* b213 and A1/3. Chem. Biol. 6, 31-41 (1999).

Stojanowic, A., Mander, G. J., Duin, E. C. & Hedderich, R. Physiological role of the F420-non-reducing hydrogenase (Mvh) from *Methanothermobacter marburgensis*. Arch. Microbiol. 180, 194-203 (2003).

Storer, A. C., Sprott, G. D. & Martin, W. G. Kinetic and physical properties of the L-malate-NAD+ oxidoreductase from *Methanospirillum hungatei* and comparison with the enzyme from other sources. Biochem. J. 193, 235-244 (1981).

Studier, F. W., (2005) Protein Expr. Purif. 41 207-234.

Stupperich, R. Recent advances in elucidation of biological corrinoid functions. FEMS Microbiol. Rev. 12, 349-366 (1993).

Šurin S, Cubonová L, Majernik Al, McDermott P, Chong J P et al. (2007) Isolation and characterization of an amiloride-resistant mutant of *Methanothermobacter thermoautotrophicus* possessing a defective Na+/H+ antiport. FEMS Microbiol Lett 269:301-308.

Tamura, K., Dudley, J., Nei, M. & Kumar, S. MEGA4: Molecular Evolutionary Genetics Analysis (MEGA) software version 4.0. Molecular biology and evolution 24, 1596-1599 (2007).

Tan, S., Evans, R. & Singh, B. Herbicidal inhibitors of amino acid biosynthesis and herbicide-tolerant crops. Amino Acids 30, 195-204 (2006).

Tatusov R L, Natale D A, Garkavtsev I V, Tatusova T A, Shankavaram U T, Rao B S, Kiryutin B, Galperin M Y, Fedorova N D, Koonin E V (2001) The COG database: new developments in phylogenetic classification of proteins from complete genomes Nucleic Acids Research 29, 22-28.

Tatusov, R. L., Galperin, M. Y., Natale, D. A. & Koonin, E. V. The COG database: a tool for genome-scale analysis of protein functions and evolution. Nucleic acids research 28, 33-36 (2000).

Tersteegen, A. & Hedderich, R. *Methanobacterium thermoautotrophicum* encodes two multisubunit membrane-bound [NiFe] hydrogenases. Transcription of the operons and sequence analysis of the deduced proteins. Eur. J. Biochem. 264, 930-943 (1999).

Thauer, R. Biodiversity and unity in biochemistry. Antonie van Leeuwenhoek 71, 21-32 (1997).

Thauer, R. K. & Bonacher, L. G. Biosynthesis of coenzyme F430, a nickel porphinoid involved in methanogenesis. In: The biosynthesis of the tetrapyrrole pigments. Wiley, Chichester (Ciba Foundation Symposium) 180, 210-227 (1994).

Thauer, R. K., Hedderich, R. & Fischer, R. Unusual coenzymes of methanogenesis from CO2 and H2. In Ferry, J. G. (ed.) Methanogenesis: ecology, physiology, biochemistry and genetics. Chapman and Hall, New York, pp. 209-252 (1993).

Thauer, R. K., Kaster, A. K., Seedorf, H., Buckel, W. & Hedderich, R. Methanogenic archaea: ecologically relevant differences in energy conservation. Nature reviews 6, 579-591 (2008).

Thompson, H., Tersteegen, A., Thauer, R. K. & Hedderich, R. Two malate dehydrogenases in *Methanobacterium thermoautotrophicum*. Arch. Microbiol. 170, 38-42 (1998).

Tietze, M. et al. Redox potentials of methanophenazine and CoB-S-S-CoM, factors involved in electron transport in Methanogenic archaea. Chembiochem 4, 333-335 (2003).

Tokura, M., Tajima, K. & Ushida, K. Isolation of *Methanobrevibacter* sp. as a ciliate-associated ruminal methanogen. J. Gen. Appl. Microbiol. 45(1), 43-47 (1999).

Tolbert, W. D., Graham, D. E., White, R. H. & Ealick, S. E. Pyruvoyl-dependent arginine decarboxylase from *Methanococcus jannaschii*: crystal structures of the self-cleaved and S53A proenzyme forms. Struct. 11, 285-94 (2003).

Tschech A, Pfennig N (1984) Growth yield increase linked to caffeate reduction in *Acetobacterium woodii*. Arch Microbiol 137:163-167.

Tumbula D, Vothknecht U C, Kim H S, Ibba M, et al. Archaeal amino-tRNA synthesis: diversity replaces dogma. Genet 152:1269-1276.

Tumbula, D. L., Becker, N. D., Chang, W-z. & Söll, D. Domain-specific recruitment of amide amino acids for protein synthesis. Nature 407, 106-110 (2000).

Ungerfeld, E. M., Rust, S. R. & Burnett, R. Increases in microbial nitrogen production and efficiency in vitro with three inhibitors of ruminal methanogenesis. Can. J. Microbiol. 53, 496-503 (2007).

Ungerfeld, E. M., Rust, S. R., Boone, D. R. & Liu, Y. (2004) Effects of several inhibitors on pure cultures of ruminal methanogens. J. Appl. Microbiol. 97, 520-526 (2004).

United Nations (1997). Kyoto Protocol to the United Nations Framework Convention on Climate Change. UNEP.IUC/99/10. Chatlelaine, Switzerland, United Nations Environment Programme's Information Unit for Conventions, for the Climate Change Secretariat. Available: http://unfccc.int/resource/docs/convkp/kpeng.pdf Accessed 2009 Sep. 30.

Vaupel, M., Dietz, H., Linder, D. & Thauer, R. K. Primary structure of cyclohydrolase (Mch) from *Methanobacterium thermoautotrophicum* (strain Marburg) and functional expression of the mch gene in *Escherichia coli*. Eur. J. Biochem. 236, 294-300 (1996).

Verdonk, M. L. et al. (2003) Proteins. 52: 609-623.

Vermeij, P., Detmers, F. J. M., Broers, F. J. M., Keltjens, J. T. & Drift, C. Purification and characterization of coenzyme F390 synthetase from *Methanobacterium thermoautrophicum* (strain ΔH). FEBS J., 226, 185-191 (1994).

Vermeij, P., Pennings, J. L. A., Maassen, S. M., Keltjens, J. T. & Vogels, G. D. Cellular levels of factor 390 and methanogenic enzymes during growth of *Methanobacterium thermautotrophicum* ?H. J. Bacteriol. 179, 6640-6648 (1997).

Vermeij, P., Vinke, E., Keltjens, J. T. & van der Drift, C. Purification and properties of coenzyme F390 hydrolase from *Methanobacterium thermoautotrophicum* (strain Marburg). Eur. J. Biochem. 234, 592-597 (1995).

Vignais, P. M., Billoud, B. & Meyer, J. Classification and phylogeny of hydrogenases. FEMS Microbiol. Rev. 25, 455-501 (2001).

Vivona S, Gardy J L, Ranachandran S, Brinkman F S L, Raghava G P S et al. (2008) Computer-aided biotechnology: from immune-informatics to reverse vaccinology. Trends Biotechnol 26: 190-200.

Volfovsky, N., Haas, B. J. & Salzberg, S. L. A clustering method for repeat analysis in DNA sequences. Genome biology 2, RESEARCH0027 (2001).

Vorholt, J. A. The active species of 'CO2' utilized by formylmethanofuran dehydrogenase from methanogenic Archaea. Eur. J. Biochem. 248, 919-924 (1997).

Wackett L P, Honek J F, Begley T P, Wallace V, Orme-Johnson W H et al. Substrate analogues as mechanistic probes of methyl-S-coenzyme M reductase. Biochem 26:6012-6018.

Wasserfallen, A. Formylmethanofuran synthesis by formylmethanofuran dehydrogenase from *Methanobacterium thermoautotrophicum* Marburg. Biochem. Biophys. Res. Comm. 199, 1256-61 (1994).

Waterhouse, A. M., Proctor, J. B., Martin, D. M., Clamp, M. & Barton, G. J. Jalview Version 2-a multiple sequence alignment editor and analysis workbench. Bioinformatics 25(9), 1189-1191 (2009).

Wedlock D N, Pedersen G, Denis M, Dey D, Janssen P H, Buddle B M (2009) Development of a vaccine to mitigate greenhouse gas emissions in agriculture: Vaccination of sheep with methanogen fractions induces antibodies that block methane production in vitro. NZ Vet J. In press.

Weidenmaier, C. & Peschel, A. Teichoic acids and related cell-wall glycopolymers in Gram-positive physiology and host interactions. Nature reviews 6, 276-287 (2008).

Weimer P. J. Manipulating ruminal fermentation: a microbial ecological perspective. J. Anim. Sci. 76, 3114-3122, (1998).

Werken van de, H. J. G., Brouns, S. J. J., & Oost, J. van der. Pentose metabolism in archaea. In: The Archaea, new models for prokaryotic biology. (Ed.) Blum P. Caister Academic Press 71-94 (2008).

Wheeler, D. L. et al. Database resources of the National Center for Biotechnology Information. Nucleic acids research 36, D13-21 (2008).

White, R. H. & Xu, H. Methylglyoxal is an intermediate in the biosynthesis of 6-deoxy-5-ketofructose-1-phosphate: a precursor for aromatic amino acid biosynthesis in *Methanocaldococcus jannaschii*. Biochem. 45, 12366-12379 (2006).

White, R. H. Biosynthesis of methanogenic cofactors. Vitam. Horm. 61, 299-337 (2001).

White, R. H. L-aspartate semialdehyde and a 6-deoxy-5-ketohexose 1-phosphate are the precursors- to the aromatic amino acids on *Methanocaldococcus jannaschii*. Biochem. 43, 7618-7627 (2004).

Whitman, W. B. & Wolfe, R. S. Activation of the methylreductase system from *Methanobacterium bryantii* by corrins, J. Bacteriol. 164, 165-172 (1985).

Whitman, W. B. & Wolfe, R. S. Inhibition by corrins of the ATP-dependent activation and the CO2 reduction by the methylreductase system in *Methanobacterium bryantii*. J. Bacteriol. 169, 87-92 (1987).

Widdel F, Kohring G W, Mayer F (1983) Studies on dissimilatory sulfate-reducing bacteria that decompose fatty acids. III. Characterization of the filamentous gliding *Desulfonema limicola* gen. nov. sp. nov., and *Desulfonema magnum* sp. nov. Arch Microbiol 134:286-94.

Wise, E. L., Graham, D. E., White, R. H. & Rayment, I. The structural determination of phosphosulfolactate synthase from *Methanococcus jannaschii* at 1.7-A resolution: an enolase that is not an enolase. J. Biol. Chem. 278, 45858-45863 (2003).

Wolin, M. J. & Miller, T. L. (2006) Int. Congr. Ser. 1293 131-137.

Wolfe, R. S. Biochemistry of methanogenesis. Biochemical Society symposium 58, 41-49 (1992).

Wolfe, R. S. My kind of biology. Annual review of microbiology 45, 1-35 (1991).

Woo, G-J., Wasserfallen, A. & Wolfe, R. S. Methyl violgen hydrogenase II, a new member of the hydrogenase family from *Methanobacterium thermoautotrophicum* ?H. J. Bacteriol. 175, 5970-5977 (1993).

Wouters, J., Oudjama, Y., Stalon, V., Droogmans, L., & Poulter, C. D. Crystal structure of the C67A mutant of isopentenyl diphosphate isomerase complexed with a mechanism-based irreversible inhibitor. Prot. 54, 216-21 (2004).

Wu, N., Pai, E. F. Crystal structures of inhibitor complexes reveal an alternate binding mode in orotidine-5'-monophosphate decarboxylase. J. Bacteriol. 277, 28080-28087 (2002).

Xing, R. Y & Whitman, W. B. Sulfometuron methyl-sensitive and -resistant acetolactate synthases of the archaebacteria *methanococcus* spp. J. Bacteriol. 169, 4486-4492 (1987).

Yokoyama, K., Nio N. & Kikuchi, Y. Properties and applications of microbial transglutaminase. Appl. Microbial. Biotechnol. 64, 447-454 (2004).

Yurist-Doutsch, S., Chaban, B., VanDyke, D. J., Jarrell, K. F. & Eichler, J. Sweet to the extreme: protein glycosylation in Archaea. Mol. Microbiol. 68, 1079-1084 (2008).

Zeikus, J. G. & Bowen, B. G. Comparative ultrastructure of methanogenic bacteria. Can. J. Microbiol. 21(2), 121-129 (1975).

Zhang, Y., White, R. H. & Ealick, S. E. Crystal structure and, function of 5-formaminoimidazole-4-carboxamide ribonucleotide synthetase from *Methanocaldococcus jannaschii*. Biochem. 47, 205-217 (2008).

Zoeiby, A. E., Sanschagrin, F., Levesque, R. C. Structure and function of the Mur enzymes: development of novel inhibitors. Mol. Microbiol. 47, 1-12 (2003).

Reference is made to sequence listing submitted herewith electronically via a text file (.txt), which is hereby incorporated by reference herein in its entirety.

All publications and patents mentioned in the above specification are herein incorporated by reference. Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the range and scope of the invention.

LENGTHY TABLES

The patent contains a lengthy table section. A copy of the table is available in electronic form from the USPTO web site (http://seqdata.uspto.gov/?pageRequest=docDetail&DocID=US09441016B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09441016B2). An electronic copy of the "Sequence Listing" will also be available from the USPTO upon request and payment of the fee set forth in 37 CFR 1.19(b)(3).

What is claimed is:

1. A vaccine composition comprising an adjuvant, and a polypeptide comprising the amino acid sequence SEQ ID NO: 7555.

2. The vaccine composition of claim 1, wherein the polypeptide comprises a conjugate or fusion molecule.

3. The vaccine composition of claim 1, wherein the vaccine composition is an animal vaccine composition against a methanogen.

4. The vaccine composition of claim 3, wherein the methanogen is *Methanobrevibacter ruminantium*.

5. The vaccine composition of claim 3, wherein the animal is a ruminant.

6. The vaccine composition of claim 5, wherein the ruminant is selected from the group consisting of cattle, sheep, goats, buffalo, moose, antelope, caribou, and deer.

7. The vaccine composition of claim 1, wherein the vaccine composition is a ruminant vaccine composition for use in reducing methane emissions.

8. A kit for reducing methanogen growth or methane production in a ruminant comprising the vaccine composition of claim 1.

9. A method of vaccinating an animal against a methanogen, comprising the step of administering to said animal, the vaccine composition according to claim 1.

10. The method of claim 9, wherein the methanogen is *Methanobrevibacter ruminantium*.

11. The method of claim 9 wherein the animal is a ruminant.

12. The method of claim 11, wherein the ruminant is selected from the group consisting of cattle, sheep, goats, buffalo, moose, antelope, caribou, and deer.

13. A method of reducing methane emissions from a ruminant, comprising vaccinating the ruminant against a methanogen according to claim 9.

* * * * *